(12) United States Patent
Kawamura et al.

(10) Patent No.: US 7,718,801 B2
(45) Date of Patent: May 18, 2010

(54) SUBSTITUTED IMIDAZOLE DERIVATIVE

(75) Inventors: Mikako Kawamura, Tsukuba (JP);
Takashi Hashihayata, Tsukuba (JP);
Satoshi Sunami, Toride (JP); Tetsuya Sugimoto, Tsukuba (JP); Fuyuki Yamamoto, Tsukuba (JP); Yoshiyuki Sato, Chiba (JP); Kaori Kamijo, Tsukuba (JP); Morihiro Mitsuya, Tsukuba (JP); Yoshikazu Iwasawa, Tsukuba (JP); Hideya Komatani, Toride (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 130 days.

(21) Appl. No.: 11/661,486

(22) PCT Filed: Aug. 30, 2005

(86) PCT No.: PCT/JP2005/016187
§ 371 (c)(1),
(2), (4) Date: Feb. 27, 2007

(87) PCT Pub. No.: WO2006/025567
PCT Pub. Date: Mar. 9, 2006

(65) Prior Publication Data
US 2008/0070894 A1 Mar. 20, 2008

(30) Foreign Application Priority Data
Aug. 31, 2004 (JP) .............................. 2004-251500

(51) Int. Cl.
*C07D 239/00* (2006.01)
*C07D 239/02* (2006.01)
(52) U.S. Cl. ...................................... 544/297; 544/242
(58) Field of Classification Search .................. 544/242, 544/297
See application file for complete search history.

(56) References Cited
FOREIGN PATENT DOCUMENTS

| JP | 2002-540097 | 11/2002 |
|---|---|---|
| JP | 2003-513977 | 4/2003 |
| WO | WO 02/076983 | 10/2002 |
| WO | WO 03/000682 | 1/2003 |
| WO | WO 03/000689 | 1/2003 |
| WO | WO 2004/014899 | 2/2004 |
| WO | WO 2004/021989 | 3/2004 |
| WO | WO 2004/043936 | 5/2004 |
| WO | WO 2005/092899 | 10/2005 |

OTHER PUBLICATIONS

Suggitt et al.; "50 Years of Preclinical Anticancer Drug Screening: Empirical to Target-Driven Approaches"; 2005; Clinical Cancer Research; 11: 971-981.*

* cited by examiner

*Primary Examiner*—Brandon J Fetterolf
*Assistant Examiner*—Anna Pagonakis
(74) *Attorney, Agent, or Firm*—Nicole M. Beeler; David A. Muthard

(57) ABSTRACT

The present invention relates to a compound represented by Formula [I] or a pharmaceutically acceptable salt or ester thereof:

wherein:
$X_1$, $X_2$, $X_3$, and $X_4$, which may be identical or different, are each C or N, provided that none to two of $X_1$, $X_2$, $X_3$, and $X_4$ is/are N;
Y is CH or N;
$R_1$, $R_1'$, $R_2$, $R_2'$, $R_3$, $R_3'$, $R_4$, and $R_4'$, which may be identical or different, are each a hydrogen atom, a lower alkyl group, or the like;
$R_5$ is a hydrogen atom or a methyl group;
$R_6$ and $R_7$, which may be identical or different, are each a hydrogen atom, a lower alkyl group, or the like;
$R_8$ and $R_8'$, which may be identical or different, are each a hydrogen atom, a lower alkyl group, or the like;
$R_9$ is an aryl group or a heteroaryl group which may be substituted; and
n is an integer from 1 to 3,
and a PLK1 inhibitor or an anticancer agent containing the same.

7 Claims, No Drawings

SUBSTITUTED IMIDAZOLE DERIVATIVE

PRIORITY CLAIM

This application is a §371 National Stage Application of PCT/JP2005/016187, filed on Aug. 30, 2005, which claims priority from Japanese Provisional Application Ser. No. 2004-251500, filed on Aug. 31, 2004.

TECHNICAL FIELD

The present invention relates to a novel substituted imidazole derivative which is useful in the field of medicine, and which inhibits proliferation of tumor cells in response to an inhibitory effect against PLK 1, thereby exhibiting an anticancer effect, and relates also to a PLK1 inhibitor and an anticancer agent containing the same.

BACKGROUND ART

Proliferation is known to be active generally in cancerous cells as compared with normal cells, and it is considered that the disordered proliferation due to an abnormality in the cell cycle control mechanism is the cause of cancer. A mitotic phase (M phase) of the cell cycle is the step of equally partitioning a chromosome into daughter cells, and a strict control in the process is essential for cell proliferation and survival. Therefore, it is believed that the inhibition of the M phase progression is an effective means for inhibiting cell proliferation, and practically, anticancer agents targeting M phase such as taxol, vincristine, or the like are achieving clinically effective results.

It has been known that many steps in the M phase progression are controlled by a protein kinase which phosphorylates proteins. A PLK (polo-like kinase) family is a serine-threonine kinase playing an important role in controlling the cell cycle including M phase, and this family includes four similar proteins of PLK1, PLK2, PLK3, and SAK (Nature Review Molecular Cell Biology (Nat. Rev. Mol. Cell Biol.), Vol. 5, 429, (2004)). Among them, PLK1 is known to participate in a plural of important stages at M phase in mammalian cells. That is, PLK1 has been reported to be participated in each step of entering the M phase, control of centrosomes, separation of chromosomes, and cytokinesis, by phosphorylating various substrates (Nature review Molecular Cell Biology (Nat. Rev. Mol. Cell Biol.), Vol. 5, 429, (2004)).

Moreover, there are many reports suggesting that PLK1 is overexpressed in various cancerous tissues in human. For example, PLK1 is acknowledged to be overexpressed in non-small-cell lung cancer (Oncogene, Vol. 14, 543, (1997)) and head and neck cancer (Cancer Research, Vol. 15, 2794, (1999)), and there are data showing that the overexpression of PLK1 is in relation with a prognosis of patients with those diseases. It is also reported that the expression of PLK1 is increased in other types of cancer such as in colon cancer, esophageal cancer, ovarian cancer, and melanoma. Such reports suggest that the overexpression of PLK1 is related to malignant alteration of cells in one way or another, and also that the function of PLK1 is important particularly in the progression of M phase in cancer cells.

From the facts, PLK1 is thought to be a possible target for anticancer approach. In fact, there are many reports on experiments for examining the inhibitory effect on the function of PLK1 against cancerous cells by using various experimental techniques. For example, from the experiment of expressing a function-inhibited PLK1 mutant in a cell by using a viral vector, it is reported that PLK1 inhibition promotes the cancerous cell-selective apoptosis (Cell growth & Differentiation, Vol. 11, 615, (2000)). There is also a report showing that PLK1 siRNA induces cancer cell growth inhibition and apoptosis (Journal of National Cancer Institute (J. Natl. Cancer Inst.), Vol. 94, 1863 (2002)). In addition, it is reported that PLK1 shRNA (Journal of National Cancer Institute (J. Natl. Cancer Inst.), Vol. 96, 862, (2004)), or antisense oligonucleotide (Oncogene, Vol. 21, 3162 (2002)) gives an antitumor effect in a mouse xenograft model. Those experimental results show that inhibition of the PLK1 activity causes promoting cancer cell growth inhibition and apoptosis, and strongly suggest that a PLK1 inhibitor may be an effective anticancer agent.

In the past, there are filed patent applications related to a compound having a PLK inhibitory effect (Pamphlet of International Publication Nos. 2004/043936, 2004/014899, etc.). However, there has not yet been reported a substituted imidazole derivative having an excellent PLK1 inhibitory effect.

DISCLOSURE OF THE INVENTION

An object of the present invention is to provide a novel substituted imidazole derivative, which exhibits a PLK1 inhibitory effect and excellent cell growth inhibitory activity based on the inhibitory effect, thereby developing an antitumor agent based on a PLK1 inhibitory effect.

In order to attain the object, the inventors of the present invention synthesized a wide range of substituted imidazole derivatives, and discovered that a compound represented by Formula [I] exhibits an excellent PLK1 inhibitory effect and cell growth inhibitory activity based on the inhibitory effect, thus completing the invention.

That is, the invention relates to a compound represented by Formula [I] or a pharmaceutically acceptable salt or ester thereof:

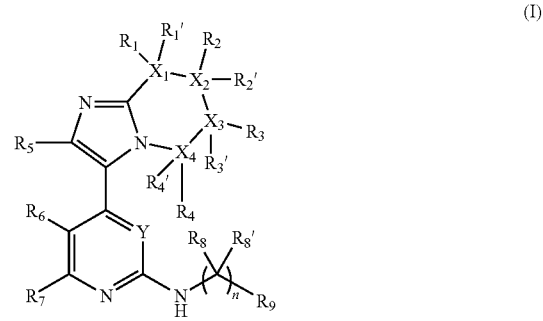

(I)

wherein:

$X_1$, $X_2$, $X_3$, and $X_4$, which may be identical or different, are each C or N, provided that none to two of $X_1$, $X_2$, $X_3$, and $X_4$ is/are N;

Y is CH or N;

$R_1$, $R_1'$, $R_2$, $R_2'$, $R_3$, $R_3'$, $R_4$, and $R_4'$, which may be identical or different, are each a hydrogen atom, a substituent selected from "Substituent Group α", a lower alkyl group which may be substituted with one or more substituents selected from "Substituent Group α", a cycloalkyl group, an aryl group or a heteroaryl group wherein the aryl group and heteroaryl group each independently may be substituted with one or more substituents, which may be identical or different, selected from the following 1) to 3):

1) a lower alkyl group,
2) a substituent selected from "Substituent Group α", and
3) a lower alkyl group substituted with a substituent selected from "Substituent Group α"), or $R_a$ wherein $R_a$ is represented by —$Z_1$—$Z_2$—$Z_3$, $Z_1$ is O or NHCO;

$Z_2$ is a single bond or $(CHW_i)_{n1}$ wherein $n_1$ is an integer from 1 to 3; i is an integer from 1 to $n_1$; $(CHW_i)_{n1}$ represents $(CHW_1)$ when $n_1=1$, $(CHW_i)_{n1}$ represents $(CHW_1)$—$(CHW_2)$ when $n_1=2$, and $(CHW_i)_{n1}$ represents $(CHW_1)$—$(CHW_2)$—$(CHW_3)$ when $n_1=3$; and $W_1$, $W_2$, and $W_3$, which may be identical or different, are each a hydrogen atom or a lower alkyl group having 1 to 2 carbon atom(s);

$Z_3$ is a lower alkoxy group or a phenyl group wherein the phenyl group may be substituted with one or more substituents selected from "Substituent Group α", provided that, when any of $X_1$, $X_2$, $X_3$, and $X_4$ is N, then any one of $R_i$ and $R_i'$ which bonds to the $X_i$ which is N, wherein i is an integer from 1 to 4, becomes N together with the $X_i$, and the other one of Ri and Ri' is as defined above; any one of $R_1$ and $R_1'$ and any one of $R_2$ and $R_2'$ may together form a double bond for $X_1$-$X_2$ bonding; and any one of $R_3$ and $R_3'$ and any one of $R_4$ and $R_4'$ may together form a double bond for $X_3$-$X_4$ bonding;

$R_5$ is a hydrogen atom or a methyl group;

$R_6$ and $R_7$, which may be identical or different, are each a hydrogen atom, a substituent selected from "Substituent Group β", a lower alkyl group which may be substituted with one or more substituents selected from "Substituent Group β", or a 5- or 6-membered aliphatic heterocyclic group selected from a pyrrolidinyl group, a piperidinyl group, and a piperazinyl group wherein the 5- or 6-membered aliphatic heterocyclic group may be substituted with one or more substituents, which may be identical or different, selected from the following 1) to 3):
1) a lower alkyl group,
2) a substituent selected from "Substituent Group β", and
3) a lower alkyl group substituted with a substituent selected from "Substituent Group β", or alternatively, $R_6$ and $R_7$ together form the following ring which is fused to a ring to which $R_6$ and $R_7$ are bonded:

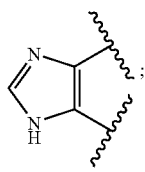

$R_8$ and $R_8'$, which may be identical or different, are each a hydrogen atom or a lower alkyl group which may be substituted with one or more substituents selected from "Substituent Group α";

$R_9$ is an aryl group or a heteroaryl group wherein the aryl group and the heteroaryl group each independently may be substituted with one or more substituents, which may be identical or different, selected from the following 1) to 9):
1) a lower alkyl group,
2) a substituent selected from "Substituent Group α",
3) a lower alkyl group substituted with a substituent selected from "Substituent Group α",
4) a 4- to 7-membered aliphatic heterocyclic group selected from an azetidinyl group, a pyrrolidinyl group, a piperidinyl group, a piperazinyl group, a 1,4-perhydrodiazepinyl group, and a morpholino group wherein:
the 4- to 7-membered aliphatic heterocyclic group may be substituted with one or more substituents, which may be identical or different, selected from the following a) to c):
a) a lower alkyl group,
b) a substituent selected from "Substituent Group α", and
c) a lower alkyl group substituted with a substituent selected from "Substituent Group α", and in the 4- to 7-membered aliphatic heterocyclic group, two hydrogen atoms binding to the same carbon atom may be replaced by an oxo group; a bond between adjacent carbon atoms constituting the heterocyclic ring may be a double bond; and nonadjacent carbon atoms constituting the heterocyclic ring may form a cross-linkage,
5) a lower alkyl group substituted with the 4- to 7-membered aliphatic heterocyclic group mentioned in 4) above,
6) —$(CH_2)_{m1}$—$NR_{10}R_{10}'$ wherein:
$m_1$ is an integer from 0 to 3,
$R_{10}$ is a hydrogen atom or a lower alkyl group,
$R_{10}'$ is:
a) a lower alkyl group substituted with a substituent selected from "Substituent Group α",
b) a 4- to 6-membered aliphatic heterocyclic group selected from an azetidinyl group, a pyrrolidinyl group, a piperidinyl group, a piperazinyl group, and a morpholino group wherein the 4- to 6-membered aliphatic heterocyclic group may be substituted with one or more substituents, which may be identical or different, selected from the following aa) to ff):
aa) a lower alkyl group,
bb) a substituent selected from "Substituent Group α",
cc) a lower alkyl group substituted with a substituent selected from "Substituent Group α",
dd) a 5- to 6-membered aliphatic heterocyclic group, which may be substituted, selected from a pyrrolidinyl group, a piperidinyl group, and a piperazinyl group,
ee) a lower alkyl group substituted with the 5- to 6-membered aliphatic heterocyclic group mentioned in dd) above, and
ff) a lower alkyl group substituted with an aromatic heterocyclic ring selected from a pyridyl group, a pyrazinyl group, and a pyrimidinyl group, which may be substituted,
c) a lower alkyl group substituted with the 4- to 6-membered aliphatic heterocyclic group mentioned in b) above,
d) a 5- to 6-membered aromatic or aliphatic heterocyclic group, which may be substituted, selected from a pyrazolyl group, a pyridyl group, a pyrazinyl group, a pyrimidinyl group, and a tetrahydropyranyl group, or
e) a cycloalkyl group having 5 to 6 carbon atoms, which may be substituted, wherein two hydrogen atoms binding to the same carbon atom in the cycloalkyl group may be replaced by an oxo group,
7) —$OR_{11}$ wherein:
$R_{11}$ is:
a) a lower alkyl group substituted with a substituent selected from "Substituent Group α", b) a 5- to 6-membered aliphatic heterocyclic group selected from a pyrrolidinyl group, a piperidinyl group, a piperazinyl group, and a morpholino group wherein the 5- to 6-membered aliphatic heterocyclic group may be substituted with one or more substituents, which may be identical or different, selected from the following aa) to cc):
  aa) a lower alkyl group,
  bb) a substituent selected from "Substituent Group α", and
  cc) a lower alkyl group substituted with a substituent selected from "Substituent Group α",
c) a lower alkyl group substituted with the 5- to 6-membered aliphatic heterocyclic group mentioned in b) above, or
d) a 5- to 6-membered aromatic heterocyclic group selected from a pyrrolyl group, an imidazolyl group, a pyrazolyl group, a pyridyl group, a pyrazinyl group, and a pyrimidinyl group, 8) $-(CH_2)_{m2}-NHCOR_{13}$ wherein:
  $m_2$ is an integer from 0 to 3,
  $R_{13}$ is:
    a) a lower alkyl group,
    b) a substituent selected from "Substituent Group α",
    c) a lower alkyl group substituted with one or more substituents selected from "Substituent Group α",
    d) a cycloalkyl group having 3 to 6 carbon atoms, which may be substituted,
    e) a lower alkyl group substituted with a 5-membered aromatic heterocyclic group selected from a pyrrolyl group, an imidazolyl group, and a pyrazolyl group, which may be substituted, or
    f) a 5- to 6-membered aliphatic heterocyclic group, which may be substituted, selected from a pyrrolidinyl group, a piperidinyl group, a piperazinyl group, and a morpholino group) and 9) $-(CH_2)_{m3}-CONR_{14}R_{14}'$ wherein:
  $m_3$ is an integer from 0 to 3,
  $R_{14}$ and $R_{14}'$, which may be identical or different, are each:
    a) a hydrogen atom,
    b) a lower alkyl group,
    c) a substituent selected from "Substituent Group α", or
    d) a lower alkyl group substituted with one or more substituents selected from "Substituent Group α",
  or alternatively, $R_{14}$ and $R_{14}'$, together with a nitrogen atom which bonds thereto, form a 5- to 6-membered aliphatic heterocyclic ring, which may be substituted, selected from a pyrrolidinyl group, a piperidinyl group, and a piperazinyl group;
n is an integer from 1 to 3; and
"Substituent Group α" and "Substituent Group β" being defined as follows:

"Substituent Group α":
a halogen atom, a hydroxy group, a nitro group, a cyano group, an amino group, a carbamoyl group, an aminosulfonyl group, a lower alkylamino group, a hydroxy-lower alkylamino group, a di-lower alkylamino group, an imino group, a lower alkylsulfonyl group, a lower alkylsulfonylamino group, a lower alkoxy group which may be substituted with 1 to 3 halogen atom(s), a lower alkoxycarbonyl group, a lower alkoxycarbonylamino group, a lower alkanoyl group which may be substituted with 1 to 3 halogen atom(s), and a carboxyl group, and "Substituent Group β":
a halogen atom, a hydroxy group, a cyano group, an amino group, a formyl group, a carbamoyl group, an aminosulfonyl group, a lower alkylamino group, a di-lower alkylamino group, a hydroxyiminomethyl group, a methoxyiminomethyl group, a lower alkoxy group, a lower alkoxycarbonyl group, a lower alkoxycarbonylamino group, a lower alkanoyl group, a lower alkanoyloxy group, a lower alkylthio group, a lower alkylsulfonyl group, a carboxyl group, and a tetrazolyl group. The compound represented by the above Formula (I) includes all of the existing enantiomers and diastereomers in addition to racemates of the compound.

Hereinafter, the symbols and terms described in the present specification will be explained.

The "lower alkyl group" in the above Formula (I) refers to a straight-chained or branched alkyl group having 1 to 6 carbon atom(s), and examples thereof include a methyl group, an ethyl group, a propyl group, an isopropyl group, a butyl group, an isobutyl group, a sec-butyl group, a tert-butyl group, a pentyl group, a hexyl group, and the like.

The "cycloalkyl group" in the above Formula (I) refers to a 3- to 8-membered aliphatic cyclic group, and examples thereof include a cyclopropyl group, a cyclobutyl group, a cyclopentyl group, a cyclohexyl group, a cycloheptyl group, a cyclooctyl group, and the like.

The "aryl group" in the above Formula (I) refers to a monocyclic, bicyclic, or tricycle aromatic hydrocarbon group having 6 to 14 carbon atoms, and specifically is a phenyl group, a naphthyl group, an indenyl group, an anthranyl group, and the like.

The "heteroaryl group" in the above Formula (I) refers to an aromatic heterocyclic group containing at least one atom selected from a nitrogen atom, an oxygen atom, and a sulfur atom in addition to carbon atoms, and examples thereof include a 5- to 7-membered monocyclic heterocyclic group, a fused-ring heterocyclic group formed by fusion of a 3- to 8-membered ring to the monocyclic heterocyclic group, and the like. Specifically, a thienyl group, a pyrrolyl group, a furyl group, a thiazolyl group, an imidazolyl group, a pyrazolyl group, an oxazolyl group, a pyridyl group, a pyrazinyl group, a pyrimidinyl group, a pyridazinyl group, an isoxazolyl group, an isoquinolyl group, an isoindolyl group, an indazolyl group, an indolyl group, a quinoxalinyl group, a quinolyl group, a benzoimidazolyl group, a benzofuranyl group, and the like may be mentioned.

The "halogen atom" in the above Formula (I) is exemplified by a fluorine atom, a chlorine atom, a bromine atom, an iodine atom, or the like, and among these, for example, a fluorine atom, a chlorine atom, and a bromine atom are preferred.

The "lower alkylamino group" in the above Formula (I) refers to a substituent formed by N-substitution of the above "lower alkyl group" to an amino group, and examples thereof include an N-methylamino group, an N-ethylamino group, an N-propylamino group, an N-isopropylamino group, an N-butylamino group, an N-isobutylamino group, an N-tert-butylamino group, an N-pentylamino group, an N-hexylamino group, and the like.

The "hydroxy-lower alkylamino group" in the above Formula (I) refers to a substituent formed by substitution of one or more of hydroxy group(s) to the above "lower alkyl amino group", and examples thereof include an N-hydroxyethylamino group, an N-hydroxypropylamino group, an N-hydroxyisopropylamino group, an N-hydroxybutylamino group, an N-hydroxyisobutylamino group, an N-hydroxytert-butylamino group, an N-hydroxypentylamino group, an N-hydroxyhexylamino group, and the like.

The "di-lower alkylamino group" in the above Formula (I) refers to a substituent formed by N,N-disubstitution of the above "lower alkyl group" to an amino group, and examples thereof include an N,N-dimethylamino group, an N,N-diethylamino group, an N,N-dipropylamino group, an N,N-diisopropylamino group, an N,N-dibutylamino group, an N,N-diisobutylamino group, an N,N-ditert-butylamino group, an N,N-dipentylamino group, an N,N-dihexylamino group, an N-ethyl-N-methylamino group, an N-methyl-N-propylamino group, and the like.

The "lower alkylsulfonyl group" in the above Formula (I) refers to a substituent formed by the bonding of the above "lower alkyl group" to a sulfur atom in a sulfonyl group, and examples thereof include a methylsulfonyl group, an ethylsulfonyl group, a butylsulfonyl group, and the like.

The "lower alkylsulfonylamino group" in the above Formula (I) refers to a substituent formed by N-substitution of the above "lower alkylsulfonyl group" to an amino group, and examples thereof include a methylsulfonylamino group, an ethylsulfonylamino group, a butylsulfonylamino group, and the like.

The "lower alkoxy group" in the above Formula (I) refers to a group formed by the bonding of the "lower alkyl group" to an oxygen atom, and examples thereof include a methoxy group, an ethoxy group, a propoxy group, an isopropoxy group, a butoxy group, an isobutoxy group, a sec-butoxy group, a tert-butoxy group, a pentyloxy group, a neopentyloxy group, a hexyloxy group, an isohexyloxy group, and the like.

The "lower alkoxycarbonyl group" in the above Formula (I) refers to a group formed by the bonding of the "lower alkoxy group" to a carbonyl group, and specific examples thereof include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, a neopentyloxycarbonyl group, a hexyloxycarbonyl group, an isohexyloxycarbonyl group, and the like.

The "lower alkoxycarbonylamino group" in the above Formula (I) refers to a group formed by N-substitution of the "lower alkoxycarbonyl group" to an amino group, and specific examples thereof include a methoxycarbonylamino group, an ethoxycarbonylamino group, a propoxycarbonylamino group, an isopropoxycarbonylamino group, a butoxycarbonylamino group, an isobutoxycarbonylamino group, a sec-butoxycarbonylamino group, a tert-butoxycarbonylamino group, a pentyloxycarbonylamino group, a neopentyloxycarbonylamino group, a hexyloxycarbonylamino group, an isohexyloxycarbonylamino group, and the like.

The "lower alkanoyl group" in the above Formula (I) refers to a group formed by the bonding of the "lower alkyl group" to a carbonyl group, and is preferably a group in which the alkyl group having 1 to 5 carbon atom(s) is bonded to a carbonyl group. For example, an acetyl group, a propionyl group, a butyryl group, an isobutyryl group, a valeryl group, an isovaleryl group, a pivaloyl group, a pentanoyl group, and the like can be included.

The "lower alkanoyloxy group" in the above Formula (I) refers to a group formed by bonding of the "lower alkanoyl group" to an oxygen atom, and examples thereof include an acetyloxy group, a propionyloxy group, a butyryloxy group, an isobutyryloxy group, a valeryloxy group, an isovaleryloxy group, a pivaloyloxy group, a pentanoyloxy group, and the like.

The "lower alkylthio group" in the above Formula (I) refers to a substituent formed by the bonding of the "lower alkyl" to a sulfur atom, and examples thereof include a methylthio group, an ethylthio group, a butylthio group, and the like.

The term "PLK" indicates a polo-like kinase.

The term "PLK1" is one of the PLK (polo-like kinase) family members constituted by PLK1, PLK2, PLK3, and SAK.

The term "PLK1 inhibitor" is a drug that inhibits a polo-like kinase 1.

The terms "pharmaceutically acceptable salt or ester" and "pharmaceutically acceptable carrier or diluent" will be explained later.

Embodiments of the compound represented by the Formula (I) will be described in more detail.

$X_1$, $X_2$, $X_3$, and $X_4$, which may be identical or different, are each C or N, provided that none to two of $X_1$, $X_2$, $X_3$, and $X_4$ is/are N, Preferably, all of $X_1$, $X_2$, $X_3$, and $X_4$ are C, or alternatively any one of $X_2$, $X_3$, and $X_4$ is N and the others are C, and more preferably, all of $X_1$, $X_2$, $X_3$, and $X_4$ are C.

Y is CH or N, and Y is preferably N.

$R_1$, $R_1'$, $R_2$, $R_2'$, $R_3$, $R_3'$, $R_4$, and $R_4'$, which may be identical or different, are each a hydrogen atom; a substituent selected from a halogen atom, a hydroxy group, a nitro group, a cyano group, an amino group, a carbamoyl group, an aminosulfonyl group, a lower alkylamino group, a hydroxy-lower alkylamino group, a di-lower alkylamino group, an imino group, a lower alkylsulfonyl group, a lower alkoxy group which may be substituted with 1 to 3 halogen atom(s), a lower alkoxycarbonyl group, a lower alkoxycarbonylamino group, a lower alkanoyl group which may be substituted with 1 to 3 halogen atom(s), and a carboxyl group (hereinafter, these are referred to as "Substituent Group α"); a lower alkyl group which may be substituted with one or more substituents selected from "Substituent Group α"; a cycloalkyl group; an aryl group; a heteroaryl group; or $R_a$ wherein:

$R_a$ is represented by $-Z_1-Z_2-Z_3$, $Z_1$ is O or NHCO; $Z_2$ is a single bond or $(CHW_i)_{n1}$, where $n_1$ is an integer from 1 to 3; i is an integer from 1 to $n_1$; $(CHW_i)_{n1}$ represents $(CHW_1)$ when $n_1=1$, $(CHW_i)_{n1}$ represents $(CHW_1)-(CHW_2)$ when $n_1=2$, and $(CHW_i)_{n1}$ represents $(CHW_1)-(CHW_2)-(CHW_3)$ when $n_1=3$; and $W_1$, $W_2$, and $W_3$, which may be identical or different, are each a hydrogen atom or a lower alkyl group having 1 to 2 carbon atom(s)); $Z_3$ is a lower alkoxy group or a phenyl group wherein the phenyl group may be substituted with one or more substituents selected from "Substituent Group α", and also the aryl group and heteroaryl group each independently may be substituted with one or more substituents, which may be identical or different, selected from the following 1) to 3):

1) a lower alkyl group,
2) a substituent selected from "Substituent Group α", and
3) a lower alkyl group substituted with a substituent selected from "Substituent Group α".

However, when any of $X_1$, $X_2$, $X_3$, and $X_4$ is N, then any one of $R_i$ and $R_i'$ bonding to the $X_i$ which is N, wherein i is an integer from 1 to 4, becomes N together with the $X_i$, and the other one of Ri and Ri' is as defined above.

Any one of $R_1$ and $R_1'$ and any one of $R_2$ and $R_2'$ may together form a double bond for $X_1$-$X_2$ bonding; and any one of $R_3$ and $R_3'$ and any one of $R_4$ and $R_4'$ may together form a double bond for $X_3$-$X_4$ bonding.

With regard to $R_1$, $R_1'$, $R_2$, $R_2'$, $R_3$, $R_3'$, $R_4$, and $R_4'$, preferably, any one of $R_1$ and $R_1'$ and any one of $R_2$ and $R_2'$ together form a double bond for $X_1$-$X_2$ bonding;

any one of $R_3$ and $R_3'$ and any one of $R_4$ and $R_4'$ together form a double bond for $X_3$-$X_4$ bonding;

the other one of $R_1$ and $R_1'$ which is not involved in forming the double bond is a substituent selected from "Substituent Group α", a lower alkyl group which may be substituted with one or more substituents selected from "Substituent Group α", a cycloalkyl group, an aryl group, or a heteroaryl group;

the other one of $R_2$ and $R_2'$ which is not involved in forming the double bond is a hydrogen atom, a substituent selected from "Substituent Group α", or a lower alkyl group which may be substituted with one or more substituents selected from "Substituent Group α", or alternatively, it becomes N together with $X_2$ which is N;

the other one of $R_3$ and $R_3'$ which is not involved in forming the double bond is a hydrogen atom, a substituent selected from "Substituent Group α", or a lower alkyl group which may be substituted with one or more substituents selected from "Substituent Group α", or alternatively, it becomes N together with $X_3$ which is N; and the other one of $R_4$ and $R_4'$ which is not involved in forming the double bond is a hydrogen atom, or alternatively, it becomes N together with $X_4$ which is N.

With regard to $R_1$, $R_1'$, $R_2$, $R_2'$, $R_3$, $R_3'$, $R_4$, and $R_4'$, preferably, any one of $R_1$ and $R_1'$ is a hydrogen atom, and the other one is a substituent selected from "Substituent Group α", a lower alkyl group which may be substituted with one or more substituents selected from "Substituent Group α", an aryl group, or a heteroaryl group; and all of $R_2$, $R_2'$, $R_3$, $R_3'$, $R_4$, and $R_4'$ are each a hydrogen atom.

With regard to $R_1$, $R_1'$, $R_2$, $R_2'$, $R_3$, $R_3'$, $R_4$, and $R_4'$, more preferably, any one of $R_1$ and $R_1'$ which is not involved in forming the double bond is a halogen atom; a cyano group; a lower alkyl group having 1 to 2 carbon atom(s), which may be substituted with 1 to 3 halogen atom(s); a lower alkoxy group having 1 to 2 carbon atom(s), which may be substituted with 1 to 3 halogen atom(s); a lower alkyl group having 1 to 3 carbon atom(s), which may be substituted with a hydroxy group; or a cyclopropyl group;

any one of $R_2$ and $R_2'$ and any one of $R_3$ and $R_3'$ both of which are not involved in forming the double bond may be identical or different from each other, and are each a hydrogen atom; a halogen atom; a cyano group; a lower alkyl group having 1 to 2 carbon atom(s) which may be substituted with 1 to 3 halogen atom(s); a lower alkoxy group having 1 to 2 carbon atom(s) which may be substituted with 1 to 3 halogen atom(s); or a lower alkyl group having 1 to 3 carbon atom(s) which may be substituted with a hydroxy group; and any one of $R_4$ and $R_4'$ which is not involved in forming the double bond is a hydrogen atom.

With regard to $R_1$, $R_1'$, $R_2$, $R_2'$, $R_3$, $R_3'$, $R_4$, and $R_4'$, more preferably, any one of $R_1$ and $R_1'$ which is not involved in forming the double bond is a fluorine atom; a chlorine atom; a bromine atom; a cyano group; a methyl group which may be substituted with 1 to 3 halogen atom(s); a methoxy group which may be substituted with 1 to 3 halogen atom(s); a lower alkyl group having 1 to 3 carbon atoms which may be substituted with a hydroxy group; or a cyclopropyl group; and any one of $R_2$ and $R_2'$, $R_3$ and $R_3'$, and $R_4$ and $R_4'$ both of which are not involved in forming the double bond are each a hydrogen atom.

$R_5$ is a hydrogen atom or a methyl group, and preferably a hydrogen atom.

$R_6$ and $R_7$, which may be identical or different, are each a hydrogen atom; a substituent selected from a halogen atom, a hydroxy group, a cyano group, an amino group, a formyl group, a carbamoyl group, an aminosulfonyl group, a lower alkylamino group, a di-lower alkylamino group, a hydroxyiminomethyl group, a methoxyiminomethyl group, a lower alkoxy group, a lower alkoxycarbonyl group, a lower alkoxycarbonylamino group, a lower alkanoyl group, a lower alkanoyloxy group, a lower alkylthio group, a lower alkylsulfonyl group, a carboxyl group, and a tetrazolyl group (hereinafter, these are referred to as "Substituent Group β"); a lower alkyl group which may be substituted with one or more substituents selected from "Substituent Group β"; or a 5- or 6-membered aliphatic heterocyclic group selected from a pyrrolidinyl group, a piperidinyl group, and a piperazinyl group wherein the 5- or 6-membered aliphatic heterocyclic group may be substituted with one or more substituents, which may be identical or different, selected from the following 1) to 3):

1) a lower alkyl group,
2) a substituent selected from "Substituent Group β", and
3) a lower alkyl group substituted with a substituent selected from "Substituent Group β", or alternatively, $R_6$ and $R_7$ together form the following ring which is fused to a ring to which $R_6$ and $R_7$ are bonded:

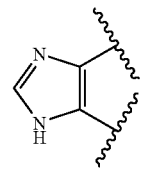

With regard to $R_6$ and $R_7$, preferably, $R_6$ is a hydrogen atom or a substituent selected from "Substituent Group β", the "Substituent Group β" is a halogen atom, a cyano group, and a lower alkoxy group, and $R_7$ is a hydrogen atom.

With regard to $R_6$ and $R_7$, more preferably, $R_6$ is a cyano group and $R_7$ is a hydrogen atom.

$R_8$ and $R_8'$, which may be identical or different, are each a hydrogen atom or a lower alkyl group which may be substituted with one or more substituents selected from "Substituent Group α", and preferably, one of $R_8$ and $R_8'$ is a hydrogen atom and the other one is a methyl group or an ethyl group; and more preferably, one of $R_8$ and $R_8'$ is a hydrogen atom and the other one is a methyl group. When a carbon atom to which $R_8$ and $R_8'$ are bonded is an asymmetric carbon, the S form is preferred.

$R_9$ is an aryl group or a heteroaryl group wherein the aryl group and the heteroaryl group each independently may be substituted with one or more substituents, which may be identical or different, selected from the following 1) to 9):

1) a lower alkyl group,
2) a substituent selected from "Substituent Group α",
3) a lower alkyl group substituted with a substituent selected from "Substituent Group α",
4) a 4- to 7-membered aliphatic heterocyclic group selected from an azetidinyl group, a pyrrolidinyl group, a piperidinyl group, a piperazinyl group, a 1,4-perhydrodiazepinyl group, and a morpholino group wherein the 4- to 7-membered aliphatic heterocyclic group may be substituted with one or more substituents, which may be identical or different, selected from the following a) to c):

a) a lower alkyl group,
b) a substituent selected from "Substituent Group α", and
c) a lower alkyl group substituted with a substituent selected from "Substituent Group α", and in the 4- to 7-membered aliphatic heterocyclic group, two hydrogen atoms binding to the same carbon atom may be replaced by an oxo group; a bond between adjacent carbon atoms constituting the heterocyclic ring may be a double bond; and nonadjacent carbon atoms constituting the heterocyclic ring may form a cross-linkage, 5) a lower alkyl group substituted with the 4- to 7-membered aliphatic heterocyclic group mentioned in 4) above, 6) —$(CH_2)_{m1}$—$NR_{10}R_{10}'$ wherein:
$m_1$ is an integer from 0 to 3,
$R_{10}$ is a hydrogen atom or a lower alkyl group,
$R_{10}'$ is:
   a) a lower alkyl group substituted with a substituent selected from "Substituent Group α",
   b) a 4- to 6-membered aliphatic heterocyclic group selected from an azetidinyl group, a pyrrolidinyl group, a piperidinyl group, a piperazinyl group, and a morpholino group wherein the 4- to 6-membered aliphatic heterocyclic group may be substituted with one or more substituents, which may be identical or different, selected from the following aa) to ff):
      aa) a lower alkyl group,
      bb) a substituent selected from "Substituent Group α",
      cc) a lower alkyl group substituted with a substituent selected from "Substituent Group α",
      dd) a 5- to 6-membered aliphatic heterocyclic group, which may be substituted, selected from a pyrrolidinyl group, a piperidinyl group, and a piperazinyl group,
      ee) a lower alkyl group substituted with the 5- to 6-membered aliphatic heterocyclic group mentioned in dd) above, and
      ff) a lower alkyl group substituted with an aromatic heterocyclic ring selected from a pyridyl group, a pyrazinyl group, and a pyrimidinyl group,
   c) a lower alkyl group substituted with the 4- to 6-membered aliphatic heterocyclic group mentioned in b) above,
   d) a 5- to 6-membered aromatic or aliphatic heterocyclic group, which may be substituted, selected from a pyrazolyl group, a pyridyl group, a pyrazinyl group, a pyrimidinyl group, and a tetrahydropyranyl group, or
   e) a cycloalkyl group having 5 to 6 carbon atoms, which may be substituted, wherein two hydrogen atoms binding to the same carbon atom in the cycloalkyl group may be replaced by an oxo group, 7) —$OR_{11}$ wherein:
$R_{11}$ is:
   a) a lower alkyl group substituted with a substituent selected from "Substituent Group α",
   b) a 5- to 6-membered aliphatic heterocyclic group selected from a pyrrolidinyl group, a piperidinyl group, a piperazinyl group, and a morpholino group wherein the 5- to 6-membered aliphatic heterocyclic group may be substituted with one or more substituents, which may be identical or different, selected from the following aa) to cc):
      aa) a lower alkyl group.
      bb) a substituent selected from "Substituent Group α", and
      cc) a lower alkyl group substituted with a substituent selected from "Substituent Group α"),
   c) a lower alkyl group substituted with the 5- to 6-membered aliphatic heterocyclic group mentioned in b) above, or
   d) a 5- to 6-membered aromatic heterocyclic group selected from a pyrrolyl group, an imidazolyl group, a pyrazolyl group, a pyridyl group, a pyrazinyl group, and a pyrimidinyl group, 8) —$(CH_2)_{m2}$—$NHCOR_{13}$ wherein:
$m_2$ is an integer from 0 to 3,
$R_{13}$ is:
   a) a lower alkyl group,
   b) a substituent selected from "Substituent Group α",
   c) a lower alkyl group substituted with one or more substituents selected from "Substituent Group α",
   d) a cycloalkyl group having 3 to 6 carbon atoms, which may be substituted,
   e) a lower alkyl group substituted with a 5-membered aromatic heterocyclic group selected from a pyrrolyl group, an imidazolyl group, and a pyrazolyl group, which may be substituted; or
   f) a 5- to 6-membered aliphatic heterocyclic group, which may be substituted, selected from a pyrrolidinyl group, a piperidinyl group, a piperazinyl group, and a morpholino group, and 9) —$(CH_2)_{m3}$—$CONR_{14}R_{14}'$ wherein:
$m_3$ is an integer from 0 to 3,
$R_{14}$ and $R_{14}'$, which may be identical or different, are each:
   a) a hydrogen atom,
   b) a lower alkyl group,
   c) a substituent selected from "Substituent Group α", or
   d) a lower alkyl group substituted with one or more substituents selected from "Substituent Group α",
or alternatively, $R_{14}$ and $R_{14}'$, together with a nitrogen atom binding thereto, form a 5- to 6-membered aliphatic heterocyclic ring which may be substituted, selected from a pyrrolidinyl group, a piperidinyl group, and a piperazinyl group.

In the 4- to 7-membered aliphatic heterocyclic group mentioned in 4) above, the phrase 'nonadjacent carbon atoms constituting the heterocyclic ring may form a cross-linkage' specifically means that nonadjacent carbon atoms constituting the heterocyclic ring may form a cross-linkage represented by —$(CH_2)_r$—, wherein r is an integer of 1 or 2, and one of the examples is the following:

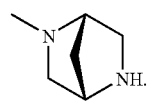

$R_9$ is preferably a phenyl group which may be substituted. That is, $R_9$ is a phenyl group wherein the phenyl group may be substituted with one or more substituents, which may be identical or different, selected from the following 1) to 8):

1) a lower alkyl group,
2) a substituent selected from "Substituent Group α",
3) a lower alkyl group substituted with a substituent selected from "Substituent Group α",
4) a 4- to 6-membered aliphatic heterocyclic group selected from an azetidinyl group, a pyrrolidinyl group, a piperidinyl group, a piperazinyl group, and a morpholino group wherein the 4- to 6-membered aliphatic heterocyclic group may be substituted with one or more substituents, which may be identical or different, selected from the following a) to c):

a) a lower alkyl group,
b) a substituent selected from "Substituent Group α", and
c) a lower alkyl group substituted with a substituent selected from "Substituent Group α". In the 4- to 6-membered aliphatic heterocyclic group; two hydrogen atoms binding to the same carbon atom may be replaced by an oxo group, a bond between adjacent carbon atoms constituting the heterocyclic ring may be a double bond; and nonadjacent carbon atoms constituting the heterocyclic ring may form a cross-linkage, 5) a lower alkyl group substituted with the 4- to 6-membered aliphatic heterocyclic group mentioned in 4) above,
6) —$NR_{10}R_{10}'$ or —$CH_2NR_{10}R_{10}'$ wherein:
$R_{10}$ is a hydrogen atom or a lower alkyl group,
$R_{10}'$ is:
   a) a lower alkyl group substituted with a substituent selected from "Substituent Group α",
   b) a 4- to 6-membered aliphatic heterocyclic group selected from an azetidinyl group, a pyrrolidinyl group, a piperidinyl group, a piperazinyl group, and a morpholino group wherein the 4- to 6-membered aliphatic heterocyclic group may be substituted with one or more substituents, which may be identical or different, selected from the following aa) to ff):
      aa) a lower alkyl group,
      bb) a substituent selected from "Substituent Group α",
      cc) a lower alkyl group substituted with a substituent selected from "Substituent Group α",
      dd) a 5- to 6-membered aliphatic heterocyclic group, which may be substituted, selected from a pyrrolidinyl group, a piperidinyl group, and a piperazinyl group,
      ee) a lower alkyl group substituted with the 5- to 6-membered aliphatic heterocyclic group mentioned in dd) above, and
      ff) a lower alkyl group substituted with an aromatic heterocyclic ring selected from a pyridyl group, a pyrazinyl group, and a pyrimidinyl group, which may be substituted,
   c) a lower alkyl group substituted with the 4- to 6-membered aliphatic heterocyclic group mentioned in b) above,
   d) a 5- to 6-membered aliphatic or aromatic heterocyclic group, which may be substituted, selected from a pyrazolyl group, a pyridyl group, a pyrazinyl group, a pyrimidinyl group, and a tetrahydropyranyl group, or
   e) a cycloalkyl group having 5 to 6 carbon atoms, which may be substituted, wherein two hydrogen atoms binding to the same carbon atom in the cycloalkyl group may be replaced by an oxo group,
7) —$OR_{11}$ wherein:
$R_{11}$ is:
a) a lower alkyl group substituted with a substituent selected from "Substituent Group α",
b) a 5- to 6-membered aliphatic heterocyclic group selected from a pyrrolidinyl group, a piperidinyl group, a piperazinyl group, and a morpholino group wherein the 5- to 6-membered aliphatic heterocyclic group may be substituted with one or more substituents, which may be identical or different, selected from the following aa) to cc):
   aa) a lower alkyl group.
   bb) a substituent selected from "Substituent Group α", and
   cc) a lower alkyl group substituted with a substituent selected from "Substituent Group α",
c) a lower alkyl group substituted with the 5- to 6-membered aliphatic heterocyclic group mentioned in b) above, or
d) a 5- to 6-membered aromatic heterocyclic group selected from a pyrrolyl group, an imidazolyl group, a pyrazolyl group, a pyridyl group, a pyrazinyl group, and a pyrimidinyl group, and
8) —$NHCOR_{13}$ or —$CH_2NHCOR_{13}$ wherein:
$R_{13}$ is:
a) a lower alkyl group,
b) a substituent selected from "Substituent Group α",
c) a lower alkyl group substituted with one or more substituents selected from "Substituent Group α",
d) a cycloalkyl group having 3 to 6 carbon atoms, which may be substituted,
e) a lower alkyl group substituted with a 5-membered aromatic heterocyclic group selected from a pyrrolyl group, an imidazolyl group, and a pyrazolyl group, which may be substituted; or
f) a 5- to 6-membered aliphatic heterocyclic group, which may be substituted, selected from a pyrrolidinyl group, a piperidinyl group, a piperazinyl group, and a morpholino group.

$R_9$ is more preferably a phenyl group wherein the phenyl group may be substituted with one or more substituents, which may be identical or different, selected from the following 1) to 5):
1) a substituent selected from "Substituent Group $\alpha_1$",
2) a 4- to 6-membered aliphatic heterocyclic group selected from an azetidinyl group, a pyrrolidinyl group, a piperidinyl group, and a piperazinyl group wherein the 4- to 6-membered aliphatic heterocyclic group may be substituted with one or more substituents, which may be identical or different, selected from the following a) to c):
   a) a lower alkyl group,
   b) a substituent selected from "Substituent Group $\alpha_1$", and
   c) a lower alkyl group substituted with a substituent selected from "Substituent Group $\alpha_1$", and in the 4- to 6-membered aliphatic heterocyclic group, two hydrogen atoms binding to the same carbon atom may be replaced by an oxo group; a bond between adjacent carbon atoms constituting the heterocyclic ring may be a double bond; and nonadjacent carbon atoms constituting the heterocyclic ring may form a cross-linkage,
3) a lower alkyl group substituted with the 5- to 6-membered aliphatic heterocyclic group mentioned in 2) above,
4) —$NR_{10}R'_{10}$ wherein:
$R_{10}$ is a hydrogen atom or a lower alkyl group having 1 to 2 carbon atom(s),
$R_{10}'$ is:
   a) a lower alkyl group substituted with a substituent selected from "Substituent Group $\alpha_1$",
   b) a 4- to 6-membered aliphatic heterocyclic group selected from an azetidinyl group, a pyrrolidinyl group, a piperidinyl group, a piperazinyl group, and a morpholino group wherein the 4- to 6-membered aliphatic heterocyclic group may be substituted with one or more substituents, which may be identical or different, selected from the following aa) to ee):
      aa) a lower alkyl group,
      bb) a substituent selected from "Substituent Group $\alpha_1$",
      cc) a lower alkyl group substituted with a substituent selected from "Substituent Group $\alpha_1$", dd) a 5- to 6-membered aliphatic heterocyclic group, which may be substituted, selected from a pyrrolidinyl group, a piperidinyl group, and a piperazinyl group, and ee) a lower alkyl group substituted with an aromatic heterocyclic ring selected from a pyridyl group, a pyrazinyl group, and a pyrimidinyl group, which may be substituted, and 5) —NHCOR$_{13}$ wherein:

R$_{13}$ is:

a) a lower alkyl group, b) a substituent selected from "Substituent Group α$_1$", or c) a lower alkyl group substituted with one or more substituents selected from "Substituent Group α$_1$". Herein, the "Substituent Group α$_1$" is a halogen atom, a hydroxy group, a cyano group, an amino group, a lower alkylamino group, a di-lower alkylamino group, a lower alkylsulfonyl group, a lower alkoxy group which may be substituted with 1 to 3 fluorine atom(s), or a lower alkanoyl group which may be substituted with 1 to 3 fluorine atom(s).

R$_9$ is even more preferably a phenyl group wherein the 3-position or 4-position of the phenyl group may be substituted with the following 1) or 2):

1) a pyrrolidinyl group or a piperazinyl group both of which may be substituted with one or more of a lower alkyl group and/or a substituent(s) selected from "Substituent Group α$_1$", or 2) —NR$_{10}$R$_{10}$' wherein:

R$_{10}$ is a hydrogen atom,

R$_{10}$' is an azetidinyl group or a piperidinyl group both of which may be substituted with a lower alkyl group optionally substituted with one or more substituents selected from "Substituent Group α$_1$".

When R$_9$ is a substituted phenyl group, the substitution position of the substituent is not particularly limited to, but the 2-position, 3-position, or 4-position, and preferably the 3-position and/or 4-position.

The number of substituent on R$_9$ is not particularly limited, but is 1, 2, or 3, preferably 1 or 2, and more preferably 1.

The preferred embodiment of R$_9$ can be represented by a phenyl group of which the 3-position or 4-position is substituted with the following substituents.

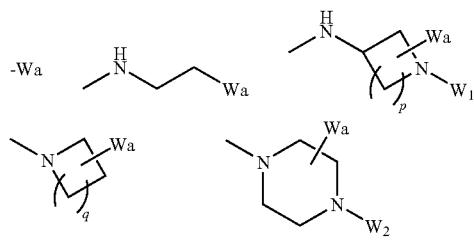

Wherein, p and q, which may be identical or different, are each 1, 2, or 3;

W$_a$ is a hydrogen atom, a lower alkyl group, or a substituent selected from "Substituent Group α$_1$"; and W$_1$ and W$_2$, which may be identical or different, are each a hydrogen atom, a lower alkyl group, a substituent selected from "Substituent Group α$_1$", or a lower alkyl group substituted with a substituent selected from "Substituent Group α$_1$".

The more preferred embodiment of R$_9$ can be represented by a phenyl group of which the 3-position or 4-position is substituted with the following substituents:

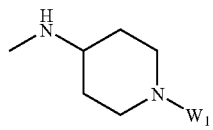 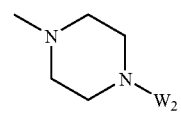

wherein, W$_1$ and W$_2$ are the same as defined above.

The particularly preferred embodiment of R$_9$ can be represented by a phenyl group of which the 3-position is substituted with the following substituent:

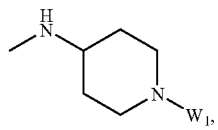

or a phenyl group of which the 4-position is substituted with the following substituent:

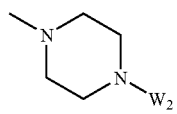

wherein W$_1$ and W$_2$ are the same as defined above.

"Substituent Group α$_1$" is:

a halogen atom, a hydroxy group, a nitro group, a cyano group, an amino group, a carbamoyl group, an aminosulfonyl group, a lower alkylamino group, a hydroxy-lower alkylamino group, a di-lower alkylamino group, an imino group, a lower alkylsulfonyl group, a lower alkoxycarbonylamino group, a lower alkoxy group which may be substituted with 1 to 3 halogen atom(s), a lower alkoxycarbonyl group, a lower alkanoyl group which may be substituted with 1 to 3 halogen atom(s), or a carboxyl group; and preferably, a halogen atom, a hydroxy group, a cyano group, an amino group, a lower alkylamino group, a di-lower alkylamino group, a lower alkylsulfonyl group, a lower alkoxy group which may be substituted with 1 to 3 fluorine atom(s), or a lower alkanoyl group which may be substituted with 1 to 3 fluorine atom(s).

"Substituent Group β" is:

a halogen atom, a hydroxy group, a cyano group, an amino group, a formyl group, a carbamoyl group, an aminosulfonyl group, a lower alkylamino group, a di-lower alkylamino group, a hydroxyiminomethyl group, a methoxyiminomethyl group, a lower alkoxy group, a lower alkoxycarbonyl group, a lower alkoxycarbonylamino group, a lower alkanoyl group, a lower alkanoyloxy group, a lower alkylthio group, a lower alkylsulfonyl group, a carboxyl group, or a tetrazolyl group; and preferably a halogen atom, a cyano group, or a lower alkoxy group.

n is an integer from 1 to 3, preferably 1.

The compound of the above Formula (I) is preferably, (a) 4-(8-methylimidazo[1,2-a]pyridin-3-yl)-2-{[(1S)-1-phenylethyl]amino}-5-pyrimidinecarbonitrile (Example 8), (b) 5-bromo-4-(8-chloroimidazo[1,2-a]pyridin-3-yl)-N-[(1S)-1-phenylethyl]-2-pyrimidinamine (Example 28),
(c) 4-(8-chloroimidazo[1,2-a]pyridin-3-yl)-2-{[(1S)-1-phenylethyl]amino}-5-pyrimidinecarbonitrile (Example 30),
(d) 5-bromo-4-[8-(difluoromethyl)imidazo[1,2-a]pyridin-3-yl]-N-[(1S)-1-phenylethyl]-2-pyrimidinamine (Example 31),
(e) 3-(5-cyano-2-{[(1S)-1-phenylethyl]amino}-4-pyrimidinyl)imidazo[1,2-a]pyridine-8-carbonitrile (Example 32),
(f) 4-[8-(difluoromethyl)imidazo[1,2-a]pyridin-3-yl]-2-{[(1S)-1-phenylethyl]amino}-5-pyrimidinecarbonitrile (Example 33),
(g) N-[(1S)-1-phenylethyl]-4-[8-(trifluoromethyl)imidazo[1,2-a]pyridin-3-yl]-2-pyrimidinamine (Example 34),
(h) 5-bromo-N-[(1S)-1-phenylethyl]-4-[8-(trifluoromethyl)imidazo[1,2-a]pyridin-3-yl]-2-pyrimidinamine (Example 35),
(i) 2-{[(1S)-1-phenylethyl]amino}-4-[8-(trifluoromethyl)imidazo[1,2-a]pyridin-3-yl]-5-pyrimidinecarbonitrile (Example 36),
(j) 2-{[(1S)-1-(3-aminophenyl)ethyl]amino}-4-[8-(difluoromethyl)imidazo[1,2-a]pyridin-3-yl]pyrimidine-5-carbonitrile (Example 80),
(k) 4-[8-(difluoromethyl)imidazo[1,2-a]pyridin-3-yl]-2-[((1S)-1-{3-[(1-methylazetidin-3-yl)amino]phenyl}ethyl)amino]pyrimidine-5-carbonitrile (Example 88),
(l) 4-[8-(difluoromethyl)imidazo[1,2-a]pyridin-3-yl]-2-{[(1S)-1-(4-piperazin-1-ylphenyl)ethyl]amino}pyrimidine-5-carbonitrile (Example 110),
(m) 4-(8-methylimidazo[1,2-a]pyridin-3-yl)-2-[((1S)-1-{3-[(1-methylpiperidin-4-yl)amino]phenyl}ethyl)amino]pyrimidine-5-carbonitrile (Example 119),
(n) 4-(8-chloroimidazo[1,2-a]pyridin-3-yl)-2-[((1S)-1-{3-[(1-methylpiperidin-4-yl)amino]phenyl}ethyl)amino]pyrimidine-5-carbonitrile (Example 123),
(o) 4-(8-chloroimidazo[1,2-a]pyridin-3-yl)-2-{[(1S)-1-(4-piperazin-1-ylphenyl)ethyl]amino}pyrimidine-5-carbonitrile (Example 132),
(p) 2-[((1S)-1-{4-[(3R)-3-aminopyrrolidin-1-yl]phenyl}ethyl)amino]-4-(8-chloroimidazo[1,2-a]pyridin-3-yl)pyrimidine-5-carbonitrile (Example 137),
(q) 4-(8-bromoimidazo[1,2-a]pyridin-3-yl)-2-{[(1S)-1-(4-piperazin-1-ylphenyl)ethyl]amino}pyrimidine-5-carbonitrile (Example 145),
(r) 4-[8-(fluoromethyl)imidazo[1,2-a]pyridin-3-yl]-2-{[(1S)-1-(4-piperazin-1-ylphenyl)ethyl]amino}pyrimidine-5-carbonitrile (Example 149),
(s) 4-[8-(fluoromethyl)imidazo[1,2-a]pyridin-3-yl]-2-{[(1S)-1-(4-piperidin-4-ylphenyl)ethyl]amino}pyrimidine-5-carbonitrile (Example 155),
(t) 4-[8-(1-hydroxyethyl)imidazo[1,2-a]pyridin-3-yl]-2-{[(1S)-1-(4-piperazin-1-ylphenyl)ethyl]amino}pyrimidine-5-carbonitrile (Example 156), or
(u) 4-(8-methoxyimidazo[1,2-a]pyridin-3-yl)-2-{[(1S)-1-(4-piperazin-1-ylphenyl)ethyl]amino}pyrimidine-5-carbonitrile (Example 158), or a pharmaceutically acceptable salt or ester thereof.

The preferred embodiment of the present specification can also be represented as follows. That is, (1) the compound of the above Formula (I), or a pharmaceutically acceptable salt or ester thereof, wherein:

all of $X_1$, $X_2$, $X_3$, and $X_4$ are C, or alternatively any one of $X_2$, $X_3$, and $X_4$ is N and the others are C;

any one of $R_1$ and $R_1'$ and any one of $R_2$ and $R_2'$ together form a double bond for $X_1$-$X_2$ bonding;

any one of $R_3$ and $R_3'$ and any one of $R_4$ and $R_4'$ together form a double bond for $X_3$-$X_4$ bonding;

the other one of $R_1$ and $R_1'$ which is not involved in forming the double bond is a substituent selected from "Substituent Group α", a lower alkyl group which may be substituted with one or more substituents selected from "Substituent Group α", a cycloalkyl group, an aryl group, or a heteroaryl group;

the other one of $R_2$ and $R_2'$ which is not involved in forming the double bond is a hydrogen atom, a substituent selected from "Substituent Group α", or a lower alkyl group which may be substituted with one or more substituents selected from "Substituent Group α", or alternatively, it becomes N together with $X_2$ which is N;

the other one of $R_3$ and $R_3'$ which is not involved in forming the double bond is a hydrogen atom, a substituent selected from "Substituent Group α", or a lower alkyl group which may be substituted with one or more substituents selected from "Substituent Group α", or alternatively, it becomes N together with $X_3$ which is N; and the other one of $R_4$ and $R_4'$ which is not involved in forming the double bond is either a hydrogen atom, or alternatively, it becomes N together with $X_4$ which is N;

(2) the compound of the above Formula (I), or a pharmaceutically acceptable salt or ester thereof, wherein:

all of $X_1$, $X_2$, $X_3$, and $X_4$ are C;

any one of $R_1$ and $R_1'$ is a hydrogen atom, and the other one is a substituent selected from "Substituent Group α", a lower alkyl group which may be substituted with one or more substituents selected from "Substituent Group α", an aryl group, or a heteroaryl group; and all of $R_2$, $R_2'$, $R_3$, $R_3'$, $R_4$, and $R_4'$ are each a hydrogen atom;

(3) the compound of (1) above, or a pharmaceutically acceptable salt or ester thereof, wherein:

one of $R_8$ and $R_8'$ is a hydrogen atom, and the other one is a methyl group or an ethyl group;

$R_9$ is a phenyl group which may be substituted; and n is 1;

(4) the compound of (3) above, or a pharmaceutically acceptable salt or ester thereof, wherein:

the "Substituent Group β" is a halogen atom, a cyano group, or a lower alkoxy group;

$R_6$ is a hydrogen atom or a substituent selected from the "Substituent Group β"; and $R_7$ is a hydrogen atom;

(5) the compound of (4) above, or a pharmaceutically acceptable salt or ester thereof, wherein Y is N;

(6) the compound of (5) above, or a pharmaceutically acceptable salt or ester thereof, wherein:

all of $X_1$, $X_2$, $X_3$, and $X_4$ are C;

any one of $R_1$ and $R_1'$ which is not involved in forming the double bond is a halogen atom; a cyano group; a lower alkyl group having 1 to 2 carbon atom(s), which may be substituted with 1 to 3 halogen atom(s); a lower alkoxy group having 1 to 2 carbon atom(s), which may be substituted with 1 to 3 halogen atom(s); a lower alkyl group having 1 to 3 carbon atom(s), which may be substituted with a hydroxy group; or a cyclopropyl group;

any one of $R_2$ and $R_2'$ and any one of $R_3$ and $R_3'$, both of which are not involved in forming the double bond, may be identical or different from each other, and are each a hydrogen atom; a halogen atom; a cyano group; a lower alkyl group having 1 to 2 carbon atom(s), which may be substituted with 1 to 3 halogen atom(s); a lower alkoxy group having 1 to 2 carbon atom(s), which may be substituted with 1 to 3 halogen atom(s); or a lower alkyl group having 1 to 3 carbon atom(s), which may be substituted with a hydroxy group; and any one of $R_4$ and $R_4'$ which is not involved in forming the double bond is a hydrogen atom;

(7) the compound of (6) above, or a pharmaceutically acceptable salt or ester thereof, wherein:

$R_5$ is a hydrogen atom, and $R_6$ is a cyano group; and any one of $R_8$ and $R_8'$ is a hydrogen atom and the other one is a methyl group;

(8) the compound of (7) above, or a pharmaceutically acceptable salt or ester thereof, wherein:

the "Substituent Group α" is a halogen atom, a hydroxy group, a cyano group, an amino group, a lower alkylamino group, a di-lower alkylamino group, a lower alkylsulfonyl group, a lower alkoxy group which may be substituted with 1 to 3 fluorine atom(s), and a lower alkanoyl group which may be substituted with 1 to 3 fluorine atom(s); and $R_9$ is a phenyl group wherein the phenyl group may be substituted with one or more substituents, which may be identical or different, selected from the following 1) to 5):

1) a substituent selected from "Substituent Group α", 2) a 4- to 6-membered aliphatic heterocyclic group selected from an azetidinyl group, a pyrrolidinyl group, a piperidinyl group, and a piperazinyl group wherein the 4- to 6-membered aliphatic heterocyclic group may be substituted with one or more substituents, which may be identical or different, selected from the following a) to c):

a) a lower alkyl group, b) a substituent selected from "Substituent Group α", and c) a lower alkyl group substituted with a substituent selected from "Substituent Group α", and in the 4- to 6-membered aliphatic heterocyclic group, two hydrogen atoms binding to the same carbon atom may be replaced by an oxo group; a bond between adjacent carbon atoms constituting the heterocyclic ring may be a double bond; and nonadjacent carbon atoms constituting the heterocyclic ring may form a cross-linkage, 3) a lower alkyl group substituted with the 5- to 6-membered aliphatic heterocyclic group mentioned in 2) above, 4) —$NR_{10}R'_{10}$ wherein:

$R_{10}$ is a hydrogen atom or a lower alkyl group having 1 to 2 carbon atom(s), $R_{10}'$ is:

a) a lower alkyl group substituted with a substituent selected from "Substituent Group α", b) a 4- to 6-membered aliphatic heterocyclic group selected from an azetidinyl group, a pyrrolidinyl group, a piperidinyl group, a piperazinyl group, and a morpholino group wherein the 4- to 6-membered aliphatic heterocyclic group may be substituted with one or more substituents, which may be identical or different, selected from the following aa) to ee):

aa) a lower alkyl group, bb) a substituent selected from "Substituent Group α", cc) a lower alkyl group substituted with a substituent selected from "Substituent Group α", dd) a 5- to 6-membered aliphatic heterocyclic group, which may be substituted, selected from a pyrrolidinyl group, a piperidinyl group, and a piperazinyl group, and ee) a lower alkyl group substituted with an aromatic heterocyclic ring selected from a pyridyl group, a pyrazinyl group, and a pyrimidinyl group, which may be substituted, and 5) —$NHCOR_{13}$ wherein:

$R_{13}$ is:

a) a lower alkyl group, b) a substituent selected from "Substituent Group α", or c) a lower alkyl group substituted with one or more substituents selected from "Substituent Group α"; or (9) the compound of (8) above, or a pharmaceutically acceptable salt or ester thereof, wherein:

any one of $R_1$ and $R_1'$ which is not involved in forming the double bond is a fluorine atom; a chlorine atom; a bromine atom; a cyano group; a methyl group which may be substituted with 1 to 3 halogen atom(s); a methoxy group which may be substituted with 1 to 3 halogen atom(s); a lower alkyl group having 1 to 3 carbon atom(s) which may be substituted with a hydroxy group; or a cyclopropyl group;

any one of $R_2$ and $R_2'$, any one of $R_3$ and $R_3'$, and any one of $R_4$ and $R_4'$, any of which are not involved in forming the double bond, are each a hydrogen atom; and $R_9$ is a phenyl group wherein the 3-position or 4-position of the phenyl group may be substituted with the following 1) or 2):

1) a pyrrolidinyl group or piperazinyl group which may be substituted with one or more of a lower alkyl group and/or a substituent(s) selected from "Substituent Group α", or 2) —$NR_{10}R_{10}'$ wherein:

$R_{10}$ is a hydrogen atom, $R_{10}'$ is an azetidinyl group or a piperidinyl group which may be substituted with a lower alkyl group optionally substituted with one or more substituents selected from "Substituent Group α".

In addition, the other embodiment of the present specification can be represented as follows. That is, a compound represented by the following Formula [$I_0$], or a pharmaceutically acceptable salt or ester thereof:

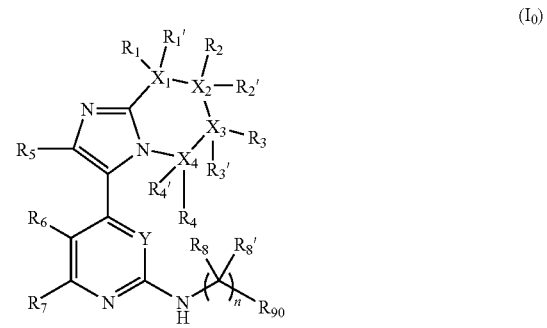

($I_0$)

wherein $X_1$, $X_2$, $X_3$, and $X_4$, which may be identical or different, are each C or N, provided that none to two of $X_1$, $X_2$, $X_3$, and $X_4$ is/are N;

Y is CH or N;

$R_1$, $R_1'$, $R_2$, $R_2'$, $R_3$, $R_3'$, $R_4$, and $R_4'$, which may be identical or different, are each a hydrogen atom, a substituent selected from "Substituent Group $α_0$", a lower alkyl group which may be substituted with one or more substituents selected from "Substituent Group $α_0$", an aryl group, or a heteroaryl group wherein the aryl group and heteroaryl group each independently may be substituted with one or more substituents, which may be identical or different, selected from the following 1) to 3):

1) a lower alkyl group, 2) a substituent selected from "Substituent Group $α_0$", and 3) a lower alkyl group substituted with a substituent selected from "Substituent Group $α_0$", or $R_a$ wherein $R_a$ is represented by —$Z_1$—$Z_2$—$Z_3$, $Z_1$ is O or NHCO;

$Z_2$ is a single bond or $(CHW_i)_{n1}$ wherein $n_1$ is an integer from 1 to 3; i is an integer from 1 to $n_1$; $(CHW_i)_{n1}$ represents $(CHW_1)$ when $n_1$=1, $(CHW_i)_{n1}$ represents $(CHW_1)$—$(CHW_2)$ when $n_1$=2, and $(CHW_i)_{n1}$ represents $(CHW_1)$—$(CHW_2)$—$(CHW_3)$ when $n_1$=3; and $W_1$, $W_2$, and $W_3$, which may be identical or different, are each a hydrogen atom or a lower alkyl group having 1 to 2 carbon atom(s));

$Z_3$ is a lower alkoxy group or a phenyl group wherein the phenyl group may be substituted with one or more substituents selected from "Substituent Group $\alpha_0$", provided that, when any of $X_1$, $X_2$, $X_3$, and $X_4$ is N, then any one of $R_i$ and $R_i'$ which bonds to the $X_i$ which is N, in which i is an integer from 1 to 4, becomes N together with the $X_i$, and the other one of Ri and Ri' is as defined above; any one of $R_1$ and $R_1'$ and any one of $R_2$ and $R_2'$ may together form a double bond for $X_1$-$X_2$ bonding; and any one of $R_3$ and $R_3'$ and any one of $R_4$ and $R_4'$ may together form a double bond for $X_3$-$X_4$ bonding;

$R_5$ is a hydrogen atom or a methyl group;

$R_6$ and $R_7$, which may be identical or different, are each a hydrogen atom, a substituent selected from "Substituent Group $\beta_0$", a lower alkyl group which may be substituted with one or more substituents selected from "Substituent Group $\beta_0$", or a 5- or 6-membered aliphatic heterocyclic group selected from a pyrrolidinyl group, a piperidinyl group, and a piperazinyl group wherein the 5- or 6-membered aliphatic heterocyclic group may be substituted with one or more substituents, which may be identical or different, selected from the followings:

1) a lower alkyl group,
2) a substituent selected from "Substituent Group $\beta_0$", and
3) a lower alkyl group substituted with a substituent selected from "Substituent Group $\beta_0$"), or alternatively, $R_6$ and $R_7$ together form the following ring which is fused to a ring to which $R_6$ and $R_7$ are bonded:

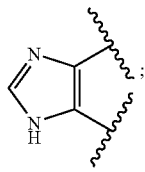

$R_8$ and $R_8'$, which may be identical or different, are each a hydrogen atom or a lower alkyl group which may be substituted with one or more substituents selected from "Substituent Group $\alpha_0$";

$R_{90}$ is an aryl group or a heteroaryl group wherein the aryl group and the heteroaryl group each independently may be substituted with one or more substituents, which may be identical or different, selected from the following 1) to 3):

1) a lower alkyl group,
2) a substituent selected from "Substituent Group $\alpha_0$",
3) a lower alkyl group substituted with a substituent selected from "Substituent Group $\alpha_0$";

n is an integer from 1 to 3; and

"Substituent Group $\alpha_0$" and "Substituent Group $\beta_0$" are defined as follows:

"Substituent Group $\alpha_0$":

a halogen atom, a hydroxy group, a cyano group, an amino group, a carbamoyl group, an aminosulfonyl group, a lower alkylamino group, a hydroxy-lower alkylamino group, a di-lower alkylamino group, a lower alkylsulfonyl group, a lower alkoxy group, a lower alkoxycarbonyl group, a lower alkanoyl group, and a carboxyl group, and "Substituent Group $\beta_0$":

a halogen atom, a hydroxy group, a cyano group, an amino group, a formyl group, a carbamoyl group, an aminosulfonyl group, a lower alkylamino group, a di-lower alkylamino group, a hydroxyiminomethyl group, a methoxyiminomethyl group, a lower alkoxy group, a lower alkoxycarbonyl group, a lower alkoxycarbonylamino group, a lower alkanoyl group, a lower alkanoyloxy group, a lower alkylthio group, a lower alkylsulfonyl group, a carboxyl group, and a tetrazolyl group.

Next, the representative processes for producing the compound of Formula (I) of the present invention will be described in the following.

Scheme 1: Process for Producing a Compound of Formula (I) from a Compound of Formula (II) or Formula (III)

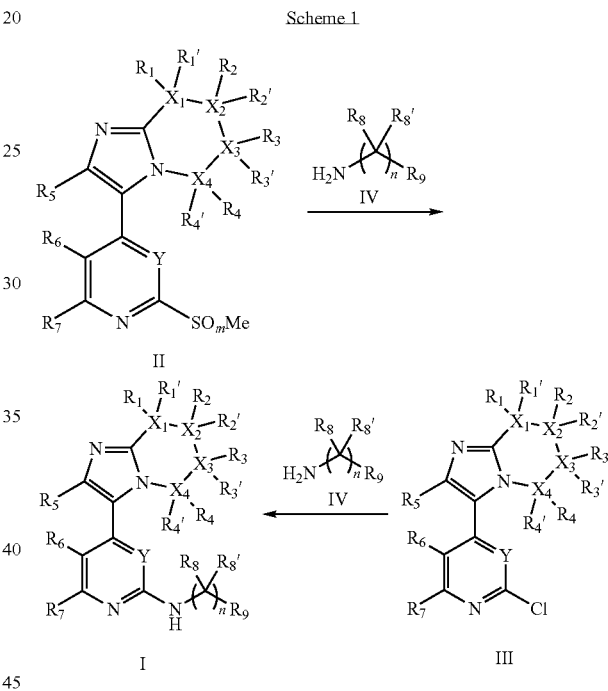

The compound of the above Formula (I) (where $X_1$, $X_2$, $X_3$, $X_4$, Y, $R_1$, $R_1'$, $R_2$, $R_2'$, $R_3$, $R_3'$, $R_4$, $R_4'$, $R_5$, $R_6$, $R_7$, $R_8$, $R_8'$, and $R_9$ are the same as defined above, and m is 1 or 2) can be synthesized by a substitution reaction between the compound of the above Formula (II) or (i) (where $X_1$, $X_2$, $X_3$, $X_4$, Y, $R_1$, $R_1'$, $R_2$, $R_2'$, $R_3$, $R_3'$, $R_4$, $R_4'$, $R_5$, $R_6$, and $R_7$ are the same as defined above) and a corresponding alkylamine of the above Formula (IV) (where n, $R_8$, $R_8'$, and $R_9$ are the same as defined above).

The substitution reaction between the compound of the above Formula (II) or Formula (U) and an alkylamine of the above Formula (IV) is preferably carried out in the presence of a base (an inorganic base such as potassium carbonate; an organic base such as triethylamine and diisopropylethylamine). The solvent for use includes chloroform, tetrahydrofuran, N,N-dimethylformamide, dimethylsulfoxide, and the like, and preferably chloroform, tetrahydrofuran, and dimethylsulfoxide. Regarding the said reaction, an alkylamine of the above Formula (IV) is used in an amount of 1 to 5 moles and preferably 2 moles, to 1 mole of the compound represented by Formula (II) or (III). The reaction temperature can be appropriately selected by those having ordinary skill in the art in accordance with the starting compound used or the reaction solvent, but the reaction temperature is usually from room temperature to the boiling point of the solvent, preferably from room temperature to 50° C. The reaction is usually completed in 1 to 120 hours, but the reaction time can be appropriately increased or decreased.

The compound of the above Formula (IV), for example, is 3-[(1S)-1-aminoethyl]aniline, 4-[(1S)-1-aminoethyl]aniline, or the like, and is either commercially available or can be synthesized from a commercially available compound by a method publicly known to those having ordinary skill in the art or a method similar thereto.

Scheme 2: Representative Process for Producing a Compound of Formula (II)

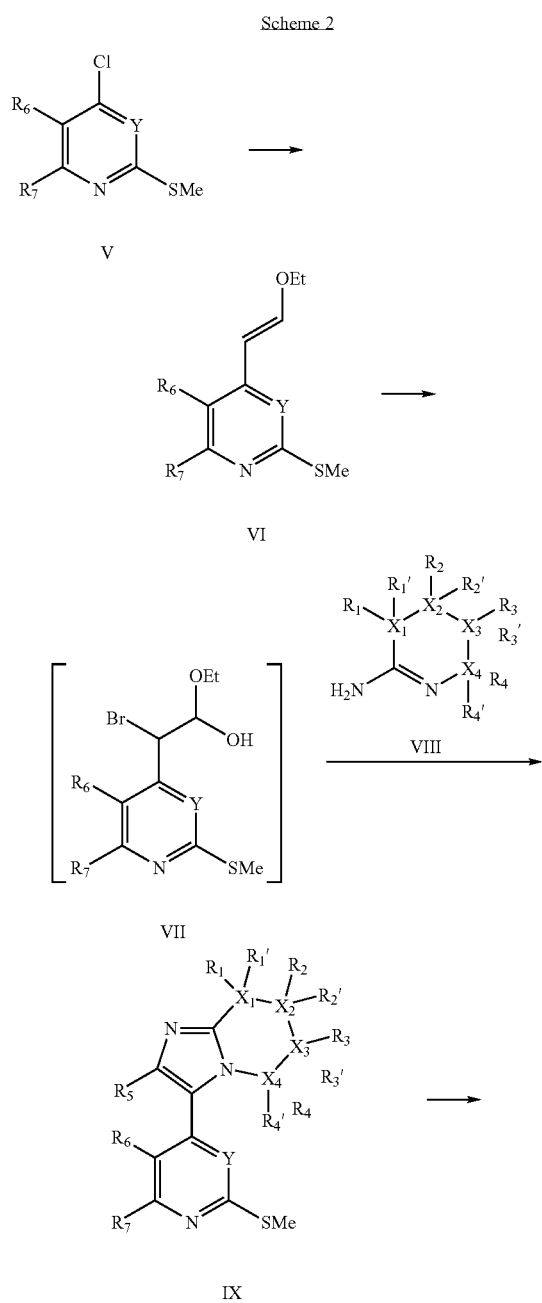

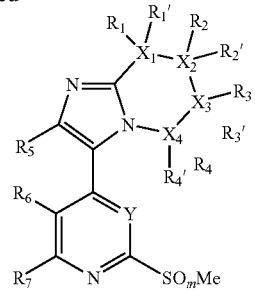

II

First, the compound of the above Formula (VI) (where $R_6$ and $R_7$ are the same as defined above) can be obtained by a coupling reaction between the compound of the above Formula (V) (where $R_6$ and $R_7$ are the same as defined above) and tris(2-ethoxyvinyl)boron in a solvent such as tetrahydrofuran, 1,4-dioxane, 1,2-dimethoxyethane, or the like, preferably in tetrahydrofuran, in the presence of a base such as palladium acetate, triphenylphosphine, aqueous solution of sodium hydroxide, or the like. In this case, the reaction temperature can be appropriately selected by those having ordinary skill in the art in accordance with the starting compound used or the reaction solvent, but the reaction temperature is usually from room temperature to the boiling point of the solvent, preferably room temperature. The reaction is usually completed in 1 to 24 hours, but the reaction time can be appropriately increased or decreased.

Next, the compound of the above Formula (IX) (where $X_1$, $X_2$, $X_3$, $X_4$, Y, $R_1$, $R_1'$, $R_2$, $R_2'$, $R_3$, $R_3'$, $R_4$, $R_4'$, $R_5$, $R_6$, and $R_7$ are the same as defined above) is synthesized in 1,4-dioxane from the compound of the above Formula (VII) (where $R_6$ and $R_7$ are the same as defined above) and the compound of the above Formula (VIII) (where $X_1$, $X_2$, $X_3$, $X_4$, $R_1$, $R_1'$, $R_2$, $R_2'$, $R_3$, $R_3'$, $R_4$, and $R_4'$ are the same as defined above, provided, however, that any one of $R_1$ and $R_1'$ and any one of $R_2$ and $R_2'$ together form a double bond for $X_1$-$X_2$ bonding, and any one of $R_3$ and $R_3'$ and any one of $R_4$ and $R_4'$ together form a double bond for $X_3$-$X_4$ bonding). Regarding the said reaction, the compound of the above Formula (VIII) is used in an amount of 1 to 3 moles and preferably 1 mole, to 1 mole of the compound represented by the above Formula (VII). The reaction temperature can be appropriately selected by those having ordinary skill in the art in accordance with the starting compound used, but the reaction temperature is usually from room temperature to the boiling point of the solvent, preferably from room temperature to 50° C. The reaction is usually completed in 1 to 24 hours, but the reaction time can be appropriately increased or decreased.

The compound of the above Formula (VII) can be prepared by reacting the compound of the above (VI) (where $R_6$ and $R_7$ are the same as defined above) with N-bromosuccinimide in 1,4-dioxane. Regarding the said reaction, N-bromosuccinimide is used in an amount of 1 to 3 moles and preferably 1 mole, to 1 mole of the compound represented by above (VI). The reaction temperature can be appropriately selected by those having ordinary skill in the art in accordance with the starting compound used, but the reaction temperature is usually from 0° C. to room temperature, preferably room temperature. The reaction is usually completed in 1 to 12 hours, but the reaction time can be appropriately increased or decreased. In addition, the obtained compound of the above Formula (VII) can be applied into the following reaction without being separated and purified.

The compound of the above Formula (II) can be synthesized by oxidizing the compound of the above Formula (IX) with m-chloroperbenzoic acid (m-CPBA) in a solvent such as dichloromethane, chloroform, N,N-dimethylformamide, or the like, preferably in chloroform or N,N-dimethylformamide. Regarding the said reaction, the m-chloroperbenzoic acid (m-CPBA) is used in an amount of 2 to 5 moles and preferably 2 moles, to 1 mole of the compound represented by the above Formula (IX). The reaction temperature can be appropriately selected by those having ordinary skill in the art in accordance with the starting compound used or the reaction solvent, but the reaction temperature is usually from 0° C. to room temperature, preferably room temperature. The reaction is usually completed in 1 to 24 hours, but the reaction time can be appropriately increased or decreased.

The compound of the above Formula (V), for example, is 4-chloro-2-methylthiopyrimidine, or the like, and the compound of the above Formula (VIII), for example, is 2-amino-3-picoline, or the like. These are either commercially available or can be synthesized from a commercially available compound by a method publicly known to those having ordinary skill in the art or a method similar thereto.

Scheme 3: Other Process for Producing a Compound of Formula (IX)

The compound of the above Formula (IX) (where Y is N, and $X_1$, $X_2$, $X_3$, $X_4$, $R_1$, $R_1'$, $R_2$, $R_2'$, $R_3$, $R_3'$, $R_4$, $R_4'$, $R_5$, $R_6$, and $R_7$ are the same as defined above) can be also synthesized by the following production process.

Scheme 3

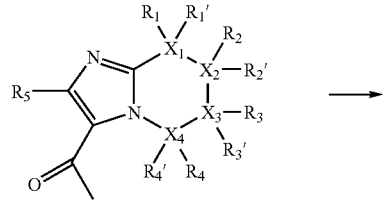

X

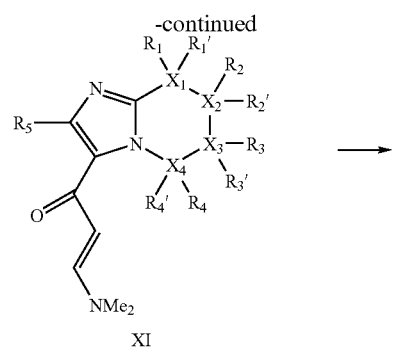

XI

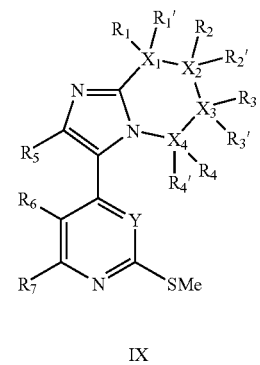

IX

First, the compound of the above Formula (XI) (where Y is N, $X_1$, $X_2$, $X_3$, $X_4$, $R_1$, $R_1'$, $R_2$, $R_2'$, $R_3$, $R_3'$, $R_4$, $R_4'$, and $R_5$ are the same as defined above) can be obtained by reacting an acyl compound of the above Formula (X) (where $X_1$, $X_2$, $X_3$, $X_4$, $R_1$, $R_1'$, $R_2$, $R_2'$, $R_3$, $R_3'$, $R_4$, $R_4'$, and $R_5$ are the same as defined above) with N,N-dimethylformamide dimethylacetal. In this case, the reaction temperature is from room temperature to the boiling point of N,N-dimethylformamide dimethylacetal, and preferably the boiling point. The reaction is usually completed in 12 to 120 hours, but the reaction time can be appropriately increased or decreased.

Next, the compound of the above Formula (IX) can be synthesized by subjecting the compound of Formula (XI) to a ring-forming reaction of the pyrimidine ring in a solvent such as methanol, ethanol, n-butanol, N,N-dimethylformamide, or the like, preferably in n-butanol, with the use of a base such as thiourea, sodium methoxide, sodium ethoxide, or the like, and then by methylation using methyl iodide. In this case, the reaction temperature is from room temperature to the boiling point of the solvent. The reaction is usually completed in 1 to 12 hours, but the reaction time can be appropriately increased or decreased.

Scheme 4: Representative Process for Producing a Compound of Formula (X)

Scheme 4

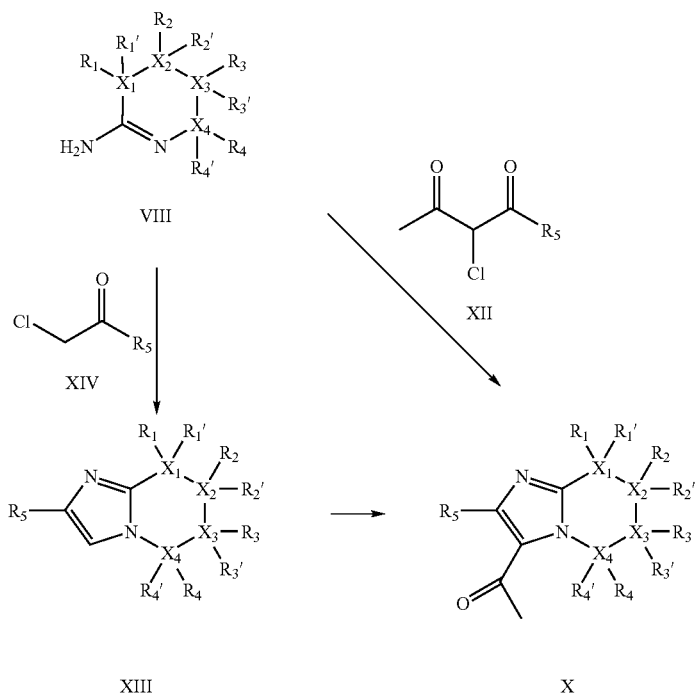

The acyl compound of the above Formula (X) (where $X_1$, $X_2$, $X_3$, $X_4$, $R_1$, $R_1'$, $R_2$, $R_2'$, $R_3$, $R_3'$, $R_4$, and $R_4'$ are the same as defined above, and $R_5$ is a methyl group, provided, however, that any one of $R_1$ and $R_1'$ and any one of $R_2$ and $R_2'$ together form a double bond for $X_1$-$X_2$ bonding, and any one of $R_3$ and $R_3'$ and any one of $R_4$ and $R_4'$ together form a double bond for $X_3$-$X_4$ bonding) can be synthesized by reacting the compound of the above (VIII) (where $X_1$, $X_2$, $X_3$, $X_4$, $R_1$, $R_1'$, $R_2$, $R_2'$, $R_3$, $R_3'$, $R_4$, and $R_4'$ are the same as defined above. While any one of $R_1$ and $R_1'$ and any one of $R_2$ and $R_2'$ together form a double bond for $X_1$-$X_2$ bonding, and any one of $R_3$ and $R_3'$ and any one of $R_4$ and $R_4'$ together form a double bond for $X_3$-$X_4$ bonding) with a chloroketone of the above Formula (XII) (where $R_5$ is the same as defined above). The reaction may be carried out by a method publicly known or a method similar thereto (Literary Documents: Bioorg. Med. Chem. Lett. 2003, 13, 3021., J. Med. Chem. 1989, 32, 2204, and the like).

In addition, the acyl compound of the above Formula (X) (where $X_1$, $X_2$, $X_3$, $X_4$, $R_1$, $R_1'$, $R_2$, $R_2'$, $R_3$, $R_3'$, $R_4$, and $R_4'$ are the same as defined above, and $R_5$ is either a hydrogen atom or a methyl group, provided, however, that any one of $R_1$ and $R_1'$ and any one of $R_2$ and $R_2'$ together form a double bond for $X_1$-$X_2$ bonding, and any one of $R_3$ and $R_3'$ and any one of $R_4$ and $R_4'$ together form a double bond for $X_3$-$X_4$ bonding) can be synthesized by Friedel-Crafts acylation of an imidazopyridine derivative of the above Formula (XIII) (where $X_1$, $X_2$, $X_3$, $X_4$, $R_1$, $R_1'$, $R_2$, $R_2'$, $R_3$, $R_3'$, $R_4$, and $R_4'$ are the same as defined above, and $R_5$ is either a hydrogen atom or a methyl group, provided, however, that any one of $R_1$ and $R_1'$ and any one of $R_2$ and $R_2'$ together form a double bond for $X_1$-$X_2$ bonding, and any one of $R_3$ and $R_3'$ and any one of $R_4$ and $R_4'$ together form a double bond for $X_3$-$X_4$ bonding). This reaction can be carried out by a conventional method (Literary Documents: J. Med. Chem. 1970, 13, 1048., Pamphlet of International Publication WO 01/014375, and the like). Also, the imidazopyridine derivative of the above Formula (XIII) can be easily prepared by using both of the compound of the above Formula (VIII) (where $X_1$, $X_2$, $X_3$, $X_4$, $R_1$, $R_1'$, $R_2$, $R_2'$, $R_3$, $R_3'$, $R_4$, and $R_4'$ are the same as defined above, provided, however, that any one of $R_1$ and $R_1'$ and any one of $R_2$ and $R_2'$ together form a double bond for $X_1$-$X_2$ bonding, and any one of $R_3$ and $R_3'$ and any one of $R_4$ and $R_4'$ together form a double bond for $X_3$-$X_4$ bonding) obtained in accordance with the conventional method and the α-halogenated carbonyl compound of the above Formula (XIV) (where $R_5$ is either a hydrogen atom or a methyl group), (Literary Documents: J. Med. Chem. 1996, 39, 2856., and the like).

By subjecting the imidazopyridine derivative of the above Formula (XIII) (where $X_1$, $X_2$, $X_3$, $X_4$, $R_1$, $R_1'$, $R_2$, $R_2'$, $R_3$, $R_3'$, $R_4$, and $R_4'$ are the same as defined above, and $R_5$ is either a hydrogen atom or a methyl group, provided, however, that any one of $R_1$ and $R_1'$ and any one of $R_2$ and $R_2'$ together forms a double bond for $X_1$-$X_2$ bonding, and any one of $R_3$ and $R_3'$ and any one of $R_4$ and $R_4'$ together forms a double bond for $X_3$-$X_4$ bonding) to a hydrogenation reaction in which Raney nickel is used as a catalyst according to a conventional method, a tetrahydroimidazopyridine derivative (XIII) (where $X_1$, $X_2$, $X_3$, $X_4$, $R_1$, $R_1'$, $R_2$, $R_2'$, $R_3$, $R_3'$, $R_4$, and $R_4'$ are the same as defined above, and $R_5$ is either a hydrogen atom or a methyl group, provided, however, that any one of $R_1$ and $R_1'$ and any one of $R_2$ and $R_2'$ do not together form a double bond for $X_1$-$X_2$ bonding, and any one of $R_3$ and $R_3'$ and any one of $R_4$ and $R_4'$ do not together form a double bond for $X_3$-$X_4$ bonding) can be synthesized.

Scheme 5: Process for Producing the Compound of Formula (III)

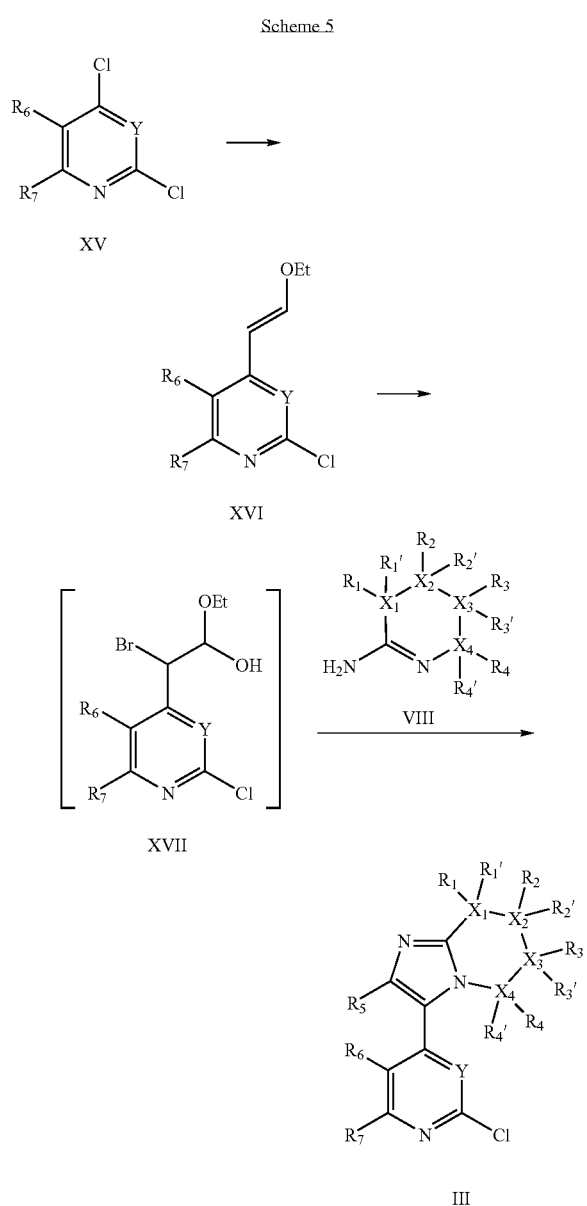

First, the compound of the above Formula (XVI) (where $R_6$ and $R_7$ are the same as defined above) can be obtained by a coupling reaction between the compound of the above Formula (XV) (where $R_6$ and $R_7$ are the same as defined above) and tris(2-ethoxyvinyl)boron in a solvent such as tetrahydrofuran, 1,4-dioxane, 1,2-dimethoxyethane, or the like, preferably in tetrahydrofuran, in the presence of a base such as palladium acetate, triphenylphosphine, aqueous solution of sodium hydroxide, or the like. In this case, the reaction temperature can be appropriately selected by those having ordinary skill in the art in accordance with the starting compound used or the reaction solvent, but the reaction temperature is usually from room temperature to the boiling point of the solvent, preferably room temperature. The reaction is usually completed in 1 to 24 hours, but the reaction time can be appropriately increased or decreased.

Here, the compound of the above Formula (XV), for example 2,6-dichloropurine or the like, is commercially available.

Next, the compound of the above Formula (III) (where $X_1$, $X_2$, $X_3$, $X_4$, $R_1$, $R_1'$, $R_2$, $R_2'$, $R_3$, $R_3'$, $R_4$, $R_4'$, $R_5$, $R_6$, and $R_7$ are the same as defined above, provided, however, that any one of $R_1$ and $R_1'$ and any one of $R_2$ and $R_2'$ together form a double bond for $X_1$-$X_2$ bonding, and any one of $R_3$ and $R_3'$ and any one of $R_4$ and $R_4'$ together form a double bond for $X_3$-$X_4$ bonding) is synthesized in 1,4-dioxane from the compound of the above Formula (XVII) (where $R_6$ and $R_7$ are the same as defined above) and the amino compound of the above Formula (VIII). Regarding the said reaction, the amino compound of the above Formula (VIII) is used in an amount of 1 to 3 moles and preferably 1 mole, to 1 mole of the compound represented by the above Formula (XVII). The reaction temperature can be appropriately selected by those having ordinary skill in the art in accordance with the starting compound used, but the reaction temperature is usually from room temperature to the boiling point of the solvent, preferably from room temperature to 50° C. The reaction is usually completed in 1 to 24 hours, but the reaction time can be appropriately increased or decreased.

The compound of the above Formula (XVII) can be prepared by reacting the compound of the above Formula (XVI) (where $R_6$ and $R_7$ are the same as defined above) with N-bromosuccinimide in 1,4-dioxane. Regarding the said reaction, N-bromosuccinimide is used in an amount of 1 to 3 moles and preferably 1 mole, to 1 mole of the compound represented by above Formula (XVI). In this case, the reaction temperature can be appropriately selected by those having ordinary skill in the art in accordance with the starting compound used, but the reaction temperature is usually from 0° C. to room temperature, preferably room temperature. The reaction is usually completed in 1 to 12 hours, but the reaction time can be appropriately increased or decreased. In addition, the obtained compound of the above Formula (XVII) can be applied into the following reaction without being separated and purified.

Scheme 6: Process for Producing the Compound of Formula (I) in which Y is CH

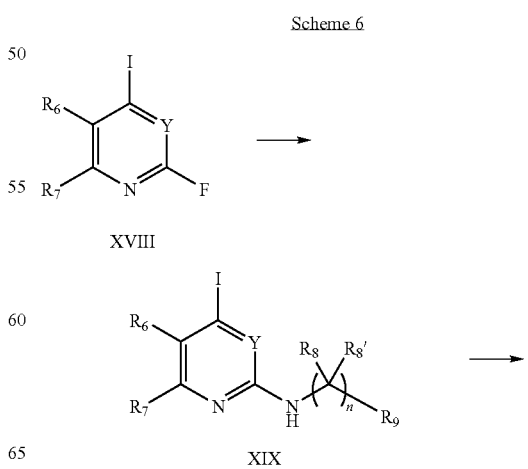

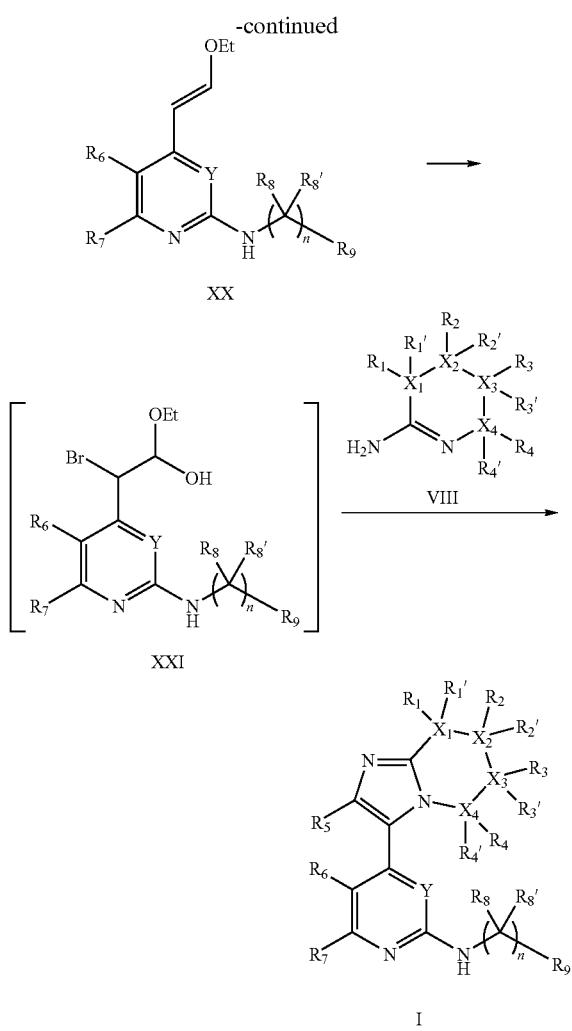

First, the compound of the above Formula (XIX) (where $R_6$, $R_7$, $R_8$, $R_8'$ and $R_9$ are the same as defined above) can be synthesized by reacting the compound of the above Formula (XVIII) (where $R_6$ and $R_7$ are the same as defined above) with the alkylamine of the above Formula (IV) (where $R_8$, $R_8'$, and $R_9$ are the same as defined above) in a solvent such as chloroform, N,N-dimethylformamide, dimethylsulfoxide, or the like, preferably in dimethylsulfoxide. Regarding the said reaction, the alkylamine of the above Formula (IV) is used in an amount of 1 to 3 mole(s) and preferably 1 mole, to 1 mole of the compound represented by the above Formula (XVIII). In this case, the reaction temperature is usually from room temperature to the boiling point of the solvent, preferably from 50 to 100° C. The reaction is usually completed in 1 to 24 hours, but the reaction time can be appropriately increased or decreased.

Next, the compound of the above Formula (XX) (where $R_6$, $R_7$, $R_8$, $R_8'$, and $R_9$ are the same as defined above) can be synthesized by introducing a vinylether group in accordance with a coupling reaction. The coupling reaction can be carried out in the same manner as in the above Scheme 2.

In addition, the compound of the above Formula (I) can be synthesized by a ring-forming reaction between the compound of the above Formula (XXI) (where $R_6$, $R_7$, $R_8$, $R_8'$, and $R_9$ are the same as defined above) and the compound of the above Formula (VIII), and the ring-forming reaction can be carried out in the same manner as in Scheme 2.

Here, the compound of the above Formula (XVIII) (where $R_6$ and $R_7$ are the same as defined above) is, for example, 2-fluoro-4-iodopyridine or the like, and is either commercially available or can be synthesized from a commercially available compound by a method publicly known or a method similar thereto (Literary Documents: J. Org. Chem. 1993, 58, 7832., and the like).

In the production processes described in the above Schemes 1 to 6, when a defined functional group is modified under the reaction conditions, those having ordinary skill in the art, if necessary, can apply a method conventionally used in synthetic organic chemistry, for example, a means for protecting or deprotecting a functional group [for example, see Protective Groups in Organic Synthesis, the third edition, written by T. W. Greene, John Wiley & Sons], thereby to obtain a desirable compound.

Introduction or conversion of $R_6$ can be conducted in any stages of the above-mentioned synthetic intermediates. Hereinafter, examples of the introduction or conversion of $R_6$ in the compound represented by the above Formula (I) will be described. In addition, a person having ordinary skill in the art can carry out the introduction or conversion of $R_6$ by using appropriate known methods, and/or the method illustrated below or a method similar thereto.

The compound of the above Formula (I) (where $R_6$ is a halogen atom, $X_1$, $X_2$, $X_3$, $X_4$, Y, $R_1$, $R_1'$, $R_2$, $R_2'$, $R_3$, $R_3'$, $R_4$, $R_4'$, $R_5$, $R_7$, $R_8$, $R_8'$, and $R_9$ are the same as defined above) can be synthesized by reacting the corresponding compound of Formula (I) (where $R_6$ is a hydrogen atom) with $R_6$—X such as N-chlorosuccinimide, N-bromosuccinimide, N-iodosuccinimide, or the like (where $R_6$ is a halogen atom, and X for example is succinimide) or with a halogenating agent such as chlorine, bromine, iodine, or the like, in a solvent such as tetrahydrofuran, water, acetic acid, methanol, ethanol, 1,4-dioxane, chloroform, dichloromethane, toluene, or the like. In this case, the reaction temperature can be appropriately selected in accordance with the starting compound used or the reaction solvent, but the reaction temperature is usually from 0° C. to the boiling point of the solvent used in the reaction. The reaction is usually completed in 1 to 24 hours, but the reaction time can be appropriately increased or decreased.

The compound of the above Formula (I) (where $R_6$ is a lower alkoxycarbonyl group, and $X_1$, $X_2$, $X_3$, $X_4$, Y, $R_1$, $R_1'$, $R_2$, $R_2'$, $R_3$, $R_3'$, $R_4$, $R_4'$, $R_5$, $R_7$, $R_8$, $R_8'$, and $R_9$ are the same as defined above) can be synthesized from a corresponding compound of Formula (I) (where $R_6$ is a bromine atom). For example, by reacting the compound of Formula (I) (where $R_6$ is a bromine atom) with carbon monoxide, in a mixed solvent prepared by adding alcohol such as methanol, ethanol, or the like to a solvent such as N,N-dimethylacetamide, N-methylpyrrolidone, N,N-dimethylformamide, or the like, and in the presence of a ligand such as 1,1'-bis(diphenylphosphino)ferrocene, a palladium catalyst such as palladium acetate (II), and a base such as sodium hydrogen carbonate or triethylamine, the corresponding compound (I) (where $R_6$ is a lower alkoxycarbonyl group) can be synthesized. In this case, the reaction temperature can be appropriately selected in accordance with the starting compound used or the reaction solvent, but the reaction temperature is usually from 50° C. to the boiling point of the solvent used in the reaction. The reaction is usually completed in 1 to 24 hours, but the reaction time can be appropriately increased or decreased.

In addition, the compound of the above Formula (I) (where $R_6$ is a hydroxycarbonyl group, and $X_1$, $X_2$, $X_3$, $X_4$, Y, $R_1$, $R_1'$, $R_2$, $R_2'$, $R_3$, $R_3'$, $R_4$, $R_4'$, $R_5$, $R_7$, $R_8$, $R_8'$, and $R_9$ are the same as defined above) can be synthesized by a hydrolysis reaction of a corresponding compound (I) (where $R_6$ is a lower alkoxycarbonyl group). For example, by subjecting the compound of the Formula (I) (where $R_6$ is a lower alkoxycarbonyl group, and $X_1$, $X_2$, $X_3$, $X_4$, Y, $R_1$, $R_1'$, $R_2$, $R_2'$, $R_3$, $R_3'$, $R_4$, $R_4'$, $R_5$, $R_7$, $R_8$, $R_8'$, and $R_9$ are the same as defined above) to a hydrolysis reaction in a solvent such as methanol, ethanol, water, tetrahydrofuran, or the like, with the use of sodium hydroxide or the like as a base, the compound (I) (where $R_6$ is a hydroxycarbonyl group) can be synthesized. In this case, the reaction temperature can be appropriately selected by those having ordinary skill in the art in accordance with the starting compound used, but the reaction temperature is usually from 0° C. to room temperature. The reaction is usually completed in 1 to 24 hours, but the reaction time can be appropriately increased or decreased.

The compound of the above Formula (I) (where $R_6$ is a carbamoyl group, and $X_1$, $X_2$, $X_3$, $X_4$, Y, $R_1$, $R_1'$, $R_2$, $R_2'$, $R_3$, $R_3'$, $R_4$, $R_4'$, $R_5$, $R_7$, $R_8$, $R_8'$, and $R_9$ are the same as defined above) can be synthesized by a condensation reaction of the corresponding compound of Formula (I) (where $R_6$ is a hydroxycarbonyl group) with amine. For example, by subjecting the compound of Formula (I) (where $R_6$ is a hydroxycarbonyl group) to a condensation reaction with amine such as ammonia, in a solvent such as tetrahydrofuran, dimethylsulfoxide, N,N-dimethylformamide, 1,4-dioxane, chloroform, or the like, with the use of a condensing agent such as 1-(3-dimethylaminopropyl)-3-ethylcarbodiimide or the like, and 1-hydroxybenzotriazol, the compound of Formula (I) (where $R_6$ is a carbamoyl group) can be synthesized. In this case, the reaction temperature can be appropriately selected by those having ordinary skill in the art in accordance with the starting compound used, but the reaction temperature is usually from room temperature to the boiling point of the solvent used. The reaction is usually completed in 1 to 24 hours, but the reaction time can be appropriately increased or decreased.

The compound of the above Formula (I) (where $R_6$ is a cyano group, and $X_1$, $X_2$, $X_3$, $X_4$, Y, $R_1$, $R_1'$, $R_2$, $R_2'$, $R_3$, $R_3'$, $R_4$, $R_4'$, $R_5$, $R_7$, $R_8$, $R_8'$, and $R_9$ are the same as defined above) can be synthesized by a dehydration reaction of the corresponding compound of Formula (I) (where $R_6$ is a carbamoyl group). For example, by subjecting the compound of Formula (I) (where $R_6$ is a carbamoyl group) to a dehydration reaction in pyridine with the use of phosphorus oxychloride, the compound of Formula (I) (where $R_6$ is a cyano group) can be synthesized. In this case, the reaction temperature can be appropriately selected by those having ordinary skill in the art in accordance with the starting compound used, but the reaction temperature is usually from room temperature to the boiling point of the solvent. The reaction is usually completed in 1 to 24 hours, but the reaction time can be appropriately increased or decreased.

Next, the PLK 1 inhibitory effect and cell proliferation inhibitory effect (cell inhibitory activity) of the compound of Formula (I) will be explained in the following.

Measurement of the Inhibitory Effect Against PLK 1 Activity (1) Preparation of PLK 1

First, a baculovirus expressing full-length human PLK1 of which N terminus is fused with GST (glutathione S-transferase) was prepared, and then the PLK1 infected into a *Spodoptera frugiperda* (Sf)9 insect cell was highly expressed as a GST-fused protein. The cells were recovered and suspended in a lysis buffer (50 mM tris-hydrochloric acid buffer (pH 7.4)/150 mM sodium chloride/1 mM EDTA (ethylenediamine tetraacetic acid)/1 mM dithiothreitol/0.1% polyoxyethylene sorbitan monolaurate) to break cells with sonicator, and supernatant was recovered after a centrifugation. The supernatant was reacted on glutathione sepharose beads, and then the beads were washed with a lysis buffer. Thereafter, the beads were reacted in a lysis buffer containing Precision Protease to recover supernatant.

(2) Preparation of PLK1-T210D

It has been known that $210^{th}$ codon of human PLK1 which originally codes for threonine can be changed to an active type by altering the site so as to code aspartic acid [Molecular and Cellular Biology (Mol. Cell. Biol.), 17th edition, 3408 (1997)]. In order to obtain a human active type PLK1 protein, cDNA of mutated PLK1 (PLK1-T210D) of which $210^{th}$ codon codes aspartic acid was prepared, by substituting a base in the $210^{th}$ codon of human PLK1 cDNA. This PLK1-T210D cDNA was integrated into a baculovirus expression vector in the same manner as in the above, expressed in insect cells, and then was purified.

(3) Measurement of PLK 1 and PLK1-T210D Activity

For the measurement of the PLK1 and PLK1-T210D activity, used as a substrate was a synthetic peptide (aspartic acid-glutamic acid-leucine-methionine-glutamic acid-alanine-serine-phenylalanine-alanine-aspartic acid-glutamine-aspartic acid-alanine-lysine), where the serine surrounding sequence of the amino acid sequence No. 198 of CDC25C, which have been reported as the site for PLK1 substrate [EMBO Report, $3^{rd}$ edition, 341 (2002)], is altered.

The reaction was carried out in accordance with the method of Toyoshima-Morimoto et al. [Nature, Vol. 410, 215-220, (2001)]. The volume of the reaction solution was 21.1 µL and the composition of the reaction buffer was 20 mM of tris-hydrochloric acid buffer (pH 7.4)/10 mM magnesium chloride/0.5 mM dithiothreitol/1 mM EGTA (ethylene glycol-bis (beta-aminoethylether)-N,N,N',N',-tetraacetic acid). Thereto, purified PLK 1, 50 µM of the substrate peptide, 50 µM of non-labeled adenosine triphosphate (ATP), and 1 µCi of [γ-33P]-labeled ATP (2000 to 4000 Ci/mmole) were added to react at 25° C. for 20 minutes. Then, 10 µL of 350 mM phosphate buffer was added to the reaction system to terminate the reaction. The resultant solution was spotted onto a multi-screen phosphocellulose filter on a 96-well plate. After the phosphocellulose filter is washed with 75 mM phosphate buffer and then dried, the radioactivity of the substrate was measured with a liquid scintillation counter. The non-labeled ATP and [γ-33P]-labeled ATP was purchased from Amersham Bioscience Corp. and the multi-screen phosphocellulose filter from Millipore Corp., respectively.

The addition of the compound of the present invention to the reaction system was carried out by adding 1.1 µL of the solution as prepared by preliminarily dissolving in dimethylsulfoxide at a 20-fold concentration of the final concentration. A control was provided by adding 1.1 µL of dimethylsulfoxide to the reaction system.

$IC_{50}$ value of the compound of the present invention for the PLK 1 and PLK1-T210D activity was determined, and the results are shown in Table 1 below.

TABLE 1

| Example No. | PLK1 inhibitory effect (nM) | PLK1-T210D inhibitory effect (nM) |
|---|---|---|
| 8 | 43 | 26 |
| 28 | — | 42 |
| 36 | — | 16 |

TABLE 1-continued

| Example No. | PLK1 inhibitory effect (nM) | PLK1-T210D inhibitory effect (nM) |
|---|---|---|
| 112 | — | 47 |
| 158 | — | 41 |

From the above, it is clear that the inhibitory activity of the compound of the present invention against PLK1 and PLK1-T210D is remarkably high.

Measurement of the Inhibitory Effect Against Cell Proliferation: Inhibitory Activity Against PLK1 at Cellular Level (1) Method of Cell Culture For the measurement of the PLK 1 inhibitory effect of the compound at the cellular level, human uterine cervix cell lines HeLaS3 cells were used. The HeLaS3 cell was obtained from American Type Culture Collection (ATTC), and cultured in a $CO_2$-incubator of saturated steam by using Dulbecco's Modified Eagle's Medium containing 10% fetal calf serum at 37° C. in the presence of 5% $CO_2$.

(2) Measurement of Inhibitory Effect of the Compound According to the Present Invention It has been reported that PLK 1 plays an important role in various stages of mitotic phase (M-phase) in mammalian cells (Nature Review Molecular Cell Biology, Vol. 5, 429, (2004)). In fact, when the mammalian cells are treated with PLK 1 siRNA to control the expression level, the cell cycle progression is inhibited and thus the cell is arrested at M phase. Also, when examining the phosphorylation level of serine, 10th residue of histone H3, which is thought to be required for a chromosome condensation in M phase, it is observed that the level is enhanced to a high level. Thus, after treating the cell with the compound according to the present invention; the phosphorylation level of histone H3 was examined by an indirect fluorescent antibody technique, the cells arrested at M phase were identified by using the level thereof as an indicator to analyze the ratio of cells arrested at M phase; and then EC50 value of each compound was calculated to evaluate the PLK 1 inhibitory effect at a cellular level.

First, HeLaS3 cells synchronized at the G1/S phase by a double-thymidine technique were seeded into lysine-treated 96-well plate (Falcon Corp.) at the ratio of 8,000 per one well, and allowed to stand still in the above-mentioned $CO_2$ incubator. After 4 hours of seeding, the compound according to the present invention, which is diluted in series, was added into each well of the plate, and further allowed to stand still in the $CO_2$ incubator. In 12 hours after the addition of the compound according to the present invention, the culture medium containing the compound according to the present invention in each well of the plate was removed, and then 100 μL of ice-cold 100% methanol (Wako Pure Chemical Industries, Ltd.) was added, to carry out cell fixation for 10 minutes and treatment for increasing the membrane permeability. Subsequently, to the wells in which the methanol was removed, 50 μL of 1% BSA/PBS was added, and then blocking was carried out for 30 minutes. Thereafter, for the primary antibody reaction, 50 μL of 1% BSA/PBS containing a 2.5 mg/mL Antiphospho Histone H3 (Ser10) antibody (Upstate Corp.) was added to the wells, and the plate was left over at room temperature for 90 minutes. After terminating the reaction, each well was once washed with PBS. Then, for the second antibody reaction, 50 μL of 1% BSA/PBS containing 1.5 mg/mL Cy5-labelled antirabbit IgG (H+L) antibody (Chemicon Ltd.) and 10 ug/mL DAPI (Sigma Ltd.), which is a nucleus staining reagent, were added to the wells, and further they were left over at room temperature for 90 minutes. After terminating the reaction, the reaction solution in wells was removed and replaced with 100 μL of PBS, and then fluorescence images were captured by using InCell Analyzer 1000 (manufactured by GE Amersham) to analyze the ratio of the cells arrested at M phase (Mitotic index) at different view angles. When the maximum value of the ratio of the cells arrested at M phase, that each drug can induce, is assumed as 100%, the drug concentration which induces 50% out of that 100% is defined as $EC_{50}$.

$EC_{50}$ values obtained by the above-mentioned method are shown in Table 2 below.

TABLE 2

| Example No. | Inhibitory effect against cell proliferation (μM) |
|---|---|
| 36 | 0.31 |
| 112 | 0.34 |
| 158 | 0.18 |

From the fact that the compound of the present invention exhibits a strong inhibitory effect against cell proliferation, it is believed to be extremely useful as an antitumor agent.

As discussed in the above, the compound according to the present invention has an excellent PLK 1 inhibitory activity and at the same time, has a strong inhibitory effect against cell proliferation. Therefore, it is believed to serve as a useful anticancer agent for strongly inhibiting the proliferation of cancerous cells. That is, a pharmaceutical composition containing the novel substituted imidazole derivative according to the invention or a pharmaceutically acceptable salt or ester thereof, or an anticancer agent containing the novel substituted imidazole derivative according to the invention or a pharmaceutically acceptable salt or ester thereof, is believed to be effective for the treatment of cancer patients. Also, the pharmaceutical composition or the anticancer agent may contain pharmaceutically acceptable carriers or diluents. Here, the term "pharmaceutically acceptable carriers or diluents" refers to excipients [e.g., fats, bees wax, semi-solid or liquid polyol, natural or hydrogenated oil, etc.]; water [e.g., distilled water, especially distilled water for injection, etc.], physiological brine, alcohol (e.g., ethanol), glycerol, polyol, aqueous glucose solution, mannitol, vegetable oil, or the like; additives [e.g. bulking agent, disintegrant, binder, lubricant, wetting agent, stabilizer, emulsifier, dispersant, preservative, sweetener, colorant, flavoring agent or aromatic substance, thickening agent, diluent, buffering substance, solvent or solubilizer, drug for attaining storage effect, salt for adjusting osmotic pressure, coating agent, or antioxidant], and the like.

The compound of the invention can also be used as a prodrug containing an ester. Here, the term 'prodrug' in general refers to a derivative of a certain drug molecule which is chemically modified, which itself shows no physiological activity but after being injected in vivo, transforms back to its original drug molecule to exhibit drug efficacy. As the prodrug of the compound according to the present invention, a compound of the above Formula (I) in which the hydroxyl group is acylated by a phosphate group can be exemplified. The prodrug/ester can be produced in accordance with the method well known or conventionally used by those having ordinary skill in the art.

Also, with regard to a tumor suitable for expecting a therapeutic effect of the compound according to the present invention, for example, human solid tumors and the like may be mentioned. Examples of the human solid tumors include cerebral cancer, head and neck cancer, esophageal cancer, thyroid cancer, small cell cancer, non-small cell cancer, breast cancer, gastric cancer, gall bladder/bile duct cancer, hepatic cancer, pancreatic cancer, colon cancer, rectal cancer, ovarian cancer, chorioepithelioma, uterine cancer, cervical cancer, renal pelvic/ureteral cancer, urinary bladder cancer, prostate cancer, penile cancer, testicular cancer, embryonal cancer, Wilms' tumor, skin cancer, malignant melanoma, neuroblastoma, osteosarcoma, Ewing's sarcoma, soft tissue sarcoma, and the like.

Next, the "pharmaceutically acceptable salt or ester thereof" described above will be explained.

When the compound according to the present invention is used as an anticancer agent or the like, the compound can be used in the form of a pharmaceutically acceptable salt thereof. Typical examples of the pharmaceutically acceptable salt include salts with alkali metals such as sodium, potassium and the like, inorganic acid salts such as hydrochloride, sulfate, nitrate, phosphate, carbonate, hydrogen carbonate, hyperchlorate and the like; organic acid salts such as, for example, acetate, propionate, lactate, maleate, fumarate, tartrate, malate, citrate, ascorbate and the like; sulfonates such as, for example, methanesulfonate, isethionate, benzenesulfonate, toluenesulfonate and the like; for example, acidic amino acid salts such as, for example, aspartate, glutamate and the like; and the like.

Preparation of the pharmaceutically acceptable salts of the compound according to the present invention can be carried out by appropriately combining methods that are conventionally used in the field of organic synthetic chemistry. Specifically, a method of subjecting a solution of the compound according to the present invention in a free form, to neutralizing titration, using an alkaline solution or an acidic solution, or the like may be mentioned.

Examples of the ester of the compound according to the present invention include methyl ester, ethyl ester, and the like. These esters can be prepared by esterifying a free carboxyl group according to conventionally used methods.

As to the dosage form used in the case of using the compound according to the present invention as an anticancer agent or the like, various forms can be selected, and for example, oral formulations such as tablet, capsule, powder, granule, liquid and the like; and sterilized liquid parenteral formulations such as solution, suspension and the like, may be mentioned.

Here, solid preparations can be prepared, without modifications, in the form of tablet, capsule, granule or powder according to conventionally used standard methods, but can be also prepared using appropriate additives. Examples of the additives include sugars such as lactose, sucrose and the like; starches of corn, wheat, rice and the like; fatty acids such as stearic acid and the like; inorganic salts such as sodium metasilicate, magnesium aluminate, anhydrous calcium phosphate, and the like; synthetic polymers such as polyvinylpyrrolidone, polyalkylene glycol and the like; fatty acid salts such as calcium stearate, magnesium stearate and the like; alcohols such as stearyl alcohol, benzyl alcohol and the like; synthetic cellulose derivatives such as methylcellulose, carboxymethylcellulose, ethylcellulose, hydroxypropylmethylcellulose and the like; and in addition to these, conventionally used additives such as water, gelatin, talc, vegetable oils, gum arabic, and the like.

These solid preparations such as tablet, capsule, granule, powder and the like may generally contain 0.1 to 100% by weight, preferably 5 to 100% by weight, more preferably 5 to 85% by weight, and particularly preferably 5 to 30% by weight, of the active ingredient.

Liquid preparations can be prepared in the form of suspension, syrup, injectable preparation or the like, using appropriate additives that are commonly used for liquid preparations, such as water, alcohols, plant-derived oils such as soybean oil, peanut oil, sesame oil and the like.

In particular, examples of appropriate solvent or diluent useful in the case of administering parenterally via intramuscular injection, intravenous injection, or subcutaneous injection, include distilled water for injection, aqueous solution of lidocaine hydrochloride (for intramuscular injection), physiological brine, aqueous glucose solution, ethanol, fluid for intravenous injection (e.g., aqueous solution of citric acid, sodium citrate and the like), electrolyte solution (e.g., for intravenous infusion, or for intravenous injection), and the like, or mixed solutions thereof.

These injectable preparations may be in a form that the active ingredient is preliminarily dissolved, or in a form that the active ingredient, as a powder or the active ingredient compounded with suitable additives, is to be dissolved at the time of use. Such injectable liquid can usually contain 0.1 to 10% by weight, preferably 1 to 5% by weight, of the active ingredient.

The liquid for oral administration, such as suspension, syrup or the like, can contain 0.5 to 10% by weight, preferably 1 to 5% by weight, of the active ingredient.

The preferred amount of the compound according to the present invention to be administered in practice can be appropriately increased or decreased in accordance with the kind of the compound to be used, the kind of the composition mixed, the frequency of administration, the specific site to be treated, and the conditions of the patient. For example, the daily dose for an adult is, in the case of oral administration, 10 to 500 mg, preferably 10 to 200 mg, and in the case of parenteral administration, preferably in the case of intravenous injection, 10 to 100 mg, preferably 10 to 30 mg, per day. In addition, the dose frequency may vary depending on the administration method and symptoms, but the administration can be conducted once, or divided into 2 to 5 portions, and preferably 2 to 3 portions.

Further, formulations including a therapeutically effective amount of the compound represented by Formula [I] according to the invention, or a pharmaceutically acceptable salt or ester thereof, can be administered simultaneously, separately, or in order, in combination with a therapeutically effective amount of an anticancer agent selected from the group consisting of anticancer alkylating agents, anticancer antimetabolites, anticancer antibiotics, plant-derived antitumor agents, anticancer platinum coordination compounds, anticancer camptothecine derivatives, anticancer tyrosine kinase inhibitors, monoclonal antibodies, interferons, biological response modifiers, and other anticancer agents, or a pharmaceutically acceptable salt or ester thereof. Here, the term "formulations" includes oral formulations and parenteral formulations. The oral formulations are exemplified by tablet, capsule, powder, granule, or the like, and the parenteral formulations are exemplified by sterilized liquid formulations such as solution, suspension, and the like, specifically is injectable preparations, drip infusion, and the like.

The term "anticancer alkylating agents" above means an alkylating agent having anticancer activity, and the "alkylating agent" here in general refers to the agent providing an alkyl group in an alkylation reaction of an organic compound in which the hydrogen atom is substituted with an alkyl group. Examples of the "anticancer alkylating agents" include nitrogen mustard N-oxide, cyclophosphamide, ifosfamide, melphalan, busulfan, mitobronitol, carboquone, thiotepa, ranimustine, nimustine, temozolomide, carmustine, and the like.

The term "anticancer antimetabolites" above refers to a metabolic antagonist having anticancer activity (antimetabolite), and the "metabolic antagonist" here in the wide sense includes substances which interfere a normal metabolic change to take place and substances which avoid producing high-energy intermediates by inhibiting an electron transport system, as they are similar in structure or function, to metabolites (vitamins, coenzymes, amino acids, sugars, etc.), which are the important factors in organisms. Examples of the "anticancer antimetabolites" include methotrexate, 6-mercaptopurine riboside, mercaptopurine, 5-fluorouracil, tegafur, doxifluridine, carmofur, cytarabine, cytarabine ocphosphate, enocitabine, S-1, gemcitabine, fludarabine, pemetrexed disodium, and the like, and preferably 5-fluorouracil, S-1, gemcitabine, and the like.

The term "anticancer antibiotics" above refers to an antibiotic having anticancer activity, and the "antibiotics" here is prepared by microorganisms, and includes substances that inhibit the growth or other functions of cells in microorganisms or other organisms. Examples of the "anticancer antibiotics" include actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus, valrubicin, and the like.

The term "plant-derived antitumor agents" includes compounds having anticancer activity exhibited by using plants as a source, and those compounds to which the chemical modification are further added. Examples of the "plant-derived antitumor agents" includes vincristine, vinblastine, vindesine, etoposide, sobuzoxane, docetaxel, paclitaxel, vinorelbine, and the like, and preferably docetaxel and paclitaxel.

The term "anticancer camptothecine derivatives" includes camptothecine per se, and refers to a compound inhibiting proliferation of cancerous cells, which is structurally related to camptothecine. The "anticancer camptothecine derivatives" is not particularly limited to, but may be exemplified by, camptothecine, 10-hydroxy camptothecine, topotecan, irinotecan, 9-aminocamptothecine, or the like, and preferably camptothecine, topotecan, and irinotecan. The irinotecan is metabolized in vivo and exhibits anticancer activity as SN-38. The camptothecine derivative is thought to have almost similar mechanism of action and activity to the camptothecine (Nitta et al, cancer and chemotherapeutics, 14, 850-857 (1987), etc.).

The term "anticancer platinum coordination compounds" above refers to a platinum coordination compound having anticancer activity, and the "platinum coordination compound" here means a platinum coordination compound that provides platinum in the form of ion. Preferable examples of the platinum compound include cisplatin; cis-diammine diaquo platinum(II)-ion; chloro(diethylenetriamine)-platinum (II) chloride; dichloro(ethylenediamine)-platinum(II); diammine(1,1-cyclobutanedicarboxylato)platinum(II) (carboplatin); spiroplatin; iproplatin; diammine(2-ethylmalonato)-platinum(II); ethylenediamine malonato platinum(II); aqua(1,2-diamino dicyclohexane)sulphato platinum(II); aqua(1,2-diamino dicyclohexane) malonato platinum(II); (1,2-diaminocyclohexane) malonato platinum (II); (4-carboxyphthalate)(1,2-diaminocyclohexane)platinum(II); (1,2-diaminocyclohexane)-(isocitrate)platinum(II); (1,2-diaminocyclohexane)oxalato platinum(II); ormaplatin; tetraplatin; carboplatin; nedaplatin; and oxaliplatin; and preferably carboplatin or oxaliplatin. In addition, other anticancer platinum coordination compounds exemplified in the present specification are publicly known and is commercially available, and/or can be produced by those having ordinary skill in the art in accordance with conventionally used techniques.

The term "anticancer tyrosine kinase inhibitors" above refers to a tyrosine kinase inhibitor having anticancer activity, and the "tyrosine kinase inhibitor" here refers to a chemical substance for inhibiting "tyrosine kinase" which involves transferring a γ-phosphate group of ATP to the hydroxyl group of a specific tyrosine in proteins. Examples of the "anticancer tyrosine kinase inhibitors" include gefitinib, imatinib, erlotinib, and the like.

The term "monoclonal antibodies" refers to an antibody produced from a monoclonal antibody-forming cell, and examples include cetuximab, bevacizumab, rituximab, alemtuzumab, trastuzumab, and the like.

The term "interferons" refers to an interferon having anticancer activity, and generally on the occasion of viral infection, is a glycoprotein having the molecular weight of about 20,000 which is produced/secreted from the most of animal cells. The interferon has functions for inhibiting proliferation of cells (tumor cells in particular) and enhancing the natural killer activity, in addition to the various immunity effector functions as well as inhibiting proliferation of virus, and is known as one of cytokines. Examples of the "interferon" include interferon α, interferon α-2a, interferon α-2b, interferon β, interferon γ-1a, interferon γ-n1, and the like.

The term "biological response modifiers" above is also known as BRM, and generally is a generic term of substances or drugs for driving to achieve individual benefits against tumors, infections, or other diseases by regulating biological reactions such as a defence mechanism possessed by organisms, and survival, proliferation, or differentiation of tissue cells. Examples of the "biological response modifiers" include krestin, lentinan, schizophyllan, picibanil, ubenimex, and the like.

The term "other anticancer agents" refers to an anticancer agent having anticancer activity which is not included in any of the above. Examples of the "other anticancer agents" include mitoxantrone, L-asparaginase, procarbazine, dacarbazine, hydroxycarbamide, pentostatin, tretinoin, alefacept, darbepoetin alfa, anastrozole, exemstane, bicalutamide, leuproreline, flutamide, fulvestrant, pegaptanib octasodium, denileukin diftitox, aldesleukin, thyrotropin alfa, arsenic trioxide, bortezomib, capecitabine, goserelin, and the like.

All of the above "anticancer alkylating agents", "anticancer antimetabolites", "anticancer antibiotics", "plant-derived antitumor agents", "anticancer platinum coordination compounds", "anticancer camptothecine derivatives", "anticancer tyrosine kinase inhibitors", "monoclonal antibodies", "interferons", "biological response modifiers", and "other anticancer agents" are publicly known and commercially available, or can be produced by those having ordinary skill in the art in accordance with methods known per se or well known/conventionally used methods.

BEST MODE FOR CARRYING OUT THE INVENTION

Examples

Hereinafter, the present invention will be described in more detail with reference to Examples, but the invention is not intended to be limited by the Examples by any means. In Examples, thin layer chromatography was performed using Silica gel $_{60}F_{254}$ (Merck & Co., Inc.) for the plate, and a UV detector for the detection. Wakogel™ C-300 or C-200 (Wako Pure Chemical Industries, Ltd.) or NH (Fuji Silysia Chemical, Ltd.) was used as the silica gel for column. In a preparative reversed phase liquid chromatography, CombiPrep Pro C18 (YMC) was used for a column, and 0.1% trifluoroacetic acid aqueous solution and 0.1% trifluoroacetic acid acetonitrile solution were used for a mobile phase. For the MS spectra, JMS-SX102A (JEOL, Co. Ltd.), or QUATTRO II (Micromass) was used, or for the LC-MS, ZMD (Micromass) was used for the measurement. For the NMR spectra, dimethylsulfoxide was used as an internal standard in the case of measuring in a deuterated dimethylsulfoxide solution, and a spectrometer such as Gemini-200 (200 MHz; Varian, Inc.), Gemini-300 (300 MHz; Varian, Inc.), Mercury 400 (400 MHz; Varian, Inc.), Inova 400 (400 MHz; Varian, Inc.), or JNM-AL 400 (400 MHz; JEOL, Co. Ltd.) was used for the measurement. All δ values were expressed in ppm.

The meanings of the abbreviations used in Examples are given below.

s: Singlet
d: Doublet
dd: Double doublet
ddd: Double double doublet
t: Triplet
dt: Double triplet
q: Quartet
dq: Double quartet
m: Multiplet
br: Broad
brs: Broad singlet
brd: Broad doublet
J: Coupling constant
Hz: Hertz
DMSO-$d_6$: Deuterated dimethylsulfoxide
$CDCl_3$: Deuterated chloroform
$CD_3OD$: Deuterated methanol
RT: Retention time

TABLE 3

| Examples | $R_1$ | $R_2$ | $R_5$ | $R_6$ | $R_7$ |
|---|---|---|---|---|---|
| 1 | H | H | H | H | H |
| 2 | H | H | H | Br | H |
| 3 | $CH_3$ | H | H | H | H |
| 4 | $CH_3$ | H | H | Br | H |
| 5 | $CH_3$ | H | H | $COOCH_3$ | H |
| 6 | $CH_3$ | H | H | COOH | H |
| 7 | $CH_3$ | H | H | $CONH_2$ | H |
| 8 | $CH_3$ | H | H | CN | H |
| 9 | $CH_3$ | H | H | $CH_2OH$ | H |
| 10 | $CH_3$ | H | H | CHO | H |
| 11 | $CH_3$ | H | H | CH=NOH | H |
| 12 | $CH_3$ | H | H | CH=NOCH$_3$ | H |
| 13 | $CH_3$ | H | H | $CHF_2$ | H |
| 14 | $CH_3$ | H | H | $NHCOOC(CH_3)_3$ | H |
| 15 | $CH_3$ | H | H | $NH_2$ | H |

TABLE 3-continued

| Examples | $R_1$ | $R_2$ | $R_5$ | $R_6$ | $R_7$ |
|---|---|---|---|---|---|
| 16 | $CH_3$ | H | H | —N(piperazine)N—CH$_3$ | H |
| 17 | $CH_3$ | H | H | —N(pyrrolidine) | H |
| 18 | $CH_3$ | H | H | $N(CH_3)_2$ | H |
| 19 | $CH_3$ | H | H | $SCH_3$ | H |
| 20 | $CH_3$ | H | H | $SO_2CH_3$ | H |

TABLE 4

| Examples | $R_1$ | $R_2$ | $R_5$ | $R_6$ | $R_7$ |
|---|---|---|---|---|---|
| 21 | $CH_3$ | H | H | I | H |
| 22 | $CH_3$ | H | H | $OCH_3$ | H |
| 23 | $CH_3$ | H | H | $NH(CH_2)_2OH$ | H |
| 24 | $CH_3$ | H | H | OH | H |
| 25 | $COOCH_3$ | H | H | Br | H |
| 26 | $CH_2OH$ | H | H | Br | H |
| 27 | $CH_2OH$ | H | H | H | H |
| 28 | Cl | H | H | Br | H |
| 29 | CN | H | H | Br | H |
| 30 | Cl | H | H | CN | H |
| 31 | $CHF_2$ | H | H | Br | H |
| 32 | CN | H | H | CN | H |
| 33 | $CHF_2$ | H | H | CN | H |

TABLE 4-continued

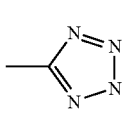

| Examples | R₁ | R₂ | R₅ | R₆ | R₇ |
|---|---|---|---|---|---|
| 34 | CF₃ | H | H | H | H |
| 35 | CF₃ | H | H | Br | H |
| 36 | CF₃ | H | H | CN | H |
| 37 | CF₃ | H | H | tetrazolyl | H |
| 38 | CH₃ | H | CH₃ | H | H |
| 39 | CH₃ | H | CH₃ | Br | H |
| 40 | H | H | CH₃ | H | H |
| 41 | H | H | CH₃ | Br | H |
| 42 | CH₃ | H | H | H | CH₃ |
| 43 | CH₃ | H | H | Br | CH₃ |

TABLE 5

| Examples | R₁ | R₂ | R₅ | R₆ | R₇ |
|---|---|---|---|---|---|
| 44 | H | H | H | H | H |
| 45 | H | H | H | Br | H |
| 46 | CH₃ | H | H | H | H |
| 47 | CH₃ | H | H | Br | H |

TABLE 6

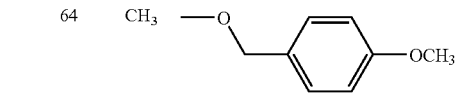

| Examples | X₁—R₁ | X₂—R₂ | X₄—R₄ | R₅ | R₆ | R₇ | Y |
|---|---|---|---|---|---|---|---|
| 51 | C—H | N | C—H | H | H | H | N |
| 52 | C—H | N | C—H | H | Br | H | N |
| 53 | C—CH₃ | N | C—H | H | H | H | N |
| 54 | C—CH₃ | C—H | N | H | CN | H | N |
| 58 | C—CH₃ | C—H | C—H | H | Br | H | CH |
| 66 | N | C—H | C—H | H | CN | H | N |

TABLE 7

| Examples | R₁ | R₂ | R₅ | R₆ | R₇ |
|---|---|---|---|---|---|
| 48 | CH₃ | COOCH₃ | H | CN | H |
| 49 | H | CH₃ | H | H | H |
| 50 | H | CH₃ | H | Br | H |
| 55 | NH₂ | H | H | CN | H |
| 56 | CH₃ | H | H | N-methylamidine | |
| 57 | H | H | H | N-methylamidine | |
| 59 | CH₃ | COOH | H | CN | H |
| 60 | CH₃ | NHCOOC(CH₃)₃ | H | CN | H |
| 61 | CH₃ | NH₂ | H | CN | H |
| 62 | CH₃ | CH₂OH | H | CN | H |
| 63 | CH₃ | CH₂NHCH₃ | H | CN | H |
| 64 | CH₃ | O-CH₂-C₆H₄-OCH₃ | H | CN | H |
| 65 | CH₃ | OH | H | CN | H |

TABLE 8

| Examples | R | R₁ | R₂ | R₅ | R₆ | R₇ |
|---|---|---|---|---|---|---|
| 67 | 1-phenylethyl with CH₃ | CH₃ | H | H | CN | H |
| 68 | 3-phenyl-3-hydroxypropyl (CH(CH₃)CH₂CH₂OH-phenyl) | CH₃ | H | H | CN | H |
| 69 | 3-phenylpropyl | CH₃ | H | H | CN | H |
| 70 | 2-thienylpropyl | CH₃ | H | H | CN | H |
| 71 | 3-pyridylethyl | CH₃ | H | H | CN | H |

TABLE 9

| Examples | R | R₁ | R₂ | R₅ | R₆ | R₇ |
|---|---|---|---|---|---|---|
| 72 | 2-chlorophenylethyl | CH₃ | H | H | CN | H |
| 73 | 3-methoxyphenylethyl | CH₃ | H | H | CN | H |
| 74 | 4-methoxyphenylethyl | CH₃ | H | H | CN | H |
| 75 | 4-aminophenylethyl | CH₃ | H | H | CN | H |
| 76 | 2-trifluoromethylphenylethyl | CH₃ | H | H | CN | H |
| 77 | 2-(4-fluorophenyl)propan-2-yl | CH₃ | H | H | CN | H |
| 78 | 2,6-difluorophenylethyl | CH₃ | H | H | CN | H |
| 79 | 2-(4-hydroxyphenyl)propan-2-yl | CH₃ | H | H | CN | H |

TABLE 10

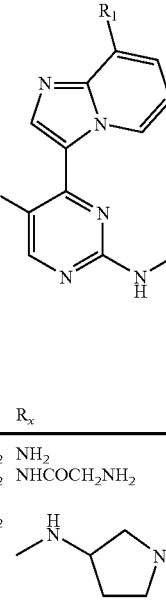

| Examples | R₁ | Rₓ | Rᵧ | *asymmetric carbon |
|---|---|---|---|---|
| 80 | CHF₂ | NH₂ | H | S form |
| 81 | CHF₂ | NHCOCH₂NH₂ | H | S form |
| 82 | CHF₂ | 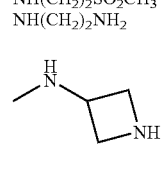 | H | S form |
| 83 | CHF₂ | NH(CH₂)₂OH | H | S form |
| 84 | CHF₂ | NH(CH₂)₂SO₂CH₃ | H | S form |
| 85 | CHF₂ | NH(CH₂)₂NH₂ | H | S form |
| 86 | CHF₂ | 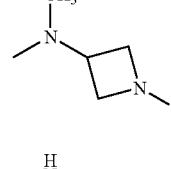 | H | S form |
| 87 | CHF₂ | 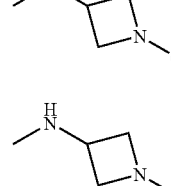 | H | S form |
| 88 | CHF₂ | 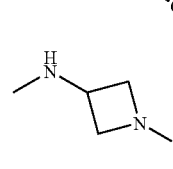 | H | S form |
| 89 | CHF₂ | 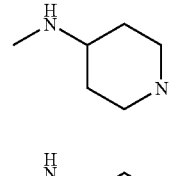 | H | S form |
| 90 | CHF₂ | 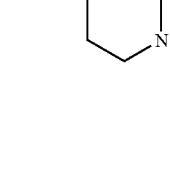 | H | S form |
| 91 | CHF₂ |  | H | S form |
| 92 | CHF₂ | 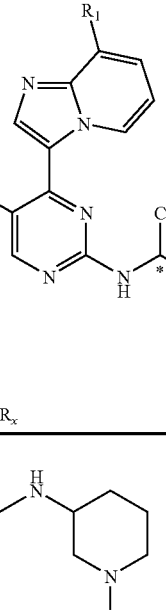 | H | S form |

TABLE 10-continued

| Examples | R₁ | Rₓ | Rᵧ | *asymmetric carbon |
|---|---|---|---|---|
| 93 | CHF₂ | 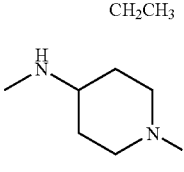 | H | S form |
| 94 | CHF₂ | 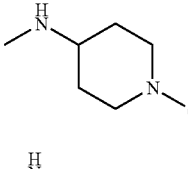 | H | S form |
| 95 | CHF₂ | 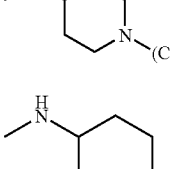 | H | S form |
| 96 | CHF₂ | 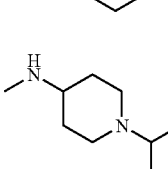 | H | S form |
| 97 | CHF₂ | 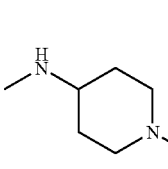 | H | S form |
| 98 | CHF₂ | 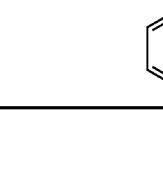 | H | S form |
| 99 | CHF₂ |  | H | S form |

TABLE 11
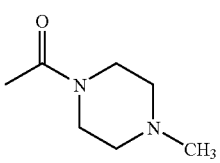
| Examples | R₁ | Rₓ | Rᵧ | *asymmetric carbon |
|---|---|---|---|---|
| 100 | CHF$_2$ | 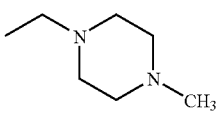 | H | racemic form |
| 101 | CHF$_2$ | 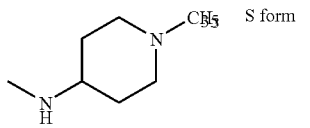 | H | racemic form |
| 102 | CHF$_2$ | CH$_2$NHCOCH$_2$NH$_2$ | H | racemic form |
| 103 | CHF$_2$ | NHCOCH(CH$_3$)NH$_2$ | H | S form |
| 104 | CHF$_2$ | H | 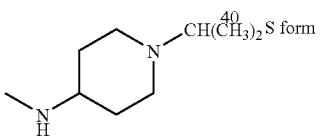 | S form |
| 105 | CHF$_2$ | H | 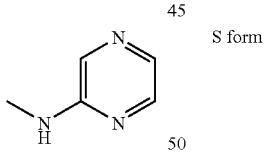 | S form |
| 106 | CHF$_2$ | H | 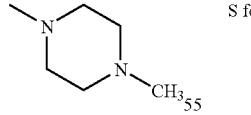 | S form |
| 107 | CHF$_2$ | H | 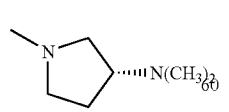 | S form |
| 108 | CHF$_2$ | H | NH(CH$_2$)$_2$N(CH$_3$)$_2$ | S form |
| 109 | CHF$_2$ | H | 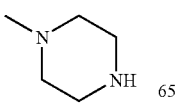 | S form |
| 110 | CHF$_2$ | H |  | S form |

TABLE 12
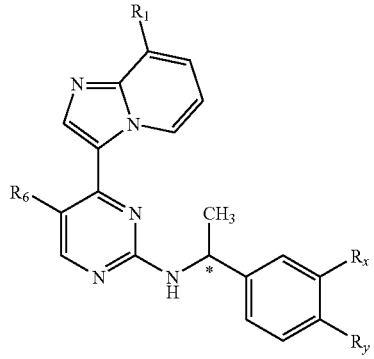
| Examples | R₁ | R₆ | Rₓ | R_y | *asymmetric carbon |
|---|---|---|---|---|---|
| 111 | CHF₂ | CN | H | 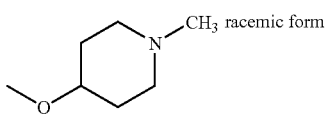 | racemic form |
| 112 | CH₃ | CN | H | NH₂ | S form |
| 113 | CH₃ | CN | H | NHSO₂CH₃ | S form |
| 114 | CH₃ | CN | H | 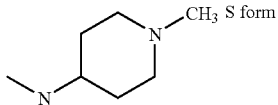 | S form |
| 115 | CH₃ | CN | H | 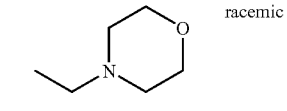 | racemic form |
| 116 | CH₃ | CN | H | CH₂NHCOCH₂NH₂ | racemic form |
| 117 | CH₃ | CN | H | CH₂SO₂CH₃ | racemic form |
| 118 | CH₃ | CN | OCH₃ | H | S form |
| 119 | CH₃ | CN | 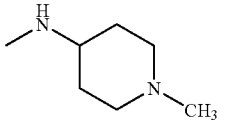 | H | S form |
| 120 | CH₂CH₃ | CN | H | 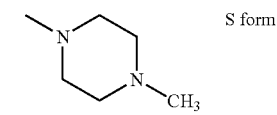 | S form |
| 121 |  | CN | H | 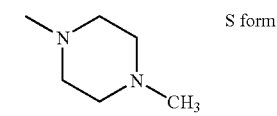 | S form |

TABLE 13
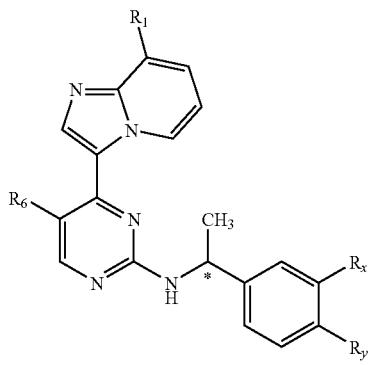
| Examples | R₁ | R₆ | Rₓ | R_y | * asymmetric carbon |
|---|---|---|---|---|---|
| 122 | CH₃ | CN | H | 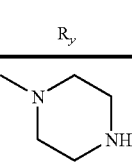 | S form |
| 123 | Cl | CN | 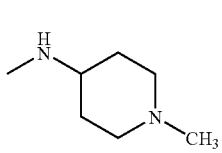 | H | S form |
| 124 | Cl | CN | 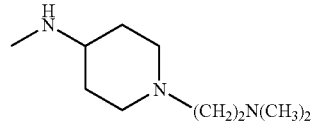 | H | S form |
| 125 | Cl | F | 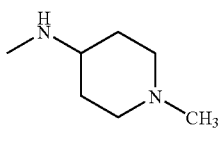 | H | S form |
| 126 | Cl | Cl | 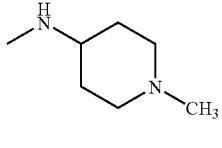 | H | S form |
| 127 | Cl | CH₃ | 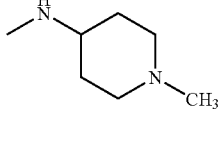 | H | S form |
| 128 | Cl | CN | 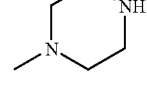 | H | S form |
| 129 | Cl | CN | 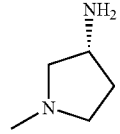 | H | S form |

TABLE 13-continued

[Structure: Imidazo[1,2-a]pyridine with R₁ substituent, connected to pyrimidine (with R₆) linked via NH-CH(CH₃)* to phenyl ring with Rx and Ry substituents]

| Examples | R₁ | R₆ | Rx | Ry | *asymmetric carbon |
|---|---|---|---|---|---|
| 130 | Cl | CN | H | 4-(methylamino)-1-methylpiperidinyl (NHCH- connected to N-CH₃ piperidine) | S form |
| 131 | Cl | CN | H | 4-methyl-piperazinyl with N-C(O)CF₃ | S form |
| 132 | Cl | CN | H | 4-methylpiperazin-1-yl (NH) | S form |

TABLE 14

[Structure: Imidazo[1,2-a]pyridine with R₁, R₂, R₃ substituents, connected to pyrimidine (with R₆) linked via NH-CH(CH₃)* to phenyl ring with Z, Rx and Ry substituents]

| Examples | R₁ | R₂ | R₃ | R₆ | Z | Rx | Ry | *asymmetric carbon |
|---|---|---|---|---|---|---|---|---|
| 133 | Cl | H | H | CN | C | H | 1,4-dimethylpiperazinyl | S form |
| 134 | Cl | H | H | CN | C | H | 1-methyl-2-oxopiperazinyl | S form |

TABLE 14-continued
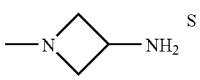
| Examples | R₁ | R₂ | R₃ | R₆ | Z | R$_x$ | R$_y$ | * asymmetric carbon |
|---|---|---|---|---|---|---|---|---|
| 135 | Cl | H | H | CN | C | H | N(CH₃)(CH₂)₂N(CH₃)₂ | S form |
| 136 | Cl | H | H | CN | C | H |  | S form |
| 137 | Cl | H | H | CN | C | H | 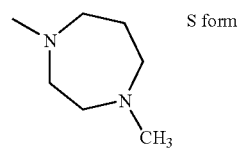 | S form |
| 138 | Cl | H | H | CN | C | H | 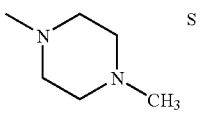 | S form |
| 139 | Cl | H | H | CN | C | Cl | 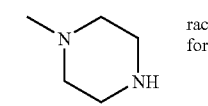 | S form |
| 140 | Cl | H | H | CN | N | — | 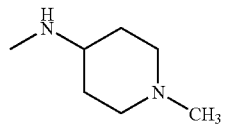 | racemic form |
| 141 | Cl | H | Cl | CN | C | 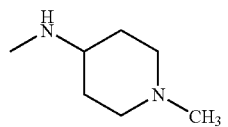 | H | S form |
| 142 | Cl | Cl | H | CN | C | 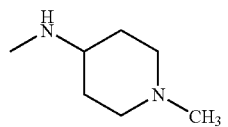 | H | S form |
| 143 | F | H | H | CN | C | H | 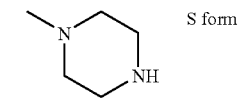 | S form |
| 144 | Br | H | H | CN | C | 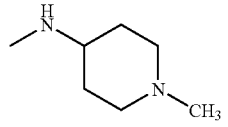 | H | S form |

TABLE 14-continued
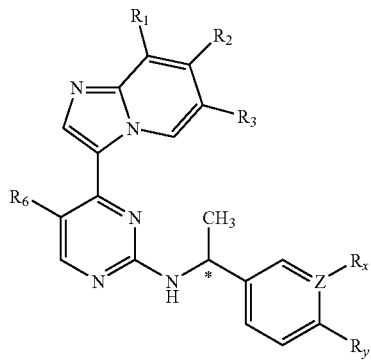
| Examples | R₁ | R₂ | R₃ | R₆ | Z | R$_x$ | R$_y$ | * asymmetric carbon |
|---|---|---|---|---|---|---|---|---|
| 145 | Br | H | H | CN | C | H | 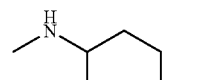 | S form |
TABLE 15
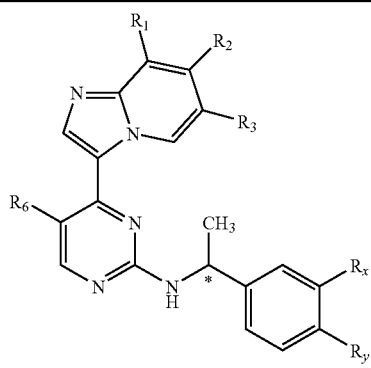
| Examples | R₁ | R₂ | R₃ | R₆ | R$_x$ | R$_y$ | * asymmetric carbon |
|---|---|---|---|---|---|---|---|
| 146 | Br | H | CH₃ | CN | 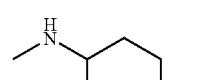 | H | S form |
| 147 | CH₂F | H | H | CN | 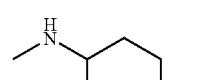 | H | S form |
| 148 | CH₂F | H | H | CN | H | 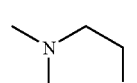 | S form |
| 149 | CH₂F | H | H | CN | H | 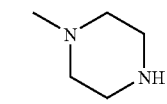 | S form |

TABLE 15-continued
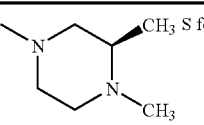
| Examples | R₁ | R₂ | R₃ | R₆ | Rₓ | Rᵧ | * asymmetric carbon |
|---|---|---|---|---|---|---|---|
| 150 | CH₂F | H | H | CN | H |  | S form |
| 151 | CH₂F | H | H | CN | H | 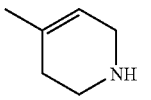 | S form |
| 152 | CH₂F | H | H | CN | H | CH₂CH₂OH | S form |
| 153 | CH₂F | H | H | CN | H | CH₂CH₂N(CH₃)₂ | S form |
| 154 | CH₂F | H | H | CN | H | 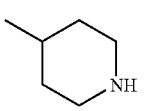 | S form |
| 155 | CH₂F | H | H | CN | H | 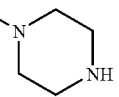 | S form |
TABLE 16
| Examples | R₁ | R₂ | R₃ | R₆ | Rₓ | Rᵧ | * asymmetric carbon |
|---|---|---|---|---|---|---|---|
| 156 | CH(CH₃)OH | H | H | CN | H | (N-methylpiperazinyl) | S form |

TABLE 16-continued

| Examples | R₁ | R₂ | R₃ | R₆ | Rₓ | Rᵧ | * asymmetric carbon |
|---|---|---|---|---|---|---|---|
| 157 | C(CH₃)₂OH | H | H | CN | methyl-N-H-(1-methylpiperidin-4-yl) | H | S form |
| 158 | OCH₃ | H | H | CN | H | 4-methylpiperazin-1-yl | S form |
| 159 | OCH₃ | CH₃ | H | CN | H | 4-methylpiperazin-1-yl | S form |
| 160 | OCH₂F | H | H | CN | H | 4-methylpiperazin-1-yl | S form |
| 161 | OCHF₂ | H | H | CN | H | methyl-NH-(1-methylpiperidin-4-yl) | S form |
| 162 | SO₂CH₃ | H | H | CN | methyl-N-H-(1-methylpiperidin-4-yl) | H | S form |

Example 1

Synthesis of 4-imidazo[1,2-a]pyridin-3-yl-N-[(1S)-phenylethyl]-2-pyrimidinamine [1] (hereinafter, referred to as the compound [1])

(1) 25 g of imidazo[1,2-a]pyridine was dissolved in 350 mL of chloroform, and 56.4 g of aluminum chloride was added under an ice-cold condition over 30 minutes. The mixture was stirred overnight at room temperature, and then heated up to the temperature of 50° C. 16 mL of acetic anhydride was added and the mixture was stirred at 50° C. for 90 minutes. After cooling the reaction solution back to room temperature, ice water was added, and a 3N aqueous solution of sodium hydroxide was further added until the mixture becomes basic. The insolubles were separated by filtration through celite, the filtrate was extracted with ethyl acetate, and the organic layer was washed with saturated brine. The layer was dried over anhydrous sodium sulfate and then filtered, and the filtrate was concentrated to obtain 1-imidazo[1,2-a]pyridine-3-ylethanone [1-1] as a brown oily product. The obtained Compound [1-1] was used in the subsequent reaction without further purification.

(2) Unpurified imidazo[1,2-a]pyridin-3-ylethanone [1-1] was dissolved in 400 mL of N,N-dimethylformamide dimethylacetal, and overheated overnight under reflux. The dimethylformamide dimethylacetal was distilled off under reduced pressure, and then diethyl ether was added to the residue. Thus obtained solid was separated by filtration and dried under reduced pressure, to obtain 5.06 g of (E)-3-(dimethylamino)-1-imidazo[1,2-a]pyridin-3-yl-2-propen-1-one [1-2] as a light brown solid.

(3) 1 g of (E)-3-(dimethylamino)-1-imidazo[1,2-a]pyridin-3-yl-2-propen-1-one [1-2] was dissolved in 10 mL of n-butanol, then 354 mg of thiourea and 377 mg of sodium methoxide were added, and the mixture was stirred at 85° C. for 2 hours. After cooling back to the room temperature, 868 μL of methyl iodide was added, and stirred at room temperature for 30 minutes. The solvent was distilled off until the volume is halved, the solid thus produced was taken and washed with diethyl ether and with water in the subsequent order, and then dried under reduced pressure to obtain 728 mg of 3-[2-methylthio-4-pyrimidinyl]imidazo[1,2-a]pyridine [1-3] as a grey solid.

(4) 150 mg of 3-[2-methylthio-4-pyrimidinyl]imidazo[1,2-a]pyridine [1-3] was dissolved in 3 mL of chloroform and 169 mg of m-chloroperbenzoic acid was added under an ice-cold condition, and stirred for 30 minutes at the same temperature. The resultant solution was added with a saturated aqueous solution of sodium sulfite and a saturated aqueous solution of sodium hydrogen carbonate, and then was extracted with chloroform. The organic layer was dried over anhydrous sodium sulfate and then the insolubles were filtered, and the filtrate was concentrated. The obtained residue was purified by silica gel column chromatography, and 160 mg of 3-[2-methylsulfonyl-4-pyrimidinyl]imidazo[1,2-a]pyridine [1-4] was obtained as a colorless amorphous substance.

(5) 73 mg of 3-[2-methylsulfonyl-4-pyrimidinyl]imidazo[1,2-a]pyridine[1-4] was dissolved in 1 mL of dimethylsulfoxide, and 109 μL of (1S)-1-phenylethylamine and 196 mg of potassium carbonate were added. The mixture solution was stirred at 80° C. for 100 minutes. After cooling back to the room temperature, the reaction mixture was filtered and purified by preparative reversed phase liquid chromatography, to obtain 11.1 mg of the target compound [1] as a pale yellow oily product.

A spectral data of the compound [1] is presented below.
$^1$H-NMR (CDCl$_3$) δ: 9.24 (br, 1H), 8.26 (d, J=5.4 Hz, 1H), 8.19 (s, 1H), 7.65 (d, J=8.1 Hz, 1H), 7.48-7.24 (m, 6H), 6.92 (d, J=5.4 Hz, 1H), 6.78-6.66 (m, 1H), 5.68-5.52 (m, 1H), 5.23-5.08 (m, 1H), 1.63 (d, J=6.9 Hz, 3H).

mass: 316 (M+1)$^+$.

Example 2

Synthesis of 5-bromo-4-imidazo[1,2-a]pyridin-3-yl-N-[(1S)-1-phenylethyl]-2-pyrimidinamine [2] (hereinafter, referred to as the compound [2])

9.1 mg of compound [1] was dissolved in 0.5 mL of acetic acid, and 1.8 μL of bromine was added thereto. The mixture was stirred at room temperature for 30 minutes, and then the acetic acid was distilled off under reduced pressure. The residue was diluted with ethyl acetate, and a saturated aqueous solution of sodium sulfite and a saturated aqueous solution of sodium hydrogen carbonate were added. The mixture was extracted with ethyl acetate, the organic layer was dried over anhydrous sodium sulfate, then the insolubles were separated by filtration, and the solvent was distilled off. The obtained residue was purified by preparative thin layer chromatography, and 8.5 mg of the target compound [2] was obtained as a pale yellow oily product.

A spectral data of the compound [2] is presented below.
$^1$H-NMR (CDCl$_3$) δ: 8.74 (s, 1H), 8.45 (s, 1H), 7.67 (d, J=12.0 Hz, 1H), 7.41-7.26 (m, 7H), 6.68-6.50 (m, 1H), 5.68-5.53 (m, 1H), 5.15-5.00 (m, 1H), 1.59 (d, J=6.9 Hz, 3H)

mass: 394, 396 (M+1)$^+$. .

Example 3

Synthesis of 4-(8-methylimidazo[1,2-a]pyridin-3-yl)-N-[(1S)-1-phenylethyl]-2-pyrimidinamine [3] (hereinafter, referred to as the compound [3])

(1) 18.27 g of 2-amino-3-picoline was dissolved in 150 mL of water, 14.2 g of sodium hydrogen carbonate and 33.2 g of chloroacetaldehyde (40% aqueous solution) were added thereto, and then stirred at room temperature for 4 hours. The solution was adjusted to pH 10 with a 3N aqueous solution of sodium hydroxide, and the mixture was extracted with ethyl acetate. The organic layer was washed with saturated brine, and then dried over anhydrous sodium sulfate. The insolubles were separated by filtration, and then the filtrate was concentrated to obtain 8-methylimidazo[1,2-a]pyridine [3-1] as a brown oily product.

(2) The target compound [3] was obtained as a pale yellow oily product, from 8-methylimidzo[1,2-a]pyridine [3-1] according to the methods of Example 1-(1) to (5).

A spectral data of the compound [3] is presented below.
$^1$H-NMR (CDCl$_3$) δ: 9.13 (br, 1H), 8.24 (d, J=5.4 Hz, 1H), 8.17 (s, 1H), 7.47-7.26 (m, 5H), 7.08 (d, J=6.9 Hz, 1H), 6.93 (d, J=5.4 Hz, 1H), 6.72-6.60 (m, 1H), 5.70-5.58 (m, 1H), 5.22-5.10 (m, 1H), 2.62 (s, 3H), 1.61 (d, J=6.9 Hz, 3H).

mass: 330 (M+1)$^+$.

Example 4

Synthesis of 5-bromo-4-(8-methylimidazo[1,2-a]pyridin-3-yl)-N-[(1S)-1-phenylethyl]-2-pyrimidinamine [4] (hereinafter, referred to as the compound [4])

4.0 mg of the target compound [4] was obtained as a pale yellow oily product, from 4.5 mg of the compound [3] according to the method of Example 2.

A spectral data of the compound [4] is presented below.
$^1$H-NMR (CDCl$_3$) δ: 8.71 (s, 1H), 8.44 (s, 1H), 7.40-7.04 (m, 7H), 6.58-6.45 (m, 1H), 5.63-5.51 (m, 1H), 5.14-5.00 (m, 1H), 2.63 (s, 3H), 1.58 (d, J=6.9 Hz, 3H).

mass: 408, 410 (M+1)$^+$.

Example 5

Synthesis of methyl 4-(8-methylimidazo[1,2-a]pyridin-3-yl)-2-{[(1S)-1-phenylethyl]amino}-5-pyrimidinecarboxylate [5] (hereinafter, referred to as the compound [5])

The mixture of 200 mg of the compound [4], 11 mg of palladium acetate (II), 27.2 mg of 1,1'-bisdiphenylphosphino ferrocene, 123 mg of sodium hydrogen carbonate, 2 ml of methanol, and 2 mL of N,N-dimethylformamide, was stirred overnight in a carbon monoxide atmosphere (3 atmospheric pressure) at 80° C. Thereafter, the reaction mixture was diluted with water, and extracted with ethyl acetate. The organic layer was washed with saturated brine, and then dried over anhydrous sodium sulfate. The insolubles were separated by filtration, the filtrate was concentrated under reduced pressure, and then the obtained residue was purified by silica gel column chromatography, to obtain 186 mg of the target compound [5] as a pale yellow solid.

A spectral data of the compound [5] is presented below.
$^1$H-NMR (CDCl$_3$) δ: 8.80 (s, 1H), 8.25 (br, 1H), 7.98 (s, 1H), 7.43-7.02 (m, 6H), 6.58-6.40 (m, 1H), 5.93-5.78 (m, 1H), 5.18-5.05 (m, 1H), 3.79 (s, 3H), 2.62 (s, 3H), 1.58 (d, J=6.9 Hz, 3H).
mass: 388 (M+1)$^+$.

Example 6

Synthesis of 4-(8-methylimidazo[1,2-a]pyridine-3-yl)-2-{[(1S)-1-phenylethyl]amino}-5-pyrimidinecarboxylic acid [6] (hereinafter, referred to as the compound [6])

10 mg of the compound [5] was dissolved in 3 mL of methanol, 51.6 μL of a 1N aqueous solution of sodium hydroxide was added thereto, and stirred at room temperature for 1 hour. 51.6 μL of a 1N aqueous solution of sodium hydroxide was further added thereto, and the mixture was stirred at 40° C. for 3 hours and a half. The reaction mixture was concentrated under reduced pressure and purified by preparative reversed phase liquid chromatography, to obtain 10.0 mg of the target compound [6] as a pale yellow solid.

A spectral data of the compound [6] is presented below.
$^1$H-NMR (DMSO-d$_6$) δ: 9.08-8.73 (m, 2H+1H×½), 8.55-8.34 (m, 1H+1H×½), 7.79-7.60 (m, 1H), 7.48-7.03 (m, 6H), 5.36-5.20 (m, 1H), 5.10-4.97 (m, 1H), 2.62 (s, 3H×½), 2.58 (s, 3H×½), 1.48 (t, J=7.5 Hz, 3H).
mass: 374 (M+1)$^+$.

Example 7

Synthesis of 4-(8-methylimidazo[1,2-a]pyridine-3-yl)-2-{[(1S)-1-phenylethyl]amino}-5-pyrimidinecarboxamide [7] (hereinafter, referred to as the compound [7])

60.0 mg of the compound [5] was dissolved in 1 mL of ethanol, 0.5 mL of 25% ammonia water was added thereto, and stirred in a sealed tube at 90° C. for 7 hours. After cooling back to the room temperature, 1 mL of 25% ammonia water was further added thereto, and the mixture was stirred overnight in a sealed tube at 120° C. The reaction mixture was cooled back to room temperature, then water was added thereto, and extracted with ethyl acetate. The organic layer was washed with saturated brine, and then dried over anhydrous sodium sulfate. The insolubles were separated by filtration, the filtrate was concentrated under reduced pressure, and then the obtained residue was purified by preparative thin layer chromatography, to obtain 7.9 mg of the target compound [7] as a white solid.

A spectral data of the compound [7] is presented below.
$^1$H-NMR (CDCl$_3$) δ: 8.62 (s, 1H), 8.33 (br, 1H), 8.14 (s, 1H), 7.45-7.03 (m, 6H), 6.64-6.43 (m, 1H), 5.98-5.80 (m, 1H), 5.79 (br, 2H), 5.25-5.04 (m, 1H), 2.61 (s, 3H), 1.59 (d, J=7.2 Hz, 3H).
mass: 373 (M+1)$^+$.

Example 8

Synthesis of 4-(8-methylimidazo[1,2-a]pyridin-3-yl)-2-{[(1S)-1-phenylethyl]amino}-5-pyrimidinecarbonitrile [8] (hereinafter, referred to as the compound [8])

6.0 mg of the compound [7] was dissolved in 1 mL of pyridine, 3.0 μL of phosphorus oxychloride was added thereto, and the mixture was stirred at room temperature for 30 minutes. After concentrating under reduced pressure, the residue was added with a saturated aqueous solution of sodium hydrogen carbonate, and extracted with ethyl acetate. The organic layer was washed with saturated brine, and then dried over anhydrous sodium sulfate. The insolubles were separated by filtration, the filtrate was concentrated under reduced pressure, and then the obtained residue was purified by preparative thin layer chromatography, to obtain 4.0 mg of the target compound [8] as a white solid.

A spectral data of the compound [8] is presented below.
$^1$H-NMR (DMSO-d$_6$) δ: 9.96 (d, J=7.5 Hz, 1H×½), 9.10-8.84 (m, 1H+1H×½), 8.80 (s, 1H×½), 8.78 (s, 1H×½), 8.74 (s, 1H×½), 8.68 (s, 1H×½), 7.58-6.95 (m, 7H), 5.28-5.20 (m, 1H×½), 5.17-5.02 (m, 1H×½), 2.60 (s, 3H×½), 2.55 (s, 3H×½), 1.53 (d, J=7.5 Hz, 3H×½), 1.51 (d, J=7.5 Hz, 3H×½).
mass: 355 (M+1)$^+$.

Example 9

Synthesis of (4-(8-methylimidazo[1,2-a]pyridin-3-yl)-2-{[(1S)-1-phenylethyl]amino}-5-pyrimidinyl)methanol [9] (hereinafter, referred to as the compound [9])

58.4 mg of the compound [5] was dissolved in 1.5 mL of tetrahydrofuran, the solution was cooled down to −78° C., then 452 μL of diisobutylaluminum hydride (1.0M toluene solution) was added thereto, and stirred in an ice bath for 1 hour. 452 μL of diisobutylaluminum hydride (1.0 M toluene solution) was further added thereto, and stirred at the same temperature for 30 minutes. Thereafter, the reaction mixture was added with sodium sulfate decahydrate, and stirred overnight. The insolubles were filtered through celite, the filtrate was concentrated under reduced pressure, and the obtained residue was purified by preparative thin layer chromatography, to obtain 34.1 mg of the target compound [9] as a white solid.

A spectral data of the compound [9] is presented below.
$^1$H-NMR (DMSO-d$_6$) δ: 8.40-8.28 (m, 2H), 7.86 (d, J=7.7 Hz, 1H), 7.43-7.15 (m, 7H), 6.67 (br, 1H), 5.26-5.23 (m, 1H), 5.15-4.96 (m, 1H), 4.45-4.30 (m, 2H), 2.52 (s, 3H), 1.46 (d, J=6.9 Hz, 3H).
mass: 360 (M+1)$^+$.

Example 10

Synthesis of 4-(8-methylimidazo[1,2-a]pyridin-3-yl)-2-{[(1S)-1-phenylethyl]amino}-5-pyrimidinecarboaldehyde [10] (hereinafter, referred to as the compound [10])

31.3 mg of the compound [9] was dissolved in 10 mL of chloroform under heating, and 118 mg of manganese dioxide was added thereto. After stirring at room temperature for 5 hours and a half, the insolubles were filtered through celite. The filtrate was concentrated under reduced pressure, and the residue was purified by preparative thin layer chromatography, to obtain 20.4 mg of the target compound [10] as a white solid.

A spectral data of the compound [10] is presented below.
$^1$H-NMR (CDCl$_3$) δ: 10.07 (s, 1H), 9.93 (s, 1H), 8.27 (d, J=7.2 Hz, 1H), 7.92 (s, 1H), 7.43-7.11 (m, 6H), 6.54 (t, J=7.2 Hz, 1H), 6.33-6.25 (m, 1H), 5.21-5.10 (m, 1H), 2.64 (s, 3H), 1.62 (d, J=6.9 Hz, 3H)
mass: 358 (M+1)$^+$. .

Example 11

Synthesis of 4-(8-methylimidazo[1,2-a]pyridin-3-yl)-2-{[(1S)-1-phenylethyl]amino}-5-pyrimidinecarboaldehyde oxime [11] (hereinafter, referred to as the compound [11])

5.1 mg of the compound [10] was dissolved in ethanol, 2.4 mg of sodium hydrogen carbonate and 1.98 mg of hydroxylamine hydrochloride were added thereto, and stirred at 60° C. for 30 minutes. The reaction mixture was concentrated under reduced pressure, and the residue was purified by preparative thin layer chromatography, to obtain 5.6 mg of the target compound [11] as a pale yellow oily product.

A spectral data of the compound [11] is presented below.
$^1$H-NMR (DMSO-$d_6$) δ: 11.15 (s, 1H), 8.83 (s, 1H), 8.43-8.36 (m, 1H), 8.31-8.22 (m, 1H), 8.07 (s, 1H), 7.84-7.68 (m, 1H), 7.42-7.18 (m, 6H), 6.75-6.63 (m, 1H), 4.55-4.46 (m, 1H), 2.51 (s, 3H), 1.47 (d, J=6.6 Hz, 3H).
mass: 373 (M+1)$^+$.

Example 12

Synthesis of 4-(8-methylimidazo[1,2-a]pyridin-3-yl)-2-{[(1S)-1-phenylethyl]amino}-5-pyrimidinecarboaldehyde o-methyloxime [12] (hereinafter, referred to as the compound [12])

6.7 mg of the target compound [12] was obtained as a pale yellow oily product, from 5.1 mg of the compound [10] and 2.39 mg of hydroxylamine methylether hydrochloride, according to the method of Example 11.

A spectral data of the compound [12] is presented below.
$^1$H-NMR (DMSO-$d_6$) δ: 8.65 (s, 1H), 8.45-8.37 (m, 2H), 8.13 (s, 1H), 7.85-7.70 (m, 1H), 7.53-7.18 (m, 6H), 6.75-6.64 (m, 1H), 5.08-4.90 (m, 1H), 3.87 (s, 3H), 2.54 (s, 3H), 1.47 (d, J=6.3 Hz, 3H).
mass: 387 (M+1)$^+$.

Example 13

Synthesis of 5-(difluoromethyl)-4-(8-methylimidazo[1,2-a]pyridin-3-yl)-N-[(1S)-1-phenylethyl]-2-pyrimidinamine [13] (hereinafter, referred to as the compound [13])

8.8 mg of the compound [10] was dissolved in 1.5 mL of dichloromethane, 9.8 μL of diethylaminosulfur trifluoride was added thereto, and stirred at room temperature for 30 minutes. 19.6 μL of diethylaminosulfur trifluoride was further added thereto, and stirred at the same temperature for 20 minutes. After adding methanol, the mixture was concentrated under reduced pressure, and the residue was purified by preparative thin layer chromatography, to obtain 1.5 mg of the target compound [13] as a colorless oily product.

A spectral data of the compound [13] is presented below.
$^1$H-NMR (DMSO-$d_6$) δ: 8.64-8.29 (m, 4H), 8.10-7.85 (m, 1H), 7.50-6.97 (m, 6H), 6.73-6.60 (m, 1H), 5.10-4.95 (m, 1H), 2.54 (s, 3H), 1.47 (d, J=6.6 Hz, 3H).
mass: 380 (M+1)$^+$.

Example 14

Synthesis of t-butyl 4-(8-methylimidazo[1,2-a]pyridin-3-yl)-2-{[(1S)-1-phenylethyl]amino}-5-pyrimidinylcarbamate [14] (hereinafter, referred to as the compound [14])

51.8 mg of the compound [6] was dissolved in a mixed solvent of 3 mL of N,N-dimethylformamide and 2 mL of 1,4-dioxane, the mixture solution was cooled to 0° C., then 54.3 μL of triethylamine and 38.9 μL of diphenylphosphoryl azide were added thereto, and stirred at room temperature for 1 hour. After adding t-butylalcohol and stirring overnight at 80° C., the reaction mixture was added with water and a saturated aqueous solution of sodium hydrogen carbonate, and extracted with ethyl acetate. The organic layer was washed with saturated brine, and then dried over anhydrous sodium sulfate. The insolubles were filtered, the filtrate was concentrated under reduced pressure, and the residue was purified by preparative thin layer chromatography, to obtain 2.7 mg of the target compound [14] as a pale yellow oily product.

A spectral data of the compound [14] is presented below.
$^1$H-NMR (CDCl$_3$) δ: 8.68 (br, 1H), 8.52 (br, 1H), 8.17 (s, 1H), 7.48-7.20 (m, 5H), 7.08-7.06 (m, 1H), 6.57-6.45 (m, 1H), 6.10-5.98 (m, 1H), 5.62-5.54 (m, 1H), 5.12-5.03 (m, 1H), 2.61 (s, 3H), 1.57 (d, J=6.9 Hz, 3H), 1.49 (s, 9H).
mass: 445 (M+1)$^+$.

Example 15

Synthesis of 4-(8-methylimidazo[1,2-a]pyridin-3-yl)-N$^2$-[(1S)-1-phenylethyl]-2,5-pyrimidindiamine [15] (hereinafter, referred to as the compound [15])

In the process for synthesizing the compound [14], the compound [15] was also produced at the same time. A part of the residue in Example 14 was purified by preparative reversed phase chromatography. After basifying the liquid with saturated aqueous solution of sodium hydrogen carbonate, the mixture was extracted with ethyl acetate, and the organic layer was dried over anhydrous sodium sulfate. The insolubles were filtered, and the filtrate was concentrated under reduced pressure to obtain 7.4 mg of the target compound [15] as a yellow oily product.

A spectral data of the compound [15] is presented below.
$^1$H-NMR (CDCl$_3$) δ: 8.62 (d, J=6.6 Hz, 1H), 8.30 (s, 1H), 8.03 (s, 1H), 7.44-7.25 (m, 5H), 7.06 (d, J=6.6 Hz, 1H), 6.51 (t, J=6.6 Hz, 1H), 5.32-5.22 (m, 1H), 5.08-4.96 (m, 1H), 3.43 (br, 2H), 2.62 (s, 3H), 1.55 (d, J=6.9 Hz, 3H).
mass: 345 (M+1)$^+$.

Example 16

Synthesis of 4-(8-methylimidazo[1,2-a]pyridin-3-yl)-5-(4-methyl-1-piperazinyl)-N-[(1S)-1-phenylethyl]-2-pyrimidinamine [16] (hereinafter, referred to as the compound [16])

(1) 100 mg of the compound [4] was dissolved in 3 mL of acetic anhydride, and stirred overnight in a sealed-tube at 150° C. After concentrating under reduced pressure, a saturated aqueous solution of sodium hydrogen carbonate was added thereto, and was extracted with ethyl acetate. The organic layer was washed with saturated brine, and then dried over anhydrous sodium sulfate. The insolubles were filtered, the filtrate was concentrated under reduced pressure, and the residue was purified by preparative thin layer chromatography, to obtain 102 mg of N-[5-bromo-4-(8-methylimidazo[1,2-a]pyridin-3-yl)-2-pyrimidinyl]-N-[(1S)-1-phenylethyl]acetamide [16-1] as a white solid.

(2) The mixture of 17 mg of N-[5-bromo-4-(8-methylimidazo[1,2-a]pyridin-3-yl)-2-pyrimidinyl]-N-[(1S)-1-phenylethyl]acetamide [16-1], 2.17 mg of bis(dibenzylideneacetone)palladium, 19 mg of 4,5-bis(diphenylphosphino)-9,9-dimethylxanthene, 17.2 mg of cesium carbonate, 5.0 μL of 1-methylpiperazine, 0.25 mL of toluene, and 0.5 mL of 1,4-dioxane, was stirred at 80° C. for 3 days. After cooling the reaction mixture back to room temperature, a saturated aqueous solution of sodium hydrogen carbonate and water were added thereto, and the mixture was extracted with ethyl acetate. The organic layer was washed with saturated brine, and then dried over anhydrous sodium sulfate. The insolubles were filtered, the filtrate was concentrated under reduced pressure, and the residue was purified by preparative reversed phase liquid chromatography, to obtain 0.6 mg of N-[4-(8-methylimidazo[1,2-a]pyridin-3-yl)-5-(4-methyl-1-piperazinyl)-2-pyrimidinyl]-N-[(1S)-1-phenylethyl]acetamide [16-2].

(3) 0.6 mg of N-[4-(8-methylimidazo[1,2-a]pyridin-3-yl)-5-(4-methyl-1-piperazinyl)-2-pyrimidinyl]-N-[(1S)-1-phenylethyl]acetamide [16-2] was dissolved in methanol, 0.1 mL of sodium methoxide (28% methanol solution) was added thereto, and stirred at 60° C. for 1 hour and 40 minutes then again stirred at 80° C. for 2 hours and 20 minutes. After concentrating under reduced pressure, the residue was purified by preparative reversed phase liquid chromatography to obtain 0.44 mg of the target compound [16] as a pale yellow oily product.

A spectral data of the compound [16] is presented below.
$^1$H-NMR (DMSO-$d_6$) δ: 8.90-7.00 (m, 10H), 5.77-5.20 (m, 1H), 4.44-4.10 (m, 1H), 2.75-2.68 (m, 4H), 2.57 (s, 3H), 2.29-2.23 (m, 4H), 1.48 (d, J=6.9 Hz, 3H), 1.28 (s, 3H).
mass: 428 (M+1)$^+$.

Example 17

Synthesis of 4-(8-methylimidazo[1,2-a]pyridin-3-yl)-N-[(1S)-1-phenylethyl]-5-(1-pyrrolidinyl)-2-pyrimidinamine [17] (hereinafter, referred to as the compound [17])

0.67 mg of the target compound [17] was obtained as a pale yellow oily product from 20 mg of the N-[5-bromo-4-(8-methylimidazo[1,2-a]pyridin-3-yl)-2-pyrimidinyl]-N-[(1S)-1-phenylethyl]acetamide [16-1] obtained in Example 16-(1) and 4.35 μL of piperidine, according to the methods of Example 16-(2) and (3).

A spectral data of the compound [17] is presented below.
$^1$H-NMR (CDCl$_3$) δ: 9.00-8.92 (m, 1H), 8.78-8.65 (m, 1H), 8.10-7.90 (m, 1H), 7.74-7.10 (m, 6H), 6.73-6.62 (m, 1H), 5.39-5.00 (m, 1H), 4.52-4.15 (m, 1H), 3.13-2.75 (m, 4H), 2.64 (s, 3H), 2.00-1.82 (m, 4H), 1.59 (d, J=6.9 Hz, 3H).
mass: 399 (M+1)$^+$.

Example 18

Synthesis of $N^5$,$N^5$-dimethyl-4-(8-methylimidazo[1,2-a]pyridin-3-yl)-$N^2$-[(1S)-1-phenylethyl]-2,5-pyrimidinediamine [18] (hereinafter, referred to as the compound [18])

2.1 mg of the target compound [18] was obtained as a pale yellow oily product from 20 mg of the N-[5-bromo-4-(8-methylimidazo[1,2-a]pyridin-3-yl)-2-pyrimidinyl]-N-[(1S)-1-phenylethyl]acetamide [16-1] obtained in Example 16-(1) and 26.4 μL of dimethylamine (2M tetrahydrofuran solution), according to the methods of Example 16-(2) and (3).

A spectral data of the compound [18] is presented below.
$^1$H-NMR (CDCl$_3$) δ: 9.20 (d, J=6.9 Hz, 1H), 8.85 (s, 1H), 8.20 (s, 1H), 7.50-7.02 (m, 6H), 6.69-6.55 (m, 1H), 5.65-5.40 (m, 1H), 5.17-5.03 (m, 1H), 2.67 (s, 6H), 2.64 (s, 3H), 1.59 (d, J=6.9 Hz, 3H)
mass: 373 (M+1)$^+$..

Example 19

Synthesis of 4-(8-methylimidazo[1,2-a]pyridin-3-yl)-5-(methylthio)-N-[(1S)-1-phenylethyl]-2-pyrimidinamine [19] (hereinafter, referred to as the compound [19])

100 mg of the compound [4] was dissolved in 2 mL of N,N-dimethylformamide, 60.6 mg of sodium methanethiolate was added, and stirred overnight at 80° C. The reaction mixture was cooled back to room temperature, water and a saturated aqueous solution of sodium hydrogen carbonate were added thereto, and extracted with ethyl acetate. The organic layer was washed with saturated brine, and then dried over anhydrous sodium sulfate. The insolubles were filtered, the filtrate was concentrated under reduced pressure, and the residue was purified by preparative thin layer chromatography, to obtain 78.5 mg of the target compound [19] as a pale yellow oily product.

A spectral data of the compound [19] is presented below.
$^1$H-NMR (CDCl$_3$) δ: 8.88 (s, 1H), 8.45 (s, 1H), 7.48-7.26 (m, 6H), 7.09 (d, J=6.7 Hz, 1H), 6.63-6.50 (m, 1H), 5.78-5.62 (m, 1H), 5.20-5.08 (m, 1H), 2.54 (s, 3H), 2.30 (s, 3H), 1.59 (d, J=6.9 Hz, 3H).
mass: 376 (M+1)$^+$.

Example 20

Synthesis of 4-(8-methylimidazo[1,2-a]pyridin-3-yl)-5-(methylsulfonyl)-N-[(1S)-1-phenylethyl]-2-pyrimidinamine [20] (hereinafter, referred to as the compound [20])

18.2 mg of the compound [19] was dissolved in 0.75 mL of N,N-dimethylformamide, 25.1 mg of m-chloroperbenzoic acid was added under an ice-cold condition, and stirred at room temperature for 1 hour. Thereto, water and a saturated aqueous solution of sodium hydrogen carbonate were added, the mixture was extracted with ethyl acetate, and the organic layer was dried over anhydrous sodium sulfate. The insolubles were filtered, the filtrate was concentrated under reduced pressure, and the residue was purified by preparative thin layer chromatography, to obtain 11.6 mg of the target compound [20] as a yellow oily product.

A spectral data of the compound [20] is presented below.
$^1$H-NMR (CDCl$_3$) δ: 9.04 (s, 1H), 8.88 (s, 1H), 8.24 (d, J=6.9 Hz, 1H), 7.50-7.08 (m, 6H), 6.50-6.39 (m, 1H), 6.18-6.10 (m, 1H), 5.20-5.06 (m, 1H), 2.99 (s, 3H), 2.59 (s, 3H), 1.51 (d, J=6.9 Hz, 3H).
mass: 408 (M+1)$^+$.

Example 21

Synthesis of 5-iodo-4-(8-methylimidazo[1,2-a]pyridin-3-yl)-N-[(1S)-1-phenylethyl]-2-pyrimidinamine [21] (hereinafter, referred to as the compound [21])

295 mg of the compound [3] was dissolved in 6 mL of chloroform, 302 mg of N-iodo succinimide was added thereto, and heated overnight under reflux. The reaction mixture was cooled back to room temperature, a saturated aqueous solution of sodium hydrogen carbonate was added thereto, and extracted with chloroform. The organic layer was washed with a saturated aqueous solution of sodium sulfite and with saturated brine in the subsequent order, and then dried over anhydrous sodium sulfate. The insolubles were filtered, the filtrate was concentrated under reduced pressure, and the residue was purified by silica gel column chromatography, to obtain 74 mg of the target compound [21] as a brown oily product.

A spectral data of the compound [21] is presented below.

$^1$H-NMR (CDCl$_3$) δ: 8.71 (s, 1H), 8.55 (s, 1H), 7.44-7.00 (m, 6H), 6.64-6.39 (m, 1H), 5.68-5.54 (m, 1H), 5.12-4.98 (m, 1H), 4.83-4.52 (m, 1H), 2.63 (s, 3H×½), 2.62 (s, 3H×½), 1.56 (d, J=6.9 Hz, 3H×½), 1.41 (d, J=6.9 Hz, 3H×½).

mass: 456 (M+1)$^+$.

Example 22

Synthesis of 5-methoxy-4-(8-methylimidazo[1,2-a] pyridin-3-yl)-N-[(1S)-1-phenylethyl]-2-pyrimidinamine [22] (hereinafter, referred to as the compound [22])

18.5 mg of the compound [21] was dissolved in 0.5 mL of methanol, then 0.77 mg of copper iodide, 1.46 mg of 1,10-phenanthroline, and 26.5 mg of cesium carbonate were added thereto, and stirred overnight in a sealed-tube at 110° C. The reaction mixture was concentrated under reduced pressure, and the residue was purified by preparative reversed phase liquid chromatography. After basifying the solution with saturated aqueous solution of sodium hydrogen carbonate, the mixture was extracted with ethyl acetate, and the organic layer was dried over anhydrous sodium sulfate. The insolubles were filtered, and the filtrate was concentrated under reduced pressure, to obtain 3.1 mg of the target compound [22] as yellow amorphous.

A spectral data of the compound [22] is presented below.

$^1$H-NMR (CDCl$_3$) δ: 9.33-9.24 (m, 1H), 8.58 (s, 1H), 7.48-7.07 (m, 7H), 6.67-6.50 (m, 1H), 5.61-5.45 (m, 1H), 5.13-5.00 (m, 1H), 3.92 (s, 3H), 2.64 (s, 3H), 1.59 (d, J=6.9 Hz, 3H).

mass: 360 (M+1)$^+$.

Example 23

Synthesis of 2-[(4-(8-methylimidazo[1,2-a]pyridin-3-yl)-2-{[(1S)-1-phenylethyl]amino}-5-pyrimidinyl) amino]ethanol [23] (hereinafter, referred to as the compound [23])

The mixture of 18.5 mg of the compound [21], 7.0 mg of bis(dibenzylideneacetone)palladium, 14.1 mg of 4,5-bis (diphenylphosphino)-9,9-dimethylxanthene, 39.7 mg of cesium carbonate, 3.7 μL of 2-aminoethanol, and 0.5 mL of 1,4-dioxane, was stirred overnight in a sealed-tube at 80° C. The reaction mixture was concentrated under reduced pressure, and the residue was purified by preparative reversed phase liquid chromatography, to obtain 2.1 mg of the target compound [23] as a yellow oily product.

A spectral data of the compound [23] is presented below.

$^1$H-NMR (CDCl$_3$) δ: 10.08-10.01 (m, 1H), 8.38-8.30 (m, 1H), 7.91-7.85 (m, 1H), 7.55-7.20 (m, 7H), 6.97-6.89 (m, 1H), 6.78-6.70 (m, 1H), 5.12-5.00 (m, 1H), 3.86-3.55 (m, 2H), 3.70 (br, 1H), 3.48-3.40 (m, 2H), 2.51 (s, 3H), 1.69 (d, J=6.9 Hz, 3H).

mass: 389 (M+1)$^+$.

Example 24

Synthesis of 4-(8-methylimidazo[1,2-a]pyridin-3-yl)-2-{[(1S)-1-phenylethyl]amino}-5-pyrimidinol [24] (hereinafter, referred to as the compound [24])

(1) The mixture of 18.5 mg of the compound [21], 2.3 mg of copper iodide, 4.5 mg of 1,10-phenanthroline, 26.5 mg of cesium carbonate, 68.3 mg of 2,4-dimethoxybenzyl alcohol, and 0.5 mL of toluene, was stirred overnight in a sealed-tube at 110° C. The reaction mixture was concentrated under reduced pressure, and the residue was purified by preparative reversed phase liquid chromatography, to obtain 3.7 mg of 5-[(2,4-dimethoxybenzyl)oxy]-4-(8-methylimidazo[1,2-a] pyridin-3-yl)-N-[(1S)-1-phenylethyl]amino}-5-pyrimidinamine [24-1].

(2) 3.7 mg of the 5-[(2,4-dimethoxybenzyl)oxy]-4-(8-methylimidazo[1,2-a]pyridin-3-yl)-N-[(1S)-1-phenylethyl] amino}-5-pyrimidinamine [24-1] was dissolved in 0.5 mL of chloroform, 0.5 mL of 4N hydrochloric acid-1,4-dioxane solution was added thereto, and stirred at room temperature for 3 hours and 40 minutes. The reaction mixture was concentrated under reduced pressure, and the residue was purified by preparative reversed phase liquid chromatography, to obtain 1.1 mg of the target compound [24] as a yellow oily product.

A spectral data of the compound [24] is presented below.

$^1$H-NMR (CDCl$_3$) δ: 9.36-9.23 (m, 1H), 9.21-9.10 (m, 1H), 8.12-8.02 (m, 1H), 7.72-7.63 (m, 1H), 7.45-7.00 (m, 8H), 5.08-4.95 (m, 1H), 2.76 (s, 3H), 1.69 (d, J=6.9 Hz, 3H).

mass: 346 (M+1)$^+$.

Example 25

Synthesis of methyl 3-(5-bromo-2-{[(1S)-1-phenylethyl]amino}-4-pyrimidinyl)imidazo[1,2-a]pyridine-8-carboxylate [25] (hereinafter, referred to as the compound [25])

(1) The mixture of 138 mg of 2-aminonicotinic acid and 6 mL of hydrochloric acid-methanol solution was stirred overnight in a sealed-tube at 90° C. The reaction mixture was concentrated under reduced pressure, the residue was added with a saturated aqueous solution of sodium hydrogen carbonate, and extracted with ethyl acetate. The organic layer was dried over anhydrous sodium sulfate, the insolubles were filtered, and the filtrate was concentrated under reduced pressure, to obtain 106 mg of 2-aminonicotinic acid methylester [25-1]. The obtained compound [25-1] was used in the subsequent reaction without further purification.

(2) 50 g of ethyl ethynyl ether (50% v/v hexane solution) was dissolved in 200 mL of tetrahydrofuran, 119 mL of borane-tetrahydrofuran complex (1.0M tetrahydrofuran solution) was added dropwise over 30 minutes under an ice-cold condition, then the reaction mixture was heated to room temperature, and further stirred for 4 hours. Thereto, 100 mL of tetrahydrofuran solution containing 19.1 g of 4-chloro-2-methylthiopyrimidine, 1.87 g of palladium acetate, 2.18 g of triphenylphosphine, and 159 mL of a 3N aqueous solution of sodium hydroxide were added, and was further stirred overnight at room temperature. Under reduced pressure, the tetrahydrofuran was distilled off, water was added to the residue, and extracted with ethyl acetate. The organic layer was washed with saturated brine, and then dried over anhydrous sodium sulfate. The insolubles were filtered, the filtrate was concentrated under reduced pressure, and the residue was purified by silica gel column chromatography, to obtain 9.7 g of 4-[(E)-2-ethoxyvinyl]-2-(methylthio)pyrimidine [25-2] as a brown oily product.

(3) 137.2 mg of the 4-[(E)-2-ethoxyvinyl]-2-(methylthio)pyrimidine [25-2] was dissolved in a mixture solvent of 5 mL of 1,4-dioxane and 2 mL of water, and 124.1 mg of N-bromosuccinimide was added thereto. After stirring at room temperature for 1 hour, 106 mg of the 2-aminonicotinic acid methylester [25-1] was added, and stirred at 85° C. for 1 hour. The reaction mixture was concentrated under reduced pressure, and the residue was purified by preparative thin layer chromatography, to obtain 106.1 mg of methyl 3-[2-(methylthio)-4-pyrimidinyl]imidazo[1,2-a]pyridine-8-carboxylate [25-3].

(4) 106.1 mg of methyl 3-[2-(methylthio)-4-pyrimidinyl]imidazo[1,2-a]pyridine-8-carboxylate [25-3] was dissolved in 1 mL of N,N-dimethylformamide, 183.1 mg of m-chloroperbenzoic acid was added, and stirred overnight at room temperature. The reaction mixture was concentrated under reduced pressure, the residue was dissolved in ethyl acetate, and washed with saturated aqueous solution of sodium hydrogen carbonate. After drying the organic layer over anhydrous sodium sulfate, the insolubles were filtered, and the filtrate was concentrated under reduced pressure, to obtain methyl 3-[2-(methylsulfonyl)-4-pyrimidinyl]imidazo[1,2-a]pyridine-8-carboxylate [25-4]. The obtained compound [25-4] was used in the subsequent reaction without further purification.

(5) The 3-[2-(methylsulfonyl)-4-pyrimidinyl]imidazo[1,2-a]pyridine-8-carboxylate [25-4] was dissolved in 3 mL of dimethylsulfoxide, then 50 µL of (1S)-(1)-phenylethylamine and 150 µL of N,N-diisopropylethylamine were added, and stirred at 90° C. for 4 hours. After cooling back the reaction mixture to room temperature, water was added, and extracted with ethyl acetate. The organic layer was dried over anhydrous sodium sulfate, then the insolubles were filtered, and the filtrate was concentrated under reduced pressure. The obtained residue was purified by preparative thin layer chromatography, to obtain methyl 3-(2-{[(1S)-1-phenylethyl]amino}-4-pyrimidinyl)imidazo[1,2-a]pyridine-8-carboxylate [25-5] was obtained.

(6) The methyl 3-(2-{[(1S)-1-phenylethyl]amino}-4-pyrimidinyl)imidazo[1,2-a]pyridine-8-carboxylate [25-5] was dissolved in 2 mL of acetic acid, 50 µL of bromine was added, and stirred at room temperature for 10 minutes. The reaction mixture was concentrated under reduced pressure, and the obtained residue was dissolved in ethyl acetate. The ethyl acetate solution was washed with a saturated aqueous solution of sodium hydrogen carbonate, and then dried over anhydrous sodium sulfate. The insolubles were filtered, the filtrate was concentrated under reduced pressure, and the residue was purified by preparative thin layer chromatography, to obtain 106.2 mg of the target compound [25] as a white solid.

A spectral data of the compound [25] is presented below.
$^1$H-NMR (CDCl$_3$) δ: 8.80 (s, 1H), 8.48 (s, 1H), 8.04 (d, J=7.2 Hz, 1H), 7.47-7.26 (m, 5H), 6.60 (br, 1H), 5.69 (br, 1H), 5.07 (br, 1H), 4.06 (s, 3H), 1.58 (d, J=7.0 Hz, 3H).
mass: 452, 454 (M+1)$^+$.

Examples 26 and 27

Synthesis of [3-(5-bromo-2-{[(1S)-1-phenylethyl]amino}-4-pyrimidinyl)imidazo[1,2-a]pyridin-8-yl]methanol [26] (hereinafter, referred to as the compound [26]), and [3-(2-{[(1S)-1-phenylethyl]amino}-4-pyrimidinyl)imidazo[1,2-a]pyridin-8-yl]methanol [27] (hereinafter, referred to as the compound [27])

50 mg of the compound [25] was dissolved in 5 mL of tetrahydrofuran, 10 mg of lithium aluminum hydride was added thereto, and stirred at room temperature for 30 minutes. To the reaction mixture, 1N aqueous solution of sodium hydroxide was added, and the organic layer was separated. The aqueous layer was extracted with ethyl acetate and mixed with the above organic layer, and then dried over anhydrous sodium sulfate. The insolubles were filtered, and the filtrate was concentrated under reduced pressure. Thereafter, the obtained residue was purified by preparative thin-layer chromatography to obtain 15.7 mg of the target compound [26] as a white solid and 10.4 mg of the target compound [27] as a pale yellow oily product.

Spectral data of the compounds [26] and [27] are presented below.

Compound [26]:
$^1$H-NMR (CDCl$_3$) δ: 8.67 (s, 1H), 8.45 (s, 1H), 7.41-7.19 (m, 7H), 6.77 (br, 1H), 5.63 (br, 1H), 5.08 (br, 1H), 5.03 (s, 2H), 1.58 (d, J=6.9 Hz, 3H).
mass: 424, 426 (M+1)$^+$.

Compound [27]:
$^1$H-NMR (CDCl$_3$) δ: 8.26 (d, J=5.3 Hz, 1H), 8.13 (s, 1H), 7.46-7.20 (m, 7H), 6.91 (d, J=5.3 Hz, 1H), 6.70 (br, 1H), 5.62 (br, 1H), 5.18-5.10 (m, 1H), 5.02 (s, 2H), 1.65 (d, J=7.7 Hz, 3H).
mass: 346 (M+1)$^+$.

Example 28

Synthesis of 5-bromo-4-(8-chloroimidazo[1,2-a]pyridin-3-yl)-N-[(1S)-1-phenylethyl]-2-pyrimidinamine [28] (hereinafter, referred to as the compound [28])

23.2 mg of the target compound [28] was obtained as a white solid, from 71 mg of 2-amino-3-chloropyridine and 107.8 mg of 4-[(E)-2-ethoxyvinyl]-2-(methylthio)pyrimidine [25-2], according to the methods of Example 25-(3) to (6).

A spectral data of the compound [28] is presented below.
$^1$H-NMR (CDCl$_3$) δ: 8.72 (s, 1H), 8.47 (s, 1H), 7.43-7.29 (m, 7H), 6.47 (br, 1H), 5.64 (br, 1H), 5.03 (br, 1H), 1.60 (d, J=6.9 Hz, 3H).
mass: 428, 430 (M+1)$^+$.

Example 29

Synthesis of 3-(5-bromo-2-{[(1S)-1-phenylethyl]amino}-4-pyrimidinyl)imidazo[1,2-a]pyridine-8-carbonitrile [29] (hereinafter, referred to as the compound [29])

20 mg of the compound [25] was dissolved in 1 mL of methanol, 1 mL of aqueous ammonia (28%) was added, and stirred in a sealed-tube at 85° C. for 1 hour and a half. After cooling the reaction mixture back to room temperature, the solid thus produced was taken, and washed with water. The obtained solid was dissolved in 1 mL of pyridine, 20 µL of phosphorus oxychloride was added, and stirred at room temperature for 5 minutes. The reaction mixture was concentrated under reduced pressure, then the residue thus obtained was neutralized with acetic acid, and extracted with ethyl acetate. After drying the organic layer over sodium sulfate, the insolubles were filtered, and the filtrate was concentrated under reduced pressure. The residue was purified by preparative thin-layer chromatography, and 3.98 mg of the target compound was obtained as a white solid.

A spectral data of the compound [29] is presented below.
$^1$H-NMR (CDCl$_3$) δ: 8.78 (s, 1H), 8.51 (s, 1H), 7.67 (d, J=6.9 Hz, 1H), 7.46-7.30 (m, 6H), 6.56 (br, 1H), 5.67 (br, 1H), 5.01 (br, 1H), 1.60 (d, J=6.9 Hz, 3H)
mass: 419, 421 (M+1)$^+$..

Example 30

Synthesis of 4-(8-chloroimidazo[1,2-a]pyridin-3-yl)-2-{[(1S)-1-phenylethyl]amino}-5-pyrimidinecarbonitrile [30] (hereinafter, referred to as the compound [30])

(1) 15 mg of methyl 4-(8-chloroimidazo[1,2-a]pyridin-3-yl)-2-{[(1S)-1-phenylethyl]amino}-5-pyrimidinecarboxylate [30-1] was obtained from 20 mg of the compound [28] according to the method of Example 5.

(2) 4-(8-chloroimidazo[1,2-a]pyridin-3-yl)-2-{[(1S)-1-phenylethyl]amino}-5-pyrimidinecarboxamide [30-2] was obtained from 15 mg of the methyl 4-(8-chloroimidazo[1,2-a]pyridin-3-yl)-2-{[(1S)-1-phenylethyl]amino}-5-pyrimidinecarboxylate [30-1] according to the method of Example 7.

(3) 1.85 mg of the target compound [30] was obtained as a white solid, from the 4-(8-chloroimidazo[1,2-a]pyridin-3-yl)-2-{[(1S)-1-phenylethyl]amino}-5-pyrimidinecarboxamide [30-2], according to the method of Example 8.

A spectral data of the compound [30] is presented below.
$^1$H-NMR (CDCl$_3$) δ: 8.98 (s, 1H×⅓), 8.90 (s, 1H×⅔), 8.72 (d, J=5.0 Hz, 1H), 8.61-8.55 (m, 1H), 7.47-7.30 (m, 6H), 6.59-6.54 (m, 1H), 6.14 (br, 1H), 5.10 (s, 1H), 1.63 (d, J=6.9 Hz, 3H).
mass: 375, 377 (M+1)$^+$.

Example 31

Synthesis of 5-bromo-4-[8-(difluoromethyl)imidazo[1,2-a]pyridin-3-yl]-N-[(1S)-1-phenylethyl]-2-pyrimidinamine [31] (hereinafter, referred to as the compound [31])

(1) 122 mg of the compound [25] was dissolved in 10 mL of tetrahydrofuran, 0.62 mL of diisobutylaluminum hydride (1.01M toluene solution) was added at −78° C., and stirred at the same temperature for 10 minutes. Thereto, a saturated aqueous solution of ammonium chloride was added, the organic layer was separated, and then dried over anhydrous sodium sulfate. The insolubles were filtered, and the residue was purified by preparative thin-layer chromatography, to obtain 72.3 mg of 3-(5-bromo-2-{[(1S)-1-phenylethyl]amino}-4-pyrimidinyl)imidazo[1,2-a]pyridine-8-carboaldehyde [31-1].

(2) 60.3 mg of the 3-(5-bromo-2-{[(1S)-1-phenylethyl]amino}-4-pyrimidinyl)imidazo[1,2-a]pyridine-8-carboaldehyde [31-1] was dissolved in 2 mL of dichloromethane, 100 μL of diethylaminosulfur trifluoride was added, and stirred at room temperature for 5 minutes. After concentrating the reaction mixture under reduced pressure, the residue thus obtained was purified by preparative thin-layer chromatography, and 48.5 mg of the target compound [31] was obtained as a white solid.

A spectral data of the compound [31] is presented below.
$^1$H-NMR (CDCl$_3$) δ: 8.73 (s, 1H), 8.48 (s, 1H), 7.59-7.30 (m, 7H), 6.61 (br, 1H), 5.68 (br, 1H), 5.03 (br, 1H), 1.59 (d, J=7.0 Hz, 3H).
mass: 444, 446 (M+1)$^+$.

Example 32

Synthesis of 3-(5-cyano-2-{[(1S)-1-phenylethyl]amino}-4-pyrimidinyl)imidazo[1,2-a]pyridine-8-carbonitrile [32] (hereinafter, referred to as the compound [32])

4.0 mg of the target compound [32] was obtained as a white solid, from 24.9 mg of the compound [29] according to the methods of Example 30-(1) to (3).

A spectral data of the compound [32] is presented below.
$^1$H-NMR (CDCl$_3$) δ: 9.04 (s, 1H×⅓), 8.96 (s, 1H×⅔), 8.86 (d, J=7.2 Hz, 1H), 8.65-8.58 (m, 1H), 7.89-7.83 (m, 1H×⅓), 7.74 (d, J=7.2 Hz, 1H×⅔), 7.50-7.32 (m, 6H), 6.66 (t, J=7.0 Hz, 1H), 6.38 (br, 1H), 5.09 (br, 1H), 1.66 (d, J=6.9 Hz, 3H).
mass: 366 (M+1)$^+$.

Example 33

Synthesis of 4-[8-(difluoromethyl)imidazo[1,2-a]pyridin-3-yl]-2-{[(1S)-1-phenylethyl]amino}-5-pyrimidinecarbonitrile [33] (hereinafter, referred to as the compound [33])

9.0 mg of the target compound [33] was obtained as a white solid, from 45.3 mg of the compound [31] according to the methods of Example 30-(1) to (3).

A spectral data of the compound [33] is presented below.
$^1$H-NMR (CDCl$_3$) δ: 8.98 (s, 1H×⅓), 8.91 (s, 1H×⅔), 8.86 (d, J=6.5 Hz, 1H), 8.61-8.56 (m, 1H), 7.70-7.76 (m, 1H×⅓), 7.63 (d, J=6.5 Hz, 1H×⅔), 7.50-7.32 (m, 6H), 6.71 (t, J=7.2 Hz, 1H), 6.10 (br, 1H), 5.11 (br, 1H), 1.66 (d, J=6.9 Hz, 3H).
mass: 391 (M+1)$^+$.

Example 34

Synthesis of N-[(1S)-1-phenylethyl]-4-[8-(trifluoromethyl)imidazo[1,2-a]pyridin-3-yl]-2-pyrimidinamine [34] (hereinafter, referred to as the compound [34])

(1) 10 g of 2-chloro-3-trifluoromethylpyridine was dissolved in 100 mL of 25% aqueous ammonia, and stirred in a sealed-tube at 175° C. for 3 days. The reaction mixture was cooled back to room temperature, and was extracted with diethyl ether. The organic layer was washed with water and with saturated brine in the subsequent order, and then dried over anhydrous sodium sulfate. After filtering the insolubles, the filtrate was concentrated under reduced pressure to obtain 8.73 g of 3-(trifluoromethyl)-2-pyridinamine [34-1] as a white solid.

(2) 23.4 mg of the target compound [34] was obtained as a pale yellow oily product, from 247 mg of 3-(trifluoromethyl)-2-pyridinamine [34-1] and 400 mg of 4-[(E)-2-ethoxyvinyl]-2-(methylthio)pyrimidine [25-2], according to the methods of Example 25-(3) to (5).

A spectral data of the compound [34] is presented below.
$^1$H-NMR (DMSO-d$_6$) δ: 10.51 (br, 1H×½), 9.49 (br, 1H×½), 8.66-8.46 (m, 1H), 8.36-8.20 (m, 1H), 8.02-7.72 (m, 2H), 7.45-7.16 (m, 7H), 5.20-4.98 (m, 1H), 1.50 (d, J=6.9 Hz, 3H).
mass: 384 (M+1)$^+$.

Example 35

Synthesis of 5-bromo-N-[(1S)-1-phenylethyl]-4-[8-(trifluoromethyl)imidazo[1,2-a]pyridin-3-yl]-2-pyrimidinamine [35] (hereinafter, referred to as the compound [35])

15.4 mg of the target compound [35] was obtained as a colorless oily product from 15.8 mg of the compound [34] according to the method of Example 2.

A spectral data of the compound [35] is presented below.
$^1$H-NMR (CDCl$_3$) δ: 8.77 (s, 1H), 8.50 (s, 1H), 7.60 (d, J=6.9 Hz, 1H), 7.42-7.33 (m, 6H), 6.66-6.48 (m, 1H), 5.73-5.58 (m, 1H), 5.09-4.90 (m, 1H), 1.59 (d, J=6.9 Hz, 3H).
mass: 462, 464 (M+1)$^+$.

Example 36

Synthesis of 2-{[(1S)-1-phenylethyl]amino}-4-[8-(trifluoromethyl)imidazo[1,2-a]pyridin-3-yl]-5-pyrimidinecarbonitrile [36] (hereinafter, referred to as the compound [36])

1.3 mg of the target compound [36] was obtained as a colorless oily product from 12.1 mg of the compound [35] according to the methods of Example 30-(1) to (3).

A spectral data of the compound [36] is presented below.
$^1$H-NMR (CDCl$_3$) δ: 8.95 (s, 1H), 8.87 (d, J=6.9 Hz, 1H), 8.58 (s, 1H), 7.66 (d, J=6.9 Hz, 1H), 7.49-7.30 (m, 5H), 6.67 (t, J=6.9 Hz, 1H), 6.22-6.15 (m, 1H), 5.15-5.02 (m, 1H), 1.65 (d, J=7.4 Hz, 3H).
mass: 409 (M+1)$^+$.

Example 37

Synthesis of N-[(1S)-1-phenylethyl]-5-(2H-tetrazole-5-yl)-4-[8-(trifluoromethyl)imidazo[1,2-a]pyridin-3-yl]-2-pyrimidinamine [37] (hereinafter, referred to as the compound [37])

10 mg of the compound [36] was dissolved in 0.5 mL of N-methyl-2-pyrrolidinone, 3.19 mg of sodium azide and 6.74 mg of triethylamine hydrochloride were added, and the mixture was stirred at 100° C. for 2 hours and 20 minutes, next stirred overnight at 150° C., and then stirred at 200° C. for 3 hours and a half. The reaction mixture was cooled back to room temperature, diluted with dimethylsulfoxide, and then purified by preparative reversed phase liquid chromatography, to obtain 2.1 mg of the target compound [37] as a brown solid.

A spectral data of the compound [37] is presented below.
$^1$H-NMR (DMSO-d$_6$) δ: 8.72-8.50 (m, 3H), 8.03-7.81 (m, 1H), 7.55-6.87 (m, 8H), 5.33-5.02 (m, 1H), 1.54-1.44 (m, 3H).
mass: 452 (M+1)$^+$.

Example 38

Synthesis of 4-(2,8-dimethylimidazo[1,2-a]pyridin-3-yl)-N-[(1S)-1-phenylethyl]-2-pyrimidinamine [38] (hereinafter, referred to as the compound [38])

(1) 2 g of 2-amino-3-picoline was dissolved in a mixture solvent of 10 mL of tetrahydrofuran and 5 mL of diethyl ether, 4.4 mL of 3-chloroacetyl acetone was added, and heated overnight under reflux. The reaction mixture was cooled back to room temperature, diluted with ethyl acetate, and then washed with water and with saturated brine in the subsequent order. After drying the organic layer over anhydrous magnesium sulfate, the insolubles were filtered, and the filtrate was concentrated under reduced pressure. The obtained residue was dissolved in a small amount of chloroform and solidified by adding hexane, to obtain 664 mg of 1-(2,8-dimethylimidazo[1,2-a]pyridin-3-yl)ethanone [38-1] as a light grey solid.

(2) 49.1 mg of the target compound [38] was obtained as a white solid from 1-(2,8-dimethylimidazo[1,2-a]pyridin-3-yl)ethanone [38-1], according to the methods of Example 1-(2) to (5).

A spectral data of the compound [38] is presented below.
$^1$H-NMR (CDCl$_3$) δ: 8.32 (d, J=5.1 Hz, 1H), 7.29-7.46 (m, 6H), 7.01 (d, J=6.6 Hz, 1H), 6.76 (d, J=5.5 Hz, 1H), 6.49 (brs, 1H), 5.93 (brs, 1H), 5.18-5.14 (m, 1H), 2.69 (s, 3H), 2.60 (s, 3H), 1.60 (d, J=7.0 Hz, 3H).
mass: 344 (M+1)$^+$.

Example 39

Synthesis of 5-bromo-4-(2,8-dimethylimidazo[1,2-a]pyridin-3-yl)-N-[(1S)-1-phenylethyl]-2-pyrimidinamine [39] (hereinafter, referred to as the compound [39])

38.2 mg of the target compound [39] was obtained as a white solid from 49 mg of the compound [38], according to the method of Example 2.

A spectral data of the compound [39] is presented below.
$^1$H-NMR (CDCl$_3$) δ: 8.45 (s, 1H), 7.37-7.23 (m, 5H), 7.18-7.14 (m, 2H), 6.98 (d, J=6.4 Hz, 1H), 5.75 (brs, 1H), 5.03 (brs, 1H), 2.61 (s, 3H), 2.47 (s, 3H), 1.54 (d, J=6.8 Hz, 3H).
mass: 422, 424 (M+1)$^+$.

Example 40

Synthesis of 4-(2-methylimidazo[1,2-a]pyridin-3-yl)-N-[(1S)-1-phenylethyl]-2-pyrimidinamine [40] (hereinafter, referred to as the compound [40])

(1) 1.39 g of 1-(2-methylimidazo[1,2-a]pyridin-3-yl)-1-ethanone [40-1] was obtained as a light brown solid from 2 g of 2-aminopyridine, according to the method of Example 38-(1).

(2) 177 mg of the target compound [40] was obtained as a white solid from 700 mg of the 1-(2-methylimidazo[1,2-a]pyridin-3-yl)-1-ethanone [40-1], according to the methods of Example 1-(2) to (5).

A spectral data of the compound [40] is presented below.
$^1$H-NMR (CDCl$_3$) δ: 8.32 (d, J=5.5 Hz, 1H), 7.52 (d, J=9.0 Hz, 1H) 7.45-7.28 (m, 6H), 7.21-7.18 (m, 1H), 6.75 (d, J=5.5 Hz, 1H), 6.55 (brs, 1H), 5.91 (brs, 1H), 5.16-5.13 (m, 1H), 2.66 (s, 3H), 1.59 (d, J=7.0 Hz, 3H).
mass: 330 (M+1)$^+$.

Example 41

Synthesis of 5-bromo-4-(2-methylimidazo[1,2-a]pyridin-3-yl)-N-[(1S)-1-phenylethyl]-2-pyrimidinamine [41] (hereinafter, referred to as the compound [41])

190.3 mg of the target compound [41] was obtained as a white solid from 177 mg of the compound [40], according to the method of Example 2.

A spectral data of the compound [41] is presented below.
$^1$H-NMR (CDCl$_3$) δ: 8.46 (s, 1H), 7.54 (d, J=8.8 Hz, 1H), 7.38-7.23 (m, 6H), 7.18 (m, 4H), 5.79 (brs, 1H), 5.05 (brs, 1H), 2.35 (s, 3H), 1.54 (d, J=6.8 Hz, 3H).
mass: 408, 410 (M+1)$^+$.

Example 42

Synthesis of 4-methyl-6-(8-methylimidazo[1,2-a]pyridin-3-yl)-N-[(1S)-1-phenylethyl]-2-pyrimidinamine [42] (hereinafter, referred to as the compound [42])

(1) 5.93 mL of 4-chloro-2-methylthiopyrimidine was dissolved in 50 mL of diethyl ether, and 100 mL of methyllithium (1M diethyl ether solution) was gradually added to the solution at −78° C. The reaction solution was stirred at 0° C.

for 1 hour, and then a solution prepared by mixing 2.3 mL of water and 15 mL of tetrahydrofuran was added thereto. The reaction solution was stirred at the same temperature for 10 minutes, and then 50 mL of a tetrahydrofuran solution containing 13.7 g of 2,3-dichloro-5,6-dicyanohydroquinone was added thereto. The reaction solution was stirred at the same temperature for 1 hour, and then 100 mL of a 1 N aqueous solution of sodium hydroxide was added to the reaction solution. The obtained reaction solution was extracted with hexane, and the organic layer was washed with a 1 N aqueous solution of sodium hydroxide and saturated brine. After drying over anhydrous magnesium sulfate, the insolubles were filtered, and the filtrate was concentrated under reduced pressure. The obtained residue was purified by silica gel column chromatography to obtain 5.1 g of 4-chloro-6-methyl-2-(methylthio)pyrimidine [42-1] as a pale yellow solid.

(2) 15 g of ethyl ethynyl ether (40% hexane solution) was dissolved in 50 mL of tetrahydrofuran, and 29 mL of a borane-tetrahydrofuran complex (1M tetrahydrofuran solution) was added to the solution at 0° C. After stirring at room temperature for 4 hours and a half, 150 mL of a tetrahydrofuran solution containing 4.0 g of the 4-chloro-6-methyl-2-(methylthio)pyrimidine [42-1], 35 mL of a 3 N aqueous solution of sodium hydroxide, 0.46 g of triphenylphosphine and 0.34 g of palladium acetate were added thereto. The obtained reaction solution was stirred at room temperature for 16 hours, and then 200 mL of water was added to the reaction solution. The reaction solution was extracted with ethyl acetate, and the organic layer was washed with saturated brine. After drying the organic layer over anhydrous magnesium sulfate, the insolubles were filtered, and the filtrate was concentrated under reduced pressure. The obtained residue was purified by silica gel column chromatography, and 4.9 g of 4-[(E)-2-ethoxyvinyl]-6-methyl-2-(methylthio)pyrimidine [42-2] was obtained as a brown oily product.

(3) 39 mg of the target compound [42] was obtained as a colorless oily product, from 500 mg of the 4-[(E)-2-ethoxyvinyl]-6-methyl-2-(methylthio)pyrimidine [42-2] and 240 µL of 2-amino-3-picoline, according to the methods of Example 25-(3) to (5).

A spectral data of the compound [42] is presented below.
$^1$H-NMR (CDCl$_3$) δ: 8.15 (s, 1H), 7.47-7.45 (m, 2H), 7.41-7.37 (m, 2H), 7.29-7.25 (m, 2H), 7.06 (d, J=6.6 Hz, 1H), 6.84 (s, 1H), 6.64-6.58 (m, 1H), 5.51 (brd, J=5.5 Hz, 1H), 5.18-5.12 (m, 1H), 2.62 (s, 3H), 2.40 (m, 3H), 1.61, (d, J=7.0 Hz, 3H).
mass: 344 (M+1).

Example 43

Synthesis of 5-bromo-4-methyl-6-(8-methylimidazo[1,2-a]pyridin-3-yl)-N-[(1S)-1-phenylethyl]-2-pyrimidinamine [43] (hereinafter, referred to as the compound [43])

37.7 mg of the target compound [43] was obtained as a colorless oily product from 37.4 mg of the compound [42], according to the method of Example 2.

A spectral data of the compound [43] is presented below.
$^1$H-NMR (CDCl$_3$) δ: 8.55 (s, 1H), 7.40-7.36 (m, 5H), 7.31-7.25 (m, 1H), 7.02 (d, J=6.7 Hz, 1H), 6.49-6.36 (m, 1H), 5.48 (brd, J=6.7 Hz, 1H), 5.08-5.00 (m, 1H), 2.61 (s, 3H), 2.57 (m, 3H), 1.53 (d, J=6.7 Hz, 3H)
mass: 422, 424 (M+1)$^+$. .

Example 44

Synthesis of N-[(1S)-1-phenylethyl]-4-(5,6,7,8-tetrahydroimidazo[1,2-a]pyridin-3-yl)-2-pyrimidinamine [44] (hereinafter, referred to as the compound [44])

(1) 1.5 g of 2-piperidone was dissolved in 75 mL of mesitylene, 248 µL of titanium tetrachloride was added thereto, and heated at 140° C. A solution obtained by dissolving 4.02 g of aminoacetoaldehyde diethyl acetal to 45 mL of mesitylene was prepared, and was added dropwise to the previous mesitylene solution over 3 hours. The mixture was stirred at 140° C. for 70 hours, then cooled back to room temperature, and was extracted with a 2N aqueous solution of hydrochloric acid. The obtained aqueous layer was basified with a 5N aqueous solution of sodium hydroxide, and then was extracted with chloroform. The organic layer was washed with saturated brine, and then dried over anhydrous sodium sulfate. The insolubles were filtered, the filtrate was concentrated under reduced pressure, and then the purification was carried out by distillation under reduced pressure (3 mmHg, 120° C.), to obtain 375 mg of 5,6,7,8-tetrahydroimidazo[1,2-a]pyridine [44-1] as a pale yellow oily product.

(2) 375 mg of the 5,6,7,8-tetrahydroimidazo[1,2-a]pyridine [44-1] was dissolved in 10 mL of carbon tetrachloride, then 546 mg of N-bromosuccinimide was added, and the mixture was heated for 30 minutes under reflux. The reaction mixture was concentrated under reduced pressure, and the residue was purified by silica gel column chromatography and then by preparative thin-layer chromatography sequentially, to obtain 155 mg of 3-bromo-5,6,7,8-tetrahydroimidazo[1,2-a]pyridine [44-2] as a pale yellow solid.

(3) 142 mg of the 3-bromo-5,6,7,8-tetrahydroimidazo[1,2-a]pyridine [44-2] was dissolved in 2.5 mL of toluene, 81.6 mg of tetrakis triphenylphosphine palladium (0) and 477 µL of tributyl(1-ethoxyvinyl)tin were added, and the mixture was stirred overnight at 120° C. The reaction mixture was cooled back to room temperature to add 10% aqueous solution of potassium fluoride, and extracted with ethyl acetate. The organic layer was washed with 10% aqueous solution of potassium fluoride and with saturated brine in the subsequent order, and then was dried over anhydrous sodium sulfate. The insolubles were filtered, the filtrate was concentrated under reduced pressure, and then the purification by silica gel column chromatography was carried out. The obtained compound was dissolved in 2 mL of chloroform, 200 µL of 10% hydrochloric acid-methanol solution was added, and the mixture was stirred for 40 minutes. The liquid was basified by adding a saturated aqueous solution of sodium hydrogen carbonate, and was extracted with chloroform. The organic layer was washed with saturated brine, and then dried over anhydrous sodium sulfate. The insolubles were filtered, the filtrate was concentrated under reduced pressure, and the obtained residue was purified by preparative thin-layer chromatography to obtain 62.2 mg of 1-(5,6,7,8-tetrahydroimidazo[1,2-a]pyridin-3-yl)ethanone [44-3] as a pale yellow oily product.

(4) 4.5 mg of the target compound [44] was obtained as a colorless oily product from 62.2 mg of the 1-(5,6,7,8-tetrahydroimidazo[1,2-a]pyridin-3-yl)ethanone [44-3], according to the methods of Example 1-(2) to (5).

A spectral data of the compound [44] is presented below.
$^1$H-NMR (CDCl$_3$) δ: 8.17 (d, J=6.3 Hz, 1H), 7.49 (s, 1H), 7.38-7.20 (m, 5H), 6.74 (d, J=6.3 Hz, 1H), 5.58-5.45 (m, 1H), 5.13-5.00 (m, 1H), 2.98-2.80 (m, 2H), 2.13-1.60 (m, 6H), 1.57 (d, J=6.9 Hz, 3H).
mass: 320 (M+1)$^+$.

Example 45

Synthesis of 5-bromo-N-[(1S)-1-phenylethyl]-4-(5,6,7,8-tetrahydroimidazo[1,2-a]pyridin-3-yl)-2-pyrimidinamine [45] (hereinafter, referred to as the compound [45])

2.2 mg of the target compound [45] was obtained as a white solid from 2.7 mg of the compound [44], according to the method of Example 2.

A spectral data of the compound [45] is presented below.
$^1$H-NMR (CDCl$_3$) δ: 8.37 (s, 1H), 7.88 (s, 1H), 7.38-7.20 (m, 5H), 5.48-5.35 (m, 1H), 5.05-4.96 (m, 1H), 2.96-2.80 (m, 2H), 1.92-1.60 (m, 6H), 1.55 (d, J=6.9 Hz, 3H).
mass: 398, 400 (M+1)$^+$.

Example 46

Synthesis of 4-(8-methyl-5,6,7,8-tetrahydroimidazo [1,2-a]pyridin-3-yl)-N-[(1S)-1-phenylethyl]-2-pyrimidinamine [46] (hereinafter, referred to as the compound [46])

(1) 1 g of 8-methylimidazo[1,2-a]pyridine [3-1] was dissolved in 20 mL of 1-butanol, and a catalytic amount of Raney nickel of was added thereto. The mixture was stirred under a hydrogen atmosphere (5 atmospheric pressure) at 65° C. for 4 days. After cooling the reaction mixture back to room temperature, the insolubles were filtered through celite, and washed with methanol. The filtrate was concentrated under reduced pressure, and the residue was purified by silica gel column chromatography, to obtain 823.3 mg of 8-methyl-5,6,7,8-tetrahydroimidazo[1,2-a]pyridine [46-1].

(2) 1-(8-methyl-5,6,7,8-tetrahydroimidazo[1,2-a]pyridin-3-yl)-1-ethanone [46-2] was obtained from 810 mg of 8-methyl-5,6,7,8-tetrahydroimidazo[1,2-a]pyridine [46-1], according to the methods of Example 44-(2) and (3).

(3) 27.3 mg of the target compound [46] was obtained as a white solid from the 1-(8-methyl-5,6,7,8-tetrahydroimidazo [1,2-a]pyridin-3-yl)-1-ethanone compound [46-2], according to the methods of Example 1-(2) to (5).

A spectral data of the compound [46] is presented below.
$^1$H-NMR (CDCl$_3$) δ: 10.04 (m, 1H), 8.13 (m, 2H), 7.37-7.25 (m, 5H), 7.00 (m, 1H), 5.01 (m, 1H), 4.30-4.27 (m, 1H×½), 4.01-3.98 (m, 1H×½), 3.63 (m, 1H×½), 3.50 (m, 1H×½), 3.35-3.31 (m, 1H×½), 3.21-3.19 (m, 1H×½), 2.14-1.87 (m, 3H), 1.66 (d, J=7.0 Hz, 3H), 1.70-1.59 (m, 1H), 1.50 (d, J=7.0 Hz, 3H×½), 1.45 (d, J=7.0 Hz, 3H×½).
mass: 334 (M+1)$^+$.

Example 47

Synthesis of 5-bromo-4-(8-methyl-5,6,7,8-tetrahydroimidazo[1,2-a]pyridin-3-yl)-N-[(1S)-1-phenylethyl]-2-pyrimidinamine [47] (hereinafter, referred to as the compound [47])

19.3 mg of the target compound [47] was obtained as a white solid from 25 mg of the target compound [46] obtained in Example 46, according to the method of Example 2.

A spectral data of the compound [47] is presented below.
$^1$H-NMR (CDCl$_3$) δ: 8.36 (s, 1H), 7.89 (s, 1H×½), 7.88 (s, 1H×½), 7.33-7.22 (m, 5H), 5.53 (br, 1H), 5.05-5.01 (m, 1H), 4.13-3.40 (m, 2H), 3.04-2.93 (m, 1H), 2.04-1.60 (m, 2H), 1.55 (d, J=7.0 Hz, 3H), 1.50-1.24 (m, 2H), 1.42 (d, J=7.0 Hz, 3H×½), 1.41 (d, J=7.0 Hz, 3H×½).
mass: 412, 414 (M+1)$^+$.

Example 48

Synthesis of methyl 3-(5-cyano-2-{[(1S)-1-phenylethyl]amino}-4-pyrimidinyl)-8-methylimidazo[1,2-a]pyridine-7-carboxylate [48] (hereinafter, referred to as the compound [48])

(1) The mixture of 1.0 g of 2-chloro-4-iodo picoline, 84 mg of palladium acetate, 218 mg of 1,1'-bisdiphenylphosphino ferrocene, 990 mg of sodium hydrogen carbonate, 10 mL of N,N-dimethylformamide, and 10 ml of methanol, was stirred overnight in a carbon monoxide atmosphere at 80° C. After cooling the reaction mixture back to room temperature, water and a saturated aqueous solution of sodium hydrogen carbonate were added thereto, and extracted with ethyl acetate. The organic layer was washed with saturated brine, and then dried over anhydrous sodium sulfate. The insolubles were filtered, the filtrate was concentrated under reduced pressure, and then the obtained residue was purified by silica gel column chromatography to obtain 522 mg of 2-chloro-3-methylisonicotinic acid methyl ester [48-1] as a colorless oily product.

(2) The mixture of 520 mg of 2-chloro-3-methylisonicotinic acid methyl ester [48-1], 161 mg of bis(dibenzylideneacetone)palladium, 324 mg of 4,5-bis(diphenylphosphino)-9,9-dimethylxanthene, 1.28 g of cesium carbonate, 564 μL of benzophenoneimine, 5 mL of 1,4-dioxane, and 5 mL of toluene, was stirred overnight at 80° C. After cooling the reaction mixture back to room temperature, water and a saturated aqueous solution of sodium bicarbonate were added, and extracted with ethyl acetate. The organic layer was washed with saturated brine, and then dried over anhydrous sodium sulfate. The insolubles were filtered, the filtrate was concentrated under reduced pressure, and the obtained residue was dissolved in 28 mL of methanol. Thereto, 1.1 g of sodium acetate and 700 mg of hydroxyamine hydrochloride were added, and stirred for 1 hour. Then, a 0.1 N aqueous solution of sodium hydroxide was added, and extracted with chloroform. The organic layer was washed with saturated brine, and then dried over anhydrous sodium sulfate. The insolubles were filtered, the filtrate was concentrated under reduced pressure, and the residue was purified by silica gel column chromatography, to obtain 92.1 mg of 2-amino-3-methylisonicotinic acid methyl ester [48-2] as a yellow solid.

(3) The mixture of 2.04 g of cis-1-ethoxy-2-tri-n-butyl stannyl ethylene (synthesized according to a method disclosed in J. Am. Chem. Soc. 1977, 99, 7365), 1.0 g of 4-chloro-2-(methylsulfonyl)-5-pyrimidinecarbonitrile (synthesized according to a method disclosed in Pamphlet of International Publication WO 2004/043936, pages 32-33), 189 mg of dichlorobis(triphenylphosphine)palladium (II), and 15 mL of acetonitrile, was heated for 4 hours under reflux. After cooling the reaction mixture back to room temperature, 1.57 g of potassium fluoride and 5 mL of water were added, and stirred at room temperature for 30 minutes. The insolubles were filtered through celite, and ethyl acetate was added to the filtrate. The obtained solution was washed with saturated brine, and then dried over anhydrous magnesium sulfate. The insolubles were filtered, the filtrate was concentrated under reduced pressure, and the obtained residue was dissolved in a small amount of ethyl acetate. Thereto, hexane was added, and the solid thus produced was taken to obtain 531.9 mg of 4-[(Z)-2-ethoxyvinyl]-2-(methylthio)-5-pyrimidinecarbonitrile [48-3] as a pink solid.

(4) 22.7 mg of the target compound [48] was obtained as a pale yellow solid, from 14 mg of the 4-[(Z)-2-ethoxyvinyl]-2-(methylthio)-5-pyrimidinecarbonitrile [48-3] and 10.5 mg of the 2-amino-3-methylisonicotinic acid methyl ester [48-2], according to the methods of Example 25-(3) to (5).

A spectral data of the compound [48] is presented below.
$^1$H-NMR (CDCl$_3$) δ: 8.93 (s, 1H), 8.73 (d, J=7.4 Hz, 1H), 8.55 (s, 1H), 7.52-7.10 (m, 6H), 6.20-6.11 (m, 1H), 5.19-5.06 (m, 1H), 3.99 (s, 3H), 2.96 (s, 3H), 1.65 (d, J=6.9 Hz, 3H).
mass: 413 (M+1)$^+$.

Example 49

Synthesis of 4-(7-methylimidazo[1,2-a]pyridin-3-yl)-N-[(1S)-1-phenylethyl]-2-pyrimidinamine [49] (hereinafter, referred to as the compound [49])

4.2 mg of the target compound [49] was obtained as a pale yellow oily product, from 94.3 mg of 4-methyl-2-pyridinamine and 171 mg of the 4-[(E)-2-ethoxyvinyl]-2-(methylthio)pyrimidine [25-2], according to the methods of Example 25-(3) to (5).

A spectral data of the compound [49] is presented below.
$^1$H-NMR (CDCl$_3$) δ: 8.90 (br, 1H), 8.37 (br, 1H), 7.77 (s, 1H), 7.53-7.28 (m, 8H), 5.19 (q, J=7.7 Hz, 1H), 2.66 (s, 3H), 1.67 (d, J=7.7 Hz, 3H).
mass: 330 (M+1)$^+$.

Example 50

Synthesis of 5-bromo-4-(7-methylimidazo[1,2-a]pyridin-3-yl)-N-[(1S)-1-phenylethyl]-2-pyrimidinamine [50] (hereinafter, referred to as the compound [50])

2.1 mg of the target compound [50] was obtained as a white solid from 2.0 mg of the target compound [49], according to the method of Example 2.

A spectral data of the compound [50] is presented below.
$^1$H-NMR (CDCl$_3$) δ: 8.71 (s, 1H), 8.42 (s, 1H), 7.50-7.28 (m, 7H), 6.50-6.42 (m, 1H), 5.80-5.72 (m, 1H), 5.12-5.05 (m, 1H), 2.42 (s, 3H), 1.60 (d, J=6.9 Hz, 3H).
mass: 408, 410 (M+1)$^+$.

Example 51

Synthesis of 4-imidazo[1,2-a]pyrazin-3-yl-N-[(1S)-1-phenylethyl]-2-pyrimidinamine [51] (hereinafter, referred to as the compound [51])

70 mg of the target compound [51] was obtained as a gray solid, from 302 mg of 2-aminopyrazine and 623 mg of the 4-[(E)-2-ethoxyvinyl]-2-(methylthio)pyrimidine [25-2], according to the methods of Example 25-(3) to (5).

A spectral data of the compound [51] is presented below.
$^1$H-NMR (DMSO-d$_6$) δ: 9.27-9.22 (m, 1H), 8.65-8.58 (m, 1H), 8.31-8.23 (m, 1H), 8.19-8.02 (m, 2H), 7.44-7.34 (m, 4H), 7.21-7.20 (m, 2H), 5.05 (brs, 1H), 1.50 (d, J=7.0 Hz, 3H)
mass: 317 (M+1)$^+$.

Example 52

Synthesis of 5-bromo-4-imidazo[1,2-a]pyrazin-3-yl-N-[(1S)-1-phenylethyl]-2-pyrimidinamine [52] (hereinafter, referred to as the compound [52])

28 mg of the target compound [52] was obtained as a white solid from 30 mg of the compound [51], according to the method of Example 2.

A spectral data of the compound [52] is presented below.
$^1$H-NMR (CDCl$_3$) δ: 9.15 (s, 1H), 8.81 (s, 1H), 8.51 (s, 1H), 7.43-7.35 (m, 6H), 5.78 (brs, 1H), 4.99 (br, 1H), 1.60 (d, J=7.0 Hz, 3H)
mass: 395, 397 (M+1)$^+$.

Example 53

Synthesis of 4-(8-methylimidazo[1,2-a]pyrazin-3-yl)-N-[(1S)-1-phenylethyl]-2-pyrimidinamine [53] (hereinafter, referred to as the compound [53])

(1) The mixture of 5 g of 2-chloro-3-methylpyrazine, 7.44 mL of benzophenoneimine, 2 g of tris(dibenzylideneacetone)(chloroform)dipalladium (0), 2.48 g of 2,2'-bis(diphenylphosphino)-1,1'-binaphthyl, 5.25 g of sodium t-butoxide, and 150 mL of toluene, was heated overnight under reflux. The reaction mixture was cooled back to room temperature, then diluted with ethyl acetated, and washed with water and with saturated brine in the subsequent order. The organic layer was dried over anhydrous magnesium sulfate. After the insolubles were filtered and the filtrate was concentrated under reduced pressure, 50 mL of 4N hydrogen chloride-1,4-dioxane solution was added to the residue, and the mixture was allowed to stand still for 1 hour. The solution was concentrated under reduced pressure, and the obtained residue was purified by silica gel column chromatography. After the solvent is distilled off, the residue was dissolved in a small amount of chloroform, and hexane was added thereto. The solid thus produced was taken, and dried under reduced pressure to obtain 2.5 g of 3-methyl-2-pyrazineamine [53-1] as an orange solid.

(2) 1.6 mg of the target compound [53] was obtained as a pale yellow oily product from 122 mg of the 3-methyl-2-pyrazineamine [53-1] and 220 mg of the 4-[(E)-2-ethoxyvinyl]-2-(methylthio)pyrimidine [25-2], according to the methods of Example 25-(3) to (5).

A spectral data of the compound [53] is presented below.
$^1$H-NMR (CD$_3$OD) δ: 7.86 (s, 2H), 7.48-7.46 (m, 3H), 7.39-7.35 (m, 4H), 7.26-7.25 (m, 1H), 4.85 (m, 1H), 2.88 (s, 3H), 1.65 (d, J=6.8 Hz, 3H)
mass: 331 (M+1)$^+$.

Example 54

Synthesis of 4-(8-methylimidazo[1,2-a]pyridazin-3-yl)-2-{[(1S)-1-phenylethyl]amino}-5-pyrimidinecarbonitrile [54] (hereinafter, referred to as the compound [54])

(1) The mixture of 1.84 g of (1S)-1-phenylethylamine, 2.65 mL of triethylamine, 2.23 g of 1H-pyrazole-1-carboxamidine hydrochloride, and 50 mL of acetonitrile, was stirred at 85° C. for 24 hours. After concentrating the reaction mixture under reduced pressure, the residue was dissolved in 75 mL of methanol. Thereto, 3.52 g of (ethoxymethylene)ethyl cyanoacetate and 4.55 mL of 1,8-diazabicyclo[5.4.0]-undeca-7-ene were added, and stirred at 65° C. for 2 days. After cooling the reaction mixture back to room temperature, water was added, and washed with ethyl acetate. The organic layer was extracted with water, and the obtained aqueous layer was mixed with the previous aqueous layer. The thus-obtained aqueous layer was acidified with hydrochloric acid, and was extracted with chloroform. The obtained organic layer was then dried over anhydrous magnesium sulfate. The insolubles were filtered, the filtrate was concentrated under reduced pressure, and the obtained residue was purified by silica gel column chromatography, to obtain 1.69 g of 6-oxo-2-{[(1S)-1-phenylethyl]amino}-1,6-dihydro-5-pyrimidinecarbonitrile [54-1] as a yellow solid.

(2) 1.69 g of the 6-oxo-2-{[(1S)-1-phenylethyl]amino}-1,6-dihydro-5-pyrimidinecarbonitrile [54-1] was dissolved in 100 mL of acetonitrile, then 5 mL of phosphorus oxychloride was added, and stirred at 85° C. for 2 hours. After concentrating the reaction mixture under reduced pressure, the obtained residue was placed in an ice bath, extracted with ethyl acetate, and the organic layer was washed with water and saturated brine in the subsequent order. After drying over anhydrous magnesium sulfate, the insolubles were filtered, and the filtrate was concentrated under reduced pressure. The obtained residue was purified by silica gel column chromatography, and 1.54 g of 4-chloro-2-{[(1S)-1-phenylethyl]amino}-5-pyrimidinecarbonitrile [54-2] was obtained as an oily product.

(3) 89 mg of 4-[(Z)-2-ethoxyvinyl]-2-{[(1S)-1-phenylethyl]amino}-5-pyrimidinecarbonitrile [54-3] was obtained from 97 mg of the 4-chloro-2-{[(1S)-1-phenylethyl]amino}-5-pyrimidinecarbonitrile [54-2], according to the method of Example 48-(3).

(4) The target compound [54] was obtained as a yellow solid, from 4-[(Z)-2-ethoxyvinyl]-2-{[(1S)-1-phenylethyl]amino}-5-pyrimidinecarbonitrile [54-3] and 4-methyl-3-pyridazinamine, according to the method of Example 25-(3).

A spectral data of the compound [54] is presented below.
$^1$H-NMR (CDCl$_3$) δ: 8.63 (s, 1H×½), 8.56 (s, 1H×½), 8.41-8.30 (m, 1H+1H×½), 8.25 (s, 1H×½), 7.43-7.24 (m, 5H), 7.01 (d, J=4.5 Hz, 1H), 6.07 (m, 1H), 5.30 (m, 1H), 2.73 (s, 3H), 1.70-1.58 (m, 3H).
mass: 356 (M+1)$^+$.

Example 55

Synthesis of 4-(8-aminoimidazo[1,2-a]pyridazin-3-yl)-2-{[(1S)-1-phenylethyl]amino}-5-pyrimidinecarbonitrile [55] (hereinafter, referred to as the compound [55])

9 mg of the target compound [55] was obtained as a yellow solid, from 14 mg of the 4-[(Z)-2-ethoxyvinyl]-2-{[(1S)-1-phenylethyl]amino}-5-pyrimidinecarbonitrile [54-3] and 2,3-pyridinediamine, according to the method of Example 25-(3).

A spectral data of the compound [55] is presented below.
$^1$H-NMR (CDCl$_3$) δ: 8.69 (s, 1H), 8.51 (s, 1H), 8.41 (m, 1H), 7.44-7.20 (m, 5H), 6.60-6.50 (m, 2H), 6.04 (m, 1H), 5.17 (m, 1H), 1.63 (d, J=7.2 Hz, 3H).
mass: 356 (M+1)$^+$.

Example 56

Synthesis of 6-(8-methylimidazo[1,2-a]pyridin-3-yl)-N-[(1S)-1-phenylethyl]-9H-purine-2-amine [56] (hereinafter, referred to as the compound [56])

(1) 5 g of 2,6-dichloropurine was added to the mixture of 1.54 g of sodium hydride and 100 mL of N,N-dimethylformamide in an ice bath, and stirred at the same temperature for 15 minutes. 6.81 mL of 2-(trimethylsilyl)ethoxymethyl chloride was added to the reaction mixture, and was stirred at the same temperature for 5 hours. The reaction mixture was added with water, and extracted with ethyl acetate. The organic layer was washed with water and saturated brine in the subsequent order, and then dried over anhydrous magnesium sulfate. The insolubles were filtered, the filtrate was concentrated under reduced pressure, and then purified by silica gel column chromatography, to obtain 6.18 g of 2,6-dichloro-9-{[2-(trimethylsilyl)ethoxy]methyl}-9H-purine [56-1] as a light brown oily product.

(2) 2 g of ethyl ethynyl ether (50% v/v hexane solution) was dissolved in 20 mL of tetrahydrofuran, and 4.7 mL of borane-tetrahydrofuran complex (1.0M tetrahydrofuran solution) was added under an ice-cold condition. After stirring the mixture at room temperature for 3 hours, 50 mL of tetrahydrofuran, 3 g of 2,6-dichloro-9-{[2-(trimethylsilyl)ethoxy]methyl}-9H-purine [56-1], 222 mg of triphenylphosphine, 63 mg of palladium acetate, and 7.0 mL of 4N aqueous solution of sodium hydroxide were added, and the mixture was heated overnight under reflux. The reaction mixture was cooled back to room temperature, diluted with ethyl acetate, and then washed with water and saturated saline in the subsequent order. The obtained organic layer was dried over anhydrous magnesium sulfate. The insolubles were filtered, the filtrate was concentrated under reduced pressure, and the residue was purified by silica gel column chromatography, to obtain 676 mg of 2-chloro-6-[(E)-2-ethoxyvinyl]-9-{[2-(trimethylsilyl)ethoxy]methyl}-9H-purine [56-2] as a light brown oily product.

(3) 200 mg of N-bromosuccinimide was added to the mixture of 400 mg of 2-chloro-6-[(E)-2-ethoxyvinyl]-9-{[2-(trimethylsilyl)ethoxy]methyl}-9H-purine [56-2], 10 mL of 1,4-dioxane, and 2 mL of water under an ice-cold condition, and stirred at the same temperature for 30 minutes. Thereto, 122 mg of 2-amino-3-picoline was added, stirred at 50° C. for 1 hour, and the reaction mixture was cooled back to room temperature. The reaction mixture was diluted with ethyl acetate, washed with water and saturated brine in the subsequent order, and the thus obtained organic layer was dried over anhydrous magnesium sulfate. The insolubles were filtered, the filtrate was concentrated under reduced pressure, and the obtained residue was purified by silica gel column chromatography, to obtain 360 mg of 2-chloro-6-(8-methylimidazo[1,2-a]pyridin-3-yl)-9-{[2-(trimethylsilyl)ethoxy]methyl}-9H-purine [56-3] as a light brown solid.

(4) The mixture of 30 mg of 2-chloro-6-(8-methylimidazo[1,2-a]pyridin-3-yl)-9-{[2-(trimethylsilyl)ethoxy]methyl}-9H-purine [56-3], 30 μL of triethylamine, 47 μL of (1S)-(1)-phenylethylamine, and 2 mL of dimethylsulfoxide, was stirred at 120° C. for 3 days. The reaction mixture was cooled back to room temperature, diluted with ethyl acetate, and washed with water and saturated brine in the subsequent order. The obtained organic layer was dried over anhydrous magnesium sulfate, the insolubles were filtered, and the filtrate was concentrated under reduced pressure. The residue was purified by preparative thin-layer chromatography, and 25 mg of 6-(8-methylimidazo[1,2-a]pyridin-3-yl)-N-[(1S)-1-phenylethyl]-9-{[2-(trimethylsilyl)ethoxy]methyl}-9H-purine-2-amine [56-4] was obtained as a white solid.

(5) 25 mg of the 6-(8-methylimidazo[1,2-a]pyridin-3-yl)-N-[(1S)-1-phenylethyl]-9-{[2-(trimethylsilyl)ethoxy]methyl}-9H-purine-2-amine [56-4] was dissolved in 10 mL of 90% trifluoroacetic acid aqueous solution, and was allowed to stand still at room temperature for 1 hour. After concentrating the reaction mixture under reduced pressure, the residue was purified by preparative reversed phase liquid chromatography to obtain 7.6 mg of a trifluoroacetate salt as the target compound [56] as a pale yellow solid.

A spectral data of the compound [56] is presented below.
$^1$H-NMR (CD$_3$OD) δ: 9.17 (s, 1H), 8.08 (s, 1H), 7.82 (d, J=6.8 Hz, 1H), 7.47-7.45 (m, 2H), 7.34-7.30 (m, 4H), 7.20-7.17 (m, 1H), 5.15-5.10 (m, 1H), 2.67 (s, 3H), 1.59 (d, J=7.0 Hz, 3H)
mass: 370 (M+1)$^+$.

Example 57

Synthesis of 6-imidazo[1,2-a]pyridin-3-yl-N-[(1S)-1-phenylethyl]-9H-purine-2-amine [57] (hereinafter, referred to as the compound [57])

3.4 mg of a trifluoroacetate salt of the target compound [57] was obtained as a pale yellow solid, from 87 mg of 2-aminopyridine and 327.5 mg of the 2-chloro-6-[(E)-2-ethoxyvinyl]-9-{[2-(trimethylsilyl)ethoxy]methyl}-9H-purine [56-2], according to the methods of Example 56-(3) to (5).

A spectral data of the compound [57] is presented below.
$^1$H-NMR (CDCl$_3$) δ: 9.26 (s, 1H), 8.08 (d, J=9.2 Hz, 1H), 7.95 (s, 1H), 7.77-7.73 (m, 1H), 7.48-7.45 (m, 2H), 7.41-7.38 (m, 2H), 7.34 (s, 2H), 7.30-7.26 (m, 1H), 7.11 (brs, 1H), 5.16-5.11 (m, 1H), 3.39-3.38 (m, 1H), 1.66 (d, J=7.0 Hz, 3H)
mass: 356 (M+1)$^+$.

Example 58

Synthesis of 5-bromo-4-(8-methylimidazo[1,2-a]pyridin-3-yl)-N-[(1S)-1-phenylethyl]-2-pyridinamine [58] (hereinafter, referred to as the compound [58])

(1) The mixture of 1 g of 2-fluoro-4-iodopyridine (synthesized according to a method disclosed in J. Org. Chem. 1993, 58, 7832-7838), 1.73 mL of (1S)-1-phenylethylamine, and 20 mL of dimethylsulfoxide, was stirred overnight at 80° C. The reaction mixture was cooled back to room temperature, then diluted with ethyl acetate, and washed with water and saturated brine in the subsequent order. The obtained organic layer was dried over anhydrous magnesium sulfate, then the insolubles were filtered, the filtrate was concentrated under reduced pressure, and the thus obtained residue was purified by silica gel column chromatography, to obtain 744 mg of 4-iodo-N-[(1S)-1-phenylethyl]-2-pyridinamine [58-1] as a light brown solid.

(2) 1.3 mL of ethyl ethynyl ether (50% v/v hexane solution) was dissolved in 10 mL of tetrahydrofuran, and in an ice bath, 2.04 mL of borane-tetrahydrofuran complex (1.0M tetrahydrofuran solution) was added dropwise over 30 minutes. Thereafter, the reaction mixture was heated to room temperature, and stirred for 3 hours. Thereto, 10 mL of tetrahydrofuran solution containing 330 mg of the 4-iodo-N-[(1S)-1-phenylethyl]-2-pyridinamine [58-1], 11.5 mg of palladium acetate, 40.2 mg of triphenylphosphine, and 1.28 mL of a 4N aqueous solution of sodium hydroxide, were added, and further stirred at room temperature for 5 hours. The reaction mixture was diluted with 150 mL of ethyl acetate, washed with water and saturated brine in the subsequent order, and the thus obtained organic layer was dried over anhydrous magnesium sulfate. The insolubles were filtered, the filtrate was concentrated under reduced pressure, and the residue was purified by silica gel column chromatography, to obtain 94 mg of 4-[(E)-2-ethoxyethenyl]-N-[(1S)-1-phenylethyl]-2-pyridinamine [58-2] as a brown oily product.

(3) 94 mg of the 4-[(E)-2-ethoxyethenyl]-N-[(1S)-1-phenylethyl]-2-pyridinamine [58-2] was dissolved in a mixed solvent of 3 mL of 1,4-dioxane and 1 mL of water, and 28 mg of N-bromosuccinimide was added thereto. After stirring at room temperature for 10 minutes, 28 mg of N-bromosuccinimide was again added, and stirred at room temperature for another 30 minutes. Thereto, 80 µL of 2-amino-3-picoline was added, and stirred at 50° C. for 1 hour. The reaction mixture was cooled back to room temperature, then diluted with ethyl acetate, and washed with water and saturated brine in the subsequent order. The organic layer was dried over anhydrous magnesium sulfate, insolubles were filtered, and the filtrate was concentrated under reduced pressure. The obtained residue was purified by preparative thin-layer chromatography, and 16 mg of the target compound [58] was obtained as a pale yellow oily product.

A spectral data of the compound [58] is presented below.
$^1$H-NMR (CDCl$_3$) δ: 8.32 (s, 1H), 7.72 (s, 1H), 7.37-7.28 (m, 6H), 7.00 (d, J=6.8 Hz, 1H), 6.56 (dd, J=6.8 Hz, 7.0 Hz, 1H), 6.23 (s, 1H), 5.26 (d, J=6.4 Hz, 1H), 4.64 (dt, J=6.4 Hz, 6.8 Hz, 1H), 1.57 (d, J=6.8 Hz, 3H)
mass: 407, 409 (M+1)$^+$.

Example 59

Synthesis of 3-(5-cyano-2-{[(1S)-1-phenylethyl]amino}-4-pyrimidinyl)-8-methylimidazo[1,2-a]pyridine-7-carboxylic acid [59] (hereinafter, referred to as the compound [59])

The mixture of 13.6 mg of the compound [48], 1 mL of methanol, 1 mL of tetrahydrofuran, 0.5 mL of water, and 165 µL of 1N aqueous solution of sodium hydroxide was stirred at 40° C. for 2 hours, then neutralized with 83 µL of a 2N aqueous solution of hydrochloric acid, and concentrated under reduced pressure. The obtained residue was purified by preparative reversed phase liquid chromatography, and 12 mg of the target compound [59] was obtained as a pale yellow solid.

A spectral data of the compound [59] is presented below.
$^1$H-NMR (DMSO-d$_6$) δ: 9.96 (d, J=7.4 Hz, 1H×½), 9.07-8.66 (m, 3H+1H×½), 7.53-7.20 (m, 6H), 5.30-5.04 (m, 1H), 4.02 (br, 1H), 2.88 (s, 3H×½), 2.83 (s, 3H×½), 1.54 (d, J=6.9 Hz, 3H×½), 1.51 (d, J=6.9 Hz, 3H×½).
mass: 399 (M+1)$^+$.

Examples 60 and 61

Synthesis of t-butyl N-[3-(5-cyano-2-{[(1S)-1-phenylethyl]amino}-4-pyrimidinyl)-8-methylimidazo[1,2-a]pyridin-7-yl]carbamate [60] (hereinafter, referred to as the compound [60]) and 4-(7-amino-8-methylimidazo[1,2-a]pyridin-3-yl)-2-{[(1S)-1-phenylethyl]amino}-5-pyrimidinecarbonitrile [61] (hereinafter, referred to as the compound [61])

7.1 µL of diphenylphosphoryl azide was added to the mixture of 9 mg of the compound [59], 9.2 µL of triethylamine, 0.3 mL of N,N-dimethylformamide, and 0.2 mL of 1,4-dioxane, in an ice bath, and stirred at room temperature for 1 hour. Subsequently, 0.1 mL of t-butylalcohol was added thereto, stirred at 80° C. for 6 hours, then cooled back to room temperature, and chloroform, water, and saturated aqueous solution of sodium hydrogen carbonate were further added. The mixture was extracted with chloroform, and the obtained organic layer was washed with saturated brine and dried over anhydrous sodium sulfate. The insolubles were filtered, the filtrate was concentrated under reduced pressure, and the obtained residue was purified by preparative reversed phase liquid chromatography, to obtain 1.6 mg of the target compound [60] as a white solid and 4.1 mg of the target compound [61] as a yellow solid.

Spectral data of the compounds [60] and [61] are presented below.

Compound [60]:
$^1$H-NMR (CDCl$_3$) δ: 8.98-8.86 (m, 1H), 8.54-8.45 (m, 1H), 7.76-7.62 (m, 1H), 7.59-7.10 (m, 6H), 6.63-6.54 (m, 1H), 6.12-6.02 (m, 1H), 5.38-5.03 (m, 1H), 2.53 (s, 3H), 1.58 (d, J=6.9 Hz, 3H), 1.26 (s, 9H).
mass: 470 (M+1)$^+$.

Compound [61]:
$^1$H-NMR (CDCl$_3$) δ: 8.83 (s, 1H), 8.67 (d, J=7.4 Hz, 1H), 8.45 (s, 1H), 7.45-7.20 (m, 6H), 6.18-5.97 (m, 1H), 5.20-5.02 (m, 1H), 4.11 (br, 2H), 2.40 (s, 3H), 1.62 (d, J=6.9 Hz, 3H).
mass: 370 (M+1)$^+$.

Example 62

Synthesis of 4-[7-(hydroxymethyl)-8-methylimidazo[1,2-a]pyridin-3-yl}-2-{[(1S)-1-phenylethyl]amino}-5-pyrimidinecarbonitrile [62] (hereinafter, referred to as the compound [62])

11.4 mg of the compound [59] was dissolved in 2 mL of tetrahydrofuran, 23.2 mg of 1,1'-carbonyldiimidazole was added, and stirred at room temperature for 6 hours. Thereto, 5.4 mg of sodium borohydride was added, stirred at the same temperature for 30 minutes, and then a saturated aqueous solution of sodium hydrogen carbonate was added. The reaction mixture was extracted with a mixture solvent of chloroform-methanol (mixing ratio of 9:1), the organic layer was washed with saturated saline, and then dried over anhydrous sodium sulfate. The insolubles were filtered, the filtrate was concentrated under reduced pressure, and the residue was purified by preparative thin-layer chromatography, to obtain 4.4 mg of the target compound [62] as a white solid.

A spectral data of the compound [62] is presented below.
$^1$H-NMR (CD$_3$OD) δ: 8.78-8.50 (m, 2H), 7.98-7.92 (m, 1H), 7.47-6.97 (m, 8H), 5.34-5.05 (m, 1H), 4.83-4.71 (m, 2H), 2.65 (s, 3H×½), 2.52 (s, 3H×½), 1.59 (d, J=6.9 Hz, 3H).
mass: 385 (M+1)$^+$.

Example 63

Synthesis of 4-{8-methyl-7-[(methylamino)methyl]imidazo[1,2-a]pyridin-3-yl}-2-{[(1S)-1-phenylethyl]amino}-5-pyrimidinecarbonitrile [63] (hereinafter, referred to as the compound [63])

3.3 μL of methanesulfonyl chloride was added to the mixture of 3.3 mg of the compound [62], 10.5 μL of N,N-diisopropylethylamine, and 1.5 mL of chloroform in an ice bath, and stirred at the same temperature for 30 minutes. In addition, 3.8 μL of N,N-diisopropylethylamine and 1.7 μL of methanesulfonyl chloride were added, and stirred at the same temperature for 25 minutes, then 19.3 mg of sodium iodide and 0.5 mL of methylamine (40% methanol solution) were added, and stirred at 60° C. for 1 hour. The reaction mixture was cooled back to room temperature, then a saturated aqueous solution of sodium hydrogen carbonate and water were added, and extracted with chloroform. The obtained organic layer was washed with saturated brine, and then dried over anhydrous sodium sulfate. The insolubles were filtered, the filtrate was concentrated under reduced pressure, and the obtained residue was purified by preparative thin-layer chromatography, to obtain 1.8 mg of the target compound [63] as a white solid.

A spectral data of the compound [63] is presented below.
$^1$H-NMR (CDCl$_3$) δ: 8.97-8.80 (m, 2H), 8.60-8.47 (m, 1H), 7.44-7.10 (m, 6H), 6.86-6.75 (m, 1H), 6.07-5.78 (m, 1H), 5.43-5.06 (m, 1H), 3.91-3.80 (m, 2H), 2.64 (s, 3H), 2.52 (s, 3H), 1.59 (d, J=6.9 Hz, 3H).
mass: 398 (M+1)$^+$.

Example 64

Synthesis of 4-{7-[(4-methoxybenzyl)oxy]-8-methylimidazo[1,2-a]pyridin-3-yl}-2-{[(1S)-1-phenylethyl]amino}-5-pyrimidinecarbonitrile [64] (hereinafter, referred to as the compound [64])

(1) The mixture of 234 mg of 2-chloro-4-iodo picoline, 17.6 mg of copper iodide, 33.3 mg of 1,10-phenanthroline, 601 mg of cesium carbonate, 230 μL of 4-methoxybenzyl alcohol, and 0.5 mL of toluene, was stirred at 110° C. for 4 hours. After adding water and a saturated aqueous solution of sodium hydrogen carbonate, the mixture was extracted with chloroform, and the organic layer was washed with saturated brine. The thus-obtained organic layer was dried over anhydrous sodium sulfate, insolubles were filtered, and the filtrate was concentrated under reduced pressure. The obtained residue was purified by preparative thin-layer chromatography, and 207 mg of 2-chloro-4-[(4-methoxybenzyl)oxy]-3-methylpyridine [64-1] as a white solid.

(2) 101 mg of 4-[(4-methoxybenzyl)oxy]-3-methyl-2-pyridinamine [64-2] was obtained as a yellow solid from 147 mg of the 2-chloro-4-[(4-methoxybenzyl)oxy]-3-methylpyridine [64-1], according to the method of Example 48-(2).

(3) 21 mg of the target compound [64] was obtained as a yellow solid from 119 mg of the 4-[(4-methoxybenzyl)oxy]-3-methyl-2-pyridinamine [64-2] and 108 mg of the 4-[(Z)-2-ethoxyvinyl]-2-(methylthio)-5-pyrimidinecarbonitrile [48-3], according to the methods of Example 25-(3) to (5).

A spectral data of the compound [64] is presented below.
$^1$H-NMR (CDCl$_3$) δ: 8.89 (s, 1H), 8.82-8.71 (m, 1H), 8.46 (s, 1H), 7.44-7.26 (m, 7H), 7.01-6.88 (m, 2H), 6.48-6.40 (m, 1H), 6.06-5.96 (m, 1H), 5.16 (s, 2H), 5.22-5.00 (m, 1H), 3.84 (s, 3H), 2.50 (s, 3H), 1.63 (d, J=6.9 Hz, 3H).
mass: 491 (M+1)$^+$.

Example 65

Synthesis of 4-(7-hydroxy-8-methylimidazo[1,2-a]pyridin-3-yl}-2-{[(1S)-1-phenylethyl]amino}-5-pyrimidinecarbonitrile [65] (hereinafter, referred to as the compound [65])

20 mg of the compound [64] was dissolved in 1.5 mL of chloroform, 1.5 mL of trifluoroacetic acid was added under an ice-cold condition, and stirred at room temperature for 30 minutes. The reaction mixture was concentrated under reduced pressure, and the obtained residue was purified by preparative reversed phase liquid chromatography to obtain 19 mg of the target compound [65] as a pale yellow oily product.

A spectral data of the compound [65] is presented below.
$^1$H-NMR (CDCl$_3$) δ: 8.63 (s, 1H), 8.56 (s, 1H), 8.33 (d, J=7.6 Hz, 1H), 7.47-7.23 (m, 6H), 7.08-7.06 (m, 1H), 6.92-6.90 (m, 1H), 5.02-4.99 (m, 1H), 2.14 (s, 3H), 1.65 (d, J=6.8 Hz, 3H)
mass: 371 (M+1)$^+$..

Example 66

Synthesis of 4-imidazo[1,2-a]pyrimidin-3-yl-2-{[(1S)-1-phenylethyl]amino}-5-pyrimidinecarbonitrile [66] (hereinafter, referred to as the compound [66])

15 mg of the target compound [66] was obtained, from 100 mg of the 4-[(Z)-2-ethoxyvinyl]-2-(methylthio)-5-pyrimidinecarbonitrile [48-3] and 48 mg of 2-pyrimidinamine, according to the methods of Example 25-(3) to (5).

A spectral data of the compound [66] is presented below.
$^1$H-NMR (CDCl$_3$) δ: 9.07 (s, 1H), 8.94-8.92 (m, 1H), 8.62-8.60 (m, 1H), 8.58 (s, 1H), 7.45-7.34 (m, 6H), 6.69-6.66 (m, 1H), 6.14-6.12 (m, 1H), 5.08-5.04 (m, 1H), 1.66 (d, J=7.2 Hz, 3H)
mass: 342 (M+1)$^+$.

Examples 67 to 78

Synthesis of 4-(8-methylimidazo[1,2-a]pyridin-3-yl)-2-{[(1S)-1-phenylpropyl]amino}-5-pyrimidinecarbonitrile [67] (hereinafter, referred to as the compound [67]), 2-[(3-hydroxy-1-phenylpropyl)amino]-4-(8-methylimidazo[1,2-a]pyridin-3-yl)-5-pyrimidinecarbonitrile [68] (hereinafter, referred to as the compound [68]), 4-(8-methylimidazo[1,2-a]pyridin-3-yl)-2-[(3-phenylpropyl)amino]-5-pyrimidinecarbonitrile [69] (hereinafter, referred to as the compound [69]), 4-(8-methylimidazo[1,2-a]pyridin-3-yl)-2-{[2-(2-thienyl)ethyl]amino}-5-pyrimidinecarbonitrile [70] (hereinafter, referred to as the compound [70]), 4-(8-methylimidazo[1,2-a]pyridin-3-yl)-2-[(3-pyridinylmethyl)amino]-5-pyrimidinecarbonitrile [71] (hereinafter, referred to as the compound [71]), 2-[(2-chlorobenzyl)amino]-4-(8-methylimidazo[1,2-a]pyridin-3-yl)-5-pyrimidinecarbonitrile [72] (hereinafter, referred to as the compound [72]), 2-[(3-methoxybenzyl)amino]-4-(8-methylimidazo[1,2-a]pyridin-3-yl)-5-pyrimidinecarbonitrile [73] (hereinafter, referred to as the compound [73]), 2-[(4-methoxybenzyl)amino]-4-(8-methylimidazo[1,2-a]pyridin-3-yl)-5-pyrimidinecarbonitrile [74] (hereinafter, referred to as the compound [74]), 2-[(4-aminobenzyl)amino]-4-(8-methylimidazo[1,2-a]pyridin-3-yl)-5-pyrimidinecarbonitrile [75] (hereinafter, referred to as the compound [75]), 4-(8-methylimidazo[1,2-a]pyridin-3-yl)-2-{[2-(trifluoromethyl)benzyl]amino}-5-pyrimidinecarbonitrile [76] (hereinafter, referred to as the compound [76]), 2-{[1-(4-fluorophenyl)ethyl]amino}-4-(8-methylimidazo[1,2-a]pyridin-3-yl)-5-pyrimidinecarbonitrile [77] (hereinafter, referred to as the compound [77]), and 2-[(2,6-difluorobenzyl)amino]-4-(8-methylimidazo[1,2-a]pyridin-3-yl)-5-pyrimidinecarbonitrile [78] (hereinafter, referred to as the compound [78])

(1) 4-(8-methylimidazo[1,2-a]pyridin-3-yl)-2-methylsulfonyl)-5-pyrimidinecarbonitrile [67-1] was obtained, from the 4-[(Z)-2-ethoxyvinyl]-2-(methylthio)-5-pyrimidinecarbonitrile [48-3] and 2-amino-3-picoline, according to the methods of Example 25-(3) and (4).

(2) Target compounds [67] to [78] were obtained from 4-(8-methylimidazo[1,2-a]pyridin-3-yl)-2-methylsulfonyl)-5-pyrimidinecarbonitrile [67-1]; and (1S)-1-phenyl-1-propanamine (for the case of Example 67), (3S)-3-amino-3-phenyl-1-propanol (for the case of Example 68), 3-phenyl-1-propanamine (for the case of Example 69), 2-(2-thienyl)-1-ethanamine (for the case of Example 70), 3-pyridinyl methanamine (for the case of Example 71), (2-chlorophenyl) methanamine (for the case of Example 72), (3-methoxyphenyl)methanamine (for the case of Example 73), (4-methoxyphenyl)methanamine (for the case of Example 74), 4-(aminomethyl)aniline (for the case of Example 75), [2-(trifluoromethyl)phenyl]methanamine (for the case of Example 76), 1-(4-fluorophenyl)-1-ethanamine (for the case of Example 77), or (2,6-difluorophenyl)methanamine (for the case of Example 78), respectively, according to the method of Example 25-(5).

Spectral data of the compounds [67] to [78] are presented below.

Compound [67]:
$^1$H-NMR (CDCl$_3$) δ: 9.62 (m, 1H×⅓), 8.98-8.80 (m, 1H+1H×⅔), 8.52 (br, 1H), 7.47-7.12 (m, 6H), 6.94 (m, 1H×⅓), 6.66 (m, 1H×⅔), 6.10 (m, 1H×⅔), 5.88 (m, 1H×⅓), 5.10 (m, 1H×⅓), 4.92 (m, 1H×⅔), 2.68 (br, 3H), 1.98 (m, 2H), 1.03 (m, 3H).
mass: 369 (M+1)$^+$.

Compound [68]:
$^1$H-NMR (CDCl$_3$) δ: 9.63 (brd, J=7.2 Hz, 1H×⅓), 8.92 (br, 1H×⅓), 8.84 (br, 1H×⅔), 8.72 (brd, J=7.2 Hz, 1H×⅔), 8.42 (br, 1H), 7.48-6.90 (m, 6H), 6.60 (m, 1H×⅔), 6.39 (m, 1H×⅓), 5.42 (m, 1H×⅓), 5.29 (m, 1H×⅔), 3.85 (m, 2H), 2.68 (br, 3H×⅓), 2.63 (br, 3H×⅔), 1.20 (m, 2H).
mass: 385 (M+1)$^+$.

Compound [69]:
$^1$H-NMR (CDCl$_3$) δ: 9.70 (m, 1H), 9.09 (s, 1H×½), 8.98 (s, 1H×½), 8.59 (s, 1H×½), 8.51 (s, 1H×½), 7.49 (m, 1H), 7.36-7.02 (m, 5H), 6.83 (m, 1H), 6.72 (m, 1H), 3.60 (m, 2H), 2.78 (m, 2H), 2.75 (s, 3H×½), 2.68 (s, 3H×½), 2.09 (m, 2H).
mass: 369 (M+1)$^+$.

Compound [70]:
$^1$H-NMR (CDCl$_3$) δ: 9.70 (brd, J=7.5 Hz, 1H×½), 9.59 (brd, J=6.9 Hz, 1H×½), 9.09 (s, 1H×½), 8.99 (s, 1H×½), 8.68 (s, 1H×½), 8.56 (s, 1H×½), 7.60 (m, 1H), 7.31-6.50 (m, 4H), 3.88 (m, 2H), 3.24 (m, 2H), 2.78 (s, 3H×½), 2.73 (s, 3H×½).
mass: 361 (M+1)$^+$.

Compound [71]:
$^1$H-NMR (CDCl$_3$) δ: 9.92 (brd, J=7.5 Hz, 1H×⅔), 9.14 (m, 1H×⅓), 9.15-8.84 (m, 2H), 8.75-8.57 (m, 2H), 8.47 (m, 1H×⅔), 8.17 (m, 1H×⅓), 7.87 (m, 1H×⅔), 7.69 (m, 1H×⅓), 7.49 (m, 1H×⅔), 7.37 (m, 1H×⅓), 7.20 (m, 1H×⅔), 6.96 (m, 1H×⅓), 4.90 (br, 2H), 2.70 (s, 3H).
mass: 342 (M+1)$^+$.

Compound [72]:
$^1$H-NMR (CDCl$_3$) δ: 9.10 (brd, J=7.5 Hz, 1H), 9.04 (s, 1H), 8.68 (s, 1H), 7.60-6.97 (m, 5H), 6.80 (m, 1H), 4.85 (brd, J=6.0 Hz, 2H), 2.71 (s, 3H).
mass: 375, 377 (M+1)$^+$.

Compound [73]:
$^1$H-NMR (CDCl$_3$) δ: 9.72 (brd, J=7.2 Hz, 1H×⅓), 9.05-8.97 (m, 1H+1H×⅔), 8.66 (s, 1H×⅓), 8.54 (s, 1H×⅔), 7.51-6.66 (m, 6H), 4.73 (m, 2H), 3.82 (s, 3H), 2.72 (s, 3H).
mass: 371 (M+1)$^+$.

Compound [74]:
$^1$H-NMR (CDCl$_3$) δ: 9.72 (brd, J=7.2 Hz, 1H×⅓), 9.17 (brd, J=6.9 Hz, 1H×⅔), 9.02 (s, 1H), 8.68 (s, 1H×⅓), 8.54 (s, 1H×⅔), 7.49 (m, 1H), 7.38-6.88 (m, 4H+1H×⅔), 6.56 (m, 1H×⅓), 4.70 (brd, J=5.7 Hz, 2H), 3.82 (s, 3H), 2.72 (s, 3H).
mass: 371 (M+1)$^+$.

Compound [75]:
$^1$H-NMR (CDCl$_3$) δ: 9.85 (m, 1H×⅓), 9.11 (m, 1H×⅔), 8.97 (s, 1H×⅓), 8.90 (s, 1H×⅔), 8.64 (s, 1H×⅓), 8.58 (s, 1H×⅔), 7.48-6.80 (m, 6H), 4.71 (m, 2H), 2.70 (s, 3H×⅓), 2.67 (s, 3H×⅔).
mass: 356 (M+1)$^+$.

Compound [76]:
$^1$H-NMR (CDCl$_3$) δ: 9.76 (m, 1H×⅓), 9.10-8.99 (m, 1H+1H×⅔), 8.71 (s, 1H×⅓), 8.64 (s, 1H×⅔), 7.82-6.80 (m, 6H), 4.98 (m, 2H), 2.70 (br, 3H).
mass: 409 (M+1)$^+$.

Compound [77]:
$^1$H-NMR (CDCl$_3$) δ: 9.77 (brd, J=7.2 Hz, 1H×⅓), 8.99 (s, 1H), 8.70 (brd, J=6.9 Hz, 1H×⅔), 8.60 (s, 1H), 7.61-6.85 (m, 6H), 5.42 (m, 1H×⅓), 5.08 (m, 1H×⅔), 2.73 (br, 3H).
mass: 373 (M+1)$^+$.

Compound [78]:
$^1$H-NMR (CDCl$_3$) δ: 9.74 (m, 1H×⅔), 9.68 (m, 1H×⅓), 9.01 (s, 1H), 8.72 (s, 1H×⅓), 8.58 (s, 1H×⅔), 7.52 (m, 1H), 7.48-6.56 (m, 4H), 4.90 (brd, J=6.3 Hz, 2H), 2.77 (s, 3H×⅔), 2.74 (s, 3H×⅓).
mass: 377 (M+1)$^+$.

Example 79

Synthesis of 2-{[1-(4-hydroxyphenyl)ethyl]amino}-4-(8-methylimidazo[1,2-a]pyridin-3-yl)-5-pyrimidinecarbonitrile [79] (hereinafter, referred to as the compound [79])

(1) 11.7 mL of t-butylchlorodiphenyl silane was added to the mixture of 5 g of 1-(4-hydroxyphenyl)-1-ethanone, 3 g of imidazole, and 70 mL of N,N-dimethylformamide, and stirred overnight at room temperature. The reaction mixture was added with 200 mL of ethyl acetate, washed with water and saturated brine in the subsequent order, and the obtained organic layer was dried over anhydrous magnesium sulfate. The insolubles were filtered, the filtrate was concentrated under reduced pressure, and the obtained residue was purified by silica gel column chromatography, to obtain 11.7 g of 1-(4-{[t-butyl(diphenyl)silyl]oxy}phenyl)-1-ethanone [79-1] as a white solid.

(2) 5 g of the 1-(4-{[t-butyl(diphenyl)silyl]oxy}phenyl)-1-ethanone [79-1] was dissolved in a mixture solvent of 50 mL of methanol and 30 mL of tetrahydrofuran, 606 mg of sodium borohydride was added thereto, and stirred at room temperature for 3 hours. The reaction mixture was added with 30 mL of water, and concentrated under reduced pressure. The residue was added with 150 mL of ethyl acetate, washed with water and saturated brine in the subsequent order, and the obtained organic layer was dried over anhydrous magnesium sulfate. The insolubles were filtered, the filtrate was concentrated under reduced pressure, and the obtained residue was purified by silica gel column chromatography, to obtain 5.02 g of 1-(4-{[t-butyl(diphenyl)silyl]oxy}phenyl)-1-ethanol [79-2] as a colorless oily product.

(3) 5.02 g of the 1-(4-{[t-butyl(diphenyl)silyl]oxy}phenyl)-1-ethanol [79-2] was dissolved in 20 mL of tetrahydrofuran, 3.45 mL of diphenylphosphoryl azide and 2.44 mL of 1,8-diazabicyclo[5.4.0]undeca-7-ene were added thereto, and stirred overnight at room temperature. The reaction mixture was added with 100 mL of ethyl acetate, washed with water and saturated brine in the subsequent order, and the obtained organic layer was dried over anhydrous magnesium sulfate. The insolubles were filtered, the filtrate was concentrated under reduced pressure, and the obtained residue was purified by silica gel column chromatography, to obtain 4.26 g of 1-[1-(4-{[t-butyl(diphenyl)silyl]oxy}phenyl)ethyl]-1,2-triazadien-2-ium [79-3] as a light brown oily product.

(4) 4.26 g of the 1-[1-(4-{[t-butyl(diphenyl)silyl]oxy}phenyl)ethyl]-1,2-triazadien-2-ium [79-3] was dissolved in 30 mL of ethanol, a catalytic amount of 10% palladium carbon catalyst was added thereto, and stirred overnight in a hydrogen atmosphere. The insolubles were filtered through celite, and washed with ethanol. The filtrate was concentrated under reduced pressure, and 3.94 g of 1-(4-{[t-butyl(diphenyl)silyl]oxy}phenyl)ethylamine [79-4] was obtained as a light brown oily product.

(5) 98 mg of 4-(8-methylimidazo[1,2-a]pyridin-3-yl)-2-{[1-(4-{[t-butyl(diphenyl)silyl]oxy}phenyl)ethyl]amino}-5-pyrimidinecarbonitrile [79-5] was obtained as a pale yellow oily product, from 100 mg of the 4-(8-methylimidazo[1,2-a]pyrimidin-3-yl)-2-methylsulfonyl)-5-pyrimidinecarbonitrile [67-1] and 400 mg of the 1-(4-{[t-butyl(diphenyl)silyl]oxy}phenyl)ethylamine [79-4], according to the method of Example 25-(5).

(6) 98 mg of the 4-(8-methylimidazo[1,2-a]pyridin-3-yl)-2-{[1-(4-{[t-butyl(diphenyl)silyl]oxy}phenyl)ethyl]amino}-5-pyrimidinecarbonitrile [79-5] was dissolved in 3 mL of tetrahydrofuran, 161 µL of tetrabutylammonium fluoride (1.0M tetrahydrofuran solution) was added thereto, and stirred at room temperature for 1 hour. The reaction mixture was added with 70 mL of ethyl acetate, washed with phosphate buffer pH 6.8, water, and saturated brine in the subsequent order, and the obtained organic layer was dried over anhydrous magnesium sulfate. The insolubles were filtered, and the filtrate was concentrated under reduced pressure. The obtained residue was dissolved in a small amount of a mixed solvent of chloroform and methanol (chloroform:methanol=9:1), solidified by hexane, and the solid thus produced was taken, to obtain 45 mg of the target compound [79] as a pale yellow solid.

A spectral data of the compound [79] is presented below.
$^1$H-NMR (DMSO-d$_6$) δ: 9.97 (d, J=6.8 Hz, 1H×⅔), 9.26 (d, J=5.9 Hz, 1H), 9.01 (d, J=6.8 Hz, 1H×⅗), 8.88 (d, J=7.4 Hz, 1H×⅗), 8.80 (d, J=8.2 Hz, 1H×⅔), 8.74-8.71 (m, 1H+1H×⅔), 8.60 (s, 1H×⅗), 7.42-7.35 (m, 1H), 7.22-7.19 (m, 2H), 7.10 (t, J=6.8 Hz, 1H×⅔), 6.93 (t, J=6.8 Hz, 1H×⅗), 6.75-6.70 (m, 2H), 5.19-5.15 (m, 1H×⅔), 5.01-4.98 (m, 1H×⅗), 2.58 (s, 3H×⅔), 2.54 (s, 3H×⅗), 1.48 (d, J=7.0 Hz, 3H×⅔), 1.46 (d, J=7.0 Hz, 3H×⅗)
mass: 371 (M+1)$^+$.

Example 80

Synthesis of 2-{[(1S)-1-(3-aminophenyl)ethyl]amino}-4-[8-(difluoromethyl)imidazo[1,2-a]pyridin-3-yl]pyrimidine-5-carbonitrile [80] (hereinafter, referred to as the compound [80])

(1) 9.6 g of 2-chloronicotinaldehyde was dissolved in 150 mL of dichloromethane, and 22.2 mL of diethylaminosulfur trifluoride was added dropwise over 10 minutes under an ice-cold condition. After stirring at 0° C. for 40 minutes, 100 mL of a saturated aqueous solution of sodium hydrogen carbonate was carefully added, and extracted with chloroform. After the organic layer was washed with saturated brine and dried over anhydrous sodium sulfate, the insolubles were filtered, and the filtrate was concentrated under reduced pressure. The obtained residue was purified by silica gel column chromatography, and 10.1 g of 2-chloro-3-(difluoromethyl)pyridine [80-1] was obtained as a light brown oily product.

(2) The mixture of 10.1 g of the 2-chloro-3-(difluoromethyl)pyridine [80-1], 1.78 g of bis(dibenzylideneacetone) palladium, 1.79 g of 4,5-bis(diphenylphosphino)-9,9-dimethylxanthene, 12.4 g of benzophenoneimine, 28.2 g of cesium carbonate, 50 mL of toluene, and 50 mL of 1,4-dioxane, was stirred overnight at 80° C. The reaction mixture was cooled back to room temperature, then 100 mL of a saturated aqueous solution of sodium hydrogen carbonate and 100 mL of water were added, and extracted with chloroform. After washing the organic layer with saturated brine, concentration was carried out under reduced pressure, and the obtained residue was dissolved in 50 mL of methanol. 61.8 mL of 2N hydrochloric acid was added and stirred for 5 minutes, and then 400 mL of 0.5 N hydrochloric acid was added and stirred for 10 minutes. The reaction solution was adjusted to pH=12 with 5N aqueous solution of sodium hydroxide, and was extracted with chloroform. After the organic layer was washed with saturated brine and dried over anhydrous sodium sulfate, the insolubles were filtered, and the filtrate was concentrated under reduced pressure. The obtained residue was purified by silica gel column chromatography, and 2.57 g of 3-(difluoromethyl)pyridine-2-amine [80-2] as a light brown oily product.

(3) 4.11 g of 4-[8-(difluoromethyl)imidazo[1,2-a]pyridin-3-yl]-2-(methylthio)pyrimidine-5-carbonitrile [80-3] was obtained as pale yellow amorphous, from 2.57 g of the 3-(difluoromethyl)pyridine-2-amine [80-2] and 4.34 g of the 4-[(Z)-2-ethoxyvinyl]-2-(methylthio)-5-pyrimidinecarbonyl [48-3], according to the method of Example 25-(3).

(4) 1.91 g of the 4-[8-(difluoromethyl)imidazo[1,2-a]pyridin-3-yl]-2-(methylthio)pyrimidine-5-carbonitrile [80-3] was dissolved in 60 mL of chloroform, 1.77 g of m-chloroperbenzoic acid was added under an ice-cold condition, and stirred at 0° C. for 30 minutes. After adding 100 mL of a saturated aqueous solution of sodium hydrogen carbonate and 100 mL of water, the reaction solution was extracted with a mixture solvent of chloroform and methanol (chloroform:methanol=9:1). After drying the organic layer over anhydrous sodium sulfate, the insolubles were filtered, and the filtrate was concentrated under reduced pressure. The obtained residue was dissolved in 60 mL of tetrahydrofuran, and added to 20 mL of a tetrahydrofuran solution prepared by 1.11 g of 3-[(1S)-1-aminoethyl]aniline (synthesized according to a method disclosed in Pamphlet of International Publication WO 00/056,331, pages 67-70) and 1.65 mL of triethylamine. The mixture was stirred at room temperature for 3 hours, 100 mL of a saturated aqueous solution of sodium hydrogen carbonate was added thereto, and extracted with ethyl acetate. The organic layer was washed with saturated brine and dried over anhydrous sodium sulfate, and then the insolubles were filtered. The filtrate was concentrated under reduced pressure, and the obtained residue was purified by preparative reversed phase liquid chromatography. The obtained eluent was basified with a saturated aqueous solution of sodium bicarbonate, and then extracted with chloroform. The organic layer was washed with saturated brine, and dried over anhydrous sodium sulfate. After the insolubles were filtered, and the filtrate was concentrated under reduced pressure, the residue was dissolved under heating in ethanol, and allowed to stand still at room temperature. The precipitate was filtered and dried under reduced pressure to obtain 1.2 g of the target compound [80] as a white solid.

A spectral data of the compound [80] is presented below.
$^1$H-NMR (CDCl$_3$) δ: 9.89-9.80 (m, 1H×⅕), 8.90-9.02 (m, 1H+1H×⅘), 8.62 (s, 1H×⅘), 8.57 (s, 1H×⅘), 7.55-7.10 (m, 3H), 6.88-6.02 (m, 4H), 6.06-5.97 (m, 1H×⅘), 5.86-5.75 (m, 1H×⅕), 5.25-5.18 (m, 1H×⅕), 5.02-4.88 (m, 1H×⅘), 3.76 (brs, 2H), 1.61 (d, J=6.8 Hz, 3H)
mass: 406 (M+1)$^+$.

Example 81

Synthesis of N-{3-[(1S)-1-({5-cyano-4-[8-(difluoromethyl)imidazo[1,2-a]pyridin-3-yl]pyrimidine-2-yl}amino)ethyl]phenyl}glycinamide [81] (hereinafter, referred to as the compound [81])

10 mg of the compound [80], 13 mg of N-t-butoxycarbonylglycine, 10 mg of 1-hydroxybenzotriazole monohydrate, and 12.9 µL of N,N-diisopropylethylamine were added in 0.5 mL of N,N-dimethylformamide, then 14.2 mg of 1-ethyl-3-(3-dimethylaminopropyl)carbodiimide hydrochloride was added thereto, and stirred at room temperature for 5 hours. Thereto, 30 mL of a saturated aqueous solution of sodium hydrogen carbonate was added, extracted with chloroform, and the organic layer was washed with saturated brine. After drying over anhydrous sodium sulfate, the insolubles were filtered, and the filtrate was concentrated under reduced pressure. The obtained residue was dissolved in 0.4 mL of chloroform, 0.4 mL of trifluoroacetic acid was added, and stirred at room temperature for 1 hour. The reaction solution was concentrated under reduced pressure, and the obtained residue was purified by preparative reversed phase liquid chromatography. The eluent was concentrated under reduced pressure, and then dissolved in methanol. The trifluoroacetic acid was removed through a weak anion-exchange resin (Bond Elute-Regular type PSA, GL Science Co., Ltd.). The solvent was distilled off under reduced pressure, and 4.0 mg of the target compound [81] was obtained as a white solid.

A spectral data of the compound [81] is presented below.
$^1$H-NMR (CDCl$_3$) δ: 10.07 (d, J=7.2 Hz, 1H×⅕), 9.04 (d, J=7.2 Hz, 1H×⅘), 8.96 (s, 1H×⅕), 8.88 (s, 1H×⅘), 8.58 (s, 1H×⅕), 8.57 (s, 1H×⅘), 7.87-6.85 (m, 9H), 5.80-5.48 (m, 1H×⅕), 5.14-5.07 (m, 1H×⅘), 3.45-3.41 (m, 2H), 2.58-2.57 (m, 2H), 1.64 (d, J=6.8 Hz, 3H)
mass: 463 (M+1)$^+$.

Example 82

Synthesis of 4-[8-(difluoromethyl)imidazo[1,2-a]pyridin-3-yl]-2-({(1S)-1-[3-(pyrrolidin-3-ylamino)phenyl]ethyl}amino)pyrimidine-5-carbonitrile [82] (hereinafter, referred to as the compound [82])

(1) 23.7 mg of the compound [80] and 10.8 mg of t-butyl 3-oxopyrrolidine-1-carboxylate were dissolved in 1.5 mL of chloroform, and then a solvent prepared by dissolving 11 mg of cyano sodium borohydride and 12 mg of zinc chloride in 585 µL of methanol, was added thereto, and stirred overnight at 50° C. After cooling back to room temperature, a saturated aqueous solution of sodium hydrogen carbonate was added, and extracted with chloroform. The organic layer was washed with saturated brine and dried over anhydrous sodium sulfate, then the insolubles were filtered, and the filtrate was concentrated under reduced pressure. The obtained residue was purified by preparative thin-layer chromatography, and 8.7 mg of t-butyl 3-({3-[(1S)-1-({5-cyano-4-[8-(difluoromethyl)imidazo[1,2-a]pyridin-3-yl]pyrimidin-2-yl}amino)ethyl]phenyl}amino)pyrrolidine-1-carboxylate [82-1] was obtained as a pale yellow oily product.

(2) 8.7 mg of the t-butyl 3-({3-[(1S)-1-({5-cyano-4-[8-(difluoromethyl)imidazo[1,2-a]pyridin-3-yl]pyrimidin-2-yl}amino)ethyl]phenyl}amino)pyrrolidine-1-carboxylate [82-1] was dissolved in 1 mL of chloroform, and 1 mL of trifluoroacetic acid was added thereto under an ice-cold condition and stirred for 30 minutes. The reaction solution was concentrated under reduced pressure, and the obtained residue was purified by preparative reversed phase liquid chromatography. The eluent was concentrated under reduced pressure, then dissolved in methanol, and the trifluoroacetic acid was removed through a weak anion-exchange resin. The solvent was distilled off under reduced pressure to obtain 6.6 mg of the target compound [82] as a white solid.

A spectral data of the compound [82] is presented below.
$^1$H-NMR (CDCl$_3$) δ: 9.10-8.96 (m, 1H+1H×⅘), 8.88 (s, 1H), 8.58 (s, 1H×⅕), 8.52 (d, J=8.0 Hz, 1H), 7.68-7.18 (m, 3H), 6.88-6.53 (m, 4H), 5.26-5.18 (m, 1H×⅕), 5.01-5.00 (m, 1H×⅘), 4.18-4.05 (m, 1H), 3.43-3.14 (m, 7H), 2.28-1.80 (m, 2H), 1.62 (d, J=6.8 Hz, 3H)
mass: 475 (M+1)$^+$.

Example 83

Synthesis of 4-[8-(difluoromethyl)imidazo[1,2-a]pyridin-3-yl]-2-[((1S)-1-{3-[(2-hydroxyethyl)amino]phenyl}ethyl)amino]pyrimidine-5-carbonitrile [83] (hereinafter, referred to as the compound [83])

(1) 122 mg of 2-[((1S)-1-{3-[(2-{[t-butyl(dimethyl)silyl]oxy}ethyl)amino]phenyl}ethyl)amino]-4-[8-(difluoromethyl)imidazo[1,2-a]pyridin-3-yl]pyrimidine-5-carbonitrile [83-1] was synthesized from 100 mg of the compound [80] and 156 mL of (t-butyldimethylsilyloxy)acetaldehyde, according to the method of Example 82-(1).

(2) 122 mg of the 2-[((1S)-1-{3-[(2-{[t-butyl(dimethyl)silyl]oxy}ethyl)amino]phenyl}ethyl)amino]-4-[8-(difluoromethyl)imidazo[1,2-a]pyridin-3-yl]pyrimidine-5-carbonitrile [83-1] was dissolved in 2 mL of tetrahydrofuran, 433 μL of tetrabutylammonium fluoride(1.0M tetrahydrofuran solution) was added under an ice-cold condition, and stirred at room temperature for 40 minutes. The reaction mixture was added with a saturated aqueous solution of sodium hydrogen carbonate, and extracted with chloroform. The organic layer was washed with saturated brine, and dried over anhydrous sodium sulfate. The insolubles were filtered, and the filtrate was concentrated under reduced pressure to obtain a residue. The residue was purified by preparative thin-layer chromatography, and 95 mg of the target compound [83] was obtained as a white solid.

A spectral data of the compound [83] is presented below.
$^1$H-NMR (CDCl$_3$) δ: 9.70 (d, J=7.2 Hz, 1H×⅕), 8.96 (s, 1H×⅕), 8.92 (d, J=7.2 Hz, 1H×⅘), 8.87 (s, 1H×⅘), 8.59 (s, 1H×⅕), 8.50 (s, 1H×⅘), 7.64-7.01 (m, 3H), 6.85-6.59 (m, 4H), 6.35-6.34 (m, 1H×⅘), 6.08-5.90 (m, 1H×⅕), 5.29-5.18 (m, 1H×⅕), 5.08-4.90 (m, 1H×⅘), 4.20 (brs, 1H), 3.87-3.84 (m, 2H), 3.49 (s, 3H), 3.31-3.29 (m, 2H), 1.61 (d, J=6.8 Hz, 3H)
mass: 450 (M+1)$^+$.

Example 84

Synthesis of 4-[8-(difluoromethyl)imidazo[1,2-a]pyridin-3-yl]-2-{[(1S)-1-(3-{[2-(methylsulfonyl)ethyl]amino}phenyl)ethyl]amino}pyrimidine-5-carbonitrile [84] (hereinafter, referred to as the compound [84])

6.5 μL of methanesulfonyl chloride was added to the mixture of 25 mg of the compound [83], 19.4 μL of N,N-diisopropylethylamine, and 0.7 mL of chloroform in an ice bath, and stirred at the same temperature for 30 minutes. Thereto, a saturated aqueous solution of sodium hydrogen carbonate was added, and was extracted with chloroform. The organic layer was washed with saturated brine, and then dried over anhydrous sodium sulfate. The insolubles were filtered and the filtrate was concentrated under reduced pressure to obtain a residue, and the residue was dissolved in 1 mL of N,N-dimethylformamide. Thereto, 28 mg of sodium methanesulfinate was added, and stirred at 90° C. for 2 hours. After cooling the reaction mixture back to room temperature, a saturated aqueous solution of sodium hydrogen carbonate was added, and extracted with chloroform. The organic layer was washed with saturated brine, and then dried over anhydrous sodium sulfate. The insolubles were filtered and the filtrate was concentrated under reduced pressure to obtain a residue. The residue was purified by preparative thin-layer chromatography, and 4.7 mg of the target compound [84] was obtained as a white solid.

A spectral data of the compound [84] is presented below.
$^1$H-NMR (CDCl$_3$) δ: 9.72-9.68 (m, 1H×⅕), 8.99-8.99 (m, 1H+1H×⅘), 8.61 (s, 1H×⅕), 8.56 (s, 1H×⅘), 7.65-7.19 (m, 3H), 6.85-6.58 (m, 4H), 6.15-6.08 (m, 1H×⅘), 5.98-5.90 (m, 1H×⅕), 5.30-5.18 (m, 1H×⅕), 5.05-4.90 (m, 1H×⅘), 4.37-4.15 (m, 3H), 3.50-3.32 (m, 2H), 2.66 (s, 3H), 1.62 (d, J=6.8 Hz, 3H)
mass: 512 (M+1)$^+$.

Example 85

Synthesis of 4-[8-(difluoromethyl)imidazo[1,2-a]pyridin-3-yl]-2-({(1S)-1-[3-(ethylamino)phenyl]ethyl}amino)pyrimidine-5-carbonitrile [85] (hereinafter, referred to as the compound [85])

8.1 mg of the target compound [85] was obtained as a white solid from 15 mg of the compound [80] and 8.8 mg of t-butyl-N-(2-oxoethyl)carbamate, according to the methods of Example 82-(1) and (2).

A spectral data of the compound [85] is presented below.
$^1$H-NMR (CDCl$_3$) δ: 9.86 (d, J=8.0 Hz, 1H×⅕), 8.99 (s, 1H×⅕), 8.94 (d, J=8.0 Hz, 1H×⅘), 8.89 (s, 1H×⅘), 8.61 (s, 1H×⅕), 8.54 (s, 1H×⅘), 7.74-7.12 (m, 3H), 6.85-6.57 (m, 4H), 6.16-6.14 (m, 1H×⅘), 8.95-5.80 (m, 1H×⅕), 5.30-5.17 (m, 1H×⅕), 5.02-4.95 (m, 1H×⅘), 4.23 (brs, 1H), 3.19-3.16 (m, 2H), 2.99-2.96 (m, 2H), 1.61 (d, J=6.8 Hz, 3H), 1.48 (brs, 2H)
mass: 449 (M+1)$^+$.

Example 86

Synthesis of 2-({(1S)-1-[3-(azetidin-3-ylamino)phenyl]ethyl}amino)-4-[8-(difluoromethyl)imidazo[1,2-a]pyridin-3-yl]pyrimidine-5-carbonitrile [86] (hereinafter, referred to as the compound [86])

4.3 mg of the target compound [86] was obtained as a white solid, from 15 mg of the target compound [80] and 9.5 mg of t-butyl-3-oxoazetidine-1-carboxylate (synthesized according to a method disclosed in page 6 in JP-A-2002-255932), according to the methods of Example 82-(1) and (2).

A spectral data of the compound [86] is presented below.
$^1$H-NMR (CDCl$_3$) δ: 9.72-9.68 (m, 1H×⅕), 8.99 (s, 1H×⅕), 8.90-8.88 (m, 1H×⅘+1H×⅘), 8.61 (s, 1H×⅕), 8.56 (s, 1H×⅘), 7.72-7.19 (m, 3H), 6.80-6.45 (m, 4H), 6.09-6.07 (m, 1H×⅘), 5.90-5.80 (m, 1H×⅕), 5.28-5.20 (m, 1H×⅕), 5.07-4.90 (m, 1H×⅘), 4.42-4.30 (m, 1H), 4.27-4.15 (m, 1H), 3.98-3.85 (m, 2H), 3.59-3.38 (m, 2H), 1.62 (d, J=6.8 Hz, 3H)
mass: 461 (M+1)$^+$.

Examples 87 and 88

Synthesis of 4-[8-(difluoromethyl)imidazo[1,2-a]pyridin-3-yl]-2-[((1S)-1-{3-[methyl(1-methylazetidin-3-yl)amino]phenyl}ethyl)amino]pyrimidine-5-carbonitrile [87] (hereinafter, referred to as the compound [87]) and 4-[8-(difluoromethyl)imidazo[1,2-a]pyridin-3-yl]-2-[((1S)-1-{3-[(1-methylazetidin-3-yl)amino]phenyl}ethyl)amino]pyrimidine-5-carbonitrile [88] (hereinafter, referred to as the compound [88])

5 mg of the compound [86] was dissolved in a mixture solvent of 0.75 mL of chloroform and 0.25 mL of tetrahydrofuran, and 4.05 µL of formaldehyde solution (37%) was added to homogenize the solution. Thereafter, 11.6 mg of sodium triacetoxyborohydride was added, and stirred at room temperature for 2 hours. Thereto, a saturated aqueous solution of sodium hydrogen carbonate was added, and extracted with chloroform. After drying the organic layer over anhydrous sodium sulfate, the insolubles were filtered and the filtrate was concentrated under reduced pressure to obtain a residue. The residue was purified by preparative thin-layer chromatography, and 1.0 mg of the target compound [87] and 0.7 mg of the target compound [88] were obtained as a white solid, respectively.

Spectral data of the compounds [87] and [88] are presented below.

Compound [87]:
$^1$H-NMR (CDCl$_3$) δ: 9.88-9.84 (m, 1H×⅕), 8.99 (s, 1H×⅕), 8.94-8.80 (m, 1H×⅘+1H×⅘), 8.61 (s, 1H×⅕), 8.57 (s, 1H×⅘), 7.76-7.19 (m, 3H), 6.83-6.62 (m, 4H), 6.13-6.08 (m, 1H×⅘), 5.98-5.90 (m, 1H×⅕), 5.30-5.20 (m, 1H×⅕), 5.10-4.90 (m, 1H×⅘), 4.20-4.07 (m, 1H), 3.95-3.70 (m, 1H), 3.10-2.92 (m, 1H), 2.84 (s, 3H), 2.50-2.40 (m, 1H), 2.39 (s, 3H), 1.63 (d, J=6.8 Hz, 3H)
mass: 489 (M+1)$^+$.

Compound [88]:
$^1$H-NMR (CDCl$_3$) δ: 9.88-9.84 (m, 1H×⅕), 8.99 (s, 1H×⅕), 8.90-8.87 (m, 1H×⅘+1H×⅘), 8.61 (s, 1H×⅕), 8.57 (s, 1H×⅘), 7.64-7.19 (m, 3H), 6.80-6.45 (m, 4H), 6.07-5.97 (m, 1H×⅘), 5.85-5.77 (m, 1H×⅕), 5.28-5.18 (m, 1H×⅕), 5.05-4.90 (m, 1H×⅘), 4.22-4.00 (m, 2H), 3.77-3.65 (m, 2H), 2.95-2.82 (m, 2H), 2.36 (s, 3H), 1.61 (d, J=6.8 Hz, 3H)
mass: 475 (M+1)$^+$.

Example 89

Synthesis of 4-[8-(difluoromethyl)imidazo[1,2-a]pyridin-3-yl]-2-[((1S)-1-{3-[(1-isopropylazetidin-3-yl)amino]phenyl}ethyl)amino]pyrimidine-5-carbonitrile [89] (hereinafter, referred to as the compound [89])

1.8 mg of the target compound [89] was obtained from 5 mg of the compound [86] and 4 µL of acetone, according to the method of Example 87.

A spectral data of the compound [89] is presented below.
$^1$H-NMR (CDCl$_3$) δ: 9.88-9.84 (m, 1H×⅕), 8.99 (s, 1H×⅕), 8.90-8.89 (m, 1H×⅘+1H×⅘), 8.61 (s, 1H×⅕), 8.56 (s, 1H×⅘), 7.65-7.19 (m, 3H), 6.82-6.46 (m, 4H), 6.07-6.05 (m, 1H×⅘), 5.92-5.80 (m, 1H×⅕), 5.28-5.18 (m, 1H×⅕), 5.03-4.90 (m, 1H×⅘), 4.35-4.00 (m, 2H), 3.80-3.62 (m, 2H), 3.02-2.85 (m, 2H), 2.42-2.28 (m, 1H), 1.61 (d, J=6.8 Hz, 3H), 0.96 (d, J=6.6 Hz, 6H)
mass: 503 (M+1)$^+$.

Example 90

Synthesis of 4-[8-(difluoromethyl)imidazo[1,2-a]pyridin-3-yl]-2-{[(1S)-1-(3-{[1-(2-fluoroethyl)azetidin-3-yl]amino}phenyl]ethyl]amino}pyrimidine-5-carbonitrile [90] (hereinafter, referred to as the compound [90])

The mixture of 15 mg of the compound [86], 10.7 mg of 2-fluoroethyl-4-methylbenzensulfonate (synthesized according to a method disclosed in Synthesis 2004, page 885), 9.0 mg of potassium carbonate, and 1 mL of dimethylsulfoxide, was stirred in a sealed-tube at 70° C. for 2 hours and a half. After cooling back to room temperature, the cooled solution was purified by preparative reversed phase liquid chromatography. The eluent was concentrated under reduced pressure, then dissolved in methanol, and trifluoroacetic acid was removed through a weak anion-exchange resin. The solvent was distilled off under reduced pressure to obtain 8.1 mg of the target compound [90] as a white solid.

A spectral data of the compound [90] is presented below.
$^1$H-NMR (CDCl$_3$) δ: 9.86-9.85 (m, 1H×⅕), 8.99 (s, 1H×⅕), 8.90-8.89 (m, 1H×⅘+1H×⅘), 8.61 (s, 1H×⅕), 8.55 (s, 1H×⅘), 7.75-7.12 (m, 3H), 6.80-6.45 (m, 4H), 6.13-6.11 (m, 1H×⅘), 5.88-5.86 (m, 1H×⅕), 5.30-5.18 (m, 1H×⅕), 5.00-4.95 (m, 1H×⅘), 4.46 (td, J=4.8, 47.6 Hz, 2H), 4.22-4.05 (m, 2H), 3.85-3.72 (m, 2H), 3.08-2.93 (m, 2H), 2.77 (td, J=4.8, 28.8 Hz, 2H), 1.61 (d, J=6.8 Hz, 3H)
mass: 507 (M+1)$^+$.

Example 91

Synthesis of 4-[8-(difluoromethyl)imidazo[1,2-a]pyridin-3-yl]-2-[((1S)-1-{3-[(1-methylpiperidin-4-yl)amino]phenyl}ethyl)amino]pyrimidine-5-carbonitrile [91] (hereinafter, referred to as the compound [91])

11.4 mg of the compound [80] was dissolved in 0.75 mL of chloroform, and 10.4 µL of 1-methyl-4-piperidone and 17.9 mg of sodium triacetoxyborohydride were added thereto. The mixture was stirred overnight at 50° C. After cooling back to room temperature, a saturated aqueous solution of sodium hydrogen carbonate was added, and extracted with chloroform. After drying the organic layer over anhydrous sodium sulfate, the insolubles were filtered and the filtrate was concentrated under reduced pressure to obtain a residue. The residue was purified by preparative thin-layer chromatography, and 12.5 mg of the target compound [91] was obtained as a pale yellow solid.

A spectral data of the compound [91] is presented below.
$^1$H-NMR (CDCl$_3$) δ: 9.86 (d, J=7.2 Hz, 1H×⅕), 8.99 (s, 1H×⅕), 8.91 (d, J=7.2 Hz, 1H×⅘), 8.89 (s, 1H×⅘), 8.62 (s, 1H×⅕), 8.55 (s, 1H×⅘), 7.74-7.11 (m, 3H), 6.85-6.53 (m, 4H), 6.12-6.11 (m, 1H×⅘), 5.96-5.85 (m, 1H×⅕), 5.28-5.17 (m, 1H×⅕), 5.05-4.88 (m, 1H×⅘), 3.72-3.60 (m, 1H), 3.38-3.22 (m, 1H), 2.82-2.79 (m, 2H), 2.34 (s, 3H), 2.18-1.90 (m, 4H), 1.62 (d, J=6.8 Hz, 3H), 1.58-1.40 (m, 2H)
mass: 503 (M+1)$^+$.

Example 92

Synthesis of 4-[8-(difluoromethyl)imidazo[1,2-a]pyridin-3-yl]-2-[((1S)-1-{3-[(1-ethylpiperidin-4-yl)amino]phenyl}ethyl)amino]pyrimidine-5-carbonitrile [92] (hereinafter, referred to as the compound [92])

5.9 mg of the target compound [92] was obtained as a white solid, from 10 mg of the compound [80] and 5.0 µL of 1-ethyl-4-piperidone, according to the method of Example 91.

A spectral data of the compound [92] is presented below.
$^1$H-NMR (CDCl$_3$) δ: 9.72-9.68 (m, 1H×⅕), 8.99 (s, 1H×⅕), 8.92-8.89 (m, 1H×⅘+1H×⅘), 8.62 (s, 1H×⅕), 8.56 (s, 1H×⅘), 7.73-7.12 (m, 3H), 6.85-6.53 (m, 4H), 6.06-6.05 (m, 1H×⅘), 5.88-5.80 (m, 1H×⅕), 5.25-5.17 (m, 1H×⅕), 5.02-4.88 (m, 1H×⅘), 3.66 (brs, 1H), 3.41-3.28 (m, 1H), 3.00-2.85 (m, 2H), 2.47 (q, J=6.0 Hz, 2H), 2.23-2.00 (m, 4H), 1.62 (d, J=6.8 Hz, 3H), 1.60-1.43 (m, 2H), 0.91 (t, J=6.0 Hz, 3H)
mass: 517 (M+1)$^+$.

Example 93

Synthesis of 4-[8-(difluoromethyl)imidazo[1,2-a]pyridin-3-yl]-2-[((1S)-1-{3-[(1-ethylpiperidin-3-yl)amino]phenyl}ethyl)amino]pyrimidine-5-carbonitrile [93] (hereinafter, referred to as the compound [93])

13.2 mg of the target compound [93] was obtained as a white solid, from 15 mg of the compound [80] and 18.2 mg of 1-ethyl-3-piperidone hydrochloride, according to the method of Example 91.
A spectral data of the compound [93] is presented below.
$^1$H-NMR (CDCl$_3$) δ: 9.88-9.84 (m, 1H×⅕), 8.99-8.99 (m, 1H+1H×⅘), 8.61 (s, 1H×⅕), 8.55 (s, 1H×⅘), 7.73-7.15 (m, 3H), 6.88-6.56 (m, 4H), 6.18-6.07 (m, 1H), 5.33-5.20 (m, 1H×⅕), 5.05-4.89 (m, 1H×⅘), 4.20-3.95 (m, 1H×⅕), 3.72-3.50 (m, 1H×⅘), 2.88-2.10 (m, 4H), 1.62 (d, J=6.8 Hz, 3H), 1.88-1.35 (m, 2H), 1.08-1.03 (m, 3H)
mass: 517 (M+1)$^+$.

Example 94

Synthesis of 4-[8-(difluoromethyl)imidazo[1,2-a]pyridin-3-yl]-2-[((1S)-1-{3-[(1-isopropylpiperidin-4-yl)amino]phenyl}ethyl)amino]pyrimidine-5-carbonitrile [94] (hereinafter, referred to as the compound [94])

6.8 mg of the target compound [94] was obtained as a white solid, from 10 mg of the compound [80] and 10.5 mg of 1-isopropyl-4-piperidone, according to the method of Example 91.
A spectral data of the compound [94] is presented below.
$^1$H-NMR (CDCl$_3$) δ: 9.86 (d, J=6.9 Hz, 1H×⅕), 8.99 (s, 1H×⅕), 8.90 (d, J=6.9 Hz, 1H×⅘), 8.89 (s, 1H×⅘), 8.61 (s, 1H×⅕), 8.55 (s, 1H×⅘), 7.64-7.14 (m, 3H), 6.86-6.53 (m, 4H), 6.10-6.08 (m, 1H×⅘), 5.92-5.80 (m, 1H×⅕), 5.28-5.15 (m, 1H×⅕), 5.02-4.89 (m, 1H×⅘), 3.78-3.50 (m, 1H), 3.38-3.20 (m, 1H), 2.97-2.72 (m, 3H), 2.34 (s, 3H), 2.39-1.84 (m, 4H), 1.62 (d, J=7.0 Hz, 3H), 1.56-1.40 (m, 2H), 1.08 (d, J=6.6 Hz, 6H)
mass: 531 (M+1)$^+$.

Example 95

Synthesis of 4-[8-(difluoromethyl)imidazo[1,2-a]pyridin-3-yl]-2-{[(1S)-1-(3-{[1-(2-hydroxyethyl)piperidin-4-yl]amino}phenyl]ethyl]amino}pyrimidine-5-carbonitrile [95] (hereinafter, referred to as the compound [95])

(1) 172 mg of 4-[8-(difluoromethyl)imidazo[1,2-a]pyridin-3-yl]-2-({(1S)-1-[3-(piperidin-4-ylamino)phenyl]ethyl}amino)pyrimidine-5-carbonitrile [95-1] was obtained as a light brown solid, from 181 mg of the compound [80] and 267 mg of 1-(t-butoxycarbonyl)-4-piperidone, according to the methods of Example 82-(1) and (2).

(2) 33.1 mg of the target compound [95] was obtained as a yellow solid, from 110 mg of the 4-[8-(difluoromethyl)imidazo[1,2-a]pyridin-3-yl]-2-({(1S)-1-[3-(piperidin-4-ylamino)phenyl]ethyl}amino)pyrimidine-5-carbonitrile [95-1] and 71.5 μL of (t-butyldimethylsilyloxy)acetoaldehyde, according to the methods of Example 83-(1) and (2).

A spectral data of the compound [95] is presented below.
$^1$H-NMR (CDCl$_3$) δ: 9.88-9.84 (m, 1H×⅕), 8.99 (s, 1H×⅕), 8.92-8.89 (m, 1H×⅘+1H×⅘), 8.62 (s, 1H×⅕), 8.56 (s, 1H×⅘), 7.64-7.19 (m, 3H), 6.85-6.53 (m, 4H), 6.08-6.07 (m, 1H×⅘), 5.88-5.80 (m, 1H×⅕), 5.28-5.18 (m, 1H×⅕), 4.99-4.96 (m, 1H×⅘), 3.67-3.60 (m, 3H), 3.40-3.25 (m, 1H), 2.90-2.87 (m, 2H), 2.80-2.65 (m, 1H), 2.57-2.54 (m, 2H), 2.25-2.20 (m, 2H), 2.05-2.03 (m, 2H), 1.61 (d, J=6.8 Hz, 3H), 1.55-1.35 (m, 2H)
mass: 533 (M+1)$^+$.

Example 96

Synthesis of 4-[8-(difluoromethyl)imidazo[1,2-a]pyridin-3-yl]-2-({(1S)-1-[3-({1-[2-(dimethylamino)ethyl]piperidin-4-yl}amino)phenyl]ethyl}amino)pyrimidine-5-carbonitrile [96] (hereinafter, referred to as the compound [96])

4.3 mg of the target compound [96] was obtained as a white solid, from 21.1 mg of the compound [95] and 99 μL of dimethylamine (2M tetrahydrofuran solution), according to the method of Example 84.
A spectral data of the compound [96] is presented below.
$^1$H-NMR (CDCl$_3$) δ: 9.88-9.84 (m, 1H×⅕), 8.99 (s, 1H×⅕), 8.91-8.89 (m, 1H×⅘+1H×⅘), 8.61 (s, 1H×⅕), 8.56 (s, 1H×⅘), 7.64-7.14 (m, 3H), 6.85-6.52 (m, 4H), 6.06-6.05 (m, 1H×⅘), 5.89-5.78 (m, 1H×⅕), 5.28-5.15 (m, 1H×⅕), 5.02-4.90 (m, 1H×⅘), 3.75-3.52 (m, 1H), 3.37-3.22 (m, 1H), 2.95-2.82 (m, 2H), 2.53-2.40 (m, 4H), 2.26 (s, 6H), 2.23-1.95 (m, 4H), 1.62 (d, J=6.9 Hz, 3H), 1.60-1.38 (m, 2H)
mass: 560 (M+1)$^+$.

Example 97

Synthesis of 4-[8-(difluoromethyl)imidazo[1,2-a]pyridin-3-yl]-2-{[(1S)-1-(3-{[1-(2-fluoroethyl)piperidin-4-yl]amino}phenyl]ethyl]amino}pyrimidine-5-carbonitrile [97] (hereinafter, referred to as the compound [97])

4.0 mg of the target compound [97] was obtained as a white solid, from 11.4 mg of the 4-[8-(difluoromethyl)imidazo[1,2-a]pyridin-3-yl]-2-({(1S)-1-[3-(piperidin-4-ylamino)phenyl]ethyl}amino)pyrimidine-5-carbonitrile [95-1] and 4.8 mg of 2-fluoroethyl-4-methylbenzensulfonate, according to the method of Example 90.
A spectral data of the compound [97] is presented below.
$^1$H-NMR (CDCl$_3$) δ: 9.88-9.84 (m, 1H×⅕), 8.99 (s, 1H×⅕), 8.92-8.90 (m, 1H×⅘), 8.61 (s, 1H×⅕), 8.56 (s, 1H×⅘), 7.78-7.14 (m, 3H), 6.86-6.53 (m, 4H), 6.08-6.06 (m, 1H×⅘), 5.92-5.80 (m, 1H×⅕), 5.28-5.15 (m, 1H×⅕), 5.03-4.90 (m, 1H×⅘), 4.58 (td, J=4.8, 47.5 Hz, 2H), 3.78-3.44 (m, 1H), 3.38-3.22 (m, 1H), 2.99-2.83 (m, 2H), 2.73 (td, J=4.8, 28.3 Hz, 2H), 2.32-2.17 (m, 2H), 2.12-1.95 (m, 2H), 1.62 (d, J=6.9 Hz, 3H), 1.60-1.40 (m, 2H)
mass: 535 (M+1)$^+$.

Example 98

Synthesis of 4-[8-(difluoromethyl)imidazo[1,2-a]pyridin-3-yl]-2-[((1S)-1-{3-[(1'-methyl-1,4'-bipiperidin-4-yl)amino]phenyl}ethyl)amino]pyrimidine-5-carbonitrile [98] (hereinafter, referred to as the compound [98])

3.5 mg of the target compound [98] was obtained as colorless amorphous, from 20 mg of the 4-[8-(difluoromethyl)imidazo[1,2-a]pyridin-3-yl]-2-({(1S)-1-[3-(piperidin-4-ylamino)phenyl)ethyl}amino)pyrimidine-5-carbonitrile [95-1] and 15.1 µL of 1-methyl-4-piperidone, according to the method of Example 91.

A spectral data of the compound [98] is presented below.
$^1$H-NMR (CDCl$_3$) δ: 9.88-9.85 (m, 1H×⅕), 8.99 (s, 1H×⅕), 8.90-8.89 (m, 1H×⅘+1H×⅘), 8.61 (s, 1H×⅕), 8.56 (s, 1H×⅘), 7.78-7.10 (m, 3H), 6.88-6.50 (m, 4H), 6.10-6.02 (m, 1H×⅘), 5.88-5.80 (m, 1H×⅕), 5.28-5.18 (m, 1H×⅕), 5.02-4.90 (m, 1H×⅘), 3.75-3.56 (m, 1H), 3.32-3.20 (m, 1H), 2.96-2.82 (m, 4H), 2.40-2.29 (m, 4H), 2.28 (s, 3H), 2.13-1.60 (m, 7H), 1.62 (d, J=6.8 Hz, 3H), 1.55-1.37 (m, 2H)
mass: 586 (M+1)$^+$.

Example 99

Synthesis of 4-[8-(difluoromethyl)imidazo[1,2-a]pyridin-3-yl]-2-{[(1S)-1-(3-{[1-(pyridin-3-ylmethyl)piperidin-4-yl]amino}phenyl)ethyl]amino}pyrimidine-5-carbonitrile [99] (hereinafter, referred to as the compound [99])

9.3 mg of the target compound [99] was obtained as a white solid, from 20 mg of the 4-[8-(difluoromethyl)imidazo[1,2-a]pyridin-3-yl]-2-({(1S)-1-[3-(piperidin-4-ylamino)phenyl]ethyl}amino}pyrimidine-5-carbonitrile [95-1] and 11.6 µL of 3-pyridinecarboxaldehyde, according to the method of Example 91.

A spectral data of the compound [99] is presented below.
$^1$H-NMR (CDCl$_3$) δ: 9.86-9.85 (m, 1H×⅕), 8.99 (s, 1H×⅕), 8.90-8.89 (m, 1H×⅘+1H×⅘), 8.61 (s, 1H×⅕), 8.55-8.51 (s, 1H+1H×⅘), 7.78-7.08 (m, 5H), 6.85-6.53 (m, 4H), 6.18-6.10 (m, 1H×⅘), 5.93-5.85 (m, 1H×⅕), 5.27-5.15 (m, 1H×⅕), 5.02-4.88 (m, 1H×⅘), 3.54 (s, 2H), 3.38-3.20 (m, 2H), 2.88-2.73 (m, 2H), 2.25-1.93 (m, 4H), 1.62 (d, J=6.8 Hz, 3H), 1.58-1.38 (m, 2H)
mass: 580 (M+1)$^+$.

Example 100

Synthesis of 4-[8-(difluoromethyl)imidazo[1,2-a]pyridin-3-yl]-2-[((1S)-1-{3-[(4-methylpiperazin-1-yl)carbonyl]phenyl}ethyl)amino]pyrimidine-5-carbonitrile [100] (hereinafter, referred to as the compound [100])

(1) 1.16 g of 3-(1-hydroxyethyl)methyl benzoate ester (synthesized according to a method disclosed in page 133 in Pamphlet of International Publication WO 00/042,045) was dissolved in 20 mL of chloroform, and 4.49 mL of triethylamine was added thereto. Under an ice-cold condition, 1.49 mL of methanesulfonyl chloride was added, and stirred at the same temperature for 40 minutes. Thereto, a saturated aqueous solution of sodium hydrogen carbonate was added, and extracted with chloroform. The organic layer was washed with saturated brine, and then dried over anhydrous sodium sulfate. The insolubles were filtered, and the filtrate was concentrated under reduced pressure. The obtained residue was dissolved in N,N-dimethylformamide, 2.09 g of sodium azide was added thereto, and stirred at 80° C. for 2 hours. After cooling the reaction solution back to room temperature, a saturated aqueous solution of sodium hydrogen carbonate was added, and extracted with ethyl acetate. The organic layer was washed with diluted brine and saturated brine in the subsequent order, and then dried over anhydrous magnesium sulfate. After filtering the insolubles, the filtrate was concentrated under reduced pressure, and thus obtained residue was purified by silica gel column chromatography, to obtain 1.21 g of methyl 3-(1-azidoethyl)benzoate [100-1] as a colorless oily product.

(2) 600 mg of the methyl 3-(1-azidoethyl)benzoate [100-1] was dissolved in 15 mL of ethanol, 200 mg of 10% palladiumcarbon catalyst was added thereto, and stirred overnight in a hydrogen atmosphere. The insolubles were filtered through celite, washed with ethanol, and then the filtrate was concentrated under reduced pressure to obtain 300 mg of methyl 3-(1-aminoethyl)benzoate [100-2] as a colorless oily product.

(3) 374 mg of methyl 3-[1-({5-cyano-4-[8-(difluoromethyl)imidazo[1,2-a]pyridin-3-yl]pyrimidin-2-yl}amino)ethyl]benzoate [100-3] was obtained as a yellow oily product, from 285 mg of the 4-[8-(difluoromethyl)imidazo[1,2-a]pyridin-3-yl]-2-(methylthio)pyrimidine-5-carbonitrile [80-3] and 242 mg of the methyl 3-(1-aminoethyl)benzoate [100-2], according to the method of Example 80-(4).

(4) 370 mg of the methyl 3-[1-({5-cyano-4-[8-(difluoromethyl)imidazo[1,2-a]pyridin-3-yl]pyrimidin-2-yl}amino)ethyl]benzoate [100-3] was suspended in a mixture solvent of 6 mL of methanol and 6 mL of tetrahydrofuran, then 4.15 mL of 1N aqueous solution of sodium hydroxide was added, and stirred at 50° C. for 30 minutes. Under an ice-cold condition, 825 µL of 5N hydrochloric acid was added, then the reaction solution was neutralized and concentrated under reduced pressure. The obtained residue was purified by preparative reversed phase liquid chromatography, and 216 mg of 3-[1-({5-cyano-4-[8-(difluoromethyl)imidazo[1,2-a]pyridin-3-yl]pyrimidin-2-yl}amino)ethyl] benzoic acid [100-4] was obtained as a pale yellow solid.

(5) 8.0 mg of the target compound [100] was obtained as a white solid, from 10 mg of the 3-[1-({5-cyano-4-[8-(difluoromethyl)imidazo[1,2-a]pyridin-3-yl]pyrimidin-2-yl}amino)ethyl] benzoic acid [100-4] and 6.1 mg of N-methylpiperazine, according to the method of Example 81.

A spectral data of the compound [100] is presented below.
$^1$H-NMR (CDCl$_3$) δ: 9.89 (d, J=6.8 Hz, 1H×⅕), 9.00-8.94 (m, 1H+1H×⅘), 8.57 (s, 1H), 8.02-7.00 (m, 7H), 6.22-6.20 (m, 1H×⅘), 5.98-5.96 (m, 1H×⅕), 5.37-5.35 (m, 1H×⅕), 5.18-5.14 (m, 1H×⅘), 3.88-3.65 (m, 2H), 3.48-3.28 (m, 2H), 2.58-2.15 (m, 4H), 2.31 (s, 3H), 1.67 (d, J=6.8 Hz, 3H)
mass: 517 (M+1)$^+$.

Example 101

Synthesis of 4-[8-(difluoromethyl)imidazo[1,2-a]pyridin-3-yl]-2-[((1S)-1-{3-[(4-methylpiperazin-1-yl)methyl]phenyl}ethyl)amino]pyrimidine-5-carbonitrile [101] (hereinafter, referred to as the compound [101])

(1) 151 mg of the 3-[1-({5-cyano-4-[8-(difluoromethyl)imidazo[1,2-a]pyridin-3-yl]pyrimidin-2-yl}amino)ethyl] benzoic acid [100-4] was dissolved in 4 mL of tetrahydrofuran, then 282 mg of N,N-carbonyldiimidazole was added, and stirred overnight at room temperature. The reaction mixture was added with 132 mg of sodium boronhydride in two additions, and stirred at room temperature for 30 minutes. Thereto, a saturated aqueous solution of sodium hydrogen carbonate was added, and extracted with ethyl acetate. The organic layer was washed with saturated brine, and dried over anhydrous sodium sulfate. The insolubles were filtered, the filtrate was concentrated under reduced pressure, and the thus obtained residue was purified by preparative thin-layer chromatography, to obtain 50 mg of 4-[8-(difluoromethyl)imidazo[1,2-a]pyridin-3-yl]-2-({1-[3-(hydroxymethyl)phenyl]ethyl}amino)pyrimidin-5-carbonitrile [101-1] as a pale yellow oily product.

(2) 3.3 mg of the target compound [101] was obtained as a white solid, from 25 mg of the 4-[8-(difluoromethyl)imidazo[1,2-a]pyridin-3-yl]-2-({1-[3-(hydroxymethyl)phenyl]ethyl}amino)pyrimidin-5-carbonitrile [101-1] and 15 mg of N-methylpiperazine, according to the method of Example 84.

A spectral data of the compound [101] is presented below.
$^1$H-NMR (CDCl$_3$) δ: 9.88 (d, J=7.2 Hz, 1H×⅕), 9.05 (d, J=7.2 Hz, 1H×⅘), 8.99 (s, 1H×⅕), 8.94 (s, 1H×⅘), 8.60 (s, 1H×⅕), 8.57 (s, 1H×⅘), 7.74-6.79 (m, 7H), 6.12-6.10 (m, 1H×⅘), 5.90-5.74 (m, 1H×⅕), 5.38-5.32 (m, 1H×⅕), 5.14-5.10 (m, 1H×⅘), 3.57-3.47 (m, 2H), 2.62-2.03 (m, 8H), 2.26 (s, 3H), 1.65 (d, J=6.8 Hz, 3H)
mass: 503 (M+1)$^+$.

Example 102

Synthesis of N-{3-[(1S)-1-({5-cyano-4-[8-(difluoromethyl)imidazo[1,2-a]pyridin-3-yl]pyrimidin-2-yl}amino)ethyl]benzyl}glycinamide [102] (hereinafter, referred to as the compound [102])

(1) 125 mg of the 4-[8-(difluoromethyl)imidazo[1,2-a]pyridin-3-yl]-2-({1-[3-(hydroxymethyl)phenyl]ethyl}amino]pyrimidin-5-carbonitrile [101-1] and 259 μL of N,N-diisopropylethylamine were dissolved in 3 mL of chloroform, then 69 μL of methanesulfonyl chloride was added under an ice-cold condition, and stirred at the same temperature for 30 minutes. Thereto, a saturated aqueous solution of sodium hydrogen carbonate was added, and extracted with chloroform. The obtained organic layer was washed with saturated brine, and dried over anhydrous sodium sulfate. The insolubles were filtered and the filtrate was concentrated under reduced pressure to obtain a residue. The residue was dissolved in 3 mL of N,N-dimethylformamide. Thereto, 97 mg of sodium azide was added, and stirred at 80° C. for 1 hour. The reaction solution was cooled back to room temperature, then a saturated aqueous solution of sodium hydrogen carbonate was added, and extracted with ethyl acetate. The obtained organic layer was washed with saturated brine, and dried over anhydrous sodium sulfate. The insolubles were filtered and the filtrate was concentrated under reduced pressure to obtain a residue. The residue was purified by preparative thin-layer chromatography, and 87 mg of 2-({1-[3-(azidomethyl)phenyl)ethyl}amino)-4-[8-(difluoromethyl)imidazo[1,2-a]pyridin-3-yl]pyrimidin-5-carbonitrile [102-1] was obtained as a light brown oily product.

(2) 87 mg of the 2-({1-[3-(azidomethyl)phenyl)ethyl}amino)-4-[8-(difluoromethyl)imidazo[1,2-a]pyridin-3-yl]pyrimidin-5-carbonitrile [102-1] was dissolved in 3 mL of ethanol, then 50 mg of 10% palladiumcarbon catalyst was added, and stirred overnight at room temperature in a hydrogen atmosphere. The insolubles were filtered through celite, the filtrate was concentrated under reduced pressure, and 76 mg of 2-({1-[3-(aminomethyl)phenyl)ethyl}amino)-4-[8-(difluoromethyl)imidazo[1,2-a]pyridin-3-yl]pyrimidin-5-carbonitrile [102-2] was obtained as a yellow solid.

(3) 5.11 mg of the target compound [102] was obtained as a pale yellow solid, from 10.4 mg of the 2-({1-[3-(aminomethyl)phenyl)ethyl}amino)-4-[8-(difluoromethyl)imidazo[1,2-a]pyridin-3-yl]pyrimidin-5-carbonitrile [102-2] and 13 mg of N-t-butoxycarbonylglycine, according to the method of Example 81.

A spectral data of the compound [102] is presented below.
$^1$H-NMR (CDCl$_3$) δ: 9.99 (d, J=6.8 Hz, 1H×⅕), 9.01 (d, J=6.8 Hz, 1H×⅘), 8.97 (s, 1H×⅕), 8.90 (s, 1H×⅘), 8.58 (s, 1H×⅕), 8.57 (s, 1H×⅘), 7.76-6.51 (m, 9H), 5.33-5.31 (m, 1H×⅕), 5.13-5.08 (m, 1H×⅘), 5.46 (s, 2H×⅕), 3.37 (s, 2H×⅘), 2.42-2.18 (m, 2H), 1.64 (d, J=7.2 Hz, 3H)
mass: 477 (M+1)$^+$.

Example 103

Synthesis of N-{4-[(1S)-1-({5-cyano-4-[8-(difluoromethyl)imidazo[1,2-a]pyridin-3-yl]pyrimidin-2-yl}amino)ethyl]phenyl}-L-alaninamide [103] (hereinafter, referred to as the compound [103])

(1) 83 mg of 4-[8-(difluoromethyl)imidazo[1,2-a]pyridin-3-yl]-2-{[(1S)-1-(4-nitrophenyl)ethyl]amino}pyrimidine-5-carbonitrile [103-1] was obtained as a pale yellow solid, from 95 mg of the 4-[8-(difluoromethyl)imidazo[1,2-a]pyridin-3-yl]-2-(methylthio)pyrimidine-5-carbonitrile [80-3] and 73 mg of (S)-α-methyl-4-nitrobenzylamine hydrochloride, according to the method of Example 80-(4).

(2) 83 mg of the 4-[8-(difluoromethyl)imidazo[1,2-a]pyridin-3-yl]-2-{[(1S)-1-(4-nitrophenyl)ethyl]amino}pyrimidine-5-carbonitrile [103-1] was dissolved in a mixture solvent of 2 mL of ethanol and 3 mL of tetrahydrofuran, then 40 mg of 10% palladiumcarbon catalyst was added, and stirred overnight at room temperature in a hydrogen atmosphere. The insolubles were filtered through celite and the filtrate was concentrated under reduced pressure to obtain a residue. The residue was purified by preparative thin-layer chromatography, and 14 mg of 2-{[(1S)-1-(4-aminophenyl)ethyl]amino}-4-[8-(difluoromethyl)imidazo[1,2-a]pyridin-3-yl]pyrimidin-5-carbonitrile [103-2] was obtained as pale yellow amorphous.

(3) 11 mg of the target compound [103] was obtained as a white solid, from 11 mg of the 2-{[(1S)-1-(4-aminophenyl)ethyl]amino}-4-[8-(difluoromethyl)imidazo[1,2-a]pyridin-3-yl]pyrimidin-5-carbonitrile [103-2] and 14 mg of N-t-butoxycarbonylalanine, according to the method of Example 81.

A spectral data of the compound [103] is presented below.
$^1$H-NMR (DMSO-d$_6$) δ: 10.38-10.36 (m, 1H), 10.20 (d, J=7.0 Hz, 1H×½), 9.16 (d, J=7.0 Hz, 1H×½), 9.05 (d, J=6.7 Hz, 1H×½), 8.97 (d, J=8.2 Hz, 1H×½), 8.79 (s, 1H×½), 8.78 (s, 1H×½), 8.75 (s, 1H×½), 8.64 (s, 1H×½), 8.10 (brs, 2H), 7.87 (d, J=7.0 Hz, 1H×½), 7.79 (d, J=6.7 Hz, 1H×½), 7.65-7.39 (m, 5H), 7.33 (t, J=7.0 Hz, 1H×½), 7.14 (t, J=7.0 Hz, 1H×½), 5.23-5.20 (m, 1H×½), 5.10-5.06 (m, 1H×½), 3.97-3.93 (m, 1H), 1.53 (d, J=7.0 Hz, 3H×½), 1.49 (d, J=7.0 Hz, 3H×½), 1.41 (t, J=7.0 Hz, 3H)
mass: 477 (M+1)$^+$.

Example 104

Synthesis of 4-[8-(difluoromethyl)imidazo[1,2-a]pyridin-3-yl]-2-[((1S)-1-{4-[(1-methylpiperidin-4-yl)amino]phenyl}ethyl)amino]pyrimidine-5-carbonitrile [104] (hereinafter, referred to as the compound [104])

7 mg of the target compound [104] was obtained as a white solid, from 20 mg of the 2-{[(1S)-1-(4-aminophenyl)ethyl]amino}-4-[8-(difluoromethyl)imidazo[1,2-a]pyridin-3-yl]pyrimidin-5-carbonitrile [103-2] and 7.4 μL of 1-methyl-4-piperidone, according to the method of Example 82-(1).

A spectral data of the compound [104] is presented below.
$^1$H-NMR (DMSO-d$_6$) δ: 10.20 (d, J=6.1 Hz, 1H×½), 9.22 (d, J=7.1 Hz, 1H×½), 8.92 (d, J=7.3 Hz, 1H×½), 8.80 (d, J=8.3 Hz, 1H×½), 8.78 (s, 1H×½), 8.76 (s, 1H×½), 8.75 (s, 1H×½), 8.63 (s, 1H×½), 7.85 (d, J=7.6 Hz, 1H×½), 7.80 (d, J=7.3 Hz, 1H×½), 7.51 (t, J=54.6 Hz, 1H×½), 7.47 (t, J=54.6 Hz, 1H×½), 7.29 (t, J=6.8 Hz, 1H×½), 7.14 (t, J=6.8 Hz, 1H×½), 7.11 (d, J=8.5 Hz, 1H), 7.09 (d, J=8.5 Hz, 1H), 6.55 (d, J=8.5 Hz, 1H), 6.52 (d, J=8.5 Hz, 1H), 5.33 (t, J=8.5 Hz, 1H), 5.15-5.07 (m, 1H×½), 4.97-4.90 (m, 1H×½), 3.13-3.08 (m, 1H), 2.70-2.65 (m, 2H), 2.13 (s, 3H×½), 2.12 (s, 3H×½), 1.98-1.90 (m, 2H), 1.84-1.79 (m, 2H), 1.47 (d, J=6.8 Hz, 3H×½), 1.44 (d, J=6.8 Hz, 3H×½), 1.37-1.29 (m, 2H)
mass: 503 (M+1)$^+$.

Example 105

Synthesis of 4-[8-(difluoromethyl)imidazo[1,2-a]pyridin-3-yl]-2-[((1S)-1-{4-[(1-isopropylpiperidin-4-yl)amino]phenyl}ethyl)amino]pyrimidin-5-carbonitrile [105] (hereinafter, referred to as the compound [105])

6 mg of the target compound [105] was obtained as a white solid, from 10 mg of the 2-{[(1S)-1-(4-aminophenyl)ethyl]amino}-4-[8-(difluoromethyl)imidazo[1,2-a]pyridin-3-yl]pyrimidin-5-carbonitrile [103-2] and 17.4 μL of 1-isopropyl-4-piperidone, according to the method of Example 82-(1).

A spectral data of the compound [105] is presented below.
$^1$H-NMR (DMSO-d$_6$) δ: 10.20 (d, J=7.1 Hz, 1H×½), 9.22 (d, J=6.6 Hz, 1H×½), 8.92 (d, J=7.3 Hz, 1H×½), 8.80 (d, J=8.3 Hz, 1H×½), 8.78 (s, 1H×½), 8.76 (s, 1H×½), 8.75 (s, 1H×½), 8.63 (s, 1H×½), 7.85 (d, J=7.3 Hz, 1H×½), 7.80 (d, J=7.6 Hz, 1H×½), 7.51 (t, J=54.4 Hz, 1H×½), 7.47 (t, J=54.4 Hz, 1H×½), 7.29 (t, J=7.1 Hz, 1H×½), 7.14 (t, J=7.1 Hz, 1H×½), 7.11-7.08 (m, 2H), 6.56-6.51 (m, 2H), 5.32 (t, J=8.4 Hz, 1H), 5.15-5.09 (m, 1H×½), 4.96-4.89 (m, 1H×½), 3.13-3.07 (m, 1H), 2.73-2.62 (m, 3H), 2.20-2.12 (m, 2H), 1.87-1.81 (m, 2H), 1.47 (d, J=6.8 Hz, 3H×½), 1.44 (d, J=6.8 Hz, 1H×½), 1.31-1.23 (m, 2H), 0.94 (d, J=6.6 Hz, 3H), 0.93 (d, J=6.6 Hz, 3H)
mass: 531 (M+1)$^+$.

Example 106

Synthesis of 4-[8-(difluoromethyl)imidazo[1,2-a]pyridin-3-yl]-2-({((1S)-1-[4-(pyrazin-2-ylamino)phenyl]ethyl}amino)pyrimidine-5-carbonitrile [106] (hereinafter, referred to as the compound [106])

(1) 2 g of S-(−)-1-(4-bromophenyl)ethylamine was dissolved in 20 mL of chloroform, and 4.18 mL of triethylamine was added thereto. Under an ice-cold condition, 2.62 g of dicarbonic acid di-t-butyl was added, and stirred at room temperature for 30 minutes. The reaction solution was diluted in 300 mL of ethyl acetate, washed with water and saturated brined in the subsequent order, and the obtained organic layer was dried over anhydrous magnesium sulfate. The insolubles were filtered and the filtrate was concentrated under reduced pressure to obtain a residue. The residue was dissolved in a small amount of chloroform and solidified by hexane, to obtain 2.6 g of t-butyl[(1S)-1-(4-bromophenyl)ethyl]carbamate [106-1] as a white solid.

(2) The mixture of 100 mg of the t-butyl[(1S)-1-(4-bromophenyl)ethyl]carbamate [106-1], 38 mg of 2-aminopyrazine, 6.8 mg of tris(dibenzylideneacetone)(chloroform)dipalladium (0), 7.7 mg of 4,5-bis(diphenylphosphino)-9,9-dimethylxanthene, 217 mg of cesium carbonate, and 3 mL of 1,4-dioxane, was stirred overnight at 100° C. After cooling the reaction mixture back to room temperature, the insolubles were filtered through celite, the filtrate was concentrated under reduced pressure, and the thus obtained residue was purified by silica gel chromatography, to obtain 50 mg of t-butyl {(1S)-1-[4-(pyrazin-2-ylamino)phenyl]ethyl}carbamate [106-2] as a pale yellow solid.

(3) 50 mg of the t-butyl{(1S)-1-[4-(pyrazin-2-ylamino)phenyl]ethyl}carbamate [106-2] was dissolved in 2 mL of chloroform, 2 mL of trifluoroacetic acid was added thereto, and stirred at room temperature for 1 hour. The reaction solution was concentrated under reduced pressure, and 51 mg of a trifluoroacetate salt of N-{4-[(1S)-1-aminoethyl]phenyl}pyrazin-2-amine [106-3] was obtained as a brown oily product.

(4) 9.2 mg of the target compound [106] was obtained as a pale yellow solid, from 37 mg of the 4-[8-(difluoromethyl)imidazo[1,2-a]pyridin-3-yl]-2-(methylthio)pyrimidine-5-carbonitrile [80-3] and 51 mg of a trifluoroacetate salt of the N-{4-[(1S)-1-aminoethyl]phenyl}pyrazin-2-amine [106-3], according to the method of Example 80-(4).

A spectral data of the compound [106] is presented below.
$^1$H-NMR (CDCl$_3$) δ: 9.83 (m, 1H×¼), 9.23 (m, 1H×¾), 8.99 (s, 1H×¼), 8.93 (s, 1H×¾), 8.62 (s, 1H×¼), 8.57 (s, 1H×¾), 8.20 (m, 1H), 8.12 (m, 1H), 8.00 (m, 1H), 7.70-7.10 (m, 5H+1H×¼), 6.88 (m, 1H×¾), 6.59 (m, 1H), 6.13 (m, 1H×¾), 5.80 (m, 1H×¼), 5.30 (m, 1H×¼), 5.10 (m, 1H×¾), 1.65 (d, J=7.6 Hz, 3H)
mass: 484 (M+1)$^+$.

Example 107

Synthesis of 4-[8-(difluoromethyl)imidazo[1,2-a]pyridin-3-yl]-2-({(1S)-1-[4-(4-methylpiperazin-1-yl)phenyl]ethyl}amino)pyrimidin-5-carbonitrile [107] (hereinafter, referred to as the compound [107])

(1) 44 mg of t-butyl{(1S)-1-[4-(4-methylpiperazin-1-yl)phenyl]ethyl}carbamate [107-1] was obtained as a light brown solid, from 100 mg of the t-butyl[(1S)-1-(4-bromophenyl)ethyl]carbamate [106-1] and 40 mg of N-methylpiperazine, according to the method of Example 106-(2).

(2) 12 mg of the target compound [107] was obtained as a pale yellow solid, from 28 mg of the 4-[8-(difluoromethyl)imidazo[1,2-a]pyridin-3-yl]-2-(methylthio)pyrimidine-5-carbonitrile [80-3] and 44 mg of the t-butyl{(1S)-1-[4-(4-methylpiperazin-1-yl)phenyl]ethyl}carbamate [107-1], according to the methods of Example 106-(3) and (4).

A spectral data of the compound [107] is presented below.
$^1$H-NMR (CDCl$_3$) δ: 9.83 (m, 1H×¼), 9.05 (d, J=7.2 Hz, 1H×¾), 8.99 (s, 1H×¼), 8.91 (s, 1H×¾), 8.62 (s, 1H×¼), 8.58 (s, 1H×¾), 7.73 (m, 1H×¼), 7.65 (m, 1H×¾), 7.50-7.19 (m, 3H), 6.99-6.90 (m, 2H+1H×¼), 6.80 (m, 1H×¾), 6.00 (m, 1H×¾), 5.80 (m, 1H×¼), 5.36 (m, 1H×¼), 5.05 (m, 1H×¾), 3.23 (m, 4H), 2.59 (m, 4H), 2.37 (s, 3H), 1.61 (d, J=6.8 Hz, 3H)
mass: 489 (M+1)$^+$.

Example 108

Synthesis of 4-[8-(difluoromethyl)imidazo[1,2-a]pyridin-3-yl]-2-{[(1S)-1-(4-{[2-(dimethylamino)ethyl]amino}phenyl]ethyl]amino}pyrimidin-5-carbonitrile [108] (hereinafter, referred to as the compound [108])

(1) 25 mg of t-butyl[(1S)-1-(4-{[2-(dimethylamino)ethyl]amino}phenyl]ethyl]carbamate [108-1] was obtained as a brown solid, from 100 mg of the t-butyl[(1S)-1-(4-bromophenyl)ethyl]carbamate [106-1] and 35 mg of N,N-dimethylethylenediamine, according to the method of Example 106-(2).

(2) 1.2 mg of the target compound [108] was obtained as a pale yellow solid, from 10 mg of the 4-[8-(difluoromethyl)imidazo[1,2-a]pyridin-3-yl]-2-(methylthio)pyrimidine-5-carbonitrile [80-3] and 25 mg of the t-butyl[(1S)-1-(4-{[2-(dimethylamino)ethyl]amino}phenyl]ethyl]carbamate [108-1], according to the methods of Example 106-(3) and (4).

A spectral data of the compound [108] is presented below.
$^1$H-NMR (CDCl$_3$) δ: 9.85 (m, 1H×⅓), 9.11 (d, J=7.2 Hz, 1H×⅔), 8.99 (s, 1H×⅓), 8.92 (s, 1H×⅔), 8.62 (s, 1H×⅓), 8.54 (s, 1H×⅔), 7.73 (m, 1H×⅓), 7.65 (d, J=7.6 Hz, 1H×⅔), 7.50-7.10 (m, 3H), 6.85 (m, 1H×⅔), 6.74-6.59 (m, 2H+1H×⅓), 6.05 (m, 1H×⅔), 5.80 (m, 1H×⅓), 5.26 (m, 1H×⅓), 5.01 (m, 1H×⅔), 3.22 (m, 2H), 2.69 (m, 2H), 2.35 (s, 6H), 1.61 (d, J=7.2 Hz, 3H)
mass: 477 (M+1)$^+$.

Example 109

Synthesis of 4-[8-(difluoromethyl)imidazo[1,2-a]pyridin-3-yl]-2-[((1S)-1-{4-[(3R)-3-(dimethylamino)pyrrolidin-1-yl]phenyl}ethyl)amino]pyrimidine-5-carbonitrile [109] (hereinafter, referred to as the compound [109])

(1) 116 mg of t-butyl((1S)-1-{4-[(3R)-3-(dimethylamino)pyrrolidin-1-yl]phenyl}ethyl)carbamate [109-1] was obtained as a light brown solid, from 100 mg of the t-butyl [(1S)-1-(4-bromophenyl)ethyl]carbamate [106-1] and 46 mg of (3R)-(+)-3-(dimethylamino)pyrrolidine, according to the method of Example 106-(2).

(2) 43 mg of the target compound [109] was obtained as a pale yellow solid, from 70 mg of the 4-[8-(difluoromethyl)imidazo[1,2-a]pyridin-3-yl]-2-(methylthio)pyrimidine-5-carbonitrile [80-3] and 116 mg of the t-butyl((1S)-1-{4-[(3R)-3-dimethylamino)pyrrolidin-1-yl]phenyl}ethyl)carbamate [109-1], according to the methods of Example 106-(3) and (4).

A spectral data of the compound [109] is presented below.
$^1$H-NMR (CDCl$_3$) δ: 9.83 (m, 1H×¼), 9.23 (d, J=6.8 Hz, 1H×¾), 8.99 (s, 1H×¼), 8.93 (s, 1H×¾), 8.62 (s, 1H×¼), 8.53 (s, 1H×¾), 7.80-7.10 (m, 4H+1H×¼), 6.85 (m, 1H×¾), 6.57 (d, J=8.4 Hz, 2H), 6.07 (m, 1H×¾), 5.80 (m, 1H×¼), 5.26 (m, 1H×¼), 5.04 (m, 1H×¾), 3.53-3.40 (m, 2H), 3.33 (m, 1H), 3.17 (m, 1H), 2.89 (m, 1H), 2.33 (s, 6H), 2.23 (m, 1H), 1.96 (m, 1H), 1.61 (d, J=6.8 Hz, 3H)
mass: 503 (M+1)$^+$.

Example 110

Synthesis of 4-[8-(difluoromethyl)imidazo[1,2-a]pyridin-3-yl]-2-{[(1S)-1-(4-piperazin-1-ylphenyl)ethyl]amino}pyrimidine-5-carbonitrile [110] (hereinafter, referred to as the compound [110])

(1) The mixture of 100 mg of the t-butyl[(1S)-1-(4-bromophenyl)ethyl]carbamate [106-1], 73 mg of 2,2,2-trifluoro-1-piperazin-1-yl-ethanone (synthesized according to a method disclosed in page 7357-7360 in Tetrahedron Lett. 1995, 41), 3.7 mg of palladium acetate, 10.7 mg of 2,2'-bis(diphenylphosphino)-1,1'-binaphthyl, 217 mg of cesium carbonate, and 3 mL of toluene, was stirred overnight at 100° C. After cooling the reaction mixture back to room temperature, the insolubles were filtered through celite, the filtrate was concentrated under reduced pressure, and the thus obtained residue was purified by preparative thin-layer chromatography, to obtain 73 mg of t-butyl((1S)-1-{4-[4-(trifluoroacetyl)piperazin-1-yl]phenyl}ethyl)carbamate [110-1] as a white solid.

(2) 34 mg of 4-[8-(difluoromethyl)imidazo[1,2-a]pyridin-3-yl]-2-[((1S)-1-{4-[4-(trifluoroacetyl)piperazin-1-yl]phenyl}ethyl)amino]pyrimidine-5-carbonitrile [110-2] was obtained as a white solid, from 38 mg of the 4-[8-(difluoromethyl)imidazo[1,2-a]pyridin-3-yl]-2-(methylthio)pyrimidine-5-carbonitrile [80-3] and 73 mg of the t-butyl((1S)-1-{4-[4-(trifluoroacetyl)piperazin-1-yl]phenyl}ethyl)carbamate [110-1], according to the methods of Example 106-(3) and (4).

(3) 34 mg of the 4-[8-(difluoromethyl)imidazo[1,2-a]pyridin-3-yl]-2-[((1S)-1-{4-[4-(trifluoroacetyl)piperazin-1-yl]phenyl}ethyl)amino]pyrimidin-5-carbonitrile [110-2] was dissolved in a mixture solvent of 5 mL of tetrahydrofuran and 1 mL of methanol, then 20 μL of 5N aqueous solution of sodium hydroxide was added thereto, and stirred at room temperature for 30 minutes. The reaction solution was diluted with chloroform, and washed with water and saturated brine in the subsequent order. The obtained organic layer was dried over anhydrous magnesium sulfate, the insolubles were filtered, and the filtrate was concentrated under reduced pressure. The obtained residue was dissolved in a small amount of chloroform and solidified by hexane, to obtain 25 mg of the target compound [110] as a white solid.

A spectral data of the compound [110] is presented below.
$^1$H-NMR (CDCl$_3$) δ: 9.84 (m, 1H×¼), 9.07 (d, J=6.8 Hz, 1H×¾), 8.99 (s, 1H×¼), 8.92 (s, 1H×¾), 8.62 (s, 1H×¼), 8.55 (s, 1H×¾), 7.70 (m, 1H×¼), 7.65 (d, J=6.4 Hz, 1H×¾), 7.49-7.09 (m, 3H), 7.01-6.88 (m, 2H+1H×¼), 6.81 (m, 1H×¾), 6.05 (m, 1H×¾), 5.80 (m, 1H×¼), 5.28 (m, 1H×¼), 5.05 (m, 1H×¾), 3.19 (m, 4H), 3.07 (m, 4H), 1.61 (d, J=6.8 Hz, 3H)
mass: 475 (M+1)$^+$.

Example 111

Synthesis of 4-[8-(difluoromethyl)imidazo[1,2-a]pyridin-3-yl]-2-[(1-{4-[(1-methylpiperidin-4-yl)oxy]phenyl}ethyl)amino]pyrimidine-5-carbonitrile [111] (hereinafter, referred to as the compound [111])

(1) 208 mg of 2-{[1-(4-{[t-butyl(diphenyl)silyl]oxy}phenyl)ethyl]amino}-4-[8-(difluoromethyl)imidazo[1,2-a]pyridin-3-yl]pyrimidine-5-carbonitrile [111-1] was obtained as a white solid, from 200 mg of the 4-[8-(difluoromethyl)imidazo[1,2-a]pyridin-3-yl]-2-(methylthio)pyrimidine-5-carbonitrile [80-3] and 264 mg of the 1-(4-{[t-butyl(diphenyl)silyl]oxy}phenyl)ethylamine [79-4], according to the method of Example 80-(4).

(2) 208 mg of the 2-{[1-(4-{[t-butyl(diphenyl)silyl]oxy}phenyl)ethyl]amino}-4-[8-(difluoromethyl)imidazo[1,2-a]pyridin-3-yl]pyrimidine-5-carbonitrile [111-1] was dissolved in 5 mL of tetrahydrofuran, then 320 μL of tetrabutylammonium fluoride (1.0M tetrahydrofuran solution) was added under an ice-cold condition, and stirred at room temperature for 1 hour. The reaction solution was diluted in 200 mL of ethyl acetate, and washed with phosphate buffer pH6.8 and saturated brine in the subsequent order. The obtained organic layer was dried over anhydrous magnesium sulfate, the insolubles were filtered, and the filtrate was concentrated under reduced pressure. The obtained residue was dissolved in a small amount of mixture solvent of chloroform and methanol (chloroform:methanol=9:1) and solidified by hexane, to obtain 107 mg of 4-[8-(difluoromethyl)imidazo[1,2-a]pyridin-3-yl]-2-{[1-(4-hydroxyphenyl)ethyl]amino}pyrimidine-5-carbonitrile [111-2] as a white solid.

(3) 10 mg of the 4-[8-(difluoromethyl)imidazo[1,2-a]pyridin-3-yl]-2-{[1-(4-hydroxyphenyl)ethyl]amino}pyrimidine-5-carbonitrile [111-2] was dissolved in 1 mL of tetrahydrofuran, then 17 mg of triphenylphosphine and 5.6 mg of 1-methyl-4-hydroxypiperidine were added and stirred. Thereto, 11 μL of diisopropyl azodicarboxylic acid was added, and stirred at 50° C. for 3 hours. The reaction mixture was cooled back to room temperature, then diluted in 100 mL of ethyl acetate, and washed with water and saturated brine in the subsequent order. The obtained organic layer was dried over anhydrous magnesium sulfate, the insolubles were filtered, and the filtrate was concentrated under reduced pressure. The obtained residue was purified by preparative thin-layer chromatography, dissolved in a small amount of chloroform, and solidified by hexane, to obtain 5.8 mg of the target compound [111] as a white solid.

A spectral data of the compound [111] is presented below.
$^1$H-NMR (DMSO-$d_6$) δ: 10.19 (d, J=7.1 Hz, 1H×½), 9.16 (d, J=6.8 Hz, 1H×½), 9.01 (d, J=7.3 Hz, 1H×½), 8.91 (d, J=8.3 Hz, 1H×½), 8.78 (s, 1H×⅖), 8.77 (s, 1H×⅗), 8.76 (s, 1H×⅖), 8.63 (s, 1H×⅗), 7.85 (d, J=7.6 Hz, 1H×½), 7.80 (d, J=7.6 Hz, 1H×½), 7.51 (t, J=54.4 Hz, 1H×½), 7.46 (t, J=54.4 Hz, 1H×½), 7.31-7.29 (m, 2H+1H×½) 7.13 (t, J=7.3 Hz, 1H×½), 6.94 (d, J=8.5 Hz, 2H×½), 6.90 (d, J=8.8 Hz, 2H×½), 5.24-5.16 (m, 1H×½), 5.08-5.01 (m, 1H×½), 4.32-4.24 (m, 1H), 2.59-2.49 (m, 2H), 2.14 (s, 3H×½), 2.13 (s, 3H×½), 2.15-2.05 (m, 2H), 1.91-1.81 (m, 2H), 1.59-1.54 (m, 1H), 1.51 (d, J=6.8 Hz, 3H×½), 1.47 (d, J=6.8 Hz, 3H×½)
mass: 504 (M+1)$^+$.

Example 112

Synthesis of 2-{[(1S)-1-(4-aminophenyl)ethyl]amino}-4-(8-methylimidazo[1,2-a]pyridin-3-yl)pyrimidine-5-carbonitrile [112] (hereinafter, referred to as the compound [112])

(1) 855 mg of 4-(8-methylimidazo[1,2-a]pyridin-3-yl)-2-(methylthio)pyrimidine-5-carbonitrile [112-1] was obtained as a brown solid, from 1 g of the 4-[(Z)-2-ethoxyvinyl]-2-(methylthio)-5-pyrimidinecarbonitrile [48-3] and 490 mg of 2-amino-3-picoline, according to the method of Example 25-(3).

(2) 350 mg of 4-(8-methylimidazo[1,2-a]pyridin-3-yl)-2-{[(1S)-1-(4-nitrophenyl)ethyl]amino}pyrimidine-5-carbonitrile [112-2] was obtained as a brown solid, from 400 mg of the 4-(8-methylimidazo[1,2-a]pyridin-3-yl)-2-(methylthio)pyrimidine-5-carbonitrile [112-1] and 204 mg of (S)-α-methyl-4-nitrobenzylamine hydrochloride, according to the method of Example 80-(4).

(3) 325 mg of the target compound [112] was obtained as a light brown solid, from 350 mg of the 4-(8-methylimidazo[1,2-a]pyridin-3-yl)-2-{[(1S)-1-(4-nitrophenyl)ethyl]amino}pyrimidine-5-carbonitrile [112-2], according to the method of Example 103-(2).

A spectral data of the compound [112] is presented below.
$^1$H-NMR (CDCl$_3$) δ: 9.62 (m, 1H×⅓), 9.03 (d, J=7.2 Hz, 1H×⅔), 8.94 (s, 1H×⅓), 8.91 (s, 1H×⅔), 8.58 (s, 1H×⅓), 8.47 (s, 1H×⅔), 7.30-7.12 (m, 3H), 6.91 (m, 1H×⅓), 6.78-6.65 (m, 2H+1H×⅔), 6.03 (m, 1H×⅓), 5.76 (m, 1H×⅔), 5.22 (m, 1H×⅓), 5.05 (m, 1H×⅔), 2.66 (s, 3H), 1.60 (d, J=6.8 Hz, 3H)
mass: 370 (M+1)$^+$.

Example 113

Synthesis of N-[4-((1S)-1-{[5-cyano-4-(8-methylimidazo[1,2-a]pyridin-3-yl)pyrimidin-2-yl]amino}ethyl)phenyl]methanesulfonamide [113] (hereinafter, referred to as the compound [113])

20 mg of the compound [112] was dissolved in 5 mL of chloroform, 25 μL of pyridine was added, then 6.3 μL of methanesulfonyl chloride was added under an ice-cold condition, and stirred at room temperature for 2 hours. Thereto, a saturated aqueous solution of sodium hydrogen carbonate was added, and extracted with chloroform. The organic layer was washed with saturated brine, and dried over anhydrous magnesium sulfate. The insolubles were filtered, the filtrate was concentrated under reduced pressure, and the thus obtained residue was purified by preparative thin-layer chromatography, to obtain 19 mg of the target compound [113] as a white solid.

A spectral data of the compound [113] is presented below.
$^1$H-NMR (CDCl$_3$) δ: 9.68 (m, 1H×¼), 8.91 (m, 1H×¼), 8.87 (s, 1H×¾), 8.81 (m, 1H×¾), 8.60-8.50 (m, 1H), 7.39 (m, 2H), 7.37-7.17 (m, 3H+1H×¼), 6.97 (m, 1H×¼), 6.69 (m, 1H×¾), 6.49 (m, 1H×¼), 5.31 (m, 1H×¼), 5.11 (m, 1H×¾), 2.99 (s, 3H×¼), 2.91 (s, 3H×¾), 2.68 (s, 3H×¼), 2.64 (s, 3H×¾), 1.62 (d, J=7.2 Hz, 3H)
mass: 448 (M+1)$^+$.

Example 114

Synthesis of 4-(8-methylimidazo[1,2-a]pyridin-3-yl)-2-[((1S)-1-{4-[(1-methylpiperidin-4-yl)amino]phenyl}ethyl)amino]pyrimidine-5-carbonitrile [114] (hereinafter, referred to as the compound [114])

7 mg of the target compound [114] was obtained as a white solid, from 24 mg of the compound [112] and 8 μL of 1-methyl-4-piperidone, according to the method of Example 82-(1).

A spectral data of the compound [114] is presented below.
$^1$H-NMR (DMSO-$d_6$) δ: 9.97 (d, J=7.3 Hz, 1H×½), 9.07 (d, J=6.8 Hz, 1H×½), 8.83 (d, J=7.3 Hz, 1H×½), 8.74 (d, J=6.8 Hz, 1H×½), 8.73 (s, 1H×½), 8.71 (s, 1H×½), 8.70 (s, 1H×½), 8.60 (s, 1H×½), 7.41 (d, J=6.8 Hz, 1H×½), 7.35 (d, J=7.1 Hz, 1H×½), 7.11-7.08 (m, 2H+1H×½), 6.96 (t, J=6.8 Hz, 1H×½), 6.54 (d, J=8.8 Hz, 1H), 6.52 (d, J=8.8 Hz, 1H), 5.34-5.30 (m, 1H), 5.15-5.07 (m, 1H×½), 4.97-4.89 (m, 1H×½), 3.15-3.07 (m, 1H), 2.72-2.66 (m, 2H), 2.58 (s, 3H×½), 2.54 (s, 3H×½), 2.15 (s, 3H×½), 2.14 (s, 3H×½), 2.01-1.97 (m, 2H), 1.84-1.79 (m, 2H), 1.47 (d, J=7.3 Hz, 3H×½), 1.44 (d, J=7.3 Hz, 3H×½), 1.34-1.30 (m, 2H)
mass: 467 (M+1)$^+$.

Example 115

Synthesis of 4-(8-methylimidazo[1,2-a]pyridin-3-yl)-2-({(1S)-1-[4-(morpholin-4-ylmethyl)phenyl]ethyl}amino)pyrimidine-5-carbonitrile [115] (hereinafter, referred to as the compound [115])

(1) To 5 mL of tetrahydrofuran solution containing 177.8 mg of lithium aluminum hydride, 3 mL of tetrahydrofuran solution containing 245 mg of methyl 4-(1-aminoethyl)benzoate (synthesized according to a method disclosed in page 115 in Pamphlet of International Publication WO 03/024,955) was added, and then stirred for 1 hour. Thereto, sodium sulfate decahydrate was added until there are no bubbles, and stirred overnight at room temperature. The mixture was filtered through celite, the filtrate was concentrated under reduced pressure, and 195 mg of [4-(1-aminoethyl)phenyl]methanol [115-1] was obtained as a colorless oily product.

(2) 175 mg of 2-({1-[4-(hydroxymethyl)phenyl]ethyl}amino)-4-(8-methylimidazo[1,2-a]pyridin-3-yl)pyrimidine-5-carbonitrile [115-2] was obtained as a white solid, from 242 mg of the 4-(8-methylimidazo[1,2-a]pyridin-3-yl)-2-(methylthio)pyrimidine-5-carbonitrile [112-1] and 195 mg of the [4-(1-aminoethyl)phenyl]methanol [115-1], according to the method of Example 80-(4).

(3) 3.8 mg of the target compound [115] was obtained as a pale yellow solid, from 30 mg of the 2-({1-[4-(hydroxymethyl)phenyl]ethyl}amino)-4-(8-methylimidazo[1,2-a]pyridin-3-yl)pyrimidine-5-carbonitrile [115-2] and 30 μL of morpholine, according to the method of Example 84.

A spectral data of the compound [115] is presented below.
$^1$H-NMR (DMSO-d$_6$) δ: 9.97 (d, J=7.0 Hz, 1H×2/5), 8.96 (d, J=6.6 Hz, 1H×3/5), 8.90 (d, J=8.2 Hz, 1H×2/5), 8.81 (d, J=7.0 Hz, 1H×3/5), 8.73-8.72 (m, 1H), 8.70 (s, 1H×2/5), 8.58 (s, 1H×3/5), 7.43-7.24 (m, 5H), 7.12 (t, J=7.0 Hz, 1H×2/5), 6.84 (t, J=7.0 Hz, 1H×3/5), 5.28-5.20 (m, 1H×2/5), 5.10-5.02 (m, 1H×3/5), 3.54-3.46 (m, 4H), 2.58 (s, 3H×2/5), 2.52 (s, 3H×3/5), 2.30-3.32 (m, 6H), 1.52 (d, J=7.0 Hz, 3H×2/5), 1.49 (d, J=7.0 Hz, 3H×3/5)
mass: 454 (M+1)$^+$.

Example 116

Synthesis of N-[4-((1S)-1-{[5-cyano-4-(8-methylimidazo[1,2-a]pyridin-3-yl)pyrimidin-2-yl]amino}ethyl)benzyl]glycinamide [116] (hereinafter, referred to as the compound [116])

(1) 51 mg of 2-({1-[4-(aminomethyl)phenyl]ethyl}amino)-4-(8-methylimidazo[1,2-a]pyridin-3-yl)pyrimidine-5-carbonitrile [116-1] was obtained as a white solid, from 75.3 mg of the 2-({1-[4-(hydroxymethyl)phenyl]ethyl}amino)-4-(8-methylimidazo[1,2-a]pyridin-3-yl)pyrimidine-5-carbonitrile [115-2], according to the methods of Example 102-(1) and (2).

(2) 5.5 mg of the target compound [116] was obtained as a pale yellow solid, from 15 mg of the 2-({1-[4-(aminomethyl)phenyl]ethyl}amino)-4-(8-methylimidazo[1,2-a]pyridin-3-yl)pyrimidine-5-carbonitrile [116-1] and 14 mg of N-t-butoxycarbonylglycine, according to the method of Example 81.

A spectral data of the compound [116] is presented below.
$^1$H-NMR (DMSO-d$_6$) δ: 9.97 (d, J=7.0 Hz, 1H×1/2), 9.04-9.00 (m, 1H), 8.94 (d, J=8.6 Hz, 1H×1/2), 8.79-8.73 (m, 2H), 8.69 (s, 1H×1/2), 8.61 (s, 1H×1/2), 7.45-7.37 (m, 2H+1H×1/2), 7.27-7.23 (m, 1H+1H×1/2), 7.14 (t, J=7.0 Hz, 1H×1/2), 6.97 (t, J=7.0 Hz, 1H×1/2), 5.25-5.17 (m, 1H×1/2), 5.14-5.06 (m, 1H×1/2), 4.30-4.29 (m, 2H), 3.57-3.54 (m, 2H), 2.58 (s, 1H×1/2), 2.54 (s, 1H×1/2), 1.51 (d, J=7.4 Hz, 3H×1/2), 1.48 (d, J=7.4 Hz, 3H×1/2)
mass: 441 (M+1)$^+$.

Example 117

Synthesis of 4-(8-methylimidazo[1,2-a]pyridin-3-yl)-2-[((1S)-1-{4-[(methylsulfonyl)methyl]phenyl}ethyl)amino]pyrimidine-5-carbonitrile [117] (hereinafter, referred to as the compound [117])

13.6 mg of the target compound [117] was obtained as a white solid, from 20 mg of the 2-({1-[4-(hydroxymethyl)phenyl]ethyl}amino)-4-(8-methylimidazo[1,2-a]pyridin-3-yl)pyrimidine-5-carbonitrile [115-2], according to the method of Example 84.

A spectral data of the compound [117] is presented below.
$^1$H-NMR (DMSO-d$_6$) δ: 9.97 (d, J=7.1 Hz, 1H×1/2), 9.00 (d, J=7.3 Hz, 1H×1/2), 8.94 (d, J=8.0 Hz, 1H×1/2), 8.86 (d, J=7.1 Hz, 1H×1/2), 8.74 (s, 1H×1/2), 8.73 (s, 1H×1/2), 8.70 (s, 1H×1/2), 8.59 (s, 1H×1/2), 7.45-7.31 (m, 5H), 7.13 (t, J=7.1 Hz, 1H×1/2), 6.91 (t, J=7.1 Hz, 1H×1/2), 5.29-5.22 (m, 1H×1/2), 5.14-5.07 (m, 1H×1/2), 4.47-4.39 (m, 2H), 2.89 (s, 3H×1/2), 2.82 (s, 3H×1/2), 2.58 (s, 3H×1/2), 2.53 (s, 3H×1/2), 1.54 (d, J=7.1 Hz, 3H×1/2), 1.51 (d, J=7.1 Hz, 3H×1/2)
mass: 447 (M+1)$^+$.

Example 118

Synthesis of 2-{[(1S)-1-(3-methoxyphenyl)ethyl]amino}-4-(8-methylimidazo[1,2-a]pyridin-3-yl)pyrimidine-5-carbonitrile [118] (hereinafter, referred to as the compound [118])

13 mg of the compound [118] was obtained as a white solid, from 20 mg of the 4-(8-methylimidazo[1,2-a]pyridin-3-yl)-2-(methylthio)pyrimidine-5-carbonitrile [112-1] and 16 mg of (S)(−)-1-(3-methoxyphenyl)ethylamine, according to the method of Example 80-(4).

A spectral data of the compound [118] is presented below.
$^1$H-NMR (CDCl$_3$) δ: 9.62 (m, 1H×1/4), 8.94 (m, 1H×1/4), 8.89 (s, 1H×3/4), 8.81 (d, J=6.8 Hz, 1H×3/4), 8.57 (m, 1H×1/4), 8.51 (s, 1H×3/4), 7.40-6.80 (m, 5H+1H×1/4), 6.64 (m, 1H×3/4), 6.09 (m, 1H×3/4), 5.53 (m, 1H×1/4), 5.30 (m, 1H×1/4), 5.09 (m, 1H×3/4), 3.81 (s, 3H), 2.71-2.63 (m, 3H), 1.62 (d, J=7.2 Hz, 3H)
mass: 385 (M+1)$^+$.

Example 119

Synthesis of 4-(8-methylimidazo[1,2-a]pyridin-3-yl)-2-[((1S)-1-{3-[(1-methylpiperidin-4-yl)amino]phenyl}ethyl)amino]pyrimidine-5-carbonitrile [119] (hereinafter, referred to as the compound [119])

(1) 22 mg of 2-{[(1S)-1-(3-aminophenyl)ethyl]amino}-4-(8-methylimidazo[1,2-a]pyridin-3-yl)pyrimidine-5-carbonitrile [119-1] was obtained in a pale yellow amorphous form, from 50 mg of the 4-(8-methylimidazo[1,2-a]pyridin-3-yl)-2-(methylthio)pyrimidine-5-carbonitrile [112-1] and 29 mg of 3-[(1S)-1-aminoethyl]aniline, according to the method of Example 80-(4).

(2) 7.1 mg of the target compound [119] was obtained as a pale yellow solid, from 11 mg of the 2-{[(1S)-1-(3-aminophenyl)ethyl]amino}-4-(8-methylimidazo[1,2-a]pyridin-3-yl)pyrimidine-5-carbonitrile [119-1] and 11 μL of 1-methyl-4-piperidone, according to the method of Example 91.

A spectral data of the compound [119] is presented below.
$^1$H-NMR (CDCl$_3$) δ: 9.64 (d, J=8.0 Hz, 1H×1/5), 8.95 (s, 1H×1/5), 8.88 (s, 1H×4/5), 8.85 (d, J=8.0 Hz, 1H×4/5), 8.58 (s, 1H×1/5), 8.52 (s, 1H×4/5), 7.30-7.14 (m, 2H), 6.71-6.52 (m, 4H), 6.01-6.00 (m, 1H×4/5), 5.88-5.78 (m, 1H×1/5), 5.27-5.15 (m, 1H×1/5), 5.03-5.00 (m, 1H×4/5), 3.75-3.50 (m, 1H), 3.38-3.18 (m, 1H), 2.73-2.38 (m, 2H), 2.69 (s, 1H×3/5), 2.64 (s, 2H+1H×2/5), 2.31 (s, 3H), 2.14-2.01 (m, 4H), 1.61 (d, J=6.8 Hz, 3H), 1.58-1.40 (m, 2H)
mass: 467 (M+1)$^+$.

Example 120

Synthesis of 4-(8-ethylimidazo[1,2-a]pyridin-3-yl)-2-({(1S)-1-[4-(4-methylpiperazin-1-yl)phenyl]ethyl}amino)pyrimidine-5-carbonitrile [120] (hereinafter, referred to as the compound [120])

(1) The mixture of 327 mg of 3-bromo-2-nitropyridine, 256.5 mg of dichlorobis(triphenylphosphine)palladium (II), 518 μL of tributyl(vinyl)tin, and 6 mL of N,N-dimethylformamide, was stirred at 80° C. for 3 hours. The reaction mixture was cooled back to room temperature, then 500 mg of potassium fluoride and 1.5 mL of water were added thereto, and stirred at room temperature for 30 minutes. The insolubles were filtered through celite, a saturated aqueous solution of sodium hydrogen carbonate was added, and extracted with ethyl acetate. The obtained organic layer was washed with saturated brine, and dried over anhydrous sodium sulfate. The insolubles were filtered, the filtrate was concentrated under reduced pressure, and then the thus obtained residue was purified by silica gel column chromatography, to obtain 236 mg of 2-nitro-3-vinylpyridine [120-1] as a pale red solid.

(2) 130 mg of the 2-nitro-vinylpyridine [120-1] was dissolved in 5 mL of ethanol, 65 mg of 10% palladiumcarbon catalyst was added thereto, and stirred overnight at room temperature in a hydrogen atmosphere. The insolubles were filtered through celite, the filtrate was concentrated under reduced pressure, and 88.7 mg of 3-ethylpyridin-2-amine [120-2] was obtained as a yellow oily product.

(3) 100 mg of 4-(8-ethylimidazo[1,2-a]pyridin-3-yl)-2-(methylthio)pyrimidine-5-carbonitrile [120-3] was obtained as a pale yellow solid, from 85 mg of the 3-ethylpyridin-2-amine [120-2] and 154 mg of the 4-[(Z)-2-ethoxyvinyl]-2-(methylthio)-5-pyrimidinecarbonyl [48-3], according to the method of Example 25-(3).

(4) 5.7 mg of the target compound [120] was obtained as a pale yellow solid, from 20 mg of the 4-(8-ethylimidazo[1,2-a]pyridin-3-yl)-2-(methylthio)pyrimidine-5-carbonitrile [120-3] and 38 mg of the t-butyl{(1S)-1-[4-(4-methylpiperazin-1-yl)phenyl]ethyl}carbamate [107-1], according to the methods of Example 106-(3) and (4).

A spectral data of the compound [120] is presented below.
$^1$H-NMR (CDCl$_3$) δ: 9.74-9.68 (m, 1H×⅕), 8.97-8.90 (m, 1H+1H×⅘), 8.57 (s, 1H×⅕), 8.49 (s, 1H×⅘), 7.35-6.65 (m, 6H), 6.12-6.06 (m, 1H×⅘), 5.82-5.73 (m, 1H×⅕), 5.31-5.20 (m, 1H×⅕), 5.12-5.00 (m, 1H×⅘), 3.25-3.16 (m, 4H), 3.30-3.15 (m, 2H), 2.63-2.47 (m, 4H), 2.35 (s, 3H), 1.61 (d, J=6.6 Hz, 3H), 1.45-1.30 (m, 3H)
mass: 467 (M+1)$^+$.

Example 121

Synthesis of 4-(8-cyclopropylimidazo[1,2-a]pyridin-3-yl)-2-({(1S)-1-[4-(4-methylpiperazin-1-yl)phenyl]ethyl}amino)pyrimidine-5-carbonitrile [121] (hereinafter, referred to as the compound [121])

(1) 1.93 g of 3-cyclopropylpyridine (synthesized according to a method disclosed in Tetrahedron Lett. 2002, 39, 6987-6990) was dissolved in 15 mL of acetic acid, then 2.4 g of hydrogen peroxide solution (31%) was added thereto, and heated overnight under reflux. The reaction mixture was concentrated under reduced pressure, the obtained residue was dissolved in chloroform, and washed with a saturated aqueous solution of sodium hydrogen carbonate and water in the subsequent order. The organic layer was dried over anhydrous sodium sulfate. The insolubles were filtered, the filtrate was concentrated under reduced pressure, and 1.47 g of 3-cyclopropylpyridine 1-oxide [121-1] was obtained as a brown oily product.

(2) 1.47 g of 3-cyclopropylpyridine-1-oxide [121-1] was dissolved in 15 mL of chloroform, and 1.89 mL of trimethylsilyl cyanide was added thereto. Subsequently, a solution prepared by dissolving 1.3 mL of dimethylcarbamoyl chloride in 5 mL of chloroform was added dropwise over 30 minutes, and was stirred overnight at room temperature. Thereto, 10 mL of 10% aqueous solution of potassium carbonate was added, and the mixture was extracted with chloroform. The organic layer was washed with saturated brine, and dried over anhydrous sodium sulfate. The insolubles were filtered and the filtrate was concentrated under reduced pressure, to obtain a residue. The residue was purified by silica gel column chromatography, and 680 mg of 3-cyclopropylpyridine-2-carbonitrile [121-2] was obtained as a white solid.

(3) The mixture of 680 mg of the 3-cyclopropylpyridine-2-carbonitrile [121-2] and 35 mL of 6N hydrochloric acid was heated overnight under reflux. The reaction mixture was concentrated under reduced pressure, and 830 mg of a hydrochloride salt of 3-cyclopropylpyridine-2-carboxylic acid [121-3] was obtained as a white solid.

(4) 830 mg of a hydrochloride salt of the 3-cyclopropylpyridine-2-carboxylic acid [121-3] was dissolved in 100 mL of 10% hydrochloric acid-methanol solution, and heated overnight under reflux. The reaction solution was concentrated under reduced pressure, a saturated aqueous solution of sodium hydrogen carbonate was added to the obtained residue, and was extracted with ethyl acetate. The organic layer was washed with saturated brine, and dried over anhydrous sodium sulfate. The insolubles were filtered, the filtrate was concentrated under reduced pressure, and 363 mg of methyl 3-cyclopropylpyridine-2-carboxylate [121-4] was obtained as a white solid.

(5) 360 mg of the methyl 3-cyclopropylpyridine-2-carboxylate [121-4] was dissolved in 4 mL of methanol, then 4 mL of 1N aqueous solution of sodium hydroxide was added thereto, and stirred at 50° C. for 30 minutes. The reaction solution was concentrated under reduced pressure, and the thus obtained residue was subjected to azeotrope twice with toluene to obtain a white solid. The obtained solid was dissolved in a mixture solvent of 4 mL of N,N-dimethylformamide and 3 mL of 1,4-dioxane, then 736 μL of triethylamine and 569 μL of diphenylphosphoryl azide were added under an ice-cold condition, and stirred at room temperature for 1 hour. Thereafter, 1.5 mL of t-butanol was added to the reaction mixture, and was stirred overnight at 80° C. After cooling the reaction mixture back to room temperature, a saturated aqueous solution of sodium hydrogen carbonate was added thereto, and extracted with chloroform. The organic layer was washed with saturated brine, and dried over anhydrous sodium sulfate. The insolubles were filtered, the filtrate was concentrated under reduced pressure, and the thus obtained residue was purified by silica gel column chromatography, to obtain 41.2 mg of 3-cyclopropylpyridine-2-amine [121-5] as a light brown oily product.

(6) 76.8 mg of 4-(8-cyclopropylimidazo[1,2-a]pyridin-3-yl)-2-(methylthio)pyrimidine-5-carbonitrile [121-6] was obtained as a pale yellow solid, from 41.2 mg of the 3-cyclopropylpyridine-2-amine [121-5] and 67.6 mg of the 4-[(Z)-2-ethoxyvinyl]-2-(methylthio)-5-pyrimidinecarbonitrile [48-3], according to the method of Example 25-(3).

(7) 11.3 mg of the target compound [121] was obtained as a pale yellow solid, from 24 mg of the 4-(8-cyclopropylimidazo[1,2-a]pyridin-3-yl)-2-(methylthio)pyrimidine-5-carbonitrile [121-6] and 39 mg of the t-butyl{(1S)-1-[4-(4-methylpiperazin-1-yl)phenyl]ethyl}carbamate [107-1], according to the methods of Example 106-(3) and (4).

A spectral data of the compound [121] is presented below.
$^1$H-NMR (CDCl$_3$) δ: 9.74-9.68 (m, 1H×⅕), 8.97-8.92 (m, 1H+1H×⅘), 8.57 (s, 1H×⅕), 8.49 (s, 1H×⅘), 7.35-6.67 (m, 6H), 6.03-5.95 (m, 1H×⅘), 5.80-5.68 (m, 1H×⅕), 5.32-5.20 (m, 1H×⅕), 5.13-5.00 (m, 1H×⅘), 3.26-3.12 (m, 4H), 2.68-2.50 (m, 5H), 2.35 (s, 3H), 1.60 (d, J=6.6 Hz, 3H), 1.30-1.12 (m, 2H), 0.96-0.83 (m, 2H)
mass: 479 (M+1)$^+$.

Example 122

Synthesis of 4-(8-methylimidazo[1,2-a]pyridin-3-yl)-2-{[(1S)-1-(4-piperazin-1-ylphenyl)ethyl]amino}pyrimidine-5-carbonitrile [122] (hereinafter, referred to as the compound [122])

(1) 12.2 mg of 4-(8-methylimidazo[1,2-a]pyridin-3-yl)-2-[((1S)-1-{4-[4-(trifluoroacetyl)piperazin-1-yl]phenyl}ethyl)amino]pyrimidine-5-carbonitrile [122-1] was obtained as a pale yellow solid, from 24.6 mg of the 4-(8-methylimidazo[1,2-a]pyridin-3-yl)-2-(methylthio)pyrimidine-5-carbonitrile [112-1] and 57.8 mg of the t-butyl((1S)-1-{4-[4-(trifluoroacetyl)piperazin-1-yl]phenyl}ethyl)carbamate [110-1], according to the methods of Example 106-(3) and (4).

(2) 5.5 mg of the target compound [122] was obtained as a white solid, from 12.2 mg of the 4-(8-methylimidazo[1,2-a]pyridin-3-yl)-2-[((1S)-1-{4-[4-(trifluoroacetyl)piperazin-1-yl]phenyl}ethyl)amino]pyrimidine-5-carbonitrile [122-1], according to the method of Example 110-(3).

A spectral data of the compound [122] is presented below.
$^1$H-NMR (CDCl$_3$) δ: 9.61 (d, J=7.2 Hz, 1H×⅕), 9.00 (d, J=7.2 Hz, 1H×⅘), 8.94 (s, 1H×⅕), 8.90 (s, 1H×⅘), 8.58 (s, 1H×⅕), 8.49 (s, 1H×⅘), 7.29-6.67 (m, 6H), 6.08-6.07 (m, 1H×⅘), 5.83-5.72 (m, 1H×⅕), 5.32-5.20 (m, 1H×⅕), 5.14-5.00 (m, 1H×⅘), 3.18-3.10 (m, 4H), 3.04-3.01 (m, 4H), 2.68 (brs, 1H), 2.65 (s, 3H), 1.61 (d, J=6.8 Hz, 3H)
mass: 439 (M+1)$^+$.

Example 123

Synthesis of 4-(8-chloroimidazo[1,2-a]pyridin-3-yl)-2-[((1S)-1-{3-[(1-methylpiperidin-4-yl)amino]phenyl}ethyl)amino]pyrimidine-5-carbonitrile [123] (hereinafter, referred to as the compound [123])

(1) 846 mg of 4-(8-chloroimidazo[1,2-a]pyridin-3-yl)-2-(methylthio)pyrimidine-5-carbonitrile [123-1] was obtained as a yellow solid, from 1 g of 2-amino-3-chloropyridine and 1.72 g of the 4-[(Z)-2-ethoxyvinyl]-2-(methylthio)-5-pyrimidinecarbonyl [48-3], according to the method of Example 25-(3).

(2) 60.8 mg of 2-{[(1S)-1-(3-aminophenyl)ethyl]amino}-4-(8-chloroimidazo[1,2-a]pyridin-3-yl)pyrimidine-5-carbonitrile [123-2] was obtained as a yellow solid, from 80 mg of the 4-(8-chloroimidazo[1,2-a]pyridin-3-yl)-2-(methylthio)pyrimidine-5-carbonitrile [123-1] and 45 mg of 3-[(1S)-1-aminoethyl]aniline, according to the method of Example 80-(4).

(3) 10.4 mg of the target compound [123] was obtained as a pale yellow solid, from 11.7 mg of the 2-{[(1S)-1-(3-aminophenyl)ethyl]amino}-4-(8-chloroimidazo[1,2-a]pyridin-3-yl)pyrimidine-5-carbonitrile [123-2] and 11.1 μL of 1-methyl-4-piperidone, according to the method of Example 91.

A spectral data of the compound [123] is presented below.
$^1$H-NMR (CDCl$_3$) δ: 9.70 (d, J=6.9 Hz, 1H×⅕), 8.98 (s, 1H×⅕), 8.89 (s, 1H×⅘), 8.79 (d, J=6.9 Hz, 1H×⅘), 8.62 (s, 1H×⅕), 8.56 (s, 1H×⅘), 7.54-6.90 (m, 2H), 6.75-6.52 (m, 4H), 6.08-6.00 (m, 1H×⅘), 5.88-5.79 (m, 1H×⅕), 5.29-5.18 (m, 1H×⅕), 5.03-4.90 (m, 1H×⅘), 3.65 (d, J=8.2 Hz, 1H), 3.35-3.29 (m, 1H), 2.88-2.70 (m, 2H), 2.30 (s, 3H), 2.18-1.96 (m, 4H), 1.62 (d, J=6.6 Hz, 3H), 1.58-1.40 (m, 2H)
mass: 487, 489 (M+1)$^+$.

Example 124

Synthesis of 4-(8-chloroimidazo[1,2-a]pyridin-3-yl)-2-({(1S)-1-[3-({1-[2-(dimethylamino)ethyl]piperidin-4-yl}amino)phenyl]ethyl}amino)pyrimidine-5-carbonitrile [124] (hereinafter, referred to as the compound [124])

(1) 184 mg of 4-(8-chloroimidazo[1,2-a]pyridin-3-yl)-2-({(1S)-1-[3-(piperidin-4-ylamino)phenyl]ethyl}amino)pyrimidine-5-carbonitrile [124-1] was obtained as a light brown solid, from 270 mg of the 2-{[(1S)-1-(3-aminophenyl)ethyl]amino}-4-(8-chloroimidazo[1,2-a]pyridin-3-yl)pyrimidine-5-carbonitrile [123-2] and 414 mg of 1-(t-butoxycarbonyl)-4-piperidone, according to the methods of Example 82-(1) and (2).

(2) 56.3 mg of 4-(8-chloroimidazo[1,2-a]pyridin-3-yl)-2-{[(1S)-1-(3-{[1-(2-hydroxyethyl)piperidin-4-yl]amino}phenyl)ethyl]amino}pyrimidine-5-carbonitrile [124-2] was obtained in a yellow amorphous form, from 88.1 mg of the 4-(8-chloroimidazo[1,2-a]pyridin-3-yl)-2-({(1S)-1-[3-(piperidin-4-ylamino)phenyl]ethyl}amino)pyrimidine-5-carbonitrile [124-1] and 59 μL of (t-butyldimethylsilyloxy)acetoaldehyde, according to the methods of Example 83-(1) and (2).

(3) 3.2 mg of the target compound [124] was obtained as a white solid, from 56.3 mg of the 4-(8-chloroimidazo[1,2-a]pyridin-3-yl)-2-{[(1S)-1-(3-{[1-(2-hydroxyethyl)piperidin-4-yl]amino}phenyl)ethyl]amino}pyrimidine-5-carbonitrile [124-2] and 200 μL of dimethylamine (2M tetrahydrofuran solution), according to the method of Example 84.

A spectral data of the compound [124] is presented below.
$^1$H-NMR (CDCl$_3$) δ: 9.70 (d, J=6.9 Hz, 1H×⅕), 8.99 (s, 1H×⅕), 8.88 (s, 1H×⅘), 8.78 (d, J=6.9 Hz, 1H×⅘), 8.62 (s, 1H×⅕), 8.56 (s, 1H×⅘), 7.53-6.90 (m, 2H), 6.70-6.52 (m, 4H), 6.06-6.04 (m, 1H×⅘), 5.88-5.80 (m, 1H×⅕), 5.27-5.18 (m, 1H×⅕), 5.02-4.90 (m, 1H×⅘), 3.69-3.57 (m, 1H), 3.33-3.22 (m, 1H), 2.93-2.83 (m, 2H), 2.53-2.38 (m, 4H), 2.25 (s, 6H), 2.20-1.95 (m, 4H), 1.61 (d, J=6.8 Hz, 3H), 1.60-1.40 (m, 2H)
mass: 544, 546 (M+1)$^+$.

Example 125

Synthesis of 4-(8-chloroimidazo[1,2-a]pyridin-3-yl)-5-fluoro-N-((1S)-1-{3-[(1-methylpiperidin-4-yl)amino]phenyl}ethyl)pyrimidine-2-amine [125] (hereinafter, referred to as the compound [125])

(1) 223 mg of 2-chloro-4-[(Z)-2-ethoxyvinyl]-5-fluoropyrimidine [125-1] was obtained as a light brown solid, from 274 mg of 2,4-dichloro-5-fluoropyrimidine, according to the method of Example 48-(3).

(2) 180 mg of 8-chloro-3-(2-chloro-5-fluoropyrimidin-4-yl)imidazo[1,2-a]pyridine [125-2] was obtained as a yellow solid, from 100 mg of the 2-chloro-4-[(Z)-2-ethoxyvinyl]-5-fluoropyrimidine [125-1] and 63.5 mg of 2-amino-3-chloropyridine, according to the method of Example 25-(3).

(3) 90 mg of the 8-chloro-3-(2-chloro-5-fluoropyrimidin-4-yl)imidazo[1,2-a]pyridine [125-2] was dissolved in 3 mL of dimethylsulfoxide, then 46.6 mg of 3-[(1S)-1-aminoethyl] aniline and 100 mg of potassium carbonate were added thereto, and stirred at 60° C. for 5 hours. The reaction mixture was cooled back to room temperature, and purified by preparative reversed phase liquid chromatography. Thereto, a saturated aqueous solution of sodium hydrogen carbonate was added, and the mixture was extracted with chloroform. The organic layer was washed with saturated brine, and dried over anhydrous sodium sulfate. The insolubles were filtered, the filtrate was concentrated under reduced pressure, and 25 mg of N-[(1S)-1-(3-aminophenyl)ethyl]-4-(8-chloroimidazo[1,2-a]pyridin-3-yl)-5-fluoropyrimidine-2-amine [125-3] was obtained as a brown oily product.

(4) 17.5 mg of the target compound [125] was obtained as a white solid, from 18.5 mg of the N-[(1S)-1-(3-aminophenyl)ethyl]-4-(8-chloroimidazo[1,2-a]pyridin-3-yl)-5-fluoropyrimidine-2-amine [125-3] and 17.8 mg of 1-methyl-4-piperidone, according to the method of Example 91.

A spectral data of the compound [125] is presented below.
$^1$H-NMR (CDCl$_3$) δ: 9.20 (brs, 1H), 8.41 (s, 1H), 8.24 (s, 1H), 7.39-7.16 (m, 2H), 6.75-6.49 (m, 4H), 5.47-5.46 (m, 1H), 4.97-4.85 (m, 1H), 3.68-3.45 (m, 1H), 3.35-3.20 (m, 1H), 2.85-2.70 (m, 2H), 2.30 (s, 3H), 2.18-1.95 (m, 4H), 1.58 (d, J=6.6 Hz, 3H), 1.56-1.40 (m, 2H)
mass: 480, 482 (M+1)$^+$.

Example 126

Synthesis of 5-chloro-4-(8-chloroimidazo[1,2-a]pyridin-3-yl)-N-((1S)-1-{3-[(1-methylpiperidin-4-yl)amino]phenyl}ethyl)pyrimidine-2-amine [126] (hereinafter, referred to as the compound [126])

11.2 mg of the target compound [126] was obtained as a light brown solid, from 300 mg of 2,4,5-trichloropyrimidine, according to the methods of Example 125-(1) to (4).

A spectral data of the compound [126] is presented below.
$^1$H-NMR (CDCl$_3$) δ: 8.72-8.60 (m, 2H), 8.35 (s, 1H), 7.36-7.17 (m, 2H), 6.72-6.52 (m, 4H), 5.63-5.50 (m, 1H), 5.00-4.83 (m, 1H), 3.77-3.47 (m, 1H), 3.33-3.20 (m, 1H), 2.88-2.72 (m, 2H), 2.31 (s, 3H), 2.20-1.96 (m, 4H), 1.56 (d, J=6.6 Hz, 3H), 1.55-1.40 (m, 2H)
mass: 496, 498 (M+1)$^+$.

Example 127

Synthesis of 4-(8-chloroimidazo[1,2-a]pyridin-3-yl)-5-methyl-N-((1S)-1-{3-[(1-methylpiperidin-4-yl)amino]phenyl}ethyl)pyrimidine-2-amine [127] (hereinafter, referred to as the compound [127])

13 mg of the target compound [127] was obtained as a light brown solid, from 500 mg of 2,4-dichloro-5-methylpyrimidine, according to the methods of Example 125-(1) to (4).

A spectral data of the compound [127] is presented below.
$^1$H-NMR (CDCl$_3$) δ: 8.85-8.68 (m, 1H), 8.24 (s, 1H), 8.07 (s, 1H), 7.34-7.12 (m, 2H), 6.72-6.48 (m, 4H), 5.45-5.38 (m, 1H), 5.00-4.83 (m, 1H), 3.33-3.25 (m, 1H), 2.89-2.78 (m, 2H), 2.35 (s, 3H), 2.32 (s, 3H), 2.20-2.10 (m, 2H), 2.05-1.95 (m, 4H), 1.54 (d, J=6.6 Hz, 3H)
mass: 476, 478 (M+1)$^+$.

Example 128

Synthesis of 4-(8-chloroimidazo[1,2-a]pyridin-3-yl)-2-{[(1S)-1-(3-piperazin-1-ylphenyl)ethyl]amino}pyrimidine-5-carbonitrile [128] (hereinafter, referred to as the compound [128])

(1) The mixture of 306 mg of 3-{(1S)-1-[(t-butoxycarbonyl)amino]ethyl}phenyl trifluoromethanesulfonate (synthesized according to a method disclosed in J. Med. Chem. 2004, 47, 2887-2896), 181 mg of 2,2,2-trifluoro-1-piperazin-1-yl-ethanone, 47.6 mg of tris(dibenzylideneacetone)(chloroform)dipalladium (0), 49.4 mg of 2-(di-t-butylphosphino)biphenyl, 246 mg of tripotassium phosphate, and 4 mL of toluene, was stirred overnight at 100° C. After cooling the reaction mixture back to room temperature, a saturated aqueous solution of sodium hydrogen carbonate was added thereto, and was extracted with ethyl acetate. The organic layer was washed with saturated brine and dried over anhydrous sodium sulfate, and the insolubles were filtered. The filtrate was concentrated under reduced pressure and purified by silica gel column chromatography, to obtain 277 mg of t-butyl((1S)-1-{3-[4-(trifluoroacetyl)piperazin-1-yl]phenyl}ethyl)carbamate [128-1] as a brown oily product.

(2) 27.7 mg of 4-(8-chloroimidazo[1,2-a]pyridin-3-yl)-2-[((1S)-1-{3-[4-(trifluoroacetyl)piperazin-1-yl]phenyl}ethyl)amino]pyrimidine-5-carbonitrile [128-2] was obtained as a pale yellow solid, from 23.6 mg of the 4-(8-chloroimidazo[1,2-a]pyridin-3-yl)-2-(methylthio)pyrimidine-5-carbonitrile [123-1] and 47 mg of the t-butyl((1S)-1-{3-[4-(trifluoroacetyl)piperazin-1-yl]phenyl}ethyl)carbamate [128-1], according to the methods of Example 106-(3) and (4).

(3) 20.7 mg of the target compound [128] was obtained as a pale yellow solid, from 27.7 mg of the 4-(8-chloroimidazo[1,2-a]pyridin-3-yl)-2-[((1S)-1-{3-[4-(trifluoroacetyl)piperazin-1-yl]phenyl}ethyl)amino]pyrimidine-5-carbonitrile [128-2], according to the method of Example 110-(3).

A spectral data of the compound [128] is presented below.
$^1$H-NMR (CDCl$_3$) δ: 9.70 (d, J=8.0 Hz, 1H×⅕), 8.99 (s, 1H×⅕), 8.89 (s, 1H×⅘), 8.79 (d, J=8.0 Hz, 1H×⅘), 8.60 (s, 1H×⅕), 8.55 (s, 1H×⅘), 7.53-6.65 (m, 6H), 6.14-6.05 (m, 1H×⅘), 5.88-5.80 (m, 1H×⅕), 5.33-5.20 (m, 1H×⅕), 5.10-4.93 (m, 1H×⅘), 3.16-3.15 (m, 4H), 3.05-3.02 (m, 4H), 2.65 (brs, 1H), 1.63 (d, J=6.8 Hz, 3H)
mass: 460, 462 (M+1)$^+$.

Example 129

Synthesis of 2-[((1S)-1-{3-[(3R)-3-aminopyrrolidin-1-yl]phenyl}ethyl)amino]-4-(8-chloroimidazo[1,2-a]pyridin-3-yl)pyrimidine-5-carbonitrile [129] (hereinafter, referred to as the compound [129])

(1) 20.4 mg of t-butyl[(1S)-1-(3-{(3R)-3-[(trifluoroacetyl)amino]pyrrolidin-1-yl}phenyl)ethyl]carbamate [129-1] was obtained as a pale yellow solid, from 97 mg of 3-{(1S)-1-[(t-butoxycarbonyl)amino]ethyl}phenyl trifluoromethanesulfonate and 57 mg of (3R)-(+)-(trifluoroacetamido)pyrrolidine, according to the method of Example 128-(1).

(2) 7.0 mg of N-{(3R)-1-[3-((1S)-1-{[4-(8-chloroimidazo[1,2-a]pyridin-3-yl)-5-cyanopyrimidin-2-yl]amino}ethyl)phenyl]pyrrolidin-3-yl}-2,2,2-trifluoroacetamide [129-2] was obtained as a pale yellow solid, from 12.8 mg of the 4-(8-chloroimidazo[1,2-a]pyridin-3-yl)-2-(methylthio)pyrimidine-5-carbonitrile [123-1] and 20.4 mg of the t-butyl[(1S)-1-(3-{(3R)-3-[(trifluoroacetyl)amino]pyrrolidin-1- yl}phenyl)ethyl]carbamate [129-1], according to the methods of Example 106-(3) and (4).

(3) 4.5 mg of the target compound [129] was obtained as a yellow solid, from 7.0 mg of the N-{(3R)-1-[3-((1S)-1-{[4-(8-chloroimidazo[1,2-a]pyridin-3-yl)-5-cyanopyrimidin-2-yl]amino}ethyl)phenyl]pyrrolidin-3-yl}-2,2,2-trifluoroacetamide [129-2], according to the method of Example 110-(3).

A spectral data of the compound [129] is presented below.
$^1$H-NMR (CDCl$_3$) δ: 9.70 (d, J=8.0 Hz, 1H×⅕), 8.95 (s, 1H×⅕), 8.88 (s, 1H×⅘), 8.80 (d, J=8.0 Hz, 1H×⅘), 8.60 (s, 1H×⅕), 8.55 (s, 1H×⅘), 7.52-6.90 (m, 2H), 6.78-6.45 (m, 4H), 6.18-6.10 (m, 1H×⅘), 5.93-5.80 (m, 1H×⅕), 5.28-5.28 (m, 1H×⅕), 5.08-4.92 (m, 1H×⅘), 3.78-3.65 (m, 1H), 3.58-3.25 (m, 3H), 3.08-2.93 (m, 1H), 2.27-2.12 (m, 1H), 1.87-1.73 (m, 1H), 1.70-1.50 (m, 2H), 1.62 (d, J=6.8 Hz, 3H)
mass: 459, 461 (M+1)$^+$.

Example 130

Synthesis of 4-(8-chloroimidazo[1,2-a]pyridin-3-yl)-2-[((1S)-1-{4-[(1-methylpiperidin-4-yl)amino]phenyl}ethyl)amino]pyrimidine-5-carbonitrile [130] (hereinafter, referred to as the compound [130])

(1) 54 mg of 4-(8-chloroimidazo[1,2-a]pyridin-3-yl)-2-{[(1S)-1-(4-nitrophenyl)ethyl]amino}pyrimidine-5-carbonitrile [130-1] was obtained as a pale yellow solid, from 76 mg of the 4-(8-chloroimidazo[1,2-a]pyridin-3-yl)-2-(methylthio)pyrimidine-5-carbonitrile [123-1] and 57 mg of (S)-α-methyl-4-nitrobenzylamine hydrochloride, according to the method of Example 80-(4).

(2) 38 mg of 2-{[(1S)-1-(4-aminophenyl)ethyl]amino}-4-(8-chloroimidazo[1,2-a]pyridin-3-yl)pyrimidine-5-carbonitrile [130-2] was obtained as a white solid, from 54 mg of the 4-(8-chloroimidazo[1,2-a]pyridin-3-yl)-2-{[(1S)-1-(4-nitrophenyl)ethyl]amino}pyrimidine-5-carbonitrile [130-1], according to the method of Example 103-(2).

(3) 6.8 mg of the target compound [130] was obtained as a white solid, from 10 mg of the 2-{[(1S)-1-(4-aminophenyl)ethyl]amino}-4-(8-chloroimidazo[1,2-a]pyridin-3-yl)pyrimidine-5-carbonitrile [130-2] and 10 μL of 1-methyl-4-piperidone, according to the method of Example 91.

A spectral data of the compound [130] is presented below.
$^1$H-NMR (DMSO-d$_6$) δ: 10.07 (d, J=7.1 Hz, 1H×½), 9.10 (d, J=7.1 Hz, 1H×½), 8.92 (d, J=7.6 Hz, 1H×½), 8.81 (d, J=8.0 Hz, 1H×½), 8.76-8.75 (m, 1H+1H×½), 8.62 (s, 1H×½), 7.78 (d, J=7.6 Hz, 1H×½), 7.73 (d, J=7.6 Hz, 1H×½), 7.16 (t, J=7.3 Hz, 1H×½), 7.10 (d, J=8.6 Hz, 2H×½), 7.08 (d, J=8.6 Hz, 2H×½), 7.01 (t, J=7.3 Hz, 1H×½), 6.54 (d, J=8.6 Hz, 2H×½), 6.52 (d, J=8.6 Hz, 2H×½), 5.33 (t, J=8.4 Hz, 1H), 5.15-5.07 (m, 1H×½), 4.96-4.88 (m, 1H×½), 3.13-3.07 (m, 1H), 2.70-2.65 (m, 2H), 2.13 (s, 3H×½), 2.12 (s, 3H×½), 1.98-1.93 (m, 2H), 1.83-1.79 (m, 2H), 1.47 (d, J=7.1 Hz, 3H×½), 1.43 (d, J=7.1 Hz, 3H×½), 1.36-1.29 (m, 2H)
mass: 487, 489 (M+1)$^+$.

Example 131

Synthesis of 4-(8-chloroimidazo[1,2-a]pyridin-3-yl)-2-[((1S)-1-{4-[4-(trifluoroacetyl)piperazin-1-yl]phenyl}ethyl)amino]pyrimidine-5-carbonitrile [131] (hereinafter, referred to as the compound [131])

17 mg of the target compound [131] was obtained as a white solid, from 20 mg of the 4-(8-chloroimidazo[1,2-a]pyridin-3-yl)-2-(methylthio)pyrimidine-5-carbonitrile [123-1] and 40 mg of the t-butyl((1S)-1-{4-[4-(trifluoroacetyl)piperazin-1-yl]phenyl}ethyl)carbamate [110-1], according to the methods of Example 106-(3) and (4).

A spectral data of the compound [131] is presented below.
$^1$H-NMR (CDCl$_3$) δ: 9.71 (m, 1H×¼), 9.07-8.92 (m, 1H+1H×¾), 8.62-8.50 (m, 1H), 7.55-7.20 (m, 3H×¾), 7.49-7.09 (m, 3H), 7.04-6.89 (m, 2H+1H×¼), 6.66 (m, 1H×¾), 6.04 (m, 1H×¾), 5.80 (m, 1H×¼), 5.28 (m, 1H×¼), 5.08 (m, 1H×¾), 3.84 (m, 2H), 3.77 (m, 2H), 3.22 (m, 4H), 1.62 (d, J=8.0 Hz, 3H)
mass: 555, 557 (M+1)$^+$.

Example 132

Synthesis of 4-(8-chloroimidazo[1,2-a]pyridin-3-yl)-2-{[(1S)-1-(4-piperazin-1-ylphenyl)ethyl]amino}pyrimidine-5-carbonitrile [132] (hereinafter, referred to as the compound [132])

4 mg of the target compound [132] was obtained as a white solid from 8 mg of the compound [131], according to the method of Example 110-(3).

A spectral data of the compound [132] is presented below.
$^1$H-NMR (CDCl$_3$) δ: 9.69 (d, J=8.0 Hz, 1H×⅓), 8.99-8.89 (m, 1H+1H×⅔), 8.62 (s, 1H×⅓), 8.55 (s, 1H×¾), 7.50 (m, 1H×⅓), 7.43 (d, J=8.0 Hz, 1H×¾), 7.37-7.20 (m, 2H), 7.01-6.89 (m, 2H+1H×¼), 6.66 (dd, J=8.0, 8.0 Hz, 1H×¾), 6.03 (m, 1H×¾), 5.79 (m, 1H×¼), 5.28 (m, 1H×¼), 5.05 (m, 1H×¾), 3.15 (m, 4H), 3.03 (m, 4H), 1.61 (d, J=6.8 Hz, 3H)
mass: 459, 461 (M+1)$^+$.

Example 133

Synthesis of 4-(8-chloroimidazo[1,2-a]pyridin-3-yl)-2-({(1S)-1-[4-(4-methylpiperazin-1-yl)phenyl]ethyl}amino)pyrimidine-5-carbonitrile [133] (hereinafter, referred to as the compound [133])

8 mg of the target compound [133] was obtained as a white solid, from 20 mg of the 4-(8-chloroimidazo[1,2-a]pyridin-3-yl)-2-(methylthio)pyrimidine-5-carbonitrile [123-1] and 37 mg of the t-butyl{(1S)-1-[4-(4-methylpiperazin-1-yl)phenyl]ethyl}carbamate [107-1], according to the methods of Example 106-(3) and (4).

A spectral data of the compound [133] is presented below.
$^1$H-NMR (CDCl$_3$) δ: 9.68 (m, 1H×⅓), 8.99-8.90 (m, 1H+1H×⅔), 8.62 (s, 1H×⅓), 8.56 (s, 1H×¾), 7.50 (m, 1H×⅓), 7.44 (m, 1H×¾), 7.38-7.21 (m, 2H), 7.00-6.90 (m, 2H+1H×¼), 6.65 (m, 1H×¾), 6.02 (m, 1H×¾), 5.79 (m, 1H×¼), 5.27 (m, 1H×¼), 5.05 (m, 1H×¾), 3.22 (m, 4H), 2.59 (m, 4H), 2.36 (s, 3H), 1.61 (d, J=6.8 Hz, 3H)
mass: 473, 475 (M+1)$^+$.

Example 134

Synthesis of 4-(8-chloroimidazo[1,2-a]pyridin-3-yl)-2-({(1S)-1-[4-(2-oxopiperazin-1-yl)phenyl]ethyl}amino)pyrimidine-5-carbonitrile [134] (hereinafter, referred to as the compound [134])

(1) 10 mg of t-butyl-4-(4-{(1S)-1-[(t-butoxycarbonyl)amino]ethyl}phenyl)-3-oxopiperazin-1-carboxylate [134-1] was obtained as a pale yellow solid, from 100 mg of the t-butyl[(1S)-1-(4-bromophenyl)ethyl]carbamate [106-1] and 85 mg of t-butyl 3-oxopiperazin-1-carboxylate, according to the method of Example 106-(2).

(2) 2 mg of the target compound [134] was obtained as a white solid, from 10 mg of the t-butyl 4-(4-{(1S)-1-[(t-butoxycarbonyl)amino]ethyl}phenyl)-3-oxopiperazin-1-carboxylate [134-1] and 5 mg of the 4-(8-chloroimidazo[1,2-a]pyridin-3-yl)-2-(methylthio)pyrimidine-5-carbonitrile [123-1], according to the methods of Example 106-(3) and (4).

A spectral data of the compound [134] is presented below.
$^1$H-NMR (CDCl$_3$) δ: 9.69 (d, J=8.0 Hz, 1H×⅓), 8.99 (s, 1H×⅓), 8.88 (s, 1H×⅔), 8.72 (d, J=8.0 Hz, 1H×⅓), 8.61 (s, 1H×⅓), 8.58 (s, 1H×⅔), 7.60-7.20 (m, 5H+1H×⅓), 6.80 (m, 1H×⅔), 6.05 (m, 1H×⅔), 5.89 (m, 1H×⅓), 5.32 (m, 1H×⅓), 5.11 (m, 1H×⅔), 3.80-3.55 (m, 4H), 3.23 (m, 2H), 1.62 (d, J=6.8 Hz, 3H)
mass: 473, 475 (M+1)$^+$.

Example 135

Synthesis of 4-(8-chloroimidazo[1,2-a]pyridin-3-yl)-2-[((1S)-1-{4-[[2-(dimethylamino)ethyl](methyl)amino]phenyl}ethyl)amino]pyrimidine-5-carbonitrile [135] (hereinafter, referred to as the compound [135])

(1) 14 mg of t-butyl((1S)-1-{4-[[2-(dimethylamino)ethyl](methyl)amino]phenyl}ethyl)carbamate [135-1] was obtained as a pale yellow solid, from 100 mg of the t-butyl [(1S)-1-(4-bromophenyl)ethyl]carbamate [106-1] and 41 mg of N,N,N'-trimethylethylenediamine, according to the method of Example 128-(1).

(2) 5.1 mg of the target compound [135] was obtained as a white solid, from 14 mg of the t-butyl((1S)-1-{4-[[2-(dimethylamino)ethyl](methyl)amino]phenyl}ethyl)carbamate [135-1] and 9 mg of the 4-(8-chloroimidazo[1,2-a]pyridin-3-yl)-2-(methylthio)pyrimidine-5-carbonitrile [123-1], according to the methods of Example 106-(3) and (4).

A spectral data of the compound [135] is presented below.
$^1$H-NMR (CDCl$_3$) δ: 9.70 (m, 1H×⅓), 9.04 (d, J=8.0 Hz, 1H×⅔), 8.97 (s, 1H×⅓), 8.92 (s, 1H×⅔), 8.63 (s, 1H×⅓), 8.54 (s, 1H×⅔), 7.67-7.40 (m, 1H), 7.23 (m, 2H), 6.95 (m, 1H×⅓), 6.80-6.65 (m, 2H+1H×⅔), 6.02 (m, 1H×⅔), 5.80 (m, 1H×⅓), 5.26 (m, 1H×⅓), 5.04 (m, 1H×⅔), 3.48 (m, 2H), 2.96 (s, 3H), 2.50 (m, 2H), 1.61 (d, J=6.8 Hz, 3H)
mass: 475, 477 (M+1)$^+$.

Example 136

Synthesis of 2-({(1S)-1-[4-(3-aminoazetidin-1-yl)phenyl]ethyl}amino)-4-(8-chloroimidazo[1,2-a]pyridin-3-yl)pyrimidine-5-carbonitrile [136] (hereinafter, referred to as the compound [136])

(1) 38 mg of t-butyl[(1S)-1-(4-{3-[(trifluoroacetyl)amino]azetidin-1-yl}phenyl)ethyl]carbamate [136-1] was obtained as a pale yellow solid, from 100 mg of the t-butyl[(1S)-1-(4-bromophenyl)ethyl]carbamate [106-1] and 67 mg of N-azetidin-3-yl-2,2,2-trifluoroacetamide, according to the method of Example 128-(1).

(2) 12 mg of N-{1-[4-((1S)-1-{[4-(8-chloroimidazo[1,2-a]pyridin-3-yl)-5-cyanopyrimidin-2-yl]amino}ethyl)phenyl]azetidin-3-yl}-2,2,2-trifluoroacetamide [136-2] was obtained as a white solid, from 38 mg of the t-butyl[(1S)-1-(4-{3-[(trifluoroacetyl)amino]azetidin-1-yl}phenyl)ethyl]carbamate [136-1] and 19 mg of the 4-(8-chloroimidazo[1,2-a]pyridin-3-yl)-2-(methylthio)pyrimidine-5-carbonitrile [123-1], according to the methods of Example 106-(3) and (4).

(3) 6.4 mg of the target compound [136] was obtained as a white solid, from 12 mg of the N-{1-[4-((1S)-1-{[4-(8-chloroimidazo[1,2-a]pyridin-3-yl)-5-cyanopyrimidin-2-yl]amino}ethyl)phenyl]azetidin-3-yl}-2,2,2-trifluoroacetamide [136-2], according to the method of Example 110-(3).

A spectral data of the compound [136] is presented below.
$^1$H-NMR (CDCl$_3$) δ: 9.69 (m, 1H×⅓), 9.10 (d, J=6.4 Hz, 1H×⅔), 8.97 (s, 1H×⅓), 8.92 (s, 1H×⅔), 8.62 (s, 1H×⅓), 8.50 (s, 1H×⅔), 7.56-7.40 (m, 1H), 7.21 (d, J=8.4 Hz, 2H), 6.95 (m, 1H×⅓), 6.70 (m, 1H×⅔), 6.48 (d, J=8.4 Hz, 2H), 6.08 (m, 1H×⅔), 5.79 (m, 1H×⅓), 5.24 (m, 1H×⅓), 5.03 (m, 1H×⅔), 4.16 (m, 2H), 3.95 (m, 1H), 3.45 (m, 2H), 1.61 (d, J=6.8 Hz, 3H)
mass: 445, 447 (M+1)$^+$.

Example 137

Synthesis of 2-[((1S)-1-{4-[(3R)-3-aminopyrrolidin-1-yl]phenyl}ethyl)amino]-4-(8-chloroimidazo[1,2-a]pyridin-3-yl)pyrimidine-5-carbonitrile [137] (hereinafter, referred to as the compound [137])

(1) 24 mg of t-butyl[(1S)-1-(4-{(3R)-3-[(trifluoroacetyl)amino]pyrrolidin-1-yl}phenyl)ethyl]carbamate [137-1] was obtained as a pale yellow solid, from 100 mg of the t-butyl [(1S)-1-(4-bromophenyl)ethyl]carbamate [106-1] and 73 mg of (3R)-(+)-(trifluoroacetamido)pyrrolidine, according to the method of Example 128-(1).

(2) 13 mg of N-{(3R)-1-[4-((1S)-1-{[4-(8-chloroimidazo[1,2-a]pyridin-3-yl)-5-cyanopyrimidin-2-yl]amino}ethyl)phenyl]pyrrolidin-3-yl}-2,2,2-trifluoroacetamide [137-2] was obtained as a white solid, from 24 mg of the t-butyl[(1S)-1-(4-{(3R)-3-[(trifluoroacetyl)amino]pyrrolidin-1-yl}phenyl)ethyl]carbamate [137-1] and 12 mg of the 4-(8-chloroimidazo[1,2-a]pyridin-3-yl)-2-(methylthio)pyrimidine-5-carbonitrile [123-1], according to the methods of Example 106-(3) and (4).

(3) 7 mg of the target compound [137] was obtained as a white solid from 10 mg of the N-{(3R)-1-[4-((1S)-1-{[4-(8-chloroimidazo[1,2-a]pyridin-3-yl)-5-cyanopyrimidin-2-yl]amino}ethyl)phenyl]pyrrolidin-3-yl}-2,2,2-trifluoroacetamide [137-2], according to the method of Example 110-(3).

A spectral data of the compound [137] is presented below.
$^1$H-NMR (CDCl$_3$) δ: 9.69 (m, 1H×⅓), 9.10 (d, J=8.0 Hz, 1H×⅔), 8.97 (s, 1H×⅓), 8.92 (s, 1H×⅔), 8.62 (s, 1H×⅓), 8.48 (s, 1H×⅔), 7.55-7.40 (m, 1H), 7.23 (d, J=8.0 Hz, 2H), 6.94 (m, 1H×⅓), 6.73 (m, 1H×⅔), 6.55 (d, J=8.0 Hz, 2H), 6.12 (m, 1H×⅔), 5.80 (m, 1H×⅓), 5.23 (m, 1H×⅓), 5.04 (m, 1H×⅔), 3.73 (m, 1H), 3.59-3.40 (m, 2H), 3.33 (m, 1H), 3.02 (m, 1H), 2.21 (m, 1H), 1.81 (m, 1H), 1.61 (d, J=6.8 Hz, 3H)
mass: 459, 461 (M+1)$^+$.

Example 138

Synthesis of 4-(8-chloroimidazo[1,2-a]pyridin-3-yl)-2-({(1S)-1-[4-(4-methyl-1,4-diazepan-1-yl)phenyl]ethyl}amino)pyrimidine-5-carbonitrile [138] (hereinafter, referred to as the compound [138])

(1) 15 mg of t-butyl{(1S)-1-[4-(4-methyl-1,4-diazepan-1-yl)phenyl]ethyl}carbamate [138-1] was obtained as a pale yellow solid, from 100 mg of the t-butyl[(1S)-1-(4-bromophenyl)ethyl]carbamate [106-1] and 46 mg of N-methylhomopiperazine, according to the method of Example 106-(2).

(2) 1.2 mg of the target compound [138] was obtained as a white solid, from 15 mg of the t-butyl{(1S)-1-[4-(4-methyl-1,4-diazepan-1-yl)phenyl]ethyl}carbamate [138-1] and 9 mg of the 4-(8-chloroimidazo[1,2-a]pyridin-3-yl)-2-(methylthio)pyrimidine-5-carbonitrile [123-1], according to the methods of Example 106-(3) and (4).

A spectral data of the compound [138] is presented below.
$^1$H-NMR (CDCl$_3$) δ: 9.69 (d, J=8.0 Hz, 1H×⅓), 9.07 (d, J=8.0 Hz, 1H×⅔), 8.97 (s, 1H×⅓), 8.92 (s, 1H×⅔), 8.63 (s, 1H×⅓), 8.54 (s, 1H×⅔), 7.67-7.10 (m, 3H), 6.93 (m, 1H×⅓), 6.75-6.60 (m, 2H+1H×⅔), 6.02 (m, 1H×⅔), 5.79 (m, 1H×⅓), 5.25 (m, 1H×⅓), 5.04 (m, 1H×⅔), 3.60 (m, 2H), 3.48 (m, 2H), 2.75 (m, 2H), 2.60 (m, 2H), 2.40 (m, 3H), 2.05 (m, 2H), 1.61 (d, J=6.8 Hz, 3H)
mass: 487, 489 (M+1)$^+$.

Example 139

Synthesis of 4-(8-chloroimidazo[1,2-a]pyridin-3-yl)-2-({(1S)-1-[3-chloro-4-(4-methylpiperazin-1-yl)phenyl]ethyl}amino)pyrimidine-5-carbonitrile [139] (hereinafter, referred to as the compound [139])

(1) 80 mg of the t-butyl{(1S)-1-[4-(4-methylpiperazin-1-yl)phenyl]ethyl}carbamate [107-1] was dissolved in 3 mL of chloroform, then 70 mg of N-chlorosuccinimide was added thereto, and stirred at room temperature for 2 hours. The reaction solution was diluted with chloroform, washed with a saturated aqueous solution of sodium hydrogen carbonate, and dried over anhydrous magnesium sulfate. The insolubles were filtered, the filtrate was concentrated under reduced pressure, and thus obtained residue was purified by preparative thin-layer chromatography, to obtain 80 mg of t-butyl{(1S)-1-[3-chloro-4-(4-methylpiperazin-1-yl)phenyl]ethyl}carbamate [139-1] as a colorless oily product.

(2) 7.5 mg of the target compound [139] was obtained as a white solid, from 15 mg of the t-butyl{(1S)-1-[3-chloro-4-(4-methylpiperazin-1-yl)phenyl]ethyl}carbamate [139-1] and 12 mg of the 4-(8-chloroimidazo[1,2-a]pyridin-3-yl)-2-(methylthio)pyrimidine-5-carbonitrile [123-1], according to the methods of Example 106-(3) and (4).

A spectral data of the compound [139] is presented below.
$^1$H-NMR (CDCl$_3$) δ: 9.70 (m, 1H×⅓), 8.98 (s, 1H×⅓), 8.93 (s, 1H×⅔), 8.86 (d, J=8.0 Hz, 1H×⅔), 8.63 (s, 1H×⅓), 8.57 (s, 1H×⅔), 7.60-7.20 (m, 3H), 7.08 (d, J=8.0 Hz, 1H), 6.99 (m, 1H×⅓), 6.70 (m, 1H×⅔), 6.04 (m, 1H×⅔), 5.80 (m, 1H×⅓), 5.26 (m, 1H×⅓), 5.03 (m, 1H×⅔), 3.10 (m, 4H), 2.60 (m, 4H), 2.37 (s, 3H), 1.61 (d, J=6.8 Hz, 3H)
mass: 507, 509 (M+1)$^+$.

Example 140

Synthesis of 4-(8-chloroimidazo[1,2-a]pyridin-3-yl)-2-{[1-(6-piperazin-1-ylpyridin-3-yl)ethyl]amino}pyrimidine-5-carbonitrile [140] (hereinafter, referred to as the compound [140])

(1) The mixture of 702 mg of 6-chloronicotinonitrile, 954 mg of t-butylpiperazin-1-carboxylate, 1.2 g of potassium carbonate, and 10 mL of N,N-dimethylacetamide, was stirred at room temperature for 3 hours, then heated to 60° C. and stirred further for 4 hours. After cooling the reaction mixture back to room temperature, water was added thereto, and was extracted with ethyl acetate. The organic layer was dried over anhydrous magnesium sulfate, the insolubles were filtered, and the filtrate was concentrated under reduced pressure. The obtained residue was purified by silica gel column chromatography, and 1.39 g of t-butyl-4-(5-cyanopyridin-2-yl)piperazin-1-carboxylate [140-1] was obtained as a white solid.

(2) 900 mg of the t-butyl-4-(5-cyanopyridin-2-yl)piperazin-1-carboxylate [140-1] was dissolved in 40 mL of tetrahydrofuran, then 2.5 mL of methylmagnesium bromide (3.0M diethyl ether solution) was added under an ice-cold condition, and stirred at the same temperature for 1 hour. Thereafter, the temperature was increased back to room temperature and stirred overnight. Thereto, a saturated aqueous solution of ammonium chloride was added under an ice-cold condition, and extracted with ethyl acetate. The organic layer was washed with saturated brine, and dried over anhydrous magnesium sulfate. The insolubles were filtered, and the filtrate was concentrated under reduced pressure. The obtained residue was dissolved in 50 mL of methanol, then 850 mg of sodium boronhydride was added under an ice-cold condition, and the mixture was stirred at the same temperature for 2 hours and a half. The reaction mixture was added with water, and extracted with chloroform. The organic layer was washed with saturated brine and dried over anhydrous magnesium sulfate, and the insolubles were filtered. The filtrate was concentrated under reduced pressure, and the thus obtained residue was purified by silica gel column chromatography, to obtain 950 mg of t-butyl 4-[5-(1-aminoethyl)pyridin-2-yl]piperazin-1-carboxylate [140-2] as a white solid.

(3) 29 mg of t-butyl 4-[5-(1-{[4-(8-chloroimidazo[1,2-a]pyridin-3-yl)-5-cyanopyrimidin-2-yl]amino}ethyl)pyridin-2-yl]piperazin-1-carboxylate [140-3] was obtained as a brown oily product, from 35 mg of the 4-(8-chloroimidazo[1,2-a]pyridin-3-yl)-2-(methylthio)pyrimidine-5-carbonitrile [123-1] and 68 mg of the t-butyl 4-[5-(1-aminoethyl)pyridin-2-yl]piperazin-1-carboxylate [140-2], according to the method of Example 80-(4).

(4) 29 mg of the t-butyl 4-[5-(1-{[4-(8-chloroimidazo[1,2-a]pyridin-3-yl)-5-cyanopyrimidin-2-yl]amino}ethyl)pyridin-2-yl]piperazin-1-carboxylate [140-3] was dissolved in 3 mL of chloroform, then 3 mL of trifluoroacetic acid was added thereto, and stirred at room temperature for 1 hour. The reaction mixture was concentrated under reduced pressure, a saturated aqueous solution of sodium hydrogen carbonate was added thereto, and was extracted with chloroform. The organic layer was dried over anhydrous magnesium sulfate, and the insolubles were filtered. The filtrate was concentrated under reduced pressure, and the obtained residue was dissolved in a small amount of chloroform and solidified by hexane, to obtain 16.6 mg of the target compound [140] as a white solid.

A spectral data of the compound [140] is presented below.
$^1$H-NMR (CDCl$_3$) δ: 9.75 (m, 1H×⅓), 9.06 (d, J=8.0 Hz, 1H×⅔), 8.94 (s, 1H×⅓), 8.90 (s, 1H×⅔), 8.60 (s, 1H×⅓), 8.55 (s, 1H×⅔), 8.22 (m, 1H), 7.60-7.40 (m, 2H), 6.97 (m, 1H×⅓), 6.85 (m, 1H×⅔), 6.69 (d, J=8.0 Hz, 1H), 5.23 (m, 1H×⅓), 5.04 (m, 1H×⅔), 3.55 (m, 2H), 3.04 (m, 2H), 1.62 (d, J=6.8 Hz, 3H)
mass: 460, 462 (M+1)$^+$.

Example 141

Synthesis of 4-(6,8-dichloroimidazo[1,2-a]pyridin-3-yl)-2-[((1S)-1-{3-[(1-methylpiperidin-4-yl)amino]phenyl}ethyl)amino]pyrimidine-5-carbonitrile [141] (hereinafter, referred to as the compound [141])

(1) 205 mg of 4-(6,8-dichloroimidazo[1,2-a]pyridin-3-yl)-2-(methylthio)pyrimidine-5-carbonitrile [141-1] was obtained as a light brown solid, from 100 mg of 2-amino-3,5-dichloropyridine and 135 mg of the 4-[(Z)-2-ethoxyvinyl]-2-(methylthio)-5-pyrimidinecarbonyl [48-3], according to the method of Example 25-(3).

(2) 12.6 mg of 2-{[(1S)-1-(3-aminophenyl)ethyl]amino}-4-(6,8-dichloroimidazo[1,2-a]pyridin-3-yl)pyrimidine-5- carbonitrile [141-2] was obtained as a light brown solid, from 50 mg of the 4-(6,8-dichloroimidazo[1,2-a]pyridin-3-yl)-2-(methylthio)pyrimidine-5-carbonitrile [141-1] and 24.4 mg of 3-[(1S)-1-aminoethyl]aniline, according to the method of Example 80-(4).

(3) 11.7 mg of the target compound [141] was obtained as a white solid, from 9.7 mg of the 2-{[(1S)-1-(3-aminophenyl)ethyl]amino}-4-(6,8-dichloroimidazo[1,2-a]pyridin-3-yl)pyrimidine-5-carbonitrile [141-2] and 8.4 μL of 1-methyl-4-piperidone, according to the method of Example 91.

A spectral data of the compound [141] is presented below.
$^1$H-NMR (CDCl$_3$) δ: 9.80 (s, 1H×4/5), 9.75 (s, 1H×1/5), 9.01 (s, 1H×4/5), 8.95 (s, 1H×1/5), 8.62 (s, 1H×1/5), 8.52 (s, 1H×4/5), 7.52 (s, 1H), 7.20-7.08 (m, 1H), 6.77-6.42 (m, 3H), 6.18-5.88 (m, 1H), 5.28-5.06 (m, 1H), 3.70-3.42 (m, 1H), 3.38-3.20 (m, 1H), 2.95-2.76 (m, 2H), 2.35 (s, 3H), 2.27-1.95 (m, 4H), 1.66 (d, J=6.6 Hz, 3H), 1.60-1.40 (m, 2H)

mass: 521, 523 (M+1)$^+$.

Example 142

Synthesis of 4-(7,8-dichloroimidazo[1,2-a]pyridin-3-yl)-2-[((1S)-1-{3-[(1-methylpiperidin-4-yl)amino]phenyl}ethyl)amino]pyrimidine-5-carbonitrile [142] (hereinafter, referred to as the compound [142])

(1) 20 mg of 4-(7,8-dichloroimidazo[1,2-a]pyridin-3-yl)-2-(methylthio)pyrimidine-5-carbonitrile [142-1] was obtained as a light brown solid, from 30 mg of 3,4-dichloropyridine-2-amine (synthesized according to a method disclosed in page 22-23 in Pamphlet of International Publication WO 97/027,205) and 40.7 mg of the 4-[(Z)-2-ethoxyvinyl]-2-(methylthio)-5-pyrimidinecarbonyl [48-3], according to the method of Example 25-(3).

(2) 9.0 mg of 2-{[(1S)-1-(3-aminophenyl)ethyl]amino}-4-(7,8-dichloroimidazo[1,2-a]pyridin-3-yl)pyrimidine-5-carbonitrile [142-2] was obtained as a white solid, from 20 mg of the 4-(7,8-dichloroimidazo[1,2-a]pyridin-3-yl)-2-(methylthio)pyrimidine-5-carbonitrile [142-1] and 24.4 mg of 3-[(1S)-1-aminoethyl]aniline, according to the method of Example 80-(4).

(3) 6.5 mg of the target compound [142] was obtained as a white solid, from 8.0 mg of the 2-{[(1S)-1-(3-aminophenyl)ethyl]amino}-4-(7,8-dichloroimidazo[1,2-a]pyridin-3-yl)pyrimidine-5-carbonitrile [142-2] and 8.4 μL of 1-methyl-4-piperidone, according to the method of Example 91.

A spectral data of the compound [142] is presented below.
$^1$H-NMR (CDCl$_3$) δ: 9.63 (d, J=7.6 Hz, 1H×1/5), 8.96 (s, 1H×1/5), 8.83 (s, 1H×4/5), 8.62 (s, 1H×1/5), 8.56 (s, 1H×4/5), 8.52 (d, J=7.6 Hz, 1H×4/5), 7.20 (dd, J=7.6 Hz, 7.6 Hz, 1H), 7.05 (d, J=7.6 Hz, 1H×1/5), 6.81 (d, J=7.6 Hz, 1H×4/5), 6.68 (d, J=7.6 Hz, 1H), 6.60-6.50 (m, 2H), 6.10-6.06 (m, 1H×4/5), 5.88-5.80 (m, 1H×1/5), 5.23-5.20 (m, 1H×1/5), 4.94-4.85 (m, 1H×4/5), 3.75-3.70 (m, 1H), 3.35-3.25 (m, 1H), 2.89-2.80 (m, 2H), 2.32 (s, 3H), 2.19-2.05 (m, 4H), 1.61 (d, J=6.8 Hz, 3H), 1.60-1.50 (m, 2H)

mass: 521, 523 (M+1)$^+$.

Example 143

Synthesis of 4-(8-fluoroimidazo[1,2-a]pyridin-3-yl)-2-{[(1S)-1-(4-piperazin-1-ylphenyl)ethyl]amino}pyrimidine-5-carbonitrile [143] (hereinafter, referred to as the compound [143])

(1) 110 mg of 4-(8-fluoroimidazo[1,2-a]pyridin-3-yl)-2-(methylthio)pyrimidine-5-carbonitrile [143-1] was obtained as a pale yellow solid, from 101 mg of 2-amino-3-fluoropyridine and 200 mg of the 4-[(Z)-2-ethoxyvinyl]-2-(methylthio)-5-pyrimidinecarbonyl [48-3], according to the method of Example 25-(3).

(2) 17 mg of the compound [143-2] was obtained as a yellow solid, from 25 mg of the 4-(8-fluoroimidazo[1,2-a]pyridin-3-yl)-2-(methylthio)pyrimidine-5-carbonitrile [143-1] and 52.8 mg of the t-butyl((1S)-1-{4-[4-(trifluoroacetyl)piperazin-1-yl]phenyl}ethyl)carbamate [110-1], according to the methods of Example 106-(3) and (4).

(3) 13.7 mg of the target compound [143] was obtained as a pale yellow solid from 17 mg of the compound [143-2], according to the method of Example 110-(3).

A spectral data of the compound [143] is presented below.
$^1$H-NMR (CDCl$_3$) δ: 9.53 (d, J=6.9 Hz, 1H×1/5), 8.92 (s, 1H×1/5), 8.90 (s, 1H×4/5), 8.83 (d, J=6.9 Hz, 1H×4/5), 8.57 (s, 1H×1/5), 8.49 (s, 1H×4/5), 7.36-6.60 (m, 6H), 6.18-6.10 (m, 1H×4/5), 5.87-5.75 (m, 1H×1/5), 5.33-5.20 (m, 1H×1/5), 5.17-5.00 (m, 1H×4/5), 3.18-3.10 (m, 4H), 3.08-2.96 (m, 4H), 2.65 (brs, 1H), 1.62 (d, J=6.8 Hz, 3H)

mass: 443 (M+1)$^+$.

Example 144

Synthesis of 4-(8-bromoimidazo[1,2-a]pyridin-3-yl)-2-[((1S)-1-{3-[(1-methylpiperidin-4-yl)amino]phenyl}ethyl)amino]pyrimidine-5-carbonitrile [144] (hereinafter, referred to as the compound [144])

(1) 516 mg of 4-(8-bromoimidazo[1,2-a]pyridin-3-yl)-2-(methylthio)pyrimidine-5-carbonitrile [144-1] was obtained as a light brown solid, from 550 mg of 2-amino-3-bromopyridine and 700 mg of the 4-[(Z)-2-ethoxyvinyl]-2-(methylthio)-5-pyrimidinecarbonyl [48-3], according to the method of Example 25-(3).

(2) 61.1 mg of 2-{[(1S)-1-(3-aminophenyl)ethyl]amino}-4-(8-bromoimidazo[1,2-a]pyridin-3-yl)pyrimidine-5-carbonitrile [144-2] was obtained as a pale yellow solid, from 100 mg of the 4-(8-bromoimidazo[1,2-a]pyridin-3-yl)-2-(methylthio)pyrimidine-5-carbonitrile [144-1] and 59 mg of 3-[(1S)-1-aminoethyl]aniline, according to the methods of Example 106-(3) and (4).

(3) 16.4 mg of the target compound [144] was obtained as a white solid, from 21.9 mg of the 2-{[(1S)-1-(3-aminophenyl)ethyl]amino}-4-(8-bromoimidazo[1,2-a]pyridin-3-yl)pyrimidine-5-carbonitrile [144-2] and 18.6 μL of 1-methyl-4-piperidone, according to the method of Example 91.

A spectral data of the compound [144] is presented below.
$^1$H-NMR (CDCl$_3$) δ: 9.72 (d, J=6.9 Hz, 1H×1/5), 8.99 (s, 1H×1/5), 8.89 (s, 1H×4/5), 8.83 (d, J=6.9 Hz, 1H×4/5), 8.62 (s, 1H×1/5), 8.54 (s, 1H×4/5), 7.72-6.80 (m, 2H), 6.70-6.52 (m, 4H), 6.06-6.04 (m, 1H×4/5), 5.88-5.80 (m, 1H×1/5), 5.28-5.15 (m, 1H×1/5), 5.05-4.89 (m, 1H×4/5), 3.74-3.45 (m, 1H), 3.35-3.18 (m, 1H), 2.87-2.68 (m, 2H), 2.30 (s, 3H), 2.18-1.94 (m, 4H), 1.61 (d, J=6.6 Hz, 3H), 1.60-1.40 (m, 2H)

mass: 531, 533 (M+1)$^+$.

Example 145

Synthesis of 4-(8-bromoimidazo[1,2-a]pyridin-3-yl)-2-{[(1S)-1-(4-piperazin-1-ylphenyl)ethyl]amino}pyrimidine-5-carbonitrile [145] (hereinafter, referred to as the compound [145])

(1) 29.5 mg of 4-(8-bromoimidazo[1,2-a]pyridin-3-yl)-2-[((1S)-1-{4-[4-(trifluoroacetyl)piperazin-1-yl]phenyl}ethyl)amino]pyrimidine-5-carbonitrile [145-1] was obtained as a white solid, from 30.3 mg of the 4-(8-bromoimidazo[1,2-a]pyridin-3-yl)-2-(methylthio)pyrimidine-5-carbonitrile [144-1] and 52.8 mg of the t-butyl((1S)-1-{4-[4-(trifluoroacetyl)piperazin-1-yl]phenyl}ethyl)carbamate [110-1], according to the methods of Example 106-(3) and (4).

(2) 21.2 mg of the target compound [145] was obtained as a pale yellow solid, from 29.5 mg of the 4-(8-bromoimidazo[1,2-a]pyridin-3-yl)-2-[((1S)-1-{4-[4-(trifluoroacetyl)piperazin-1-yl]phenyl}ethyl)amino]pyrimidine-5-carbonitrile [145-1], according to the method of Example 110-(3).

A spectral data of the compound [145] is presented below.
$^1$H-NMR (CDCl$_3$) δ: 9.75-9.73 (m, 1H×⅕), 8.92-8.90 (m, 1H+1H×⅕), 8.62 (s, 1H×⅕), 8.54 (s, 1H×⅘), 7.70-6.59 (m, 6H), 6.09-6.07 (m, 1H×⅘), 5.86-5.72 (m, 1H×⅕), 5.28-5.20 (m, 1H×⅕), 5.07-5.03 (m, 1H×⅘), 3.17-3.10 (m, 4H), 3.05-3.03 (m, 4H), 2.67 (brs, 1H), 1.61 (d, J=6.6 Hz, 3H)
mass: 503, 505 (M+1)$^+$.

Example 146

Synthesis of 4-(8-bromo-6-methylimidazo[1,2-a]pyridin-3-yl)-2-[((1S)-1-{3-[(1-methylpiperidin-4-yl)amino]phenyl}ethyl)amino]pyrimidine-5-carbonitrile [146] (hereinafter, referred to as the compound [146])

(1) 216 mg of 4-(8-bromo-6-methylimidazo[1,2-a]pyridin-3-yl)-2-(methylthio)pyrimidine-5-carbonitrile [146-1] was obtained as a pale yellow solid, from 169 mg of 2-amino-3-bromo-5-methylpyridine and 200 mg of the 4-[(Z)-2-ethoxyvinyl]-2-(methylthio)-5-pyrimidinecarbonyl [48-3], according to the method of Example 25-(3).

(2) 30.8 mg of 2-{[(1S)-1-(3-aminophenyl)ethyl]amino}-4-(8-bromo-6-methylimidazo[1,2-a]pyridin-3-yl)pyrimidine-5-carbonitrile [146-2] was obtained as a pale yellow solid, from 53.6 mg of the 4-(8-bromo-6-methylimidazo[1,2-a]pyridin-3-yl)-2-(methylthio)pyrimidine-5-carbonitrile [146-1] and 24.4 mg of 3-[(1S)-1-aminoethyl]aniline, according to the methods of Example 106-(3) and (4).

(3) 16.4 mg of the target compound [146] was obtained as a white solid, from 17.7 mg of the 2-{[(1S)-1-(3-aminophenyl)ethyl]amino}-4-(8-bromo-6-methylimidazo[1,2-a]pyridin-3-yl)pyrimidine-5-carbonitrile [146-2] and 14.6 μL of 1-methyl-4-piperidone, according to the method of Example 91.

A spectral data of the compound [146] is presented below.
$^1$H-NMR (CDCl$_3$) δ: 9.47-9.30 (m, 1H), 8.96-8.83 (m, 1H), 8.65-8.40 (m, 1H), 7.60-7.46 (m, 1H), 7.30-7.10 (m, 1H), 6.77-6.45 (m, 2H), 6.25-5.80 (m, 1H), 5.34-5.10 (m, 1H), 3.82-3.50 (m, 1H), 3.37-3.16 (m, 1H), 2.88-2.78 (m, 2H), 2.29 (s, 3H), 2.32-2.25 (m, 3H), 2.33-1.92 (m, 4H), 1.66 (d, J=6.6 Hz, 3H), 1.60-1.40 (m, 2H)
mass: 545, 547 (M+1)$^+$.

Example 147

Synthesis of 4-[8-(fluoromethyl)imidazo[1,2-a]pyridin-3-yl]-2-[((1S)-1-{3-[(1-methylpiperidin-4-yl)amino]phenyl}ethyl)amino]pyrimidine-5-carbonitrile [147] (hereinafter, referred to as the compound [147])

(1) To 100 mL of tetrahydrofuran solution containing 5.7 g of lithium aluminum hydride, 20 mL of tetrahydrofuran solution containing 13.8 g of 2-aminonicotinic acid was added, and heated for 2 hours under reflux. After cooling the reaction mixture back to room temperature, sodium sulfate decahydrate was slowly added until there are no bubbles, and stirred for 2 hours at room temperature. The insolubles were filtered through celite, the filtrate was concentrated under reduced pressure, and 10.7 g of (2-aminopyridin-3-yl)methanol [147-1] was obtained as a white solid.

(2) 6.76 g of 4-[8-(hydroxymethyl)imidazo[1,2-a]pyridin-3-yl]-2-(methylthio)pyrimidine-5-carbonitrile [147-2] was obtained as a light brown solid, from 4.31 g of the (2-aminopyridin-3-yl)methanol [147-1] and 7.0 g of the 4-[(Z)-2-ethoxyvinyl]-2-(methylthio)-5-pyrimidinecarbonitrile [48-3], according to the method of Example 25-(3).

(3) 4.23 g of the 4-[8-(hydroxymethyl)imidazo[1,2-a]pyridin-3-yl]-2-(methylthio)pyrimidine-5-carbonitrile [147-2] was dissolved in 500 mL of chloroform, then 5.2 mL of bis-(2-methoxyethyl)aminosulfur trifluoride was added thereto at −40° C., and stirred at the same temperature for 1 hour. 2.6 mL of bis-(2-methoxyethyl)aminosulfur trifluoride was further added, and stirred at the same temperature for 1 hour. Thereto, a saturated aqueous solution of sodium hydrogen carbonate was slowly added, and the mixture was extracted with chloroform. The organic layer was washed with water and saturated brine in the subsequent order, and dried over anhydrous magnesium sulfate. The insolubles were filtered, the filtrate was concentrated under reduced pressure, and the thus obtained residue was dissolved in a small amount of chloroform and solidified by adding diethyl ether, to obtain 3.43 g of 4-[8-(fluoromethyl)imidazo[1,2-a]pyridin-3-yl]-2-(methylthio)pyrimidine-5-carbonitrile [147-3] as a light brown solid.

(4) 9.0 mg of 2-{[(1S)-1-(3-aminophenyl)ethyl]amino}-4-[8-(fluoromethyl)imidazo[1,2-a]pyridin-3-yl]pyrimidine-5-carbonitrile [147-4] was obtained as a pale yellow solid, from 20 mg of the 4-[8-(fluoromethyl)imidazo[1,2-a]pyridin-3-yl]-2-(methylthio)pyrimidine-5-carbonitrile [147-3] and 18 mg of 3-[(1S)-1-aminoethyl]aniline, according to the method of Example 80-(3).

(5) 4.3 mg of the target compound [147] was obtained as a white solid, from 9.0 mg of the 2-{[(1S)-1-(3-aminophenyl)ethyl]amino}-4-[8-(fluoromethyl)imidazo[1,2-a]pyridin-3-yl]pyrimidine-5-carbonitrile [147-4] and 7.4 μL of 1-methyl-4-piperidone, according to the method of Example 91.

A spectral data of the compound [147] is presented below.
$^1$H-NMR (CDCl$_3$) δ: 9.75-9.74 (m, 1H×⅕), 8.95 (s, 1H×⅕), 8.89-8.86 (m, 1H×⅘+1H×⅘), 8.60 (s, 1H×⅕), 8.55 (s, 1H×⅘), 7.55-7.43 (m, 1H), 7.23-7.06 (m, 1H), 6.82-6.53 (m, 4H), 6.04-5.76 (m, 3H), 5.26-5.18 (m, 1H×⅕), 5.03-4.96 (m, 1H×⅘), 3.67-3.63 (m, 1H), 3.32-3.26 (m, 1H), 2.85-2.79 (m, 2H), 2.32 (s, 3H), 2.13-2.01 (m, 4H), 1.61 (d, J=6.8 Hz, 3H), 1.56-1.49 (m, 2H)
mass: 485 (M+1)$^+$.

Example 148

Synthesis of 4-[8-(fluoromethyl)imidazo[1,2-a]pyridin-3-yl]-2-({(1S)-1-[4-(4-methylpiperazin-1-yl)phenyl]ethyl}amino)pyrimidine-5-carbonitrile [148] (hereinafter, referred to as the compound [148])

11.3 mg of the target compound [148] was obtained as a white solid, from 15 mg of the 4-[8-(fluoromethyl)imidazo[1,2-a]pyridin-3-yl]-2-(methylthio)pyrimidine-5-carbonitrile [147-3] and 33.4 mg of the t-butyl{(1S)-1-[4-(4-methylpiperazin-1-yl)phenyl]ethyl}carbamate [107-1], according to the methods of Example 106-(3) and (4).

A spectral data of the compound [148] is presented below.
$^1$H-NMR (DMSO-d$_6$) δ: 10.11 (d, J=7.3 Hz, 1H×½), 9.12 (d, J=7.1 Hz, 1H×½), 8.95 (d, J=7.3 Hz, 1H×½), 8.85 (d, J=8.3 Hz, 1H×½), 8.75 (s, 1H×½), 8.74 (s, 1H×½), 8.73 (s, 1H×½), 8.61 (s, 1H×½), 7.69 (d, J=6.8 Hz, 1H×½), 7.63 (d, J=6.8 Hz, 1H×½), 7.27-7.24 (m, 2H+1H×½), 7.10 (t, J=7.3 Hz, 1H×½), 6.93 (d, J=8.8 Hz, 2H×½), 6.89 (d, J=8.8 Hz, 2H×½), 5.83 (d, J=47.1 Hz, 2H×½), 5.79 (d, J=47.1 Hz, 2H×½), 5.20-5.13 (m, 1H×½), 5.05-4.98 (m, 1H×½), 3.08-3.05 (m, 4H), 2.43-2.38 (m, 4H), 2.19 (s, 3H×½), 2.18 (s, 3H×½), 1.49 (d, J=6.8 Hz, 3H×½), 1.46 (d, J=6.1 Hz, 3H×½)

mass: 471 (M+1)$^+$.

Example 149

Synthesis of 4-[8-(fluoromethyl)imidazo[1,2-a]pyridin-3-yl]-2-{[(1S)-1-(4-piperazin-1-ylphenyl)ethyl]amino}pyrimidine-5-carbonitrile [149] (hereinafter, referred to as the compound [149])

(1) 13 mg of 4-[8-(fluoromethyl)imidazo[1,2-a]pyridin-3-yl]-2-[((1S)-1-{4-[4-(trifluoroacetyl)piperazin-1-yl]phenyl}ethyl)amino]pyrimidine-5-carbonitrile [149-1] was obtained as a white solid, from 22 mg of the 4-[8-(fluoromethyl)imidazo[1,2-a]pyridin-3-yl]-2-(methylthio)pyrimidine-5-carbonitrile [147-3] and 42.6 mg of the t-butyl((1S)-1-{4-[4-(trifluoroacetyl)piperazin-1-yl]phenyl}ethyl)carbamate [110-1], according to the methods of Example 106-(3) and (4).

(2) 5.1 mg of the target compound [149] was obtained as a white solid, from 13 mg of the 4-[8-(fluoromethyl)imidazo[1,2-a]pyridin-3-yl]-2-[((1S)-1-{4-[4-(trifluoroacetyl)piperazin-1-yl]phenyl}ethyl)amino]pyrimidine-5-carbonitrile [149-1], according to the method of Example 110-(3).

A spectral data of the compound [149] is presented below.
$^1$H-NMR (DMSO-d$_6$) δ: 10.11 (d, J=7.1 Hz, 1H×½), 9.12 (d, J=7.3 Hz, 1H×½), 8.95 (d, J=7.3 Hz, 1H×½), 8.86 (d, J=8.1 Hz, 1H×½), 8.75 (s, 1H×½), 8.74 (s, 1H×½), 8.73 (s, 1H×½), 8.61 (s, 1H×½), 7.69 (d, J=7.2 Hz, 1H×½), 7.63 (d, J=7.2 Hz, 1H×½), 7.27-7.23 (m, 2H+1H×½), 7.09 (t, J=7.1 Hz, 1H×½), 6.91 (d, J=8.8 Hz, 2H×½), 6.87 (d, J=8.8 Hz, 2H×½), 5.83 (d, J=47.1 Hz, 2H×½), 5.79 (d, J=47.1 Hz, 2H×½), 5.21-5.13 (m, 1H×½), 5.04-4.96 (m, 1H×½), 2.99-2.96 (m, 4H), 2.80-2.76 (m, 4H), 1.50 (d, J=6.8 Hz, 3H×½), 1.46 (d, J=6.8 Hz, 3H×½)

mass: 457 (M+1)$^+$.

Example 150

Synthesis of 2-[((1S)-1-{4-[(3R)-3,4-dimethylpiperazin-1-yl]phenyl}ethyl)amino]-4-[8-(fluoromethyl)imidazo[1,2-a]pyridin-3-yl]pyrimidine-5-carbonitrile [150] (hereinafter, referred to as the compound [150])

(1) 500 mg of t-butyl(3R)-3-methylpiperazin-1-carboxylate and 400 μL of formaldehyde solution (37%) were dissolved in 5 mL of chloroform, then a solution prepared by dissolving 151 mg of cyanotrihydro sodium borate and 163 mg of zinc chloride in 8 mL of methanol was added thereto, and stirred overnight at room temperature. The reaction mixture was diluted in 100 μL of chloroform, washed with a saturated aqueous solution of sodium hydrogen carbonate, and dried over anhydrous magnesium sulfate. The insolubles were filtered, the filtrate was concentrated under reduced pressure, and the obtained residue was dissolved in 4 mL of chloroform. Thereto, 4 mL of trifluoroacetic acid was added, and stirred at room temperature for 1 hour and a half. The reaction solution was concentrated under reduced pressure, the obtained residue was dissolved in methanol, and the trifluoroacetic acid was removed through a weak anion-exchange resin. The solvent was distilled off under reduced pressure, and 46 mg of (2R)-1,2-dimethylpiperazine [150-1] was obtained as a brown oily product.

(2) 10 mg of t-butyl((1S)-1-{4-[(3R)-3,4-dimethylpiperazin-1-yl]phenyl}ethyl)carbamate [150-2] was obtained as a brown oily product, from 100 mg of the t-butyl[(1S)-1-(4-bromophenyl)ethyl]carbamate [106-1] and 46 mg of the (2R)-1,2-dimethylpiperazine [150-1], according to the method of Example 128-(1).

(3) 5.0 mg of the target compound [150] was obtained as a pale yellow solid, from 10 mg of the t-butyl((1S)-1-{4-[(3R)-3,4-dimethylpiperazin-1-yl]phenyl}ethyl)carbamate [150-2] and 7.5 mg of the 4-[8-(fluoromethyl)imidazo[1,2-a]pyridin-3-yl]-2-(methylthio)pyrimidine-5-carbonitrile [147-3], according to the methods of Example 106-(3) and (4).

A spectral data of the compound [150] is presented below.
$^1$H-NMR (DMSO-d$_6$) δ: 10.11 (d, J=6.8 Hz, 1H×½), 9.13 (d, J=7.3 Hz, 1H×½), 8.95 (d, J=7.3 Hz, 1H×½), 8.85 (d, J=8.3 Hz, 1H×½), 8.75 (s, 1H×½), 8.74 (s, 1H×½), 8.73 (s, 1H×½), 8.61 (s, 1H×½), 7.69 (d, J=7.8 Hz, 1H×½), 7.63 (d, J=6.3 Hz, 1H×½), 7.26-7.23 (m, 2H+1H×½), 7.10 (t, J=7.1 Hz, 1H×½), 6.92 (d, J=8.8 Hz, 2H×½), 6.88 (d, J=8.8 Hz, 2H×½), 5.83 (d, J=47.1 Hz, 2H×½), 5.79 (d, J=47.1 Hz, 2H×½), 5.21-5.13 (m, 1H×½), 5.05-4.97 (m, 1H×½), 3.49-3.44 (m, 2H), 2.79-2.64 (m, 2H), 2.34-2.26 (m, 1H), 2.19-2.07 (m, 5H), 1.49 (d, J=7.0 Hz, 3H×½), 1.46 (d, J=7.0 Hz, 3H×½), 1.34-1.30 (m, 2H)

mass: 485 (M+1)$^+$.

Example 151

Synthesis of 2-[((1S)-1-{4-[(1S,4S)-2,5-diazabicyclo[2.2.1]hept-2-yl]phenyl}ethyl)amino]-4-[8-(fluoromethyl)imidazo[1,2-a]pyridin-3-yl]pyrimidine-5-carbonitrile [151] (hereinafter, referred to as the compound [151])

(1) 226 mg of t-butyl(1S,4S)-2,5-diazabicyclo[2.2.1]heptane-2-carboxylate was suspended in 5 mL of tetrahydrofuran, and 476 μL of triethylamine was added thereto. 194 μL of trifluoroacetic anhydride was added to the mixture, and stirred at room temperature for 1 hour. The reaction mixture was added with water, and extracted with ethyl acetate. The organic layer was washed with saturated brine, and dried over anhydrous sodium sulfate. The insolubles were filtered, the filtrate was concentrated under reduced pressure, and the thus obtained residue was purified by silica gel column chromatography, to obtain 204 mg of (t-butyl(1S,4S)-5-(trifluoroacetyl)-2,5-diazabicyclo[2.2.1]heptane-2-carboxylate [151-1] as a light brown oily product.

(2) 204 mg of the (t-butyl(1S,4S)-5-(trifluoroacetyl)-2,5-diazabicyclo[2.2.1]heptane-2-carboxylate [151-1] was dissolved in 3 mL of chloroform, then 3 mL of trifluoroacetic acid was added thereto, and stirred at room temperature for 1 hour. The reaction solution was concentrated under reduced pressure, the obtained residue was dissolved in methanol, and the trifluoroacetic acid was removed through a weak anion-exchange resin. The solvent was distilled off under reduced pressure, and 156 mg of (1S,4S)-2-(trifluoroacetyl)-2,5-diazabicyclo[2.2.1]heptane [151-2] was obtained as a brown oily product.

(3) 156 mg of t-butyl((1S)-1-{4-[(1S,4S)-5-(trifluoroacetyl)-2,5-diazabicyclo[2.2.1]hept-2-yl]phenyl}ethyl)carbamate [151-3] was obtained as a light brown solid, from 100 mg of the t-butyl[(1S)-1-(4-bromophenyl)ethyl]carbamate

[106-1] and 156 mg of the (1S,4S)-2-(trifluoroacetyl)-2,5-diazabicyclo[2.2.1]heptane [151-2], according to the method of Example 110-(1).

(4) 12 mg of 4-[8-(fluoromethyl)imidazo[1,2-a]pyridin-3-yl]-2-[((1S)-1-{4-[(1S,4S)-5-(trifluoroacetyl)-2,5-diazabicyclo[2.2.1]hept-2-yl]phenyl}ethyl)amino]pyrimidine-5-carbonitrile [151-4] was obtained as a light brown solid, from 97 mg of the t-butyl((1S)-1-{4-[(1S,4S)-5-(trifluoroacetyl)-2,5-diazabicyclo[2.2.1]hept-2-yl]phenyl}ethyl)carbamate [151-3] and 38 mg of the 4-[8-(fluoromethyl)imidazo[1,2-a]pyridin-3-yl]-2-(methylthio)pyrimidine-5-carbonitrile [147-3], according to the methods of Example 106-(3) and (4).

(5) 1.0 mg of the target compound [151] was obtained as a white solid from 12 mg of the 4-[8-(fluoromethyl)imidazo[1,2-a]pyridin-3-yl]-2-[((1S)-1-{4-[(1S,4S-5-(trifluoroacetyl)-2,5-diazabicyclo[2.2.1]hept-2-yl]phenyl}ethyl)amino]pyrimidine-5-carbonitrile [151-4], according to the method of Example 110-(3).

A spectral data of the compound [151] is presented below.
1H-NMR (CDCl$_3$) δ: 9.75-9.70 (m, 1H×¼), 9.25-8.95 (m, 1H+1H×¾), 8.65-8.63 (s, 1H×¼), 8.51 (s, 1H×¾), 8.10-7.98 (m, 2H), 7.60-6.40 (m, 5H), 6.00-5.80 (m, 2H), 5.10-4.40 (m, 3H), 3.90-3.10 (m, 5H), 2.30-1.80 (m, 2H), 1.61 (d, J=6.6 Hz, 3H)
mass: 469 (M+1)$^+$.

Example 152

Synthesis of 4-[8-(fluoromethyl)imidazo[1,2-a]pyridin-3-yl]-2-({(1S)-1-[4-(2-hydroxyethyl)phenyl]ethyl}amino)pyrimidine-5-carbonitrile [152] (hereinafter, referred to as the compound [152])

(1) The mixture of 50 mg of the t-butyl[(1S)-1-(4-bromophenyl)ethyl]carbamate [106-1], 223.4 mg of dichlorobis(triphenylphosphine)palladium (II), 31.2 mg of potassium vinyltrifluoroborate, 27.9 µL of triethylamine, 0.5 mL of tetrahydrofuran, and 0.5 mL of methanol, was stirred overnight at 100° C. The reaction mixture was cooled back to room temperature, water was added thereto, and was extracted with chloroform. The organic layer was washed with saturated brine, and dried over anhydrous sodium sulfate. The insolubles were filtered, the filtrate was concentrated under reduced pressure, and the obtained residue was purified by preparative thin-layer chromatography, to obtain 24.2 mg of t-butyl[(1S)-1-(4-vinylphenyl)ethyl]carbamate [152-1] as a white solid.

(2) 24.2 mg of the t-butyl[(1S)-1-(4-vinylphenyl)ethyl]carbamate [152-1] was dissolved in 1 mL of tetrahydrofuran, then 783 µL of 9-borabicyclo[3.3.1]nonane (9-BBN, 0.5M tetrahydrofuran solution) was added dropwise over 2 minutes under an ice-cold condition, and stirred overnight at room temperature. Thereto, 0.2 mL of a 3N aqueous solution of sodium hydroxide and 0.2 mL of hydrogen peroxide solution (35%) were added, and stirred at room temperature for 10 hours. The reaction mixture was added with water and extracted with chloroform, and the organic layer was washed with saturated brine and then dried over anhydrous sodium sulfate. The insolubles were filtered, the filtrate was concentrated under reduced pressure, and the obtained residue was purified by preparative thin-layer chromatography. The obtained compound was dissolved in 1.5 mL of N,N-dimethylformamide, then 14.2 mg of benzoic acid and 21.3 mg of 4-dimethylaminopyridine were added and stirred to homogenize the solution, and 22.3 mg of 1-ethyl-3-(3-dimethylaminopropyl)carbodiimide hydrochloride was added and stirred overnight at room temperature. Thereto, water was added, and the mixture was extracted with chloroform. The organic layer was washed with saturated brine, and then dried over anhydrous sodium sulfate. The insolubles were filtered, the filtrate was concentrated under reduced pressure, and the thus obtained residue was purified by preparative thin-layer chromatography, to obtain 15.2 mg of 2-(4-{(1S)-1-[(t-butoxycarbonyl)amino]ethyl}phenyl)ethylbenzoate [152-2] as a white solid.

(3) 13.5 mg of 2-{4-[(1S)-1-({5-cyano-4-[8-(fluoromethyl)imidazo[1,2-a]pyridin-3-yl]pyrimidin-2-yl}amino)ethyl]phenyl}ethylbenzoate [152-3] was obtained as a white solid, from 15.2 mg of the 2-(4-{(1S)-1-[(t-butoxycarbonyl)amino]ethyl}phenyl)ethylbenzoate [152-2] and 20.1 mg of the 4-[8-(fluoromethyl)imidazo[1,2-a]pyridin-3-yl]-2-(methylthio)pyrimidine-5-carbonitrile [147-3], according to the methods of Example 106-(3) and (4).

(4) 13.5 mg of the 2-{4-[(1S)-1-({5-cyano-4-[8-(fluoromethyl)imidazo[1,2-a]pyridin-3-yl]pyrimidin-2-yl}amino)ethyl]phenyl}ethylbenzoate [152-3] was dissolved in a mixture solvent of 2 mL of tetrahydrofuran and 2 mL of methanol, then 1 mL of a 1N aqueous solution of sodium hydroxide was added thereto, and stirred at room temperature for 1 and a half hours. Thereto, 1 mL of 1N hydrochloric acid was added, and the mixture was extracted with a mixture solvent of chloroform and methanol (chloroform:methanol=9:1). The organic layer was washed with saturated brine and then dried over anhydrous sodium sulfate, and the insolubles were filtered. The filtrate was concentrated under reduced pressure, and the obtained residue was purified by preparative thin-layer chromatography, to obtain 8.3 mg of the target compound [152] as a white solid.

A spectral data of the compound [152] is presented below.
$^1$H-NMR (CDCl$_3$) δ: 9.73 (d, J=7.6 Hz, 1H×⅓), 8.94 (s, 1H×⅓), 8.91 (d, J=7.6 Hz, 1H×⅔), 8.87 (s, 1H×⅔), 8.58 (s, 1H×⅓), 8.52 (s, 1H×⅔), 7.52 (d, J=7.6 Hz, 1H×⅓), 7.45 (d, J=7.6 Hz, 1H×⅔), 7.35 (d, J=8.0 Hz, 2H), 7.29 (d, J=8.0 Hz, 2H), 7.06 (dd, J=7.6, 7.6 Hz, 1H×⅓), 6.74 (dd, J=7.6, 7.6 Hz, 1H×⅔), 6.19-6.14 (m, 1H×⅔), 5.86-5.74 (m, 2H+1H×⅓), 5.36-5.28 (m, 1H×⅓), 5.16-5.08 (m, 1H×⅔), 3.87 (t, J=6.4 Hz, 2H), 2.88 (t, J=6.4 Hz, 2H), 1.63 (d, J=6.4 Hz, 3H)
mass: 417 (M+1)$^+$.

Example 153

Synthesis of 2-[((1S)-1-{4-[2-(dimethylamino)ethyl]phenyl}ethyl)amino]-4-[8-(fluoromethyl)imidazo[1,2-a]pyridin-3-yl]pyrimidine-5-carbonitrile [153] (hereinafter, referred to as the compound [153])

5.9 mg of the target compound [153] was obtained as a white solid, from 7.0 mg of the compound [152] and 2 mL of dimethylamine (2M tetrahydrofuran solution), according to the method of Example 84.

A spectral data of the compound [153] is presented below.
$^1$H-NMR (CDCl$_3$) δ: 9.74 (d, J=7.6 Hz, 1H×⅓), 8.94 (s, 1H×⅓), 8.89 (d, J=7.6 Hz, 1H×⅔), 8.88 (s, 1H×⅔), 8.59 (s, 1H×⅓), 8.54 (s, 1H×⅔), 7.52 (d, J=7.6 Hz, 1H×⅓), 7.45 (d, J=7.6 Hz, 1H×⅔), 7.31 (d, J=8.0 Hz, 2H), 7.27-7.25 (m, 2H), 7.07 (dd, J=7.6, 7.6 Hz, 1H×⅓), 6.74 (dd, J=7.6, 7.6 Hz, 1H×⅔), 6.10-6.05 (m, 1H×⅔), 5.95-5.78 (m, 2H+1H×⅓), 5.35-5.25 (m, 1H×⅓), 5.12-5.08 (m, 1H×⅔), 2.81 (t, J=8.0 Hz, 2H), 2.54 (t, J=8.0 Hz, 2H), 2.30 (s, 6H), 1.62 (d, J=6.8 Hz, 3H)
mass: 444 (M+1)$^+$.

Example 154

Synthesis of 4-[8-(fluoromethyl)imidazo[1,2-a]pyridin-3-yl]-2-({(1S)-1-[4-(1,2,3,6-tetrahydropyridin-4-yl)phenyl]ethyl}amino)pyrimidine-5-carbonitrile [154] (hereinafter, referred to as the compound [154])

(1) 2 g of 1-(trifluoroacetyl)piperidin-4-one (synthesized according to a method disclosed in page 24 in JP-A-63-227599) was dissolved in 20 mL of tetrahydrofuran, then 11.3 mL of lithium bis(trimethylsilyl)amide (1.0M tetrahydrofuran solution) was added at −78° C., and stirred at the same temperature for 10 minutes. Thereto, a solution prepared by dissolving 3.7 g of N-phenyltrifluoromethane sulfonimide in 9 mL of tetrahydrofuran was added, and the temperature of −78° C. was elevated to room temperature over 3 hours under stirring. Water was added to terminate the reaction, and extracted with ethyl acetate. The organic layer was washed with saturated brine, and then dried over anhydrous magnesium sulfate. The insolubles were filtered and the filtrate was concentrated under reduced pressure, to obtain 3.12 g of the compound [154-1] as a light brown oily product. The 1-(2,2,2-trifluoroacetyl)-1,2,3,6-tetrahydropyridin-4-yl trifluoromethanesulfonate [154-1] was used in the subsequent reaction without further purification.

(2) 1 g of 1-(2,2,2-trifluoroacetyl)-1,2,3,6-tetrahydropyridin-4-yl trifluoromethanesulfonate [154-1] was dissolved in 30 mL of 1,4-dioxane, then 85 mg of 1,1'-bis(diphenylphosphino)ferrocene, 125 mg of dichlorobis(triphenylphosphine)palladium (II), 2.98 g of cesium carbonate, and 775 mg of bis(pinacolato)diboron were added thereto, and stirred overnight at 80° C. After cooling the reaction mixture back to room temperature, water was added, and was extracted with ethyl acetate. The organic layer was washed with saturated brine, and then dried over anhydrous magnesium sulfate. The insolubles were filtered, the filtrate was concentrated under reduced pressure, and the thus obtained residue was purified by silica gel column chromatography, to obtain 400 mg of 4-(4,4,5,5-tetramethyl-1,3,2-dioxaborolan-2-yl)-1-(trifluoroacetyl)-1,2,3,6-tetrahydropyridine [154-2] as a brown oily product.

(3) 400 mg of the 4-(4,4,5,5-tetramethyl-1,3,2-dioxaborolan-2-yl)-1-(trifluoroacetyl)-1,2,3,6-tetrahydropyridine [154-2] was dissolved in 10 mL of N,N-dimethylformamide, then 196 mg of the t-butyl[(1S)-1-(4-bromophenyl)ethyl]carbamate [106-1], 54 mg of [1,1'-bis(diphenylphosphino)ferrocene]dichloropalladium (II), and 181 mg of potassium carbonate were added thereto, and stirred overnight at 80° C. The reaction mixture was cooled back to room temperature, then diluted in 100 mL of ethyl acetate, and washed with water and saturated brine in the subsequent order. The obtained organic layer was dried over anhydrous magnesium sulfate, and the insolubles were filtered. The filtrate was concentrated under reduced pressure, and the obtained residue was purified by silica gel column chromatography, to obtain 100 mg of t-butyl((1S)-1-{4-[1-(trifluoroacetyl)-1,2,3,6-tetrahydropyridin-4-yl]phenyl}ethyl)carbamate [154-3] as a white solid.

(4) 10 mg of 4-[8-(fluoromethyl)imidazo[1,2-a]pyridin-3-yl]-2-[((1S)-1-{4-[1-(trifluoroacetyl)-1,2,3,6-tetrahydropyridin-4-yl]phenyl}ethyl)amino]pyrimidine-5-carbonitrile [154-4] was obtained as a white solid, from 50 mg of the t-butyl((1S)-1-{4-[1-(trifluoroacetyl)-1,2,3,6-tetrahydropyridin-4-yl]phenyl}ethyl)carbamate [154-3] and 34 mg of the 4-[8-(fluoromethyl)imidazo[1,2-a]pyridin-3-yl]-2-(methylthio)pyrimidine-5-carbonitrile [147-3], according to the methods of Example 106-(3) and (4).

(5) 5.6 mg of the target compound [154] was obtained as a pale yellow solid, from the 10 mg of the 4-[8-(fluoromethyl)imidazo[1,2-a]pyridin-3-yl]-2-[((1S)-1-{4-[1-(trifluoroacetyl)-1,2,3,6-tetrahydropyridin-4-yl]phenyl}ethyl)amino]pyrimidine-5-carbonitrile [154-4], according to the method of Example 110-(3).

A spectral data of the compound [154] is presented below.
$^1$H-NMR (DMSO-$d_6$) δ: 10.11 (d, J=7.1 Hz, 1H×½), 9.12-9.02 (m, 1H), 8.94 (d, J=8.0 Hz, 1H×½), 8.76 (s, 1H×½), 8.75 (s, 1H×½), 8.73 (s, 1H×½), 8.61 (s, 1H×½), 7.70 (d, J=6.3 Hz, 1H×½), 7.63 (d, J=6.3 Hz, 1H×½), 7.43-7.36 (m, 4H), 7.26 (t, J=7.1 Hz, 1H×½), 7.03 (t, J=7.1 Hz, 1H×½), 6.15-6.14 (m, 1H), 5.84 (d, J=47.1 Hz, 2H×½), 5.78 (d, J=47.1 Hz, 2H×½), 5.27-5.20 (m, 1H×½), 5.12-5.05 (m, 1H×½), 3.35-3.33 (m, 2H), 2.91-2.86 (m, 2H), 2.33-2.29 (m, 2H), 1.53 (d, J=7.1 Hz, 3H×½), 1.50 (d, J=7.1 Hz, 3H×½)
mass: 454 (M+1)$^+$.

Example 155

Synthesis of 4-[8-(fluoromethyl)imidazo[1,2-a]pyridin-3-yl]-2-{[(1S)-1-(4-piperidin-4-ylphenyl)ethyl]amino}pyrimidine-5-carbonitrile [155] (hereinafter, referred to as the compound [155])

(1) 50 mg of the t-butyl((1S)-1-{4-[1-(trifluoroacetyl)-1,2,3,6-tetrahydropyridin-4-yl]phenyl}ethyl)carbamate [154-3] was dissolved in 3 mL of tetrahydrofuran, then a catalytic amount of 10% palladiumcarbon catalyst was added thereto, and stirred at room temperature for 1 hour in a hydrogen atmosphere. The insolubles were filtered through celite, the filtrate was concentrated under reduced pressure, and 53.3 mg of t-butyl((1S)-1-{4-[1-(trifluoroacetyl)piperidin-4-yl]phenyl}ethyl)carbamate [155-1] was obtained as a white solid.

(2) 13.5 mg of 4-[8-(fluoromethyl)imidazo[1,2-a]pyridin-3-yl]-2-[((1S)-1-{4-[1-(trifluoroacetyl)piperidin-4-yl]phenyl}ethyl)amino]pyrimidine-5-carbonitrile [155-2] was obtained as a pale yellow solid, from 53.3 mg of the t-butyl((1S)-1-{4-[1-(trifluoroacetyl)piperidin-4-yl]phenyl}ethyl)carbamate [155-1] and 36 mg of the 4-[8-(fluoromethyl)imidazo[1,2-a]pyridin-3-yl]-2-(methylthio)pyrimidine-5-carbonitrile [147-3], according to the methods of Example 106-(3) and (4).

(3) 5.6 mg of the target compound [155] was obtained as a white solid, from 10 mg of the 4-[8-(fluoromethyl)imidazo[1,2-a]pyridin-3-yl]-2-[((1S)-1-{4-[1-(trifluoroacetyl)piperidin-4-yl]phenyl}ethyl)amino]pyrimidine-5-carbonitrile [155-2], according to the method of Example 110-(3).

A spectral data of the compound [155] is presented below.
$^1$H-NMR (DMSO-$d_6$) δ: 10.11 (d, J=6.8 Hz, 1H×½), 9.01-8.97 (m, 1H), 8.92 (d, J=8.3 Hz, 1H×½), 8.75 (s, 1H), 8.73 (s, 1H×½), 8.61 (s, 1H×½), 7.70 (d, J=6.8 Hz, 1H×½), 7.63 (d, J=7.1 Hz, 1H×½), 7.43-7.36 (m, 4H), 7.26 (t, J=7.1 Hz, 1H×½), 7.34-7.32 (m, 2H), 7.27-7.17 (m, 2H+1H×½), 7.01 (t, J=7.1 Hz, 1H×½), 5.84 (d, J=47.1 Hz, 2H×½), 5.78 (d, J=47.1 Hz, 2H×½), 5.26-5.19 (m, 1H×½), 5.09-5.03 (m, 1H×½), 3.00-2.94 (m, 2H), 2.56-2.51 (m, 2H), 1.65-1.60 (m, 2H), 1.52 (d, J=6.8 Hz, 3H×½), 1.49 (d, J=7.1 Hz, 3H×½)
mass: 456 (M+1)$^+$.

Example 156

Synthesis of 4-[8-(1-hydroxyethyl)imidazo[1,2-a]pyridin-3-yl]-2-{[(1S)-1-(4-piperazin-1-ylphenyl)ethyl]amino}pyrimidine-5-carbonitrile [156] (hereinafter, referred to as the compound [156])

(1) 3.2 g of 4-(8-acetylimidazo[1,2-a]pyridin-3-yl)-2-(methylthio)pyrimidine-5-carbonitrile [156-1] was obtained as a light brown solid, from 2 g of 2-amino-3-acetylpyridine and 3.25 g of the 4-[(Z)-2-ethoxyvinyl]-2-(methylthio)-5-pyrimidinecarbonyl [48-3], according to the method of Example 25-(3).

(2) 46.6 mg of 4-(8-acetylimidazo[1,2-a]pyridin-3-yl)-2-[((1S)-1-{4-[4-(trifluoroacetyl)piperazin-1-yl]phenyl}ethyl)amino]pyrimidine-5-carbonitrile [156-2] was obtained as a white solid, from 100 mg of the 4-(8-acetylimidazo[1,2-a]pyridin-3-yl)-2-(methylthio)pyrimidine-5-carbonitrile [156-1] and 156 mg of the t-butyl((1S)-1-{4-[4-(trifluoroacetyl)piperazin-1-yl]phenyl}ethyl)carbamate [110-1], according to the methods of Example 106-(3) and (4).

(3) 42.2 mg of 4-(8-acetylimidazo[1,2-a]pyridin-3-yl)-2-{[(1S)-1-(4-piperazin-1-ylphenyl)ethyl]amino}pyrimidine-5-carbonitrile [156-3] was obtained as a yellow solid, from 46.6 mg of the 4-(8-acetylimidazo[1,2-a]pyridin-3-yl)-2-[((1S)-1-{4-[4-(trifluoroacetyl)piperazin-1-yl]phenyl}ethyl)amino]pyrimidine-5-carbonitrile [156-2], according to the method of Example 110-(3).

(4) 39 mg of the 4-(8-acetylimidazo[1,2-a]pyridin-3-yl)-2-{[(1S)-1-(4-piperazin-1-ylphenyl)ethyl]amino}pyrimidine-5-carbonitrile [156-3] was dissolved in a mixture solvent of 1 mL of tetrahydrofuran and 1 mL of methanol, then 2.8 mg of sodium boronhydride was added thereto, and stirred at room temperature for 15 minutes. Thereto, a saturated aqueous solution of sodium hydrogen carbonate was added, and the mixture was extracted with a mixture solvent of chloroform and methanol (chloroform:methanol=9:1). The organic layer was washed with saturated brine and dried over anhydrous sodium sulfate. The insolubles were filtered, and then the filtrate was concentrated under reduced pressure. The obtained residue was purified by preparative thin-layer chromatography, and 31.9 mg of 4-[8-(1-hydroxyethyl)imidazo[1,2-a]pyridin-3-yl]-2-{[(1S)-1-(4-piperazin-1-ylphenyl)ethyl]amino}pyrimidine-5-carbonitrile [156-4] was obtained as a two kinds of diastereomer mixture.

(5) 31.9 mg of the 4-[8-(1-hydroxyethyl)imidazo[1,2-a]pyridin-3-yl]-2-{[(1S)-1-(4-piperazin-1-ylphenyl)ethyl]amino}pyrimidine-5-carbonitrile [156-4] which is two kinds of diastereomer mixture was separated on Chiralpak AD-H (manufactured by Daicel Chemical Industries Ltd.) using hexane-isopropanol-diethylamine as an eluent.

Conditions for separation are as follows.

Column: ChiralpakAD-H (manufactured by Daicel Chemical Industries, Ltd.), diameter of 20 mm, length of 250 mm Eluent: Hexane-isopropanol-diethylamine (30:70:0.1)

Flow rate: 15 mL/min

The obtained eluent was concentrated under reduced pressure to obtain 11.1 mg of the target compound [156] which is one of the diastereomers (RT=13 min) as a white solid and 11.8 mg of 4-[8-(1-hydroxyethyl)imidazo[1,2-a]pyridin-3-yl]-2-{[(1S)-1-(4-piperazin-1-ylphenyl)ethyl]amino}pyrimidine-5-carbonitrile [156-5] which is the other one of the diastereomers (RT=17 min) as a white solid.

A spectral data of the compound [156] is presented below.

$^1$H-NMR (CDCl$_3$) δ: 9.63 (d, J=7.2 Hz, 1H×⅕), 8.98 (d, J=7.2 Hz, 1H×⅘), 8.90 (s, 1H×⅕), 8.86 (s, 1H×⅘), 8.58 (s, 1H×⅕), 8.51 (s, 1H×⅘), 7.30-6.67 (m, 6H), 6.17-6.05 (m, 1H×⅘), 5.86-5.77 (m, 1H×⅕), 5.40-5.22 (m, 1H+1H×⅕), 5.12-5.00 (m, 1H×⅘), 3.14-3.06 (m, 4H), 3.04-3.01 (m, 4H), 2.60 (brs, 1H), 2.02 (brs, 1H), 1.68 (d, J=4.0 Hz, 3H), 1.61 (d, J=6.8 Hz, 3H)

mass: 469 (M+1)$^+$.

Example 157

Synthesis of 4-[8-(1-hydroxy-1-methylethyl)imidazo[1,2-a]pyridin-3-yl]-2-[((1S)-1-{3-[(1-methylpiperidin-4-yl)amino]phenyl}ethyl)amino]pyrimidine-5-carbonitrile [157] (hereinafter, referred to as the compound [157])

(1) 100 mg of the 4-(8-acetylimidazo[1,2-a]pyridin-3-yl)-2-(methylthio)pyrimidine-5-carbonitrile [156-1] was dissolved in 5 mL of tetrahydrofuran, then 577 μL of methylmagnesium bromide (0.84M tetrahydrofuran solution) was added in an ice-cold condition, and stirred overnight at room temperature. 200 μL of methylmagnesium bromide was further added and stirred at room temperature for 4 hours, then a saturated aqueous solution of ammonium chloride was added to terminate the reaction. The reaction solution was extracted with chloroform, and the organic layer was dried over anhydrous magnesium sulfate. The insolubles were filtered, the filtrate was concentrated under reduced pressure, and the thus obtained residue was purified by preparative thin-layer chromatography, to obtain 18 mg of 4-[8-(1-hydroxy-1-methylethyl)imidazo[1,2-a]pyridin-3-yl]-2-(methylthio)pyrimidine-5-carbonitrile [157-1] as a brown solid.

(2) 15.2 mg of 2-{[(1S)-1-(3-aminophenyl)ethyl]amino}-4-[8-(1-hydroxy-1-methylethyl)imidazo[1,2-a]pyridin-3-yl]pyrimidine-5-carbonitrile [157-2] was obtained as a light brown solid, from 18 mg of the 4-[8-(1-hydroxy-1-methylethyl)imidazo[1,2-a]pyridin-3-yl]-2-(methylthio)pyrimidine-5-carbonitrile [157-1] and 11 mg of 3-[(1S)-1-aminoethyl]aniline, according to the method of Example 80-(4).

(3) 2.9 mg of the target compound [157] was obtained as a pale yellow solid, from 15 mg of the 2-{[(1S)-1-(3-aminophenyl)ethyl]amino}-4-[8-(1-hydroxy-1-methylethyl)imidazo[1,2-a]pyridin-3-yl]pyrimidine-5-carbonitrile [157-2] and 9 μL of 1-methyl-4-piperidone, according to the method of Example 91.

A spectral data of the compound [157] is presented below.

$^1$H-NMR (DMSO-d$_6$) δ: 10.03 (d, J=5.8 Hz, 1H×⅓), 8.93-8.89 (m, 1H×⅔+1H×⅔), 8.82 (d, J=8.3 Hz, 1H×⅓), 8.74 (s, 1H×⅔), 8.73 (s, 1H×⅓), 8.71 (s, 1H×⅓), 8.54 (s, 1H×⅔), 7.70 (d, J=7.3 Hz, 1H×⅓), 7.59 (d, J=6.3 Hz, 1H×⅔), 7.20 (d, J=7.1 Hz, 1H×⅓), 7.06-6.96 (m, 1H+1H×⅔), 6.57-6.53 (m, 2H), 6.43-6.39 (m, 1H), 5.51-5.48 (m, 1H+1H×⅔), 5.41 (d, J=7.6 Hz, 1H×⅓), 5.15-5.09 (m, 1H×⅓), 4.95-4.89 (m, 1H×⅔), 3.08 (brs, 1H), 2.68-2.60 (m, 2H), 2.14 (s, 3H×⅔), 2.06 (s, 3H×⅓), 1.95-1.75 (m, 4H), 1.72 (s, 3H×⅓), 1.71 (s, 3H×⅓), 1.68 (s, 3H×⅔), 1.67 (s, 3H×⅔), 1.50-1.46 (m, 3H), 1.38-1.23 (m, 2H)

mass: 511 (M+1)$^+$.

Example 158

Synthesis of 4-(8-methoxyimidazo[1,2-a]pyridin-3-yl)-2-{[(1S)-1-(4-piperazin-1-ylphenyl)ethyl]amino}pyrimidine-5-carbonitrile [158] (hereinafter, referred to as the compound [158])

(1) 190 mg of 4-(8-hydroxyimidazo[1,2-a]pyridin-3-yl)-2-(methylthio)pyrimidine-5-carbonitrile [158-1] was obtained as an orange solid, from 100 mg of the 2-amino-3-hydroxypyridine and 200 mg of the 4-[(Z)-2-ethoxyvinyl]-2-(methylthio)-5-pyrimidinecarbonyl [48-3], according to the method of Example 25-(3).

(2) 150 mg of the 4-(8-hydroxyimidazo[1,2-a]pyridin-3-yl)-2-(methylthio)pyrimidine-5-carbonitrile [158-1] was dissolved in 3 mL of dimethylsulfoxide, then 293 mg of potassium carbonate and 40 μL of methyl iodide were added thereto, and stirred at room temperature for 30 minutes. The reaction solution was diluted in 200 mL of chloroform, and washed with water. Then, the organic layer was dried over anhydrous magnesium sulfate. The insolubles were filtered, and the filtrate was concentrated under reduced pressure. The obtained residue was dissolved in a small amount of a mixed solvent of chloroform and methanol (chloroform:methanol=9:1), and solidified by hexane, to obtain 58 mg of 4-(8-methoxyimidazo[1,2-a]pyridin-3-yl)-2-(methylthio)pyrimidine-5-carbonitrile [158-2] as a brown solid.

(3) 11.3 mg of 4-(8-methoxyimidazo[1,2-a]pyridin-3-yl)-2-[((1S)-1-{4-[4-(trifluoroacetyl)piperazin-1-yl]phenyl}ethyl)amino]pyrimidine-5-carbonitrile [158-3] was obtained as a white solid, from 11 mg of the 4-(8-methoxyimidazo[1,2-a]pyridin-3-yl)-2-(methylthio)pyrimidine-5-carbonitrile [158-2] and 15 mg of the t-butyl((1S)-1-{4-[4-(trifluoroacetyl)piperazin-1-yl]phenyl}ethyl)carbamate [110-1], according to the methods of Example 106-(3) and (4).

(4) 3.7 mg of the target compound [158] was obtained as a pale yellow solid, from 11.3 mg of the 4-(8-methoxyimidazo[1,2-a]pyridin-3-yl)-2-[((1S)-1-{4-[4-(trifluoroacetyl)piperazin-1-yl]phenyl}ethyl)amino]pyrimidine-5-carbonitrile [158-3], according to the method of Example 110-(3).

A spectral data of the compound [158] is presented below.
$^1$H-NMR (DMSO-$d_6$) δ: 9.70 (d, J=6.8 Hz, 1H×½), 8.92 (d, J=7.3 Hz, 1H×½), 8.83 (d, J=8.3 Hz, 1H×½), 8.76 (d, J=6.6 Hz, 1H×½), 8.72 (s, 1H×½), 8.71 (s, 1H×½), 8.65 (s, 1H×½), 8.52 (s, 1H×½), 7.25-7.23 (m, 2H), 7.10-6.86 (m, 4H), 5.20-5.13 (m, 1H×½), 5.04-4.96 (m, 1H×½), 3.98 (s, 3H×½), 3.96 (s, 3H×½), 2.99-2.97 (m, 4H), 2.83-2.79 (m, 4H), 1.49 (d, J=6.8 Hz, 3H×½), 1.46 (d, J=6.8 Hz, 3H×½)
mass: 455 (M+1)$^+$.

Example 159

Synthesis of 4-(8-methoxy-7-methylimidazo[1,2-a]pyridin-3-yl)-2-{[(1S)-1-(4-piperazin-1-ylphenyl)ethyl]amino}pyrimidine-5-carbonitrile [159] (hereinafter, referred to as the compound [159])

(1) 1.36 mL of isopropylamine was dissolved in 8 mL of tetrahydrofuran, 3.64 mL of n-butyllithium (2.66M hexane solution) was added at −78° C. and stirred at the same temperature for 10 minutes, and then the temperature was elevated to 0° C. and stirred for 1 hour. The reaction mixture was again cooled back to −78° C., a solution prepared by dissolving 950 mg of 2-phenyl[1,3]oxazolo[4,5-b]pyridine (synthesized according to a method disclosed in Synthetic Commun. 1992, 22 (20), 2891-1901) in 28 mL of tetrahydrofuran was added thereto, and stirred at the same temperature for 30 minutes. A solution prepared by dissolving 0.36 mL of methyl iodide to 16 mL of tetrahydrofuran was added to the reaction solution, and stirred at the same temperature for 5 hours. After terminating the reaction by adding water and then elevating the temperature to room temperature, the reaction solution was extracted with chloroform and the organic layer was washed with saturated brine. The organic layer was dried over anhydrous sodium sulfate, the insolubles were filtered, and the filtrate was concentrated under reduced pressure, and the thus obtained residue was purified by silica gel column chromatography, to obtain 86 mg of 7-methyl-2-phenyl[1,3]oxazolo[4,5-b]pyridine[159-1] as a light blue solid.

(2) 86 mg of the 7-methyl-2-phenyl[1,3]oxazolo[4,5-b]pyridine [159-1] was dissolved in a mixture solvent of 4 mL of tetrahydrofuran and 4 mL of ethanol, 1.64 mL of an aqueous solution of sodium hydroxide 33% was added thereto, and heated overnight under reflux. After cooling back to room temperature, the reaction solution was concentrated under reduced pressure. To the obtained residue, 5 mL of dichloromethane and 3.4 mL of an aqueous solution of sodium hydroxide 33% were added and stirred. Thereto, 28 μL of methyl iodide and 30.5 μL of Adogen 464 (phase transfer catalyst, Aldrich Corporation) were added, and stirred overnight at room temperature. Water was added, the reaction solution was extracted with chloroform, and the organic layer was washed with phosphate buffer pH 7.0, water, and saturated brine in the subsequent order. The organic layer was dried over anhydrous sodium sulfate, the insolubles were filtered, the filtrate was concentrated under reduced pressure, and the thus obtained residue was purified by preparative thin-layer chromatography, to obtain 4.2 mg of 3-methoxy-4-methylpyridin-2-amine [159-2] as a light brown solid.

(3) 2.8 mg of 4-(8-methoxy-7-methylimidazo[1,2-a]pyridin-3-yl)-2-(methylthio)pyrimidine-5-carbonitrile [159-3] was obtained as a pale yellow solid, from 4.2 mg of the 3-methoxy-4-methylpyridin-2-amine [159-2] and 6.7 mg of the 4-[(Z)-2-ethoxyvinyl]-2-(methylthio)-5-pyrimidinecarbonyl [48-3], according to the method of Example 25-(3).

(4) 3.6 mg of 4-(8-methoxy-7-methylimidazo[1,2-a]pyridin-3-yl)-2-[((1S)-1-{4-[4-(trifluoroacetyl)piperazin-1-yl]phenyl}ethyl)amino]pyrimidine-5-carbonitrile [159-4] was obtained as a pale yellow solid, from 2.8 mg of the 4-(8-methoxy-7-methylimidazo[1,2-a]pyridin-3-yl)-2-(methylthio)pyrimidine-5-carbonitrile [159-3] and 4 mg of the t-butyl((1S)-1-{4-[4-(trifluoroacetyl)piperazin-1-yl]phenyl}ethyl)carbamate [110-1], according to the methods of Example 106-(3) and (4).

(5) 3.0 mg of the target compound [159] was obtained as a pale yellow solid, from 3.6 mg of the 4-(8-methoxy-7-methylimidazo[1,2-a]pyridin-3-yl)-2-[((1S)-1-{4-[4-(trifluoroacetyl)piperazin-1-yl]phenyl}ethyl)amino]pyrimidine-5-carbonitrile [159-4], according to the method of Example 110-(3).

A spectral data of the compound [159] is presented below.
$^1$H-NMR (CDCl$_3$) δ: 9.40 (d, J=6.4 Hz, 1H×⅕), 8.90 (s, 1H×⅕), 8.86 (s, 1H×⅘), 8.83 (d, J=6.4 Hz, 1H×⅘), 8.56 (s, 1H×⅕), 8.48 (s, 1H×⅘), 7.35-7.25 (m, 2H), 6.94 (d, J=8.0 Hz, 2H), 6.79 (d, J=6.4 Hz, 1H×⅕), 6.57 (d, J=6.4 Hz, 1H×⅘), 6.05-5.97 (m, 1H×⅘), 5.79-5.72 (m, 1H×⅕), 5.30-5.25 (m, 1H×⅕), 5.12-5.05 (m, 1H×⅘), 4.21 (s, 3H), 3.20-3.15 (m, 4H), 3.07-3.02 (m, 4H), 2.36 (s, 3H), 1.61 (d, J=6.8 Hz, 3H)
mass: 469 (M+1)$^+$.

Example 160

Synthesis of 4-[8-(fluoromethoxy)imidazo[1,2-a]pyridin-3-yl]-2-{[(1S)-1-(4-piperazin-1-ylphenyl)ethyl]amino}pyrimidine-5-carbonitrile [160] (hereinafter, referred to as the compound [160])

(1) 100 mg of the 4-(8-hydroxyimidazo[1,2-a]pyridin-3-yl)-2-(methylthio)pyrimidine-5-carbonitrile [158-1] was dissolved in 3 mL of N,N-dimethylformamide, 146 mg of potassium carbonate and 216 mg of fluoromethyl 4-methylbenzenesulfonate (synthesized according to a method disclosed in page 555 to 566 in J. Labelled Compd. Radio pharm. 2003, 46) were added, and stirred at 80° C. for 5 hours. After cooling the reaction mixture back to room temperature, a saturated aqueous solution of sodium hydrogen carbonate was added, and was extracted with a mixture solvent of chloroform and methanol (chloroform:methanol=9:1). The organic layer was washed with saturated brine, and dried over anhydrous sodium sulfate. The insolubles were filtered, and the filtrate was concentrated under reduced pressure. The obtained residue was dissolved in a small amount of a mixture solvent of chloroform and methanol (chloroform:methanol=9:1), and solidified by adding diethyl ether, to obtain 44.1 mg of 4-[8-(fluoromethoxy)imidazo[1,2-a]pyridin-3-yl]-2-(methylthio)pyrimidine-5-carbonitrile [160-1] as a brown solid.

(2) 15.9 mg of 4-[8-(fluoromethoxy)imidazo[1,2-a]pyridin-3-yl]-2-[((1S)-1-{4-[4-(trifluoroacetyl)piperazin-1-yl]phenyl}ethyl)amino]pyrimidine-5-carbonitrile [160-2] was obtained as yellow amorphous, from 27.6 mg of the 4-[8-(fluoromethoxy)imidazo[1,2-a]pyridin-3-yl]-2-(methylthio)pyrimidine-5-carbonitrile [160-1] and 52.8 mg of the t-butyl ((1S)-1-{4-[4-(trifluoroacetyl)piperazin-1-yl]phenyl}ethyl)carbamate [110-1], according to the methods of Example 106-(3) and (4).

(3) 11.3 mg of the target compound [160] was obtained as a pale yellow solid, from 13.6 mg of the 4-[8-(fluoromethoxy)imidazo[1,2-a]pyridin-3-yl]-2-[((1S)-1-{4-[4-(trifluoroacetyl)piperazin-1-yl]phenyl}ethyl)amino]pyrimidine-5-carbonitrile [160-2], according to the method of Example 110-(3).

A spectral data of the compound [160] is presented below.
$^1$H-NMR (CDCl$_3$) δ: 9.52 (d, J=7.2 Hz, 1H×⅕), 8.90-8.82 (m, 1H+1H×⅘), 8.60 (s, 1H×⅕), 8.52 (s, 1H×⅘), 7.29-6.66 (m, 6H), 6.13-6.11 (m, 1H×⅘), 5.97 (d, J=52.0 Hz, 2H), 5.85-5.77 (m, 1H×⅕), 5.33-5.20 (m, 1H×⅕), 5.12-5.00 (m, 1H×⅘), 3.15-3.08 (m, 4H), 3.06-3.03 (m, 4H), 2.65 (brs, 1H), 1.62 (d, J=6.8 Hz, 3H)
mass: 473 (M+1)$^+$.

Example 161

Synthesis of 4-[8-(difluoromethoxy)imidazo[1,2-a]pyridin-3-yl]-2-[((1S)-1-{4-[(1-methylpiperidin-4-yl)amino]phenyl}ethyl)amino]pyrimidine-5-carbonitrile [161] (hereinafter, referred to as the compound [161])

(1) 20 mg of the 4-(8-hydroxyimidazo[1,2-a]pyridin-3-yl)-2-(methylthio)pyrimidine-5-carbonitrile [158-1] was dissolved in 1 mL of acetonitrile, then 20 mg of potassium carbonate and 13 mg of sodium chlorodifluoroacetate were added, and stirred overnight at 90° C. After cooling the reaction mixture back to room temperature, diluted in 100 mL of chloroform, and washed with water and dried over anhydrous magnesium sulfate. The insolubles were filtered, then the filtrate was concentrated under reduced pressure and purified by preparative thin-layer chromatography, to obtain 15 mg of 4-[8-(difluoromethoxy)imidazo[1,2-a]pyridin-3-yl]-2-(methylthio)pyrimidine-5-carbonitrile [161-1] as a light brown solid.

(2) 8.3 mg of 4-[8-(difluoromethoxy)imidazo[1,2-a]pyridin-3-yl]-2-{[(1S)-1-(4-nitrophenyl)ethyl]amino}pyrimidine-5-carbonitrile [161-2] was obtained as a yellow solid, from 15 mg of the 4-[8-(difluoromethoxy)imidazo[1,2-a]pyridin-3-yl]-2-(methylthio)pyrimidine-5-carbonitrile [161-1] and 14 mg of (S)-α-methyl-4-nitrobenzylamine hydrochloride, according to the method of Example 80-(4).

(3) 7.9 mg of 2-{[(1S)-1-(4-aminophenyl)ethyl]amino}-4-[8-(difluoromethoxy)imidazo[1,2-a]pyridin-3-yl]pyrimidine-5-carbonitrile [161-3] was obtained as a white solid, from 8.3 mg of the 4-[8-(difluoromethoxy)imidazo[1,2-a]pyridin-3-yl]-2-{[(1S)-1-(4-nitrophenyl)ethyl]amino}pyrimidine-5-carbonitrile [161-2], according to the method of Example 103-(2).

(4) 3.2 mg of the target compound [161] was obtained as a white solid, from 7.9 mg of the 2-{[(1S)-1-(4-aminophenyl)ethyl]amino}-4-[8-(difluoromethoxy)imidazo[1,2-a]pyridin-3-yl]pyrimidine-5-carbonitrile [161-3] and 3 μL of 1-methyl-4-piperidone, according to the method of Example 82-(1).

A spectral data of the compound [161] is presented below.
$^1$H-NMR (DMSO-d$_6$) δ: 9.95 (d, J=7.1 Hz, 1H×½), 8.99 (d, J=6.1 Hz, 1H×½), 8.91 (d, J=7.3 Hz, 1H×½), 8.80 (d, J=8.3 Hz, 1H×½), 8.76 (s, 1H×½), 8.75 (s, 1H×½), 8.73 (s, 1H×½), 8.58 (s, 1H×½), 7.59 (t, J=73.7 Hz, 1H×½), 7.56 (t, J=73.7 Hz, 1H×½), 7.40 (d, J=7.1 Hz, 1H×½), 7.35 (d, J=7.6 Hz, 1H×½), 7.16 (t, J=7.3 Hz, 1H×½), 7.11-7.07 (m, 2H), 7.01 (t, J=7.3 Hz, 1H×½), 6.55 (d, J=8.6 Hz, 1H×½), 6.52 (d, J=8.6 Hz, 1H×½), 5.33 (t, J=8.0 Hz, 1H), 5.15-5.08 (m, 1H×½), 4.96-4.89 (m, 1H×½), 3.15-3.07 (m, 1H), 2.72-2.65 (m, 2H), 2.15 (s, 3H×½), 2.14 (s, 3H×½), 2.01-1.97 (m, 2H), 1.84-1.80 (m, 2H), 1.47 (d, J=6.8 Hz, 3H×½), 1.44 (d, J=6.8 Hz, 3H×½), 1.38-1.29 (m, 2H)
mass: 519 (M+1)$^+$.

Example 162

Synthesis of 2-[((1S)-1-{3-[(1-methylpiperidin-4-yl)amino]phenyl}ethyl)amino]-4-[8-(methylsulfonyl)imidazo[1,2-a]pyridin-3-yl]pyrimidine-5-carbonitrile [162] (hereinafter, referred to as the compound [162])

(1) The mixture of 800 mg of 2-chloro-3-(methylsulfonyl)pyridine (synthesized according to a method disclosed in J. Org. Chem. 1979, 44, 3080-3082) and 60 mL of aqueous ammonia, was stirred overnight in a sealed-tube at 175° C. After cooling back to room temperature, the mixture was extracted with diethyl ether, and the organic layer was washed with saturated brine and dried over anhydrous sodium sulfate. The insolubles were filtered. The filtrate was concentrated under reduced pressure, and 473 mg of 3-(methylsulfonyl)pyridine-2-amine [162-1] was obtained as a light orange solid.

(2) 473 mg of 4-[8-(methylsulfonyl)imidazo[1,2-a]pyridin-3-yl]-2-(methylthio)pyrimidine-5-carbonitrile [162-2] was obtained as a pale yellow solid, from 470 mg of the 3-(methylsulfonyl)pyridine-2-amine [162-1] and 4-[(Z)-2-ethoxyvinyl]-2-(methylthio)-5-pyrimidinecarbonyl [48-3], according to the method of Example 25-(3).

(3) 44.6 mg of 2-{[(1S)-1-(3-aminophenyl)ethyl]amino}-4-[8-(methylsulfonyl)imidazo[1,2-a]pyridin-3-yl]pyrimidine-5-carbonitrile [162-3] was obtained, from 100 mg of the 4-[8-(methylsulfonyl)imidazo[1,2-a]pyridin-3-yl]-2-(methylthio)pyrimidine-5-carbonitrile [162-2] and 47.3 mg of 3-[(1S)-1-aminoethyl]aniline, according to the method of Example 80-(4).

(4) 15.2 mg of the target compound [162] was obtained as a yellow solid, from 15.1 mg of the 2-{[(1S)-1-(3-aminophenyl)ethyl]amino}-4-[8-(methylsulfonyl)imidazo[1,2-a]pyridin-3-yl]pyrimidine-5-carbonitrile [162-3] and 12.8 μL of 1-methyl-4-piperidone, according to the method of Example 91.

A spectral data of the compound [162] is presented below.
$^1$H-NMR (CDCl$_3$) δ: 8.92-8.89 (m, 2H), 8.61 (s, 1H×⅕), 8.59 (s, 1H×⅘), 8.13 (d, J=7.3 Hz, 1H×⅕), 8.04 (d, J=7.3 Hz, 1Hx⅘), 7.33-7.12 (m, 1H), 6.89-6.56 (m, 4H), 6.17-6.10 (m, 1Hx⅘), 6.02-5.92 (m, 1H×⅕), 5.26-5.17 (m, 1H×⅕), 5.00-4.87 (m, 1Hx⅘), 3.76-3.60 (m, 1H), 3.56 (s, 3Hx⅕), 3.52 (s, 3Hx⅘), 3.37-3.20 (m, 1H), 2.90-2.75 (m, 2H), 2.32 (s, 3H), 2.26-1.96 (m, 4H), 1.62 (d, J=6.8 Hz, 3H), 1.60-1.42 (m, 2H) mass: 531 (M+1)$^+$.

INDUSTRIAL APPLICABILITY

Since the compound of the present invention has an excellent inhibitory effect against PLK1 and cell proliferation, it is expected to serve as a useful anticancer agent in the field of medicine.

The invention claimed is:
1. A compound represented by Formula [I]:

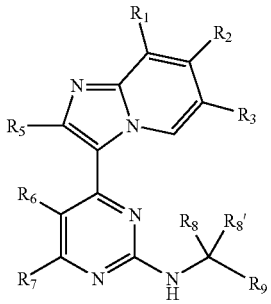

wherein:
$R_1$, $R_2$, and $R_3$, which may be identical or different, are each a hydrogen atom, a substituent selected from "Substituent Group α", a lower alkyl group which may be substituted with one or more substituents selected from "Substituent Group α", a cycloalkyl group, an aryl group or a heteroaryl group wherein the aryl group and heteroaryl group each independently may be substituted with one or more substituents, which may be identical or different, selected from the following 1) to 3):
1) a lower alkyl group,
2) a substituent selected from "Substituent Group α", and
3) a lower alkyl group substituted with a substituent selected from "Substituent Group α", or $R_a$ wherein $R_a$ is represented by —$Z_1$—$Z_2$—$Z_3$,
$Z_1$ is O or NHCO;
$Z_2$ is a single bond or $(CHW_i)_{n1}$ wherein $n_1$ is an integer from 1 to 3; i is an integer from 1 to $n_1$; $(CHW_i)_{n1}$ represents $(CHW_1)$ when $n_1$=1, $(CHW_i)_{n1}$ represents $(CHW_1)$—$(CHW_2)$ when $n_1$=2, and $(CHW_i)_{n1}$ represents $(CHW_1)$—$(CHW_2)$—$(CHW_3)$ when $n_1$=3; and $W_1$, $W_2$, and $W_3$, which may be identical or different, are each a hydrogen atom or a lower alkyl group having 1 to 2 carbon atom(s);
$Z_3$ is a lower alkoxy group or a phenyl group wherein the phenyl group may be substituted with one or more substituents selected from "Substituent Group α",
$R_5$ is a hydrogen atom or a methyl group;
$R_6$ and $R_7$, which may be identical or different, are each a hydrogen atom, a substituent selected from "Substituent Group β", a lower alkyl group which may be substituted with one or more substituents selected from "Substituent Group β", or a 5- or 6-membered aliphatic heterocyclic group selected from a pyrrolidinyl group, a piperidinyl group, and a piperazinyl group wherein the 5- or 6-membered aliphatic heterocyclic group may be substituted with one or more substituents, which may be identical or different, selected from the following 1) to 3):
1) a lower alkyl group,
2) a substituent selected from "Substituent Group β", and
3) a lower alkyl group substituted with a substituent selected from "Substituent Group β",
$R_8$ and $R_8'$, which may be identical or different, are each a hydrogen atom or a lower alkyl group which may be substituted with one or more substituents selected from "Substituent Group α";
$R_9$ is a phenyl group wherein the phenyl group may be substituted with one or more substituents, which may be identical or different, selected from the following 1) to 5):
1) a substituent selected from "Substituent Group α",
2) a 4- to 6-membered aliphatic heterocyclic group selected from an azetidinyl group, a pyrrolidinyl group, a piperidinyl group, and a piperazinyl group wherein the 4- to 6-membered aliphatic heterocyclic group may be substituted with one or more substituents, which may be identical or different, selected from the following a) to c):
a) a lower alkyl group,
b) a substituent selected from "Substituent Group α", and
c) a lower alkyl group substituted with a substituent selected from "Substituent Group α", and in the 4- to 6-membered aliphatic heterocyclic group, two hydrogen atoms binding to the same carbon atom may be replaced by an oxo group; a bond between adjacent carbon atoms constituting the heterocyclic ring may be a double bond; and nonadjacent carbon atoms constituting the heterocyclic ring may form a cross-linkage,
3) a lower alkyl group substituted with the 5- to 6-membered aliphatic heterocyclic group mentioned in 2) above,
4) —$NR_{10}R'_{10}$ wherein:
$R_{10}$ is a hydrogen atom or a lower alkyl group having 1 to 2 carbon atom(s),
$R_{10}'$ is:
a) a lower alkyl group substituted with a substituent selected from "Substituent Group α", or
b) a 4- to 6-membered aliphatic heterocyclic group selected from an azetidinyl group, a pyrrolidinyl group, a piperidinyl group, a piperazinyl group, and a morpholino group wherein the 4- to 6-membered aliphatic heterocyclic group may be substituted with one or more substituents, which may be identical or different, selected from the following aa) to ee):
aa) a lower alkyl group,
bb) a substituent selected from "Substituent Group α",
cc) a lower alkyl group substituted with a substituent selected from "Substituent Group α",
dd) a 5- to 6-membered aliphatic heterocyclic group, which may be substituted, selected from a pyrrolidinyl group, a piperidinyl group, and a piperazinyl group, and
ee) a lower alkyl group substituted with an aromatic heterocyclic ring selected from a pyridyl group, a pyrazinyl group, and a pyrimidinyl group, which may be substituted, and 5) —NHCOR$_{13}$ wherein:
R$_{13}$ is:
a) a lower alkyl group,
b) a substituent selected from "Substituent Group α", or
c) a lower alkyl group substituted with one or more substituents selected from "Substituent Group α".

"Substituent Group α" and "Substituent Group β" are defined as follows:
"Substituent Group α":
a halogen atom, a hydroxy group, a nitro group, a cyano group, an amino group, a carbamoyl group, an aminosulfonyl group, a lower alkylamino group, a hydroxy-lower alkylamino group, a di-lower alkylamino group, an imino group, a lower alkylsulfonyl group, a lower alkylsulfonylamino group, a lower alkyl group which may be substituted with 1 to 3 halogen atom(s), a lower alkoxycarbonyl group, a lower alkoxycarbonylamino group, a lower alkanoyl group which may be substituted with 1 to 3 halogen atom(s), and a carboxyl group; and
"Substituent Group β":
a halogen atom, a hydroxy group, a cyano group, an amino group, a formyl group, a carbamoyl group, an aminosulfonyl group, a lower alkylamino group, a di-lower alkylamino group, a hydroxy-lower alkylamino group, a hydroxyiminomethyl group, a methoxyiminomethyl group, a lower alkoxy group, a lower alkoxycarbonyl group, a lower alkoxycarbonylamino group, a lower alkanoyl group, a lower alkanoyloxy group, a lower alkylthio group, a lower alkylsulfonyl group, a carboxyl group, and a tetrazolyl group.

2. The compound according to claim 1, wherein:
the "Substituent Group β" is a halogen atom, a cyano group, and a lower alkoxy group; R$_6$ is a hydrogen atom or a substituent selected from the "Substituent Group β"; and R$_7$ is a hydrogen atom;
one of R$_8$ and R$_8$' is a hydrogen atom, and the other one is a methyl group or an ethyl group.

3. The compound according to claim 2, wherein:
R$_1$ is a halogen atom; a cyano group; a lower alkyl group having 1 to 2 carbon atom(s), which may be substituted with 1 to 3 halogen atom(s); a lower alkoxy group having 1 to 2 carbon atom(s), which may be substituted with 1 to 3 halogen atom(s); a lower alkyl group having 1 to 3 carbon atom(s), which may be substituted with a hydroxy group; or a cyclopropyl group;
R$_2$ and R$_3$ may be identical or different from each other, and are each a hydrogen atom; a halogen atom; a cyano group; a lower alkyl group having 1 to 2 carbon atom(s), which may be substituted with 1 to 3 halogen atom(s); a lower alkoxy group having 1 to 2 carbon atom(s), which may be substituted with 1 to 3 halogen atom(s); or a lower alkyl group having 1 to 3 carbon atom(s), which may be substituted with a hydroxy group.

4. The compound according to claim 3, wherein R$_5$ is a hydrogen atom; R$_6$ is a cyano group; and any one of R$_8$ and R$_8$' is a hydrogen atom and the other one is a methyl group.

5. The compound according to claim 4, wherein:
the "Substituent Group α" is a halogen atom, a hydroxy group, a cyano group, an amino group, a lower alkylamino group, a di-lower alkylamino group, a lower alkylsulfonyl group, a lower alkoxy group which may be substituted with 1 to 3 fluorine atom(s), and a lower alkanoyl group which may be substituted with 1 to 3 fluorine atom(s).

6. The compound according to claim 5, wherein:
R$_1$ is a fluorine atom; a chlorine atom; a bromine atom; a cyano group; a methyl group which may be substituted with 1 to 3 halogen atom(s); a methoxy group which may be substituted with 1 to 3 halogen atom(s); a lower alkyl group having 1 to 3 carbon atom(s), which may be substituted with a hydroxy group; or a cyclopropyl group;
R$_2$ and R$_3$ are each a hydrogen atom; and
R$_9$ is a phenyl group wherein the 3-position or 4-position of the phenyl group may be substituted with the following 1) or 2):
1) a pyrrolidinyl group or piperazinyl group which may be substituted with one or more of a lower alkyl group and/or a substituent(s) selected from "Substituent Group α", or
2) —NR$_{10}$R$_{10}$' wherein:
R$_{10}$ is a hydrogen atom,
R$_{10}$' is an azetidinyl group or a piperidinyl group which may be substituted with a lower alkyl group optionally substituted with one or more substituents selected from "Substituent Group α".

7. The compound according to claim 1, which is:
(a) 4-(8-methylimidazo [1,2-a]pyridin-3-yl)-2-{[(1S)-1-phenylethyl]amino}-5-pyrimidinecarbonitrile,
(b) 5-bromo-4-(8-chloroimidazo[1,2-a]pyridin-3-yl)-N-[(1S)-1-phenylethyl]-2-pyrimidinamine,
(c) 4-(8-chloroimidazo[1,2-a]pyridin-3-yl)-2-{[(1S)-1-phenylethyl]amino}-5-pyrimidinecarbonitrile,
(d) 5-bromo-4-[8-(difluoromethyl)imidazo[1,2-a]pyridin-3-yl]-N-[(1S)-1-phenylethyl]-2-pyrimidinamine,
(e) 3-(5-cyano-2-{[(1S)-1-phenylethyl]amino}-4-pyrimidinyl)imidazo[1,2-a]pyridine-8-carbonitrile,
(f) 4-[8-(difluoromethyl)imidazo[1,2-a]pyridin-3-yl]-2-{[(1S)-1-phenylethyl]amino}-5-pyrimidinecarbonitrile,
(g) N-[(1S)-1-phenylethyl]-4-[8-(trifluoromethyl)imidazo[1,2-a]pyridin-3-yl]-2-pyrimidinamine,
(h) 5-bromo-N-[(1S)-1-phenylethyl]-4-[8-(trifluoromethyl)imidazo[1,2-a]pyridin-3-yl]-2-pyrimidinamine,
(i) 2-{[(1S)-1-phenylethyl]amino}-4-[8-(trifluoromethyl)imidazo[1,2-a]pyridin-3-yl]-5-pyrimidinecarbonitrile,
(j) 2-{[(1S)-1-(3-aminophenyl)ethyl]amino}-4-[8-(difluoromethyl)imidazo[1,2-a]pyridin-3-yl]pyrimidine-5-carbonitrile,
(k) 4-[8-(difluoromethyl)imidazo[1,2-a]pyridin-3-yl]-2-[((1S)-1-{3-[(1-methylazetidin-3-yl)amino]phenyl}ethyl)amino]pyrimidine-5-carbonitrile,
(l) 4-[8-(difluoromethyl)imidazo[1,2-a]pyridin-3-yl]-2-{[(1S)-1-(4-piperazin-1-ylphenyl)ethyl]amino}pyrimidine-5-carbonitrile,
(m) 4-(8-methylimidazo[1,2-a]pyridin-3-yl)-2-[((1S)-1-{3-[(1-methylpiperidin-4-yl)amino]phenyl}ethyl)amino]pyrimidine-5-carbonitrile,
(n) 4-(8-chloroimidazo[1,2-a]pyridin-3-yl)-2-[((1S)-1-{3-[(1-methylpiperidin-4-yl)amino]phenyl}ethyl)amino]pyrimidine-5-carbonitrile,
(o) 4-(8-chloroimidazo[1,2-a]pyridin-3-yl)-2-{[(1S)-1-(4-piperazin-1-ylphenyl)ethyl]amino}pyrimidine-5-carbonitrile,
(p) 2-[((1S)-1-{4-[(3R)-3-aminopyrrolidin-1-yl]phenyl}ethyl)amino]-4-(8-chloroimidazo[1,2-a]pyridin-3-yl)pyrimidine-5-carbonitrile,
(q) 4-(8-bromoimidazo[1,2-a]pyridin-3-yl)-2-{[(1S)-1-(4-piperazin-1-ylphenyl)ethyl]amino}pyrimidine-5-carbonitrile,
(r) 4-[8-(fluoromethyl)imidazo[1,2- a]pyridin-3-yl]-2-{[(1S)-1-(4-piperazin-1-ylphenyl)ethyl]amino}pyrimidine-5-carbonitrile, (s) 4-[8-(fluoromethyl)imidazo [1,2-a]pyridin-3-yl]-2-{[(1S)-1-(4-piperidin-4-ylphenyl)ethyl]amino}pyrimidine-5-carbonitrile, (t) 4-[8-(1-hydroxyethyl)imidazo[1,2-a]pyridin-3-yl]-2-{[(1S)-1-(4-piperazin-1-ylphenyl)ethyl]amino}pyrimidine-5-carbonitrile, or (u) 4-(8-methoxyimidazo[1,2-a]pyridin-3-yl)-2-{[(1S)-1-(4-piperazin-1-ylphenyl)ethyl]amino}pyrimidine-5-carbonitrile.

* * * * *